United States Patent
Messmann et al.

(10) Patent No.: US 12,240,870 B2
(45) Date of Patent: Mar. 4, 2025

(54) SEQUENCING METHOD FOR CAR T CELL THERAPY

(71) Applicants: Purdue Research Foundation, West Lafayette, IN (US); ENDOCYTE, INC., West Lafayette, IN (US); SEATTLE CHILDREN'S HOSPITAL, Seattle, WA (US)

(72) Inventors: Richard Messmann, Brighton, MI (US); Christopher Paul Leamon, West Lafayette, IN (US); Haiyan Chu, West Lafayette, IN (US); Yingjuan June Lu, West Lafayette, IN (US); Philip Stewart Low, West Lafayette, IN (US); Michael C. Jensen, Bainbridge Island, WA (US); James Matthaei, Seattle, WA (US); Navin Robert Charles Pinto, Seattle, WA (US); Julie Ruggieri Park, Seattle, WA (US)

(73) Assignees: Purdue Research Foundation, West Lafayette, IN (US); Endocyte, Inc, West Lafayette, IN (US); Seattle Children's Hospital, Seattle, WA (US)

( * ) Notice: Subject to any disclaimer, the term of this patent is extended or adjusted under 35 U.S.C. 154(b) by 969 days.

(21) Appl. No.: 16/971,801

(22) PCT Filed: Feb. 22, 2019

(86) PCT No.: PCT/US2019/019191
§ 371 (c)(1),
(2) Date: Aug. 21, 2020

(87) PCT Pub. No.: WO2019/165237
PCT Pub. Date: Aug. 29, 2019

(65) Prior Publication Data
US 2021/0346431 A1  Nov. 11, 2021

Related U.S. Application Data

(60) Provisional application No. 62/634,573, filed on Feb. 23, 2018, provisional application No. 62/656,265, (Continued)

(51) Int. Cl.
*A61K 39/00* (2006.01)
*A61K 47/55* (2017.01)
(Continued)

(52) U.S. Cl.
CPC ........ *A61K 47/551* (2017.08); *A61K 39/4611* (2023.05); *A61K 39/4631* (2023.05);
(Continued)

(58) Field of Classification Search
CPC A61K 39/46; A61K 39/4611; A61K 39/4631; A61K 2039/545; A61K 2239/38
See application file for complete search history.

(56) References Cited

U.S. PATENT DOCUMENTS

| 4,690,915 A | 9/1987 | Rosenberg |
| 4,946,778 A | 8/1990 | Ladner et al. |

(Continued)

FOREIGN PATENT DOCUMENTS

| CN | 102775500 A | 11/2012 |
| CN | 106132436 A | 11/2016 |

(Continued)

OTHER PUBLICATIONS

Rodgers et al, Switch-mediated activation and retargeting of CAR-T cells for B-cell malignancies, Proc. Nat'l. Acad. Sci. e459-e468, available online Jan. 12, 2016.*

(Continued)

*Primary Examiner* — Kevin K Hill
(74) *Attorney, Agent, or Firm* — Schwegman Lundberg & Woessner, P.A.

(57) ABSTRACT

The present disclosure relates to methods of treating a patient with a cancer by administering to the patient a composition comprising CAR T cells and administering to (Continued)

the patient a small molecule linked to a targeting moiety by a linker. The disclosure also relates to compositions for use in such methods.

14 Claims, 20 Drawing Sheets

Related U.S. Application Data filed on Apr. 11, 2018, provisional application No. 62/724,345, filed on Aug. 29, 2018, provisional application No. 62/736,730, filed on Sep. 26, 2018.

(51) Int. Cl.
*A61P 35/00* (2006.01)
*C07K 14/705* (2006.01)

(52) U.S. Cl.
CPC .. *A61K 39/464404* (2023.05); *A61K 39/4646* (2023.05); *A61P 35/00* (2018.01); *C07K 14/705* (2013.01); *A61K 2239/38* (2023.05)

(56) References Cited

U.S. PATENT DOCUMENTS

| | | |
|---|---|---|
| 5,087,616 A | 2/1992 | Myers et al. |
| 5,116,964 A | 5/1992 | Capon et al. |
| 5,202,238 A | 4/1993 | Fell, Jr. et al. |
| 5,216,132 A | 6/1993 | Basi |
| 5,359,046 A | 10/1994 | Capon et al. |
| 5,372,930 A | 12/1994 | Colton et al. |
| 5,482,856 A | 1/1996 | Fell, Jr. et al. |
| 5,514,582 A | 5/1996 | Capon et al. |
| 5,525,503 A | 6/1996 | Rudd et al. |
| 5,538,866 A | 7/1996 | Israeli et al. |
| 5,670,148 A | 9/1997 | Sherwin et al. |
| 5,686,281 A | 11/1997 | Roberts |
| 5,712,149 A | 1/1998 | Roberts |
| 5,714,147 A | 2/1998 | Capon et al. |
| 5,741,899 A | 4/1998 | Capon et al. |
| 5,747,292 A | 5/1998 | Greenberg et al. |
| 5,830,755 A | 11/1998 | Nishimura et al. |
| 5,834,256 A | 11/1998 | Finer et al. |
| 5,837,544 A | 11/1998 | Capon et al. |
| 5,843,728 A | 12/1998 | Seed et al. |
| 5,851,828 A | 12/1998 | Seed et al. |
| 5,858,740 A | 1/1999 | Finer et al. |
| 5,861,156 A | 1/1999 | George et al. |
| 5,906,936 A | 5/1999 | Eshhar et al. |
| 5,908,638 A | 6/1999 | Huber et al. |
| 5,912,170 A | 6/1999 | Seed et al. |
| 5,912,172 A | 6/1999 | Eshhar et al. |
| 5,914,109 A | 6/1999 | Zolla-Pazner et al. |
| 5,935,818 A | 8/1999 | Israeli et al. |
| 5,969,102 A | 10/1999 | Bram et al. |
| 6,004,781 A | 12/1999 | Seed |
| 6,004,811 A | 12/1999 | Seed et al. |
| 6,005,004 A | 12/1999 | Katz et al. |
| 6,077,947 A | 6/2000 | Capon et al. |
| 6,083,751 A | 7/2000 | Feldhaus et al. |
| 6,103,521 A | 8/2000 | Capon et al. |
| 6,117,656 A | 9/2000 | Seed |
| 6,132,718 A | 10/2000 | Hansen |
| 6,218,187 B1 | 4/2001 | Finer et al. |
| 6,261,787 B1 | 7/2001 | Davis et al. |
| 6,319,494 B1 | 11/2001 | Capon et al. |
| 6,392,013 B1 | 5/2002 | Seed et al. |
| 6,406,697 B1 | 6/2002 | Capon et al. |
| 6,407,221 B1 | 6/2002 | Capon et al. |
| 6,410,014 B1 | 6/2002 | Seed et al. |
| 6,410,319 B1 | 6/2002 | Raubitschek et al. |
| 6,432,403 B1 | 8/2002 | Philips |
| 6,451,995 B1 | 9/2002 | Cheung et al. |
| 6,521,602 B1 | 2/2003 | Patel et al. |
| 6,524,572 B1 | 2/2003 | Li |
| 6,699,972 B1 | 3/2004 | Roffler et al. |
| 6,753,162 B1 | 6/2004 | Seed et al. |
| 6,759,243 B2 | 7/2004 | Kranz et al. |
| 6,770,749 B2 | 8/2004 | Ellenhorn et al. |
| 6,953,668 B1 | 10/2005 | Israeli et al. |
| 7,037,647 B1 | 5/2006 | Israeli et al. |
| 7,049,136 B2 | 5/2006 | Seed et al. |
| 7,052,906 B1 | 5/2006 | Lawson et al. |
| 7,070,995 B2 | 7/2006 | Jensen |
| 7,105,159 B1 | 9/2006 | Israeli et al. |
| 7,217,421 B1 | 5/2007 | McArthur et al. |
| 7,265,209 B2 | 9/2007 | Jensen |
| 7,320,787 B2 | 1/2008 | Seed et al. |
| 7,348,004 B2 | 3/2008 | Peters et al. |
| 7,354,587 B1 | 4/2008 | Hansen |
| 7,354,762 B2 | 4/2008 | Jensen |
| 7,381,408 B2 | 6/2008 | Mezo et al. |
| 7,404,956 B2 | 7/2008 | Peters et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,482,005 B2 | 1/2009 | Kim |
| 7,514,537 B2 | 4/2009 | Jensen |
| 7,569,663 B2 | 8/2009 | Tykocinski et al. |
| 7,572,891 B2 | 8/2009 | Belldegrun et al. |
| 7,618,817 B2 | 11/2009 | Campbell |
| 7,632,497 B2 | 12/2009 | Stavenhagen |
| 7,655,461 B2 | 2/2010 | Finn et al. |
| 7,666,424 B2 | 2/2010 | Cheung et al. |
| 7,723,111 B2 | 5/2010 | Hwu et al. |
| 7,741,465 B1 | 6/2010 | Eshhar et al. |
| 7,871,817 B2 | 1/2011 | Voss et al. |
| 7,906,620 B2 | 3/2011 | Eisenbach et al. |
| 7,919,079 B2 | 4/2011 | Simmons et al. |
| 7,939,059 B2 | 5/2011 | Yang et al. |
| 7,994,298 B2 | 8/2011 | Zhang et al. |
| 7,998,736 B2 | 8/2011 | Morgan et al. |
| 8,105,830 B2 | 1/2012 | Weidanz et al. |
| 8,148,154 B2 | 4/2012 | Cheung et al. |
| 8,163,887 B2 | 4/2012 | Hansen |
| 8,211,422 B2 | 7/2012 | Eshhar et al. |
| RE43,586 E | 8/2012 | Israeli et al. |
| 8,252,914 B2 | 8/2012 | Zhang et al. |
| 8,324,353 B2 | 12/2012 | Jensen |
| 8,389,282 B2 | 3/2013 | Sadelain et al. |
| 8,399,645 B2 | 3/2013 | Campana et al. |
| 8,409,577 B2 | 4/2013 | Thompson et al. |
| 8,450,112 B2 | 5/2013 | Li et al. |
| 8,465,743 B2 | 6/2013 | Rosenberg et al. |
| 8,486,911 B2 | 7/2013 | Okada et al. |
| 8,497,118 B2 | 7/2013 | Jensen |
| 8,741,306 B2 | 6/2014 | Belldegrun et al. |
| 8,802,374 B2 | 8/2014 | Jensen |
| 8,809,050 B2 | 8/2014 | Vera et al. |
| 8,822,196 B2 | 9/2014 | Rosenberg et al. |
| 8,822,647 B2 | 9/2014 | Jensen |
| 8,859,229 B2 | 10/2014 | Rabinovich et al. |
| 8,877,199 B2 | 11/2014 | Rader et al. |
| 8,906,682 B2 | 12/2014 | June et al. |
| 8,911,993 B2 | 12/2014 | June et al. |
| 8,932,830 B2 | 1/2015 | Peters et al. |
| 8,946,385 B2 | 2/2015 | Kawai |
| 8,956,860 B2 | 2/2015 | Vera et al. |
| 9,023,621 B2 | 5/2015 | Gurney et al. |
| 9,040,669 B2 | 5/2015 | Cheung et al. |
| 9,062,127 B2 | 6/2015 | Voss et al. |
| 9,074,000 B2 | 7/2015 | Scheinberg et al. |
| 9,089,520 B2 | 7/2015 | Brenner |
| 9,101,584 B2 | 8/2015 | June et al. |
| 9,101,609 B2 | 8/2015 | Tan et al. |
| 9,102,760 B2 | 8/2015 | June et al. |
| 9,102,761 B2 | 8/2015 | June et al. |
| 9,111,061 B2 | 8/2015 | Otsuka et al. |
| 9,133,436 B2 | 9/2015 | Riley et al. |
| 9,156,915 B2 | 10/2015 | Waldman et al. |
| 9,163,258 B2 | 10/2015 | Riddell et al. |
| 9,175,308 B2 | 11/2015 | Shiku et al. |

(56) References Cited

U.S. PATENT DOCUMENTS

| | | |
|---|---|---|
| 9,181,527 B2 | 11/2015 | Sentman |
| 9,211,321 B2 | 12/2015 | Karlsson-Parra et al. |
| 9,212,229 B2 | 12/2015 | Schonfeld et al. |
| 9,220,728 B2 | 12/2015 | Sadelain et al. |
| 9,226,936 B2 | 1/2016 | Hu et al. |
| 9,233,125 B2 | 1/2016 | Davila et al. |
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,865 B2 | 8/2016 | Powell et al. |
| 9,402,888 B2 | 8/2016 | Ertl et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell, Jr. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana et al. |
| 9,623,049 B2 | 4/2017 | Eshhar et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |
| 9,663,756 B1 | 5/2017 | Lipkens et al. |
| 9,663,763 B2 | 5/2017 | Sentman |
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |
| 9,701,758 B2 | 7/2017 | Cooper et al. |
| 9,708,384 B2 | 7/2017 | Scholler et al. |
| 9,714,278 B2 | 7/2017 | June et al. |
| 9,717,745 B2 | 8/2017 | He |
| 9,725,519 B2 | 8/2017 | Masuko et al. |
| 9,733,245 B2 | 8/2017 | Kawai |
| 9,738,726 B2 | 8/2017 | Dimitrov et al. |
| 9,745,368 B2 | 8/2017 | Milone et al. |
| 9,765,142 B2 | 9/2017 | Dimitrov et al. |
| 9,765,156 B2 | 9/2017 | June et al. |
| 9,765,330 B1 | 9/2017 | Niazi et al. |
| 9,765,342 B2 | 9/2017 | Kochenderfer |
| 9,777,061 B2 | 10/2017 | Ebersbach et al. |
| 9,777,064 B2 | 10/2017 | Wang et al. |
| 9,783,591 B2 | 10/2017 | June et al. |
| 9,789,174 B2 | 10/2017 | Karlsson-Parra et al. |
| 9,790,267 B2 | 10/2017 | Kaplan |
| 9,790,278 B2 | 10/2017 | Sentman et al. |
| 9,790,282 B2 | 10/2017 | Orentas et al. |
| 9,790,467 B2 | 10/2017 | Kevlahan et al. |
| 9,796,783 B2 | 10/2017 | Ågerstam et al. |
| 9,802,997 B2 | 10/2017 | Mahr et al. |
| 9,803,022 B2 | 10/2017 | Ho et al. |
| 9,808,486 B2 | 11/2017 | Georgiou et al. |
| 9,809,581 B2 | 11/2017 | Chen et al. |
| 9,815,901 B2 | 11/2017 | Brogdon et al. |
| 9,815,908 B2 | 11/2017 | Schonfeld et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,840,548 B2 | 12/2017 | Mahr et al. |
| 9,845,362 B2 | 12/2017 | Mukherjee |
| 9,849,092 B2 | 12/2017 | Peyman |
| 9,855,297 B2 | 1/2018 | Duchateau et al. |
| 9,855,298 B2 | 1/2018 | Bot et al. |
| 9,856,322 B2 | 1/2018 | Campana et al. |
| 9,856,497 B2 | 1/2018 | Qi et al. |
| 9,856,501 B2 | 1/2018 | O'Keefe |
| 9,856,756 B2 | 1/2018 | Mahr et al. |
| 9,862,775 B2 | 1/2018 | Kwon et al. |
| 9,868,774 B2 | 1/2018 | Orentas et al. |
| 9,868,951 B2 | 1/2018 | Hu et al. |
| 9,873,894 B2 | 1/2018 | Conway et al. |
| 9,879,087 B2 | 1/2018 | DeSander et al. |
| 9,885,021 B2 | 2/2018 | Bollard et al. |
| 9,889,160 B2 | 2/2018 | Jantz et al. |
| 9,889,161 B2 | 2/2018 | Jantz et al. |
| 9,890,393 B2 | 2/2018 | Duchateau et al. |
| 9,914,909 B2 | 3/2018 | Brown et al. |
| 10,117,897 B2 | 11/2018 | Sadelain et al. |
| 11,311,576 B2 | 4/2022 | Jensen et al. |
| 11,759,480 B2 | 9/2023 | Low et al. |
| 11,779,602 B2 | 10/2023 | Low et al. |
| 2001/0031252 A1 | 10/2001 | Low et al. |
| 2002/0004052 A1 | 1/2002 | Berd et al. |
| 2002/0018783 A1 | 2/2002 | Sadelain et al. |
| 2002/0111474 A1 | 8/2002 | Capon et al. |
| 2002/0132983 A1 | 9/2002 | Junghans |
| 2003/0077249 A1 | 4/2003 | Bebbington et al. |
| 2003/0170238 A1 | 9/2003 | Gruenberg et al. |
| 2003/0171546 A1 | 9/2003 | Jensen |
| 2003/0175288 A1 | 9/2003 | Itoh |
| 2003/0215427 A1 | 11/2003 | Jensen |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2006/0018878 A1 | 1/2006 | Cooper et al. |
| 2006/0067920 A1 | 3/2006 | Jensen |
| 2006/0155115 A1 | 7/2006 | Jakobsen et al. |
| 2007/0031438 A1 | 2/2007 | Junghans |
| 2007/0036773 A1 | 2/2007 | Cooper et al. |
| 2008/0051380 A1 | 2/2008 | Auerbach et al. |
| 2008/0188000 A1 | 8/2008 | Reik et al. |

(56) References Cited

U.S. PATENT DOCUMENTS

| | | |
|---|---|---|
| 2009/0011984 A1 | 1/2009 | Yla-Herttuala et al. |
| 2009/0191172 A1 | 7/2009 | Cooper et al. |
| 2009/0202501 A1 | 8/2009 | Zhang et al. |
| 2009/0257994 A1 | 10/2009 | Jensen |
| 2009/0324630 A1 | 12/2009 | Jensen |
| 2010/0135974 A1 | 6/2010 | Eshhar et al. |
| 2010/0178276 A1 | 7/2010 | Sadelain et al. |
| 2010/0278830 A1 | 11/2010 | Shoemaker et al. |
| 2011/0172254 A1 | 7/2011 | Leamon et al. |
| 2011/0178279 A1 | 7/2011 | Williams et al. |
| 2012/0093842 A1 | 4/2012 | Eshhar et al. |
| 2012/0213783 A1 | 8/2012 | Rosenberg et al. |
| 2012/0302466 A1 | 11/2012 | Sentman |
| 2013/0058936 A1 | 3/2013 | Bruenker et al. |
| 2013/0143895 A1 | 6/2013 | McAllister et al. |
| 2013/0149337 A1 | 6/2013 | Cooper et al. |
| 2013/0156794 A1 | 6/2013 | Eshhar et al. |
| 2013/0287748 A1 | 10/2013 | June et al. |
| 2013/0287752 A1 | 10/2013 | Davila et al. |
| 2013/0309258 A1 | 11/2013 | June et al. |
| 2013/0309267 A1 | 11/2013 | Simmons et al. |
| 2013/0323834 A1 | 12/2013 | Brenner |
| 2013/0344066 A1 | 12/2013 | Faham et al. |
| 2014/0004132 A1 | 1/2014 | Brenner et al. |
| 2014/0004137 A1 | 1/2014 | Ovaa et al. |
| 2014/0017170 A1 | 1/2014 | Irvine et al. |
| 2014/0050708 A1 | 2/2014 | Powell et al. |
| 2014/0099309 A1 | 4/2014 | Powell, Jr. et al. |
| 2014/0120136 A1 | 5/2014 | Katsikis et al. |
| 2014/0134142 A1 | 5/2014 | Smith et al. |
| 2014/0134720 A1 | 5/2014 | Stauss et al. |
| 2014/0227237 A1 | 8/2014 | June et al. |
| 2014/0234348 A1 | 8/2014 | Scholler et al. |
| 2014/0255363 A1 | 9/2014 | Metelitsa et al. |
| 2014/0271582 A1 | 9/2014 | Forman et al. |
| 2014/0271635 A1 | 9/2014 | Brogdon et al. |
| 2014/0274909 A1 | 9/2014 | Orentas et al. |
| 2014/0286973 A1 | 9/2014 | Powell, Jr. |
| 2014/0286987 A1 | 9/2014 | Spencer et al. |
| 2014/0294861 A1 | 10/2014 | Scholler et al. |
| 2014/0301993 A1 | 10/2014 | Powell, Jr. et al. |
| 2014/0308259 A1 | 10/2014 | Scholler et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0356398 A1 | 12/2014 | Riddell et al. |
| 2014/0378389 A1 | 12/2014 | Robbins et al. |
| 2015/0073154 A1 | 3/2015 | Davis |
| 2015/0110760 A1 | 4/2015 | Zhang et al. |
| 2015/0139943 A1 | 5/2015 | Campana et al. |
| 2015/0152181 A1 | 6/2015 | Sentman et al. |
| 2015/0211023 A1 | 7/2015 | Shiboleth et al. |
| 2015/0225470 A1 | 8/2015 | Zhang et al. |
| 2015/0225480 A1 | 8/2015 | Powell, Jr. |
| 2015/0238631 A1 * | 8/2015 | Kim .................. A61K 39/385 530/391.9 |
| 2015/0283178 A1 | 10/2015 | June et al. |
| 2015/0306141 A1 | 10/2015 | Jensen et al. |
| 2015/0307564 A1 | 10/2015 | Young et al. |
| 2015/0307842 A1 | 10/2015 | Sentman |
| 2015/0314014 A1 | 11/2015 | Lauermann |
| 2015/0320799 A1 | 11/2015 | Low et al. |
| 2015/0328292 A1 | 11/2015 | Spencer et al. |
| 2015/0368342 A1 | 12/2015 | Wu et al. |
| 2016/0008398 A1 | 1/2016 | Sadelain et al. |
| 2016/0046700 A1 | 2/2016 | Foster et al. |
| 2016/0046724 A1 | 2/2016 | Brogdon et al. |
| 2016/0046729 A1 | 2/2016 | Schonfeld et al. |
| 2016/0051651 A1 | 2/2016 | Brogdon et al. |
| 2016/0058857 A1 | 3/2016 | Spencer et al. |
| 2016/0068601 A1 | 3/2016 | Brogdon et al. |
| 2016/0076056 A1 | 3/2016 | Reik et al. |
| 2016/0096892 A1 | 4/2016 | Brogdon et al. |
| 2016/0120907 A1 | 5/2016 | Sentman |
| 2016/0129109 A1 | 5/2016 | Davila et al. |
| 2016/0136190 A1 | 5/2016 | Weichert et al. |
| 2016/0151465 A1 | 6/2016 | Slawin et al. |
| 2016/0166613 A1 | 6/2016 | Spencer et al. |
| 2016/0175359 A1 | 6/2016 | Spencer et al. |
| 2016/0185861 A1 | 6/2016 | Bedoya et al. |
| 2016/0222119 A1 | 8/2016 | Scholler et al. |
| 2016/0243258 A1 | 8/2016 | Scharenberg et al. |
| 2016/0250258 A1 | 9/2016 | Delaney et al. |
| 2016/0340649 A1 | 11/2016 | Brown et al. |
| 2016/0361360 A1 | 12/2016 | Chang et al. |
| 2017/0002017 A1 | 1/2017 | Andrez et al. |
| 2017/0015746 A1 | 1/2017 | Jensen |
| 2017/0029531 A1 | 2/2017 | Crane |
| 2017/0029774 A1 | 2/2017 | Jensen et al. |
| 2017/0044240 A1 | 2/2017 | Wagner et al. |
| 2017/0081411 A1 | 3/2017 | Engels et al. |
| 2017/0087185 A1 | 3/2017 | Crane et al. |
| 2017/0152297 A1 | 6/2017 | Jensen |
| 2017/0166877 A1 | 6/2017 | Bayle et al. |
| 2017/0209543 A9 | 7/2017 | Jensen |
| 2017/0224733 A1 | 8/2017 | Badie et al. |
| 2017/0267742 A1 | 9/2017 | Jensen et al. |
| 2017/0306303 A1 | 10/2017 | Taunton et al. |
| 2017/0340672 A1 | 11/2017 | Wu et al. |
| 2017/0342124 A1 | 11/2017 | Scholler et al. |
| 2017/0356010 A1 | 12/2017 | Frost et al. |
| 2017/0360910 A1 | 12/2017 | Wang et al. |
| 2017/0368098 A1 | 12/2017 | Chen et al. |
| 2018/0009891 A1 | 1/2018 | Jensen |
| 2018/0016539 A1 | 1/2018 | Ding et al. |
| 2018/0022795 A1 | 1/2018 | Milone et al. |
| 2018/0022828 A1 | 1/2018 | Schonfeld et al. |
| 2018/0142198 A1 | 5/2018 | Sharei et al. |
| 2018/0142239 A1 | 5/2018 | Yu et al. |
| 2018/0214527 A1 | 8/2018 | Wang et al. |
| 2018/0282692 A1 | 10/2018 | Rawlings et al. |
| 2018/0320133 A1 | 11/2018 | Forman et al. |
| 2018/0327781 A1 | 11/2018 | Scharenberg et al. |
| 2019/0000881 A1 | 1/2019 | Sadelain et al. |
| 2019/0016776 A1 | 1/2019 | Jensen et al. |
| 2019/0091308 A1 | 3/2019 | Low et al. |
| 2019/0161531 A1 | 5/2019 | Pule et al. |
| 2019/0209611 A1 | 7/2019 | Eckardt et al. |
| 2019/0224237 A1 | 7/2019 | Jensen et al. |
| 2019/0255109 A1 | 8/2019 | Low et al. |
| 2019/0292517 A1 | 9/2019 | Cheung et al. |
| 2019/0388468 A1 | 12/2019 | Lock et al. |
| 2020/0023009 A1 | 1/2020 | Low et al. |
| 2020/0054676 A1 | 2/2020 | Low et al. |
| 2020/0087399 A1 | 3/2020 | Jensen et al. |
| 2020/0123224 A1 | 4/2020 | Scharenberg |
| 2020/0354477 A1 | 11/2020 | Jensen et al. |
| 2020/0405760 A1 | 12/2020 | Low et al. |
| 2021/0147871 A1 | 5/2021 | Scharenberg et al. |
| 2021/0308267 A1 | 10/2021 | Low et al. |
| 2021/0317407 A1 | 10/2021 | Jensen et al. |
| 2021/0340573 A1 | 11/2021 | Scharenberg et al. |
| 2022/0000996 A1 | 1/2022 | Low et al. |
| 2022/0017920 A1 | 1/2022 | Scharenberg et al. |
| 2022/0257652 A1 | 8/2022 | Jensen et al. |
| 2022/0280648 A1 | 9/2022 | Low et al. |
| 2022/0409747 A1 | 12/2022 | Low et al. |
| 2023/0068879 A1 | 3/2023 | Jensen et al. |
| 2023/0172981 A1 | 6/2023 | Jensen et al. |
| 2023/0322925 A1 | 10/2023 | Jensen et al. |
| 2023/0348624 A1 | 11/2023 | Scharenberg et al. |

FOREIGN PATENT DOCUMENTS

| | | |
|---|---|---|
| CN | 106163547 A | 11/2016 |
| CN | 112105382 | 12/2020 |
| EP | 0340793 A2 | 11/1989 |
| EP | 2177230 A1 | 4/2010 |
| EP | 10009345 | 9/2010 |
| EP | 2537416 B1 | 11/2014 |
| EP | 2614077 B1 | 8/2016 |
| JP | 2015525765 A | 9/2015 |
| JP | 2016534995 A | 11/2016 |
| JP | 2017507919 A | 3/2017 |

(56) References Cited

FOREIGN PATENT DOCUMENTS

| | | |
|---|---|---|
| TW | 201834668 | 10/2018 |
| TW | 202000229 | 1/2020 |
| WO | WO-8604356 A1 | 7/1986 |
| WO | WO-9210591 A1 | 6/1992 |
| WO | WO-9215671 A1 | 9/1992 |
| WO | WO-9530014 A1 | 11/1995 |
| WO | WO-9723613 A2 | 7/1997 |
| WO | WO-9734634 A1 | 9/1997 |
| WO | WO-9958572 A1 | 11/1999 |
| WO | WO-0014257 | 3/2000 |
| WO | WO-0023573 A2 | 4/2000 |
| WO | WO-0191625 A2 | 12/2001 |
| WO | WO-02088334 A1 | 11/2002 |
| WO | WO-2005079836 A1 | 9/2005 |
| WO | WO-2005084716 A2 | 9/2005 |
| WO | WO-2006029879 A2 | 3/2006 |
| WO | WO-2006036445 A2 | 4/2006 |
| WO | WO-2008031577 A1 | 3/2008 |
| WO | WO-2008045437 A2 | 4/2008 |
| WO | WO-2008057437 A2 | 5/2008 |
| WO | WO-2008121420 A1 | 10/2008 |
| WO | WO-2009091826 A2 | 7/2009 |
| WO | WO-2009117117 A1 | 9/2009 |
| WO | WO-2010025177 A1 | 3/2010 |
| WO | WO-2011041093 A1 | 4/2011 |
| WO | WO-2011059836 A2 | 5/2011 |
| WO | WO-2012028241 A1 | 3/2012 |
| WO | WO-2012031744 A1 | 3/2012 |
| WO | WO-2012054825 A1 | 4/2012 |
| WO | WO-2012079000 A1 | 6/2012 |
| WO | WO-2012082841 A2 | 6/2012 |
| WO | WO-2012099973 A2 | 7/2012 |
| WO | WO-2012129514 A1 | 9/2012 |
| WO | WO-2012138475 A1 | 10/2012 |
| WO | WO-2013019615 A2 | 2/2013 |
| WO | WO-2013039889 A1 | 3/2013 |
| WO | WO-2013044225 A1 | 3/2013 |
| WO | WO-2013063419 A2 | 5/2013 |
| WO | WO-2013067492 A1 | 5/2013 |
| WO | WO-2013071154 A1 | 5/2013 |
| WO | WO-2013088446 A1 | 6/2013 |
| WO | WO-2013093809 A1 | 6/2013 |
| WO | WO-2013112986 A1 | 8/2013 |
| WO | WO-2013123061 A1 | 8/2013 |
| WO | WO-2013126726 A1 | 8/2013 |
| WO | WO-2013166321 A1 | 11/2013 |
| WO | WO-2013177247 A1 | 11/2013 |
| WO | WO-2014011984 A1 | 1/2014 |
| WO | WO-2014011987 A1 | 1/2014 |
| WO | WO-2014031687 A1 | 2/2014 |
| WO | WO-2014039523 A1 | 3/2014 |
| WO | WO-2014043441 A1 | 3/2014 |
| WO | WO-2014055668 A1 | 4/2014 |
| WO | WO-2014055771 A1 | 4/2014 |
| WO | WO-2014068388 A1 | 5/2014 |
| WO | WO-2014099671 A1 | 6/2014 |
| WO | WO-2014100385 A1 | 6/2014 |
| WO | WO-2014100615 A1 | 6/2014 |
| WO | WO-2014124143 A1 | 8/2014 |
| WO | WO-2014127261 A1 | 8/2014 |
| WO | WO-2014130635 A1 | 8/2014 |
| WO | WO-2014152177 A1 | 9/2014 |
| WO | WO-2014153002 A1 | 9/2014 |
| WO | WO-2015057834 A1 | 4/2015 |
| WO | WO-2015057852 A1 | 4/2015 |
| WO | WO-2015107075 A1 | 7/2015 |
| WO | WO-2015123496 A1 | 8/2015 |
| WO | WO-2015164594 A1 | 10/2015 |
| WO | WO-2015188135 A1 | 12/2015 |
| WO | WO-2016025322 A1 | 2/2016 |
| WO | WO-2016025454 A2 | 2/2016 |
| WO | WO-2016054520 A2 | 4/2016 |
| WO | WO-2016073755 A2 | 5/2016 |
| WO | WO-2016098078 A2 | 6/2016 |
| WO | WO-2016102965 A1 | 6/2016 |
| WO | WO-2016109668 A1 | 7/2016 |
| WO | WO-2016132366 A1 | 8/2016 |
| WO | WO2016149665 | 9/2016 |
| WO | WO-2016154621 A1 | 9/2016 |
| WO | WO 2016/168766 A1 | 10/2016 |
| WO | WO-2016168769 A1 | 10/2016 |
| WO | WO-2016168773 A2 | 10/2016 |
| WO | WO-2016201300 A1 | 12/2016 |
| WO | WO-2016210447 A1 | 12/2016 |
| WO | WO-2017025638 A1 | 2/2017 |
| WO | WO-2017029511 A1 | 2/2017 |
| WO | WO-2017029512 A1 | 2/2017 |
| WO | WO-2017035362 A1 | 3/2017 |
| WO | WO-2017062628 A1 | 4/2017 |
| WO | WO-2017068360 A1 | 4/2017 |
| WO | WO-2017068361 A1 | 4/2017 |
| WO | WO-2017114497 A1 | 7/2017 |
| WO | WO-2017123548 A1 | 7/2017 |
| WO | WO-2017136829 A1 | 8/2017 |
| WO | WO-2017137758 A1 | 8/2017 |
| WO | WO-2017137759 A1 | 8/2017 |
| WO | WO-2017143094 A1 | 8/2017 |
| WO | WO-2017143150 A1 | 8/2017 |
| WO | WO-2017165245 A2 | 9/2017 |
| WO | WO-2017165571 A1 | 9/2017 |
| WO | WO2017177149 | 10/2017 |
| WO | WO-2017180587 A2 | 10/2017 |
| WO | WO-2017214167 A1 | 12/2017 |
| WO | WO-2017214170 A2 | 12/2017 |
| WO | WO-2017216561 A1 | 12/2017 |
| WO | WO-2017216562 A1 | 12/2017 |
| WO | WO-2018013797 A1 | 1/2018 |
| WO | WO-2018031694 A1 | 2/2018 |
| WO | WO-2018075794 A1 | 4/2018 |
| WO | WO-2018075807 A1 | 4/2018 |
| WO | WO-2018075813 A1 | 4/2018 |
| WO | WO-2018080541 A1 | 5/2018 |
| WO | WO-2018102761 A1 | 6/2018 |
| WO | WO-2018111763 A1 | 6/2018 |
| WO | WO-2018111834 A1 | 6/2018 |
| WO | WO-2018115146 A1 | 6/2018 |
| WO | WO-2018148224 A1 | 8/2018 |
| WO | WO-2018152451 A1 | 8/2018 |
| WO | WO 2018/160622 A1 | 9/2018 |
| WO | WO-2018165194 A1 | 9/2018 |
| WO | WO-2018165198 A1 | 9/2018 |
| WO | WO-2018170150 A2 | 9/2018 |
| WO | WO-2018175453 A1 | 9/2018 |
| WO | WO-2018213332 A1 | 11/2018 |
| WO | WO-2019028190 A1 | 2/2019 |
| WO | WO-2019033050 A1 | 2/2019 |
| WO | WO 2019/144091 A1 | 7/2019 |
| WO | WO 2019/144095 A1 | 7/2019 |
| WO | WO-2019156795 A1 | 8/2019 |
| WO | WO-2019165237 A1 | 8/2019 |
| WO | WO-2019210057 A1 | 10/2019 |
| WO | WO-2020033129 A1 | 2/2020 |
| WO | WO-2020033272 A1 | 2/2020 |
| WO | WO-2021007109 A1 | 1/2021 |
| WO | WO-2021055641 A1 | 3/2021 |
| WO | WO-2021076788 A2 | 4/2021 |
| WO | WO-2021154839 A1 | 8/2021 |
| WO | WO-2021158523 A1 | 8/2021 |
| WO | WO-2021158534 A1 | 8/2021 |
| WO | WO-2021178887 A1 | 9/2021 |
| WO | WO-2022015955 A1 | 1/2022 |
| WO | WO-2022109162 A1 | 5/2022 |
| WO | WO-2022164935 A1 | 8/2022 |

OTHER PUBLICATIONS

Wu et al, Remote control of therapeutic T cells through a small molecule-gated chimeric receptor Science 350(6258): doi: 10.1126/science.aaab4077, 12 pages, Sep. 24, 2015.*

Farkas et al, Proarrhythmic Effects of Intravenous Quinidine, Amiodarone, D-Sotalol, and Almokalant in the Anesthetized Rabbit Model of Torsade de Pointes, J. Cardiovasc. Pharmacol. 39: 287-297, 2002.*

(56) References Cited

OTHER PUBLICATIONS

Ren et al, Safety Strategies of Genetically Engineered T Cells in Cancer Immunotherapy, Current Pharmaceutical Design, 24: 78- 83; available online Jan. 1, 2018.*
Lu et al, Preclinical pharmacokinetics, tissue distribution, and antitumor activity of a folate-hapten conjugate-targeted immunotherapy in hapten-immunized mice, Molecular Cancer Therapeutics 5(12): 3258-3267, 2006.*
Amato et al, A Phase I Study of Folate Immune Therapy (EC90 Vaccine Administered With GPI-0100 Adjuvant Followed by EC17) in Patients With Renal Cell Carcinoma, J. Immunother. 36(4): 268-275, 2013.*
Extended European Search report issued by the European Patent Office for Application No. 23169858.0, dated Oct. 30, 2023, 9 pages.
GenBank: AMZ04818.1, Zah, E. et al., dated Apr. 24, 2016, 6 pages.
Kanduluru et al., "Design, Synthesis, and Evaluation of a Neurokinin-1 Receptor-Targeted Near-IR Dye for Fluorescence-Guided Surgery of Neuroendocrine Cancers," Bioconjugate Chem. 27, 2157-2165 (2016).
Sang et al., "The research development of Chimeric Antigen Receptor T-cells in hematological malignancies," Practical Oncology Journal, vol. 30, No. 5, (Oct. 28, 2016), pp. 473-476.
Zah et al., "T Cells Expressing CD19/CD20 Bispecific Chimeric Antigen Receptors Prevent Antigen Escape by Malignant B Cells," Cancer Immunology Research, Jun. 2016, vol. 4 (6), pp. 498-508.
Extended European Search Report issued by the European Patent Office for Application No. 19757681.2, dated Nov. 25, 2021, 9 pages.
Gu et al., "Abstract LB-187: New methods for controlling CAR T cell-mediated cytokine storms : Cancer Research", Proceedings: AACR Annual Meeting 2017, (Jul. 1, 2017), Retrieved from the Internet Sep. 28, 2021: URL:https://cancerres.aacrjournals.org/content/77/13 Supplement/LB-187, 2 pages.
Lu et al: "Preclinical Evaluation of Bispecific Adaptor Molecule Controlled Folate Receptor CAR-T Cell Therapy With Special Focus on Pediatric Malignancies", Frontiers in Oncology, vol. 9, pp. 1-20 (2019).
PCT Search Report and Written Opinion prepared for PCT/US2019/019191, completed Jun. 11, 2019.
Abate-Daga, et al., "Abstracts for the 25th Annual Scientific Meeting of the International Society for Biological Therapy of Cancer," Journal of Immunotherapy (2010); 33(8): 859-920.
Abken, H. et al. "Chimeric T-Cell Receptors: Highly Specific Tools To Target Cytotoxic T-Lymphocytes To Tumour Cells," Cancer Treatment Reviews (1997); 23:97-112.
Abken, H., et al., "Tuning tumor-specific T-cell activation: a matter of costimulation?" Trends in Immunology vol. 23 No. 5 May 2002: 240-45.
Abstracts for the 26th Annual Scientific Meeting of the Society for Immunotherapy of Cancer (SITC), J Immunother., vol. 34, No. 9, Nov.-Dec. 2011 (62 pp.).
Airenne et al., "Recombinant avidin and avidin-fusion proteins", Biomolecular Engineering 16 (1999) 87-92.
Alcover et al., "A soluble form of the human CD5 alpha chain expressed in the baculovirus system: Biochemical characterization and binding to MHC Class 1", Molecular Immunology, vol. 30, No. 1, pp. 55-67, 1993.
Alexander et al., "Indoleamine 2,3-Dioxygenase Expression in Transplanted NOD Islets Prolongs Graft Survival After Adoptive Transfer of Diabetogenic Splenocytes," Diabetes 2002, vol. 51 pp. 356-365.
Alonso-Camino et al. "CARbodies: Human Antibodies Against Cell Surface Tumor Antigens Selected From Repertoires Displayed on T Cell Chimeric Antigen Receptors." (2013) Mol Ther Nucl Acids 2, e93 (11 pages).
Altenschmidt, U. et al. "Adoptive transfer of in vitro-targeted, activated T lymphocytes results in total tumor regression," J. Immunol. (1997); 159:5509-15.

Altenschmidt, U., et al., "Specific cytotoxic T lymphocytes in gene therapy," J. Mol. Med. (1997); 75, 259-266.
Altschul et al., "Local Alignment Statistics, [27] Multiple Alignment and Phylogenetic Trees," Methods in Enzymology 266:460-480 (1996).
Altschul, S.F., et al., "Basic local alignment search tool," J. Mol. Biol. 215:403-410 (Oct. 5, 1990).
Altvater, B., et al., "284 (CD244) Signaling by Recombinant Antigen-specific Chimeric Receptors Costimulates Natural Killer Cell Activation to Leukemia and Neuroblastoma Cells", Clin Cancer Res 2009; 15( 15) Aug. 1, 2009: 4857-66.
Alvarez-Vallina et al., Antigen-spedfic targeting of CD28-mediated T cell co-stirnulation usinfJ chimeric single-chain antibody variable fragment-CDW receptorn, Eur. „J. Immunol, •1996, 26, 2304-2309.
Amin et al., "The Eighth Edition AJCC Cancer Staging Manual Continuing to Build a Bridge From a Population-Based to a More "Personalized" Approach to Cancer Staging," CA Cancer J Cun 67(2):93-99 (2017).
An, Z., et al., "IgG2m4, an engineered antibody isotype with reduced Fc function", MAbs (2009); 1(6): 572-579.
Ang et al., "Generating a Chimeric Antigen Receptor To Redirect T-Cell Specificity after Infusion", Molecular Therapy vol. 19, Supplement 1, May 2011, SI37-SI38.
Arch, R. H. et al. (1998). 4-1BB and Ox40 are members of a tumor necrosis factor (TNF)-nerve growth factor receptor subfamily that bind TNF receptor-associated factors and activate nuclear factor kappaB. Molecular and Cellular Biology 18(1):558-565.
Aruffo et al., "Molecular cloning of a CD28 eDNA by a high-efficiency COS cell expression system," Proc. Natl. Acad. Sci. USA (1987); 84: 8573-8577.
Baba et al., "N-Linked Carbohydrate on Human Leukocyte Antigen-C and Recognition by Natural Killer Cell Inhibitory Receptors", Human Immunology 61, 1202-1218 (2000).
Baniyash et al., "The T Cell Antigen Receptor Zeta Chain Is Tyrosine Phosphorylated upon Activation" The Journal of Biological Chemistry, vol. 263, No. 34, Issue of Dec. 5, pp. 18225-18230.
Barber, et al., "Chimeric NKG2D expressing T cells eliminate immunosuppression and activate immunity within the ovarian tumor microenvironment," J. Immunol. (2009); 183:6939-6947.
Barber et al. "Chimeric NKG2D Receptor-Bearing T Cells as Immunotherapy for Ovarian Cancer," Cancer Res. (2007);67(10): 5003-5008.
Barber, et al., "Chimeric NKG2D Receptor-Expressing T Cells as an Immunotherapy for Multiple Myeloma," Exp Hematol. (Oct. 2008); 36(10):1318-28.
Barber, et al., "Immunotherapy with chimeric NKG2D receptors leads to long-term tumor-free survival and development of host antitumor immunity in murine ovarian cancer," J. immunol 180:72-78 (2008).
Barber, et al., J Immunol. (Aug. 1, 2014); 193(3): 1513, pp. 1-2: (Erratum to Barber et al. "Immunotherapy with chimeric NKG2D receptors leads to long-term tumor-free survival and development of host antitumor immunity in murine ovarian cancer," J. Immunol. (2008); 180:72-78).
Barocas, Daniel A., et al., "A Population-based Study of Renal Cell Carcinoma and Prostate Cancer in the Same Patients," 2006, BJU International, vol. 97, pp. 33-36.
Barrett et al., Chimeric Antigen Receptor Therapy for Cancer Annual Review of Medicine vol. 65: 333-347 (2014).
Bauer, A, et al., "Differential signal transduction via T-cell receptor CD3'2, CD3C-,v, and CD3'q2 isoforms," Proc. Natl. Acad. Sci. USA (1991); 88: 3842-3846.
Bauer; et al., "Activation of NK cells and T cells by NKG2D, a receptor for stress-inducible MICA." Science. Jul. 30, 1999; 285(5428):727-9.
Baum et al. "Retrovirns vectors: toward the plentivirns?" (2006) Molecular Therapy: The Journal of the American Society of Gene Therapy. 13:1050-1063.
Becker, M. L. B., et al., "Expression of a hybrid immunoglobulin-T cell receptor protein in transgenic mice," Cell (1989); 58:911-921.
Bedzyk, WD et al., "Active site structure and antigen binding properties of idiotypically cross-reactive anti-fluorescein monoclonal antibodies," J Bioi Chem., 1990, 265,133-138.

(56) References Cited

OTHER PUBLICATIONS

Bejcek, B, et al., "Development and Characterization of Three Recombinant Single Chain Antibody Fragments (scFvs) Directed against the CD19 Antigen!," Cancer Research 55, (1995); 2346-2351.
Berger, C., et al., Analysis of trans gene-specific immune responses that limit the in vivo persistence of adoptively transferred HSV-TK-modified donor T cells after allogeneic hematopoietic cell transplantation. Blood, 2006. 1 07(6): p. 2294-302.
Berger et al., "Safety of targeting ROR1 in primates with chimeric antigen receptor modified T cells," Cancer Immunology Research, 3(2):206-216 (2015).
Berget al., "Section 3.2 Primary Structure: Amino Acids Are Linked by Peptide Bonds to Form Polypeptide Chains" Biochemistry. 5th Ed. New York. W.H. Freeman; 2002, pp. 1-16.
Betancur et al., "Nonpeptide antagonists of neuropeptide receptors: tools for research and therapy," Trends Pharmacol Sci. 18(10): 372-386 (1997).
Blast Search page for "P20334[209-256]" (2 pages), retrieved from http://www.uniprot.org/blasV?about=P20334[209-256]&key=Topological %20domain on Oct. 14, 2016.
Bluemel et al., "Epitope distance to the target cell membrane and antigen size determine the potency of T cell-mediated lysis by BiTE antibodies specific for a large melanoma surface antigen," Cancer Immunol Immunother 59(8):1197-1209 (2010).
Boder et al., "Directed evolution of antibody fragments with monovalent femtomolar antigen-binding affinity," Proc Natl Acad Sci U S A 97(20):10701-10705 (2000).
Bolhuis et al. "Preparation for a phase 1/11 study using autologous gene modified T lymphocytes for treatment of metastatic renal cancer patients.," Adv. Exp. Med. Biol. (1998); 451:547-555.
Boomer et al., "Cutting Edge: A Double-Mutant Knockin of the CD28 Ymnm and PYAP Motifs Reveals a Critical Role for the YMNM Motif in Regulation of T Cell Proliferation and Bcl-x L Expression" The Journal of Immunology. 2014; 192, pp. 3465-3469.
Boomer, J, et al.,. "An Enigmatic Tail of CD28 Signaling," Washington University School of Medicine (2010); 1-20.
Boulassel et al., "Immunotherapy for B-Cell Neoplasms using T Cells expressing Chimeric Antigen Receptors: From antigen choice to clinical implementation," Sultan Qaboos Univ Med J 12(3):273-285 (2012).
Boursier et al., "Evidence for an Extended Structure of the T-cell Co-receptor CD8a as Deduced from the Hydrodynamic Properties of Soluble Forms of the Extracellular Region*," The Journal of Biological Chemistry 1993, vol. 268, No. 3, Issue of Jan. 25, pp. 2013-2020.
Brennan et al., "Carbohydrate Recognition by a Natural Killer Cell Receptor, Ly-49C*," The Journal of Biological Chemistry 1995, vol. 270, No. 17, Issue of Apr. 28, pp. 9691-9694.
Brentjens et al. "CD19-targeted T cells rapidly induce molecular remissions in adults with chemotherapy-refractory acute lymphoblastic leukemia", Science Translational Medicine, (2013); 5(177):177ra38, 10 pages.
Brentjens et al., "Eradication of systemic B-cell tumors by genetically targeted human T lymphocytes co-stimulated by CD80 and interleukin-15," Nature Medicine 9(3): 279-286 (2003).
Brentjenset al., "Treatment of chronic lymphocytic leukemia with genetically targeted autologous T cells: case report of an unforeseen adverse event in a phase I clinical trialm" Mol Ther 18(4):666-668 (2010).
Bridgeman, J.S., et al., "Structural and biophysical determinants of alpha beta T-cell antigen recognition," Immunology (Jan. 2012); 135(1 ): 9-18 (First published: Dec. 7, 2011 ).
Bruhnns et al., "Differential Roles of N- and C-Terminal Immunoreceptor Tyrosine-Based Inhibition Motifs During Inhibition of Cell Activation by Killer Cell Inhibitory Receptors," The Journal of Immunology 1999; 162:3168-3175.
Bukczynski et al., "Costimulatory ligand 4-1 BBL (CD137L) as an efficient adjuvant of human antiviral cytotoxic T cell responses," Proc. Natl. Acad. Sci. USA, 2004, 101: 1291-1296.
Cambier, et al., "Antigen and Fe receptor signaling. The awesome power of the immunoreceptor tyrosine-based activation motif (ITAM)," J Immunol. (Oct. 1, 1995); 155(7):3281-5.
Camerini, D, et al., "The T cell activation antigen CD27 is a member of the nerve growth factor/tumor necrosis factor receptor gene family," The Journal of Immunology (1991); 3165-3169.
Cameron et al., "Identification of a Titin-Derived HLA-AI-Presented Peptide as a Cross-Reactive Target for Engineered MAGE A3-Directed T Cells," Sci Transl Med 197(5):197ra103; 1-11 (2013).
Canfield, S.M. et al., "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).
Cannons et al., "4-IBB ligand induces cell division, sustains survival, and enhances effector function of CD4 and CDS T cells with similar efficacy," J Immunol. Aug. 2001, 167(3): 1313-1324.
Carlens et al. "Ex vivo T lymphocyte expansion for retroviral transduction: influence of serum-free media on variations in cell expansion rates and lymphocyte subset distribution." (2000) Exp Hematol 28(10): 1137-46.
Carpenito C., et al., Control of large, established tumor xenografts with genetically retargeted human T cells containing CD28 and CD137 domains. Proc Natl Acad Sci U S A. Mar. 3, 2009;106(9):3360-5. doi: 10.1073/pnas.0813101106. Epub Feb. 11, 2009. PMID: 19211796; PMCID: PMC2651342.
Carpenter, R. O., et al. "B-cell Maturation Antigen is a Promising Target for Adoptive T-cell Therapy of Multiple Myeloma," Clinical Cancer Research, 2013, vol. 19(8), pp. 2048-2060.
Cartellieri, M. el al., "Chimeric antigen receptor-engineered T cells for immunotherapy of cancer," J. Biomedicine and Biotechnology, 2010, Article ID 956304. 13 pages.
Cavalieri et al. "Human T lymphocytes transduced by lentiviral vectors in the absence of TCR activation maintain an intact immune competence." (2003) Blood. 102(2): 497-505.
"Chain A, 4m5.3 Anti-Fluorescein Single Chain Antibody Fragment (Scfv)" (4 pages), retrieved from https://www.ncbi.nlm.nih.gov/protein/62738392?report=genbank&log$=protalign&blast_rank=I&RID=UWAEY60801 Ron Oct. 12, 2016.
Chalupny et al., "T-cell activation molecule 4-IBB binds to extracellular matrix proteins," Proc. Natl. Acad. Sci., USA, 89: 103360-10364 (Nov. 1992).
Chang et al., "A Chimeric Receptor with NKG2D Specificity Enhances Natural Killer Cell Activation and Killing of Tumor Cells", Cancer Res 2013;73:1777-1786. Published online Jan. 9, 2013.
Cheadle et al., "Chimeric antigen receptors for T-cell based therapy" Methods Mol Biol. 2012; 907:645-66.
Chen, et al. "Chimeric antigen receptor (CAR)-directed adoptive immunotherapy: a new era m targeted cancer therapy," Stem Cell Investig. (Jan. 18, 2014); 1:2 (2 pages).
Chen et al. "Fusion protein linkers: property, design and functionality," Adv Drug Deliv Rev. (2013); 65: 1357-1369 (Epub Sep. 29, 2012).
Cheng et al., "Hapten-directed targeting to single-chain antibody receptors," Cancer Gene Therapy, 11(5):380-388 (2004).
Cho C. "Rapid identification of cytokine release syndrome after haploidentical PBSC transplantation and successful therapy with tocilizumab." Bone Marrow Transplant. Dec. 2016;51 (12): 1620-1621, Epub Sep. 26, 2016.
Cho et al., "Macromolecular versus small-molecule therapeutics: drug discovery, development and clinical considerations" TI BTECH, vol. 14, May 1996, pp. 153-158.
Chothia, et al., "Conformations of immunoglobulin hypervariable regions," Nature, Dec. 28, 1989, vol. 342, pp. 877-883.
Cianciulli, A. et al., "Folic Acid Is Able to Polarize the Inflammatory Response in LPS Activated Microglia by Regulating Multiple Signaling Pathways", Mediators of Inflammation, 2016, 10 pages.
Clay, et al., "Efficient transfer of a tumor antigen-reactive TCR to human peripheral blood lymphocytes confers anti-tumor reactivity," J. Immunol. (1999); 163:507-153.

(56) References Cited

OTHER PUBLICATIONS

Cohen et al. "Recognition of fresh human tumor by human peripheral blood lymphocytes transduced with a bicistronic retroviral vector encoding a murine anti-p53 TCR" J Immunol. 175:5799-5808 (2005).
Colcher, D. et al. "In vivo tumor targeting of a recombinant single-chain antigen-binding protein.," J. Nat. Cancer Inst. (1990); 82:1191-1197.
Cole et al., "The molecular determinants of CD8 co-receptor function," Immunology 137(2):139-148 (2012).
"Common Terminology Criteria for Adverse Events (CTCAE)" National Cancer Institute Common Toxicity Criteria version 4.03 (NCI-CTCAE v4.03 (2010) (196 pages).
Cooper et al., "Enhanced antilymphoma efficacy of CD19-redirected influenza MP1-specific CTLs by cotransfer of T cells modified to present influenza MP1," Blood 2005, vol. 105 No. 4 pp. 1622-1631.
Cooper et al., Sequence Listing, Compositions and Methods Related to a Human CD19-Specific Chimeric Antigen Receptor (H-CAR), U.S. Appl. No. 61/020,991, filed Jan. 14, 2008, 5 pages.
Cooper, Laurence JN, et al. "T-cell clones can be rendered specific for CD19: Toward the selective augmentation of the graft-versus-B-lineage leukemia effect." Blood (2003); 101.4: 1637-1644.
Cooper, "Test-driving CARs," Blood (Sep. 15, 2008); 112(6):2172-3.
Cordaro, T. A et al. "Tumor size at the time of adoptive transfer determines whether tumor rejection occurs," Eur. J. Immunol. (2000); 30: 1297-1307.
Croft, M., "The role of TNF superfamily members in T-cell function and diseases" Nature Reviews, Immunology, vol. 9, Apr. 2009, pp. 271-285.
Dai, et al., "Chimeric Antigen Receptors Modified T-Cells for Cancer Therapy," J Natl Cancer Inst (2016); 108(7): djv439 (14 pages) (First published online Jan. 27, 2016).
Dall, Peter et al. "In vivo cervical cancer growth inhibition by genetically engineered cytotoxic T cells." Cancer Immunol. Immunother. (Jan. 2005); 54(1):51-60.
Darcy, P. K. et al., "Expression in cytotoxic T lymphocytes of a single-chain anti-carcinoembryonic antigen antibody. Redirected Fas ligand-mediated lysis of colon carcinoma," Eur. J. Immunol. (1998); 28:1663-72.
Davila et al., "CD19 CAR-targeted T cells induce long-term remission and B Cell Aplasia in an immunocompetent mouse model of B cell acute lymphoblastic leukemia," PLoS One 8(4) e61338 (2013), 14 pages.
Davila M. L. et al: "Efficacy and toxicity management of 19-28z CART cell therapy in B cell acute lymphoblastic leukemia" Sci Transl Med. Feb. 19, 2014;6(224):224-25.
Davila Marco L. et al: "CD19-Targeted T Cells for Hematologic Malignancies •Clinical Experience to Date", Cancer Journal, vol. 21, No. 6, Jan. 1, 2015 (Jan. 1, 2015), pp. 470-474.
Davila ML, et al., "How do CARs work?: Early insights from recent clinical studies targeting CD19," Oncoimmunology (Dec. 2012 I); 1(9):1577-1583.
Debelouchina et al., "A molecular engineering toolbox for the structural biologist" Quarterly Reviews of Biophysics, 2017, 50, e7, pp. 1-41.
Definition of "Protein", Concise Dictionary of Biomedicine and Molecular Biology, 2nd Edition, Pei-Show Juo, PhD, 2002,p. 903.
Deng et al., "Antitumor activity of NKG2D Car-T cells against human colorectal cancer cells in vitro and in vivo," Am J Cancer Res 9(5)945-958 (2019).
Diefenbach et al., "The innate immune response to tumors and its role in the induction of T-cell immunity," Immunological Reviews 2002, vol. 188: 9-21.
Dotti, et al., "Design and development of therapies using chimeric antigen receptor-expressing T cells." Immunol Rev. (2014); 257 (1): 107-126, 35 pages. First published: Dec. 13, 2013.
Dubrovska et al., "A chemically induced vaccine strategy for prostate cancer," ACS Chem Biol 6(11):1223-1231 (2011).

Duncan et al., Localization of the binding site for the human high-affinity Fe receptor on IgG, Nature 1998, vol. 332 pp. 563-564.
Ertl et al., "Considerations for the Clinical Application of Chimeric Antigen Receptor T Cells: Observations from a Recombinant DNA Advisory Committee Symposium Held Jun. 15, 2010," Cancer Research 71(9): 3175-3181 (2011).
Eshhar, et al, "Design of Cytotoxic T Lymphocytes with Antibody-Type Specificity against Tumor Cells Using Chimeric T cR," Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar et al., Specific activation and targeting of cytotoxic lymphocytes through chimeric single chains consisting of antibody-binding domains and the or subunits of the immunoglobulin and T-cell receptors, Proc. Natl. Acad. Sci. USA 90:720-724 (1993).
Eshhar, Z., et al., "Chimeric T cell receptor which incorporates the anti-tumour specificity of a monoclonal antibody with the cytolytic activity ofT cells: a model system for immunotherapeutical approach," Br J Cancer. Suppl. (Jul. 1990); 10: 27-29.
Eshhar, Z., et al., "Functional expression of chimeric receptor genes in human T cells," J. Immunol. Meth. (2001); 248: 67-76.
Extended European Search Report issued by the European Patent office for Application No. 18761400.3, dated Sep. 24, 2020, 7 pages.
Extended European Search Report issued by the European Patent Office for Application No. 19204092.1, dated Mar. 16, 2020, 8 pages.
Extended European Search Report issued by the European Patent Office for Application No. 19740881.8, dated Oct. 10, 2021, 9 pages.
Extended European Search report issued by the European Patent Office for Application No. 19741309.9, dated Oct. 5, 2021, 12 pages.
Extended European Search Report issued by the European Patent Office for Appliction No. EP17779919, dated Nov. 6, 2019, 7 pages.
Fang, R.H., et al., "Lipid-insertion Enables Targeting Functionalization of Erythrocyte Membrane-cloaked Nanoparticles," Nanoscale, Oct. 2013, vol. 5(19), pp. 8884-8888.
FDA Approval Letter dated Apr. 23, 2014, for Biologics License Application for Sylvant™ (siltuximab), 12 pages.
FDA Approval Letter dated Jan. 8, 2010, for Biologics License Application for Acternra (tocilizumab), 9 pages.
Fedorov VD, et al., "PD-1- and CTLA-4-based inhibitory chimeric antigen receptors (iCARs) divert off-target immunotherapy responses," Sci Transl Med. (Dec. 11, 2013); 5(215):215ral72 (12 pages).
Feng et al., "Convergence on a Distinctive Assembly Mechanism by Unrelated Families of Activating Immune Receptors", Immunity, vol. 22, 427-438, Apr. 2005.
Feng et al., The Assembly of Diverse Immune Receptors Is Focused on a Polar Membrane-Embedded Interaction Site, 2006. PLoS Biol 4(5)e142: 0768-0779.
Ferrone, S., et al., "How much longer will tumor cells fool the immune system," Immunol. Today (2000); 21: 70-72.
Figini, M, et al., "Conversion of murine antibodies to human antibodies and their optimization for ovarian cancer therapy targeted to the folate receptor," Cancer ImmunolImmunother (Apr. 2009); 58(4):531-46 (Epub Aug. 15, 2008).
Figini, M., et al., "Panning phage antibody libraries on cells: isolation of human Fab fragments against ovanan carcinoma using guided selection," Cancer Res (Mar. 1, 1998); 58(5):991-996.
Finney et al., "Activation of resting human primary T cells with chimeric receptors: costimulation from CD28, inducible costimulator, CD134, and CD137 in series with signals from the TCR zeta chain," J. Immunol., 172(1):104-113, Jan. 2004.
Finney et al., "Chimeric Receptors Providing Both Primary and Costimulatory Signaling in T Cells from a Single Gene Product," J Immunol161, 2791-2797 (1998).
Fitzer-Attas et al., "Harnessing Syk family tyrosine kinases as signaling domains for chimeric single chain of the variable domain receptors: optimal design for T cell activation," J. Immunol., 160(1): 145-54, Jan. 1998.
Foell et al., "CD137-mediated T cell co-stimulation terminates existing autoimmune disease in SLE-prone NZB/NZW FI mice.," Ann NY Acad Sci. Apr. 2003; 987:230-5.

(56) References Cited

OTHER PUBLICATIONS

Frecha et al., "Advances in the field of lentivector-based transduction of T and B lymphocytes for gene therapy." Mol Ther. (2010); 18.10: 1748-1757.
Friedmann-Morvinski, D., et al., "Redirected primary T cells harboring a chimeric receptor require co stimulation for their antigen-specific activation," Blood (2005); 105(8): 3087-3093.
Frost et al., "In Vitro Evaluation of Avidin Antibody Pretargeting Using 211At-Labeled and Biotinylated Poly-L-Lysine as Effector Molecule*," Cancer 2010, Cancer Therapy With Antibodies and Immunoconjugates, Supplement to Cancer, pp. 1101-1110.
Fujita, K.et al., "Prolonged disease-free period in patients with advanced epithelial ovarian cancer after adoptive transfer of tumor-infiltrating lymphocytes." Clin. Cancer Res., 1995, 1, 501-507.
Gade et al., "Targeted elimination of prostate cancer by genetically directed human T lymphocytes," Cancer Res. (2005); 65:9080-9088.
Gargalionis et al, "The molecular rationale of Src inhibition in colorectal carcinomas," Int. J. Cancer, 134:2019-2029 (2013).
Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-1149.
Gilboa, E., "How tumors escape immune destruction and what we can do about it," Cancer Immunol. Immunother. (1999); 48: 382-385.
Gilham et al., CAR-T cells and solid tumors: tuning T cells to challenge an inveterate foe, Trends in Molecular Medicine 18(7):377-384 (2012).
Gilham et al., "Primary polyclonal human T lymphocytes targeted to carcino-embryonic antigens and neural cell adhesion molecule tumor antigens by CD3zeta-based chimeric immune receptors," J. Immunother, (Mar.-Apr. 2002); 25 (2): 139-151.
Gill et al., "Preclinical targeting of human acute myeloid leukemia and myeloablation using chimeric antigen receptor-modified T cells," Blood (2014); 123(15): 2343-54 (pub online Mar. 4, 2014).
Gillies, S.D. et al., "Targeting Human Cytotoxic T Lymphocytes to Kill Heterologous Epidermal Growth Factor Receptor-Bearing Tumor Cells," The Journal of Immunology (1991); 146(3): 1067-1071.
Gong, et al., "Cancer Patient T Cells Genetically Targeted to Prostate Specific Membrane Antigen Specifically Lyse Prostate Cancer Cells and Release Cytokines in Response to Prostate-Specific Membrane Antigen," Neoplasia (1999); 1:123-7.
Gong, M. C., et al., "Prostate-specific membrane antigen (PSMA)-specific monoclonal antibodies in the treatment of prostate and other cancers," Cancer Metastasis Rev. (1999); 18: 483-490.
Gonzalez et al., "Genetic engineering of cytolytic T lymphocytes for adoptive T-cell therapy of neuroblastoma," J Gene Med (2004); 6:704-711.
Goverman, J. et al., "Chimeric immunoglobulin-T cell receptor proteins form functional receptors: implications forT cell receptor complex formation and activation," Cell (1990); 60:929-939.
Grada et al., "TanCAR: a novel bispecific chimeric antigen receptor for cancer immunotherapy," Molecular Therapy—Nucleic Acids (2013): 2(7): Article No. e1 05 (internal pp. 1-11) (e-pub. Jul. 9, 2013).
Greenfield, E. A, Nguyen, K. A & Kuchroo, V. K. CD28/B7 co-stimulation: a review. Crit. Rev. Immunol. 18,389-41 8 (1998).
Griffioen, M., et al., "Retroviral transfer of human CD20 as a suicide gene for adoptive T-cell therapy," Haematologica (2009); 94(9): 1316-20.
Griffiths et al., "The Nature of DNA" Modern Genetic Analysis. New York: W.H. Freeman; 1999, pp. 1-11.
Grosenbach et al., "A recombinant vector expressing transgenes for four T-cell costimulatory molecules (OX40L, B7-1, ICAM-1, LFA-3) induces sustained CD4+ and CDS+ T-cell activation, protection from apoptosis, and enhanced cytokine production," Cellular Immunology 222 (2003) 45-57.

Gross et al., "Chimaeric T-cell receptors specific to a B-lymphoma idiotype: a model for tumour immunotherapy," Biochem. Soc. Trans. (Nov. 1995); 23(4):1079-82.
Gross et al., "Development and study of chimeric immunoglobulin/T cell receptor molecules as functional receptors that endow T cells with antibody-type specificity," Ph.D. Thesis presented to the Feinberg Graduate School, The Wiezmann Institute of Science, Rehovot, Israel (1990); 1-70.
Gross, G. et al., "Endowing T cells with antibody specific using chimeric T cell receptors," Department of Chemical Immunology, FASEB J. (Dec. 1992); 6(15):3370-8.
Gross, G. et al., "Generation of effector T cells expressing chimeric T cell receptor with antibody type-specificity," Transplant. Proc. (1989); 21 (1 Pt 1):127-130.
Gross, Gideon, Tova Waks, and Zelig Eshhar. "Expression of immunoglobulin-T-cell receptor chimeric molecules as functional receptors with antibody-type specificity." Proceedings of the National Academy of Sciences 86.24 (1989): 10024-10028.
Grupp, Advances in T-cell therapy for All, Best Practice & Research Clinical Haematology, vol. 27, No. 3-4, Sep. 1, 2014 (Sep. 1, 2014), pp. 222-228.
Grupp, S.A. et al., "Chimeric antigen receptor-modified T cells for acute lymphoid leukemia", N Engl J Med. (2013); 368(16): 1509-1518.
Gruss et al., "Tumor Necrosis Factor Ligand Superfamily: Involvement in the Pathology of Malignant Lymphomas" Blood, vol. 85, No. 12, Jun. 15, 1995, pp. 3378-3404.
Guinn et al., "4-IBBL Cooperates with B7-I and B7-2 in Converting a B Cell Lymphoma Cell Line into a Long-Lasting Antitumor Vaccine," The Journal of Immunology 162:5003-5010 (1999).
Habib-Agahi ,H., Phan, T.T. and Searle, P.F. Co-stimulation with 4-IBB ligand allows extended T-cell proliferation, synergizes with CD80/CD86 and can reactivate anergic T cells Int. Immunol. 19 (12), 1383-1394 (2007).
Hackett et al. "A transposon and transposase system for human application" (2010) Molecular Therapy: The Journal of the American Society of Gene Therapy. 18:674-683.
Hansen et al., "Description of an Ectothermic TCR Coreceptor, CD8 a, in Rainbow Trout," J. Immunol., 164, 3132-3139, 2000.
Hanson, H. L. et al. Eradication of established tumors by Cds+ T cell adoptive immunotherapy. Immunity 13, 265-276 (2000).
Harper et al., "CTLA-4 and CD28 Activated Lymphocyte Molecules are Closely Related in Both Mouse and Human as to Sequence, Message, Expression, Gene Structure, and Chromosomal Location", The Journal of Immunology, vol. 147, 1037-1044, No. 3, 1991.
Hatakeyama et al., "Transmembrane Signaling of Interleukin 2 Receptor," J. Exp. Med. 1987, vol. 166 pp. 362-375.
Hayes, N., et al., "Redirecting Mouse CTL Against Colon Carcinoma: Superior Signaling Efficacy of Single-Chain Variable Domain Chimeras Containing TCR-zeta vs Fe epsilon RI-gamma," J Immunol 166:182-187 (2001).
Hege et al., "Safety, tumor trafficking and immunogenicity of chimeric antigen receptor (CAR)-T cells specific for TAG-72 in colorectal cancer," Journal for Immuno Therapy of Cancer 2017, 5:22.
Hege et al., "Systemic T Cell-independent Tumor Immunity after Transplantation of Universal Receptor-modified Bone Marrow into SCID Mice", J. Exp. Med. vol. 184 Dec. 1996 pp. 2261-2269.
Hekele, A. et al., "Growth retardation of tumors by adoptive transfer of cytotoxic T lymphocytes reprogrammed by CD44v6-specific scFv:zeta-chimera," Int. J. Cancer (1996); 68(2):232-8.
Helen E Heslop: "Safer Cars", Molecular Therapy, vol. 18, No. 4, Apr. 1, 2010, XP55609534.
Hennig I.M., et al., "Substance-P Receptors in Human Primary Neoplasms: Tumoral and Vascular Localization," International Journal of Cancer, 1995, vol. 61(6), pp. 786-792.
Herron et al., "High resolution structures of the 4-4-20 Fab-fluorescein complex in two solvent systems: effects of solvent on structure and antigen-binding affinity," Biophys J 67(6):2167-2183 (1994).
Heslop, "Genetic engineering ofT-cell receptors: TCR takes to titin," Blood (Aug. 8, 2013); 122(6):853-4.

(56) References Cited

OTHER PUBLICATIONS

Heuser, et al., "T-cell activation by recombinant immunoreceptors: impact of the intracellular signalling domain on the stability of receptor expression and antigen-specific activation of grafted T-cells," Gene Therapy (2003); 10: 1408-1419.

Ho, et al., "Adoptive Immunotherapy: Engineering T Cell Responses as Biologic Weapons for Tumor Mass Destruction," Cancer Cell (May 2003); 3:431-7.

Hombach, et al., "Adoptive Immunotherapy with Genetically Engineered T Cells: Modification of the IgGI Fe 'Spacer' Domain in the Extracellular Moiety of Chimeric Antigen Receptors Avoids 'Off-Target' Activation and Unintended Initiation of an Innate Immune Response," Gene Ther. (Oct. 2010); 17(10):1206-13.

Hombach, et al., J Immunol (2004); 173: 695: (Erratum to Hombach, et al., Tumor-specific T cell activation by recombinant immunoreceptors: CD3 zeta signaling and CD28 costimulation are simultaneously required for efficient IL.

Hombach et al., "T cell activation by recombinant FcRI-chain immune receptors: an extracellular spacer domain impairs antigen-dependent T cell activation but not antigen recognition," Gene Therapy 7: 1067-1075 (2000).

Hombach, et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule," J Immunol. (2001); 167:6123-6131.

Honegger et al., "A mutation designed to alter crystal packing permits structural analysis of a tight-binding fluorescein-scFv complex," Protein Science 14(10): 2537-2549 (2005).

Hong, Soon-Sun et al., "A Novel Small-Molecule Inhibitor Targeting the IL-6 Receptor β Subunit, Glycoprotein 130," J Immunol 2015; 195:237-245; Prepublished online May 29, 2015;doi: 10.4049/jimmunol.1402908 http://www.jimmunol.org/content/195/1/237.

Huang, J., et al., Modulation by IL-2 of CD70 and CD27 expression on CDS+ T cells: importance for the therapeutic effectiveness of cell transfer immunotherapy J. Immunol. 176 (12), 7726-7735 (2006).

Hudecek et al., "Receptor affinity and extracellular domain modifications affect tumor recognition by ROR1-specific chimeric antigen receptor T-cells," Clin Cancer Res. 19(12):3153-3164 (2013).

Hughes M. S. et al., Transfer of a TCR gene derived from a patient with a marked antitumor response conveys highly active T-cell effector functions. Hum Gene Ther Apr. 2005; 16( 4):457-72).

Hunter et al., "Inhibition of Fey Receptor-Mediated Phagocytosis by a Nonphagocytic Fey Receptor," Blood, vol. 91, No. 5 (Mar. 1, 1998): pp. 1762-1768.

Hutchins et al., "Site-Specific Coupling and Sterically Controlled Formation of Multimeric Antibody Fab Fragments with Unnatural Amino Acids. Journal of Molecular Biology," J Mol Biol 406(4):595-603 (2011).

Hutloff, A. et al.. "ICOS is an inducible T-cell costimulator structurally and functionally related to CD28," Nature. 1999, 397, 263-266.

Hwu, et al, "The Genetic Modification ofT Cells for Cancer Therapy: An Overview of Laboratory and Clinical Trials," Cancer Detection and Prevention (1994); 18(1):43-50.

Hwu, P., et al., "In Vivo Antitumor Activity of T Cells Redirected with Chimeric Antibody/T-Cell Receptor Genes," Cancer Research (Aug. 1, 1995); 55: 3369-3373.

Hwu, P. et al., "Lysis of Ovarian Cancer Cells by Human Lymphocytes Redirected with a Chimeric Gene Composed of an Antibody Variable Region and the Fc Receptor gamma-Chain," The Journal of Experimental Medicine (1993); 178, 361-366.

Imai, C. et al., "Chimeric receptors with 4-IBB signaling capacity provoke potent cytotoxicity against acute lymphoblastic leukemia," Leukemia, 2004, 18, 676-684.

Imai, K., et al., "Comparing Antibody and Small-Molecule Therapies for Cancer"; https://www.medscape.com/viewarticle/550008 (26 pages), 2006.

International Search Report and Written Opinion dated Mar. 27, 2019 for PCT/US2019/014478, 8 pages.

International Search Report and Written Opinion issued by the International Searching Authorigy for Application No. PCT/US2017/026618, completed Aug. 30, 2017, 12 pages.

International Search Report issued in Appl. No. PCT/US2019/014472 (Apr. 26, 2019), 15 pages.

International Search Report prepared for PCT/US2013/076986, mailed Apr. 28, 2014, 15 pages.

Irving, B.A. et al. (1991). The cytoplasmic domain of the T cell receptor chain is sufficient to couple to receptor-associated signal transduction pathways, Cell 64:891-901.

Isakov et al., "PKC-theta-mediated signal delivery from the TCRICD28 surface receptors", Frontiers in Immunology, T Cell Biology, Aug. 2012, vol. 3, Article 273, pp. 1-12.

Israeli, R. S., et al., "Expression of the prostate-specific membrane antigen," Cancer Res. (1994); 54, 1807-1811.

Janeway et al., "Appendix I. Immunologists' Toolbox" Immunobiology: The Immune System in Health and Disease. 5th ed. New York: Garland Science; 2001 (101 pages).

Janeway et al., "The structure of a typical antibody molecule" Immunobiology: The Immune System in Health and Disease. 5th Ed. New York: Garland Science; 2001, pp. 1-11.

Jang, I, et al., "Human 4-IBB (CD137) Signals Are Mediated by TRAF2 and Activate Nuclear Factor-kB," Biochemical And Biophysical Research Communications (1998); 613-620.

Jena, B. et al. "Redirecting T-cell specificity by introducing a tumor-specific chimeric antigen receptor" Blood, (Aug. 19, 2010); 116(7):1035-1044.

Jensen, M. C., et al., Abstract #98: "Targeting Pre-B Acute Lymphoblastic Leukemia With T Cell Clones Engineered To Express A CD19-Specific Chimeric Immunoreceptor," Blood (Nov. 16, 2000); 96(11):26A.

Jensen, M. C., et al., "Human T lymphocyte genetic modification with naked DNA," Molecular Therapy (2000); 1:49- 55.

Jensen, M.C., et al., Antitransgene rejection responses contribute to attenuated persistence of adoptively transferred CD20/CD19-specific chimeric antigen receptor redirected T cells in humans. Bioi Blood Marrow Transplant, 2010.16(9): p. 1245-56.

Jensen, Met al. "CD20 Is A Molecular Target For scFvFc[zeta] Receptor Redirected T Cells: Implications for Cellular Immunotherapy of CD20+ Malignancy," Biology of Blood and Marrow Transplantation (1998); 4:75-83.

Johnson et al., "Kabat database and its applications: 30 years after the first variability plot," Nucleic Acids Res., 28(1): 214-218 (2000).

Johnson, L. A. et al., "Gene therapy with human and mouse T-cell receptors mediates cancer regression and targets normal tissues expressing cognate antigen," Blood , vol. 114, No. 3, pp. 535-546 (Jul. 2009).

Jonnalagadda et al., "Chimeric Antigen Receptors With Mutated IgG4 Fe Spacer Avoid Fe Receptor Binding and Improve T Cell Persistence and Antitumor Efficacy," Molecular Therapy 2015, vol. 23, No. 4, pp. 757-768.

Jung, S. et al., "Selection for improved protein stability by phage display," J. Mol. Bioi., 1999, 294, 163-180.

Jung, S, et al. "Improving in vivo folding and stability of a single-chain Fv antibody fragment by loop grafting." Protein Eng. Aug. 1997; 10(8):959-66.

Junghans RP, "Is it safer CARs that we need, or safer rules of the road?," Mol Ther. (Oct. 2010); 18(10):1742-3.

Kabat et al., Abstract, Sequence of Proteins of Immunological Interest, US Public Health Services, NIH, Bethesda, MD, Publication No. 91-3242, 3 pages, (1991).

Kagoya, Y., et al., Transient stimulation expands superior antitumor T cells for adoptive therapy. JCI Insight, 2017. 2(2): p. e89580 (13 pages).

Kalos, et al., "T Cells with Chimeric Antigen Receptors Have Potent AntitumorEffects and Can Establish Memory in Patients with Advanced Leukemia", Sci Transl Med. Aug. 10, 2011; 3(95): 95ra73. doi:10.1126/scitranslmed.3002842.

Kandalaft, L. et al., "A phase I clinical trial of adoptive transfer of folate receptor-alpha redirected autologous T cells for recurrent ovarian cancer," Journal of Translational Medicine, 2012, 10:157, 10 pages.

(56) References Cited

OTHER PUBLICATIONS

Kang, S. et al: "Therapeutic uses of anti-interleukin-6 receptor antibody", International Immunology, vol. 27, No. 1, Aug. 20, 2014 (Aug. 20, 2014), pp. 21-29.

Karachaliou et al., "Common Co-activation of AXL and CDCPI in EGFR-mutation-positive Non-small cell Lung Cancer Associated with Poor Prognosis," EBioMedicine (2017) https://doi.org/1 0/1 016/j.ebiom.2018.02.001, 16 pages.

Kariv et al., Analysis of the Site of Interaction of CD28 with Its Counterreceptors COSO and CD86 and Correlation with Function, 157 J. Immunol.29-38 (1996).

Katz et al., "Recognition of HLA-Cw4 but Not HLA-Cw6 by the NK Cell Receptor Killer Celllg-Like Receptor Two-Domain Short Tail No. 4", J Immunol2001; 166:7260-7267.

Kenderian, et al; "CD33-specific chimeric antigen receptor T cells exhibit potent preclinical activity against human acute myeloid leukemia," Leukemia (Aug. 2015); 29(8): 1637-47 (Epub Feb. 27, 2015).

Kennedy, M. et al., "Optical imaging of metastatic tumors using a folate-targeted fluorescent probe," J. Biomed. Opt., 2003, 8, 636-641.

Kershaw et al., "Gene-Engineered T Cells as a Superior Adjuvant Therapy for Metastatic Cancer," The Journal of Immunology 173(3): 2143-2150 (2004).

Kershaw, M. H. et al., "A Phase I Study on Adoptive Immunotherapy Using Gene-Modified T Cells for Ovarian Cancer," Clin Cancer Res, 12(20):6106-6115 (Oct. 2006).

Kim et al., "NMR Structural Studies of Interactions of a Small, Nonpeptidyl Tpo Mimic with the Thrombopoietin Receptor Extracellular Juxtamembrane and Transmembrane Domains," J Biol Chem (2007) 282(19)14253-14261.

Kim et al., "Protein conjugation with genetically encoded unnatural amin acids," Current Opinion in Chemical Biology 17(3):412-419 (2013).

Kim et al., "Therapeutic Potential of 4-1BB (CD137) As a Regulator for Effector CDS+ T Cells," Journal of Hematotherapy & Stem Cell Research (2001) 10:441-449.

Kim M.S., et al., "Redirection of Genetically Engineered CAR-T cells using Bifunctional Small Molecules," Journal of the American Chemical Society, 2015, vol. 137(8), pp. 2832-2835, and supplemental data, pp. S1-S8.

Kintzing et al., "Emerging Strategies for Developing Next-Generation Protein Therapeutics for Cancer Treatment" Trends in Pharmacological Sciences, vol. 37, No. 12, Dec. 2016, pp. 993-1008.

Klotz et al., "Macromolecule—Small Molecule Interactions. Strong Binding by Intramolecularly Cross-Linked Polylysine" Biochemistry. Vol. 10, No. 6, Mar. 16, 1971, pp. 923-926.

Kochenderfer, J. et al., "Eradication of B-lineage cells and regression of lymphoma in a patient treated with autologous T cells genetically engineered to recognize CD19," Blood, 2010, 116,4099-4102.

Kochenderfer, et al., "Construction and Pre-clinical Evaluation of an Anti-CD19 Chimeric Antigen Receptor," J Immunother. Sep. 2009, 32(7): 689-702, 26 pages.

Kochenderfer, J. et al., "B-cell depletion and remissions of malignancy along with cytokine-associated toxicity in a clinical trial of anti-CD19 chimeric-antigen-receptor-transduced T cells", Blood (2012); 119(12):2709-2720.

Kochenderfer, J. et al., "Treating B-cell cancer with T cells expressing anti-CD19 chimeric antigen receptors", Nat Rev Clin Oncol. (2013); 10(5):267-276.

Kochenderfer, J.N., et al., "Adoptive transfer of syngeneic T cells transduced with a chimeric antigen receptor that recognizes murine CD19 can eradicate lymphoma and normal B cells.," Blood (2010); 116(19):3875-3886.

Kolmar et al., "Alternative binding proteins: biological activity and therapeutic potential of cystine-knot miniproteins," The FEBS Journal, 2008, 275, 26684-26690.

Kowolik, C. et al., "CD28 costimulation provided through a CD19-specific chimeric antigen receptor enhances in vivo persistence and antitumor efficacy of adoptively transferred T cells", Cancer Res. (2006); 66(22): 10995-11004.

Kowolik, et al., "CD28-costimulation provided through a CD-19-specific chimeric immunoreceptor enhances in vivo persistence and anti-tumor efficacy of adoptively transferred T cells," Blood 106(11): 1278, 4 pages (2005) (Retrieved from http://www.bloodjournal.org/contenU106/11/1278).

Kozak, M. et al., "At least six nucleotides preceding the AUG initiator codon enhance translation in mammalian cells," Journal of Molecular Biology, vol. 196(4):947-950 (1987).

Kranz et al., "Partial elucidation of an anti-hapten repertoire in BALB/c mice comparative characterization of several monoclonal antiFLuorescyl antibodies," Mol Immunol (1981) 18(10), 889-898.

Krause, A., et al., "Genetic approaches to sustain the function of tumor-specific T-lymphocytes," Mol. Ther. (2000); 1 (S260): 713.

Krause et al., "Antigen-dependent CD28 Signaling Selectively Enhances Survival and Proliferation in Genetically Modified Activated Human Primary T Lymphocytes," J. Exp. Med. 188(4):619-626 (1998).

Kularatne, S.A. et al., "Prostate-Specific Membrane Antigen Targeted Imaging and Therapy of Prostate Cancer Using a PSMA Inhibitor as a Homing Ligand," Molecular Pharmaceutics, 2009, vol. 6, No. 3, pp. 780-789.

Kunik et al., "Paratome: an online tool for systematic identification of antigen-binding regions in antibodies based on sequence or structure," Nucl Acids Res. 40:W521-W524 (2012).

Kuwana, Y. et al., "Expression of chimeric receptor composed of immunoglobulin-derived V regions and T-cell receptor-derived C regions," Biochem. Biophys. Res. Comm. (1987); 149:960-968.

Kwon, B, et al., "eDNA sequences of two inducible T-cell genes," eDNA sequences of two inducible T-cell genes (1989); 86: 1963-1967.

Kwon, B, et al., "Expression Characteristics of Two Potential T Cell Mediator Genes," Cellular Immunology (1989); 414-422.

Lafage-Pochitaloff M, Costello R, Couez D, Simonetti J, Mannoni P, Mawas C, Olive D. "Human CD28 and CTLA-41g superfamily genes are located on chromosome 2 at bands q33-q34" Immunogenetics 31(3):198-201 (1990).

Lamers et al., "Immune responses to transgene and troviral vector in patients treated with ex vivo-engineered T Cells." Blood 2011, 117(1): 72-82.

Lamers et al., "Treatment of Metastatic Renal Cell Carcinoma With Autologous T-Lymphocytes Genetically Retargeted Against Carbonic Anhydrase IX: First Clinical Experience," Journal of Clinical Oncology 24(13): e20-e22 (2006).

Laroche et al., "Characterization of a Recombinant Single-chain Molecule Comprising the Variable Domains of a Monoclonal Antibody Specific for Human Fibrin Fragment D-dimer*," The Journal of Biological Chemistry 1991, vol. 266, No. 25, Issue of Sep. 5, pp. 16343-16349.

Latza, U. et al., "The human OX40 homolog: eDNA structure, expression and chromosomal assignment of the ACT35 antigen," Eur. J. [Immunol., 1994, 24, 677-683.

Le; Robert Q. et al. "FDA Approval Summary: Tocilizumab for Treatment of ChimericAntigen Receptor T Cell-Induced Severe or Life-Threatening CytokineRelease Syndrome," The Oncologist 23:943-947 (2018).

Lee, D, et al., "4-1BB Signaling Activates the T Cell Factor 1 Effector/b-Catenin Pathway with Delayed Kinetics via ERK Signaling and Delayed PI3K/AKT Activation to Promote the Proliferation of CDS+ T Cells," PLOS One (2013); 8: 1-11.

Lee et al., Erratum, "Current concepts in the diagnosis and management of cytokine release syndrome," Blood, Sep. 15, 2016, vol. 128, No. 11, 2 pages.

Lee et al. "Current concepts in the diagnosis and management of cytokine release syndrome", Blood, The Journal of the American Society of Hematology, (2014); 124(2):188-195.

Lee et al., "Use of a Single CAR T Cell and Several Bispecific Adapters Facilitates Eradication of Multiple Antigenically Different Solid Tumors," Cancer Res 79:387-396 (2019).

(56) References Cited

OTHER PUBLICATIONS

Lefranc, MP. et al., "IMGT unique numbering for immunoglobulin and T cell receptor variable domains and Ig superfamily V-like domains," Developmental & Comparative Immunology, Jan. 2003, 27(1), pp. 55-77.
Letourneur et al. "T-cell and basophil activation through the cytoplasmic tail of T-cell-receptor zeta family proteins" Proc. Natl. Acad. Sci USA (1991); 88:8905-8909.
Li et al, "CAIX-specific CAR-T Cells and Sunitinib Show Synergistic Effects Against Metastatic Renal Cancer Models," Journal of Immunotherapy 4316-4328 (2020).
Liebowitz, D. N., Lee, K. P. & June, C.H. Co-stimulatory approaches to adoptive immunotherapy. Curr. Opin. Oncol. 10, 533-541 (1998).
Lin et al., "Transglutaminase-catalyzed site-specific conjugation of small-molecule probes to proteins in vitro and on the surface of living cells," J. Am. Chem. Soc. (2006); 128:4542-4543.
Lineberger, "CD33-directed therapy with gemtuzumab ozogamicin in acute myeloid leukemia: progress in understanding cytotoxicity and potential mechanisms of drug resistance", Leukemia 19(2): 176-182 (2005).
Linette, G.P., et al., "Cardiovascular toxicity and titin cross-reactivity of affinity-enhanced T cells in myeloma and melanoma," Blood (Aug. 8, 2013); 122(6): 863-71 (Epub Jun. 14, 2013).
Liou et al., "A chimeric mouse-human antibody that retains specificity for HIV gp 120 and mediates the lysis of HIV-infected cells," J Immunol1989; 143: 3967-3975.
Liu H, et al., "Monoclonal antibodies to the extracellular domain of prostate-specific membraneantigen also react with tumor vascular endothelium," Cancer Res. (1997); 57(17): 3629-3634.
Lodish et al., "Hierarchical Structure of Proteins" Molecular Cell Biology. 4th Ed. New York: W.H. Freeman; 2000. pp.1-25.
Long, A. H., et al., 4-IBB costimulation ameliorates T cell exhaustion induced by tonic signaling of chimeric antigen receptors. Nat Med, 2015. 21(6): p. 581-90.
Love et al., "ITAM-mediated Signaling by the T-Cell Antigen Receptor," Cold Spring Harbor D Perspectives in Biology, 2(6): a002485-a002485 (2010), pp. 1-11.
Lowin_Kropf et al., "Cytoskeletal Polarization ofT Cells Is Regulated by an Immunoreceptor Tyrosine-based Activation Motif-dependent Mechanism," The Journal of Cell Biology 1998, vol. 140, No. 4, pp. 861-871.
Lu et al., "Folate-targeted dinitrophenyl hapten immunotherapy: effect of linker chemistry on antitumor activity and allergic potential," Mol. Pharm., 2007, 695-706.
Lu et al., "Strategy to prevent drug-related hypersensitivity in folate-targeted hapten immunotherapy of cancer," AAPS J 11(3):628-638 (2009).
Lu, Y. et al., "Preclinical pharmacokinetics, tissue distribution, and antitumor activity of a folate-hapten conjugate-targeted immunotherapy in hapten-immunized mice", Molecular Cancer Therapeutics, 2006, vol. 5, No. 12, pp. 3258-3267.
Lueders et al., "The Long Terminal Repeat of an Endogenous Intracisternal A—Particle Gene Functions as a Promoter When Introduced into Eukaryotic Cells by Transfection" Molecular and Cellular Biology, vol. 4, No. 10, Oct. 1984, pp. 2128-2135.
Lustgarten, J., et al., "Specific Elimination of IgE Production Using T Cell Lines Expressing Chimeric T Cell Receptor Genes," European Journal of Immunology (1995); 25(10):2985-2991.
Ma et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," C. Gene Therapy 11: 297-306 (2004).
Ma et al., "Targeting of antigens to B lymphocytes via CD19 as a means for tumor vaccine development," Journal of Immunology 190(11):5588-5599 (2013).
Ma J.S.Y., et al., "Versatile Strategy for Controlling the Specificity and Activity of Engineered T cells," Proceedings of the National Academy of Sciences, 2016, vol. 113(4), pp. E450-E458.
Ma, Q., et al., "Genetically engineered T cells as adoptive immunotherapy of cancer," Cancer Chemother Biol Response Modif (2002); 20: 315-41.
Maeda, et al., "Tumor vascular permeability and the EPR effect in macromolecular therapeutics: a review," Journal of Controlled Release 65 (2000), pp. 271-284 (14 pages).
Maher, J., Immunotherapy of malignant disease using chimeric antigen receptor engrafted T cells. International Scholarly Research Notices Oncology, 2012:278093 (2012).
Maher, John, et al. "Human T-lymphocyte cytotoxicity and proliferation directed by a single chimeric TCR/CD28 receptor." Nature Biotechnology (2002); 20.1: 70-75.
Makabe et al., "Thermodynamic consequences of mutations in Vernier zone residues of a humanized anti-human epidermal growth factor receptor murine antibody," Journal of Biological Chemistry, 283(2):1156-1166 (2008).
Manual pCDH Vectors (System Biosciences) (21 pages), Nov. 18, 2013.
Marincola, F. M., et al., "Escape of human solid tumors from T cell recognition: molecular mechanisms and functional significance," Adv. Immunol. (2000); 74: 181-273.
Martin et al., "Modeling antibody hypervariable loops: a combined algorithm,"Proc Natl Acad Sci (USA), 86:9268-9272 (1989).
Maude Shannon L. et al. "Chimeric Antigen Receptor T Cells for Sustained Remissions in Leukemia" N Engl J Med. Oct. 16, 2014;371(16):1507-17.
Maude, S.L. et al., "Managing Cytokine Release Syndrome Associated With Novel T Cell-Engaging Therapies" Cancer J. Mar.-Apr. 2014; 20(2): 119-22.
Maus et al., "Antibody-modified T cells: CARs take the front seat for hematologic malignancies," Blood 123(17):2626-2635 (2014).
Maus et al., "Ex vivo expansion of polyclonal and antigen-specific cytotoxic T lymphocytes by artificial APCs expressing ligands for the T-cell receptor, CD28 and 4-IBB," Nature Biotechnology, Nature Publishing Group, New York, NY, US, vol. 20, No. 2, Feb. 1, 2002, pp. 143-148.
Maus, et al., "Zoom Zoom: racing CARs for multiple myeloma," Clin Cancer Res. (Apr. 15, 2013); 19(8):1917-9 (Epub Feb. 26, 2013).
Maus, M.V., et al., T cells expressing chimeric antigen receptors can cause anaphylaxis in humans. Cancer Immunol Res, 2013. 1(1): p. 26-31.
Mcguinness et al., "Anti-tumor activity of human T cells expressing the CC49-zeta chimeric immune receptor," Hum Gene Ther. Jan. 20, 1999;10(2):165-73.
Medstrand et al., "Long Terminal Repeats Are Used as Alternative Promoters for the Endothelin B Receptor and Apolipoprotein C-1 Genes in Humans", The Journal of Biological Chemistry, vol. 276, No. 3, Issue of Jan. 19, pp. 1896-1903, 2001.
Melero, I, et al., "Amplification of tumor immunity by gene transfer of the co-stimulatory 4-IBB ligand: synergy with the CD28 co-stimulatory pathway," Bristol-Myers Squibb Pharmaceutical Research Institute ( 1998); 1116-1121.
Melief, C. J. et al., "Strategies for immunotherapy of cancer," Adv. Immunol. (2000); 75:235-282.
Midelfort, KS, et al., "Substantial Energetic Improvement with Minimal Structural Perturbation in a High Affinity Mutant Antibody," J. Mal. Bioi., 343, 685-701, 2004.
Miguel Muñoz, Rafael Coveñas, "Substance P," Encyclopedia of Endocrine Diseases (Second Edition), vol. 1, pp. 571-578 (2018).
Milone et al., "Chimeric receptors containing CD137 signal transduction domains mediate enhanced survival of T cells and increased antileukemic efficacy in vivo," Mol Ther. (2009) 17(8):1453-1464.
Molecular Cloning A Laboraory Manual, 4th Edition, Cold Spring Harbor Laboratory Press, (2012) Green and Sambrook, TOC, 34 pages (2012).
Mooney et al., "Concise Review: Neural Stem Cell-Mediated Targeted Cancer Therapies" Stem Cells Translational Medicine, 2018, pp. 740-747.
Moore et al., "Application of dual affinity retargeting molecules to achieve optimal redirected T-cell killing of B-cell lymphoma," Blood, The Journal of the American Society of Hematalogy, Apr. 2011, 117(17), pp. 4542-4551.

(56) References Cited

OTHER PUBLICATIONS

Moore et al., "Characterisation of salmon and trout CD8a and CD8l3," Molecular Immunology 42 (2005) 1225-1234.
Moretta et al., "Activating Receptors and Coreceptors Involved in Human Natural Killer Cell-Mediated Cytolysis," Annu. Rev. Immunol. 2001. 19:197-223.
Morgan, R. A. et al., "Cancer Regression in Patients After Transfer of Genetically Engineered Lymphocytes," Science, vol. 314, pp. 126-129 (Oct. 2006).
Morgan RA et al., "Case Report of a Serious Adverse Event Following the Administration of T Cells Transduced With a Chimeric Antigen Receptor Recognizing Erbb2," Molecular Therapy 18(4):843-851 (2010).
Moritz, D. et al., "Cytotoxic T lymphocytes with a grafted recognition specificity for ERBB2-expressing tumor cells," Proc Natl Acad Sci U S A. May 10, 1994; 91(10): 4318-4322.
Morrison, C, "CAR-T Field Booms as Next-Generation Platforms Attract Big Players," Nature Biotechnology (Jun. 2015); 33: 571-72.
Muller T, et al., "Expression of a CD20-specific chimeric antigen receptor enhances cytotoxic activity of NK cells and overcomes NK-resistance of lymphoma and leukemia cells," Cancer Immunol. Immunother. (2008); 57: 411-423.
Mungra et al., "Targeted human cytolytic fusion proteins at the cutting edge harnessing the apoptosis-inducing properties of human enzymes for the selective elimination of tumor cells," Oncotarget. 10(8):897-915 (2019).
Munn et al., "Role of Low-Affinity Fe Receptors in Antibody-dependent Tumor Cell Phagocytosis by Human Monocyte-derived Macrophages," Cancer Research 51, 1117-1123, Feb. 15, 1991.
Nam, K, et al., "Cross-Linking of 4-IBB Activates TCR-Signaling Pathways in CDS• T Lymphocytes," The Journal of Immunology174(4):1898-1905 (2005).
National Cancer Institute. CAR T-Cell Therapy: Engineering Patients' Immune Cells to Treat Their Cancers, Cancer Research Updates, Updated: Oct. 16, 2014; 5 pages; retrieved Nov. 17, 2014 from http://www.cancer.gov/cancertopics/research-updates/2013/CAR-T-Cells.
Nelson, Aaron L., "Antibody fragments," mAbs 2010, Landes Bioscience, vol. 2, Issue 1, pp. 77-83.
Nieba, L., et al., "Disrupting the hydrophobic patches at the antibody variable/constant domain interface: improved in vivo folding and physical characterization of an engineered scFv fragment," Protein Eng. 10(4):435-444 (1997).
Nolan K F, et al., "Bypassing immunization: optimized design of 'designer T cells' against carcinoembryonic antigen (CEA)-expressing tumors, and lack of suppression by soluble CEA," Clinical Cancer Research (Dec. 1999); 5(12): 3928-3941.
Oelke et al., "Ex vivo induction and expansion of antigen-specific cytotoxic T cells by HLA-Ig-coated artificial antigen-presenting cells," Nature Medicine (2003); 9(5):619- 624.
Oelsner, S., et al., "Continuously expanding CAR NK-92 cells display selective cytotoxicity against B-cellleukemia and lymphoma", Cytotherapy, 2017; 19: 235-249.
Okazaki et al., "PD-I immunoreceptor inhibits B cell receptormediated signaling by recruiting src homology 2-domain-containing tyrosine phosphatase 2 to phosphotyrosine", PNAS Nov. 20, 2001, vol. 98, No. 24, 13866-13871.
Orr, B., "Rapid method for measuring ScFv thermal stability by yeast surface display," Biotechnol Prog., 2003. 19, 631-638.
Pages et al., "Two Distinct Intracytoplasmic Regions of the T-cell Adhesion Molecule CD28 Participate in Phosphatidylinositol 3-Kinase Association" The Journal of Biological Chemistry, vol. 271, No. 16, Apr. 19, 1996, pp. 9403-9409.
Paillard, F. "Immunotherapy with T cells bearing chimeric antitumor receptors," Hum. Gene Ther. (1999); 10: 151-153.
Paillasse, M, et al., "Insights into the Cholecystokinin 2 Receptor Binding Site and Processes of Activation," The American Society for Pharmacology and Experimental Therapeutics (2006); 70:1935-1945.

Pameijer, Colette RJ, et al. "Conversion of a tumor-binding peptide identified by phage display to a functional chimeric T cell antigen receptor." Cancer Gene Therapy (2007); 14.1: 91-97.
Park et al., "Treating cancer with genetically engineered T cells" Trends Biotechnol. Nov. 29, 2011(11): 550-557.
Parkhurst et al. "Characterization of genetically modified T-cell receptors that recognize the CEA:691-699 peptide in the context of HLA-A2.1 on human colorectal cancer cells" (2009) Clin Cancer Res. Jan. 1, 2009;15(1):169-80.
Patel et al., "T-cell killing of heterogenous tumor or viral targets with bispecific chimeric immune receptors," Cancer Gene Therapy (2000); 7(8): 1127-1134.
Patel Jainam et al: "Cancer Cartography: charting out a new approach to cancer immunotherapy", Immunotherapy. 2014;6(6):675-8.
PCT Search Report and Written Opinion prepared for PCT/US2018/020095, completed Jul. 17, 2018, 12 pages.
Peng-Cheng, "Evaluation of a Carbonic Anhydrase IX-Targeted near-Infrared Dye for Fluorescence-Guided Surgery of Hypoxic Tumors," Mol. Pharmaceutics, 13:1618-1625 (2016).
PeproTech, Recombinant Human 4-IBB Receptor, https://www.peprotech.com/recombinant- human-4-1 bb-receptor, downloaded Jul. 25, 2018, 5 pages, dated 2017.
Pierce, et al., "Computational Design of the Affinity and Specificity of a Therapeutic T Cell Receptor" PLOS Computational Biology (Feb. 13, 2014); 10(2): e1003478 (11 pages).
Pinto et al, "Molecular cloning and characterization of sea bass (*Dicentrarchus labrax* L.) CD8a," Veterinary Immunology and Immunopathology, 110, 169-177, 2006.
Pizarro, J.C., et al., "Structural and functional characterization of a monoclonal antibody specific for the preSI region of hepatitis B virus," FEBS letters (2001); 509: 463-468.
Pollok et al., Inducible T cell antigen 4-IBB. Analysis of expression and function, J Immunol1993; 150:771-781.
Porter DI, et al. Chimeric antigen receptor T cells persist and induce sustained remissions in relapsed refractory chronic lymphocytic leukemia . Science translational medicine. 2015;7(303)303-39. doi 10. I 126iscitranslmed.aac5415. PubMed PMID26333935.
Porter et al., Chimeric antigen receptor-modified T cells in chronic lymphoid leukemia, New England Journal of Medicine 355(8):725-733 (2011).
Prasad et al., "T-cell antigen CD28 interacts with the lipid kinase phosphalidylinosilol 3-kinase by a cytoplasmic Tyr P)—Met-Xaa-Mel motif," Proc. Nall. Acad. Sci. U.S.A. 91(7): 2832-2838 (1994).
Product brochure for the Engineered Autologous Cell Therapy (eACT™) Platform, available from Kite Pharma, retrieved Oct. 25, 2015 from http://www.kitepharma.com/c/products/eact.php.
Protein Lounge, 4-IBB Pathway, http://www.proteinlounge.com/Pathway/4-1BB%20Pathway, downloaded Jul. 25, 2018, 1 page.
Pule et al., "Artificial T-cell receptors," Cytotherapy (2003) 5(3)211-226.
Pule et al., "Virus-specific T cells engineered to coexpress tumor-specific receptors: persistence and antitumor activity in individuals with neuroblastoma," Nat. Med. (2008); 14: 1264-1270.
Qin et al., "Incorporation of a hinge domain improves the expansion of chimeric antigen receptor T cells," Journal of Hematology & Oncology (2017) 10:68, 11 pages.
Rabu et al., "Production of Recombinant Human Trimeric CD137L (4-1BBL), Cross-linking is Essential to its T Cell Co-Stimulation Activity," The Journal of Biological Chemistry vol. 280, No. 50, pp. 41472-41481, Dec. 16, 2005.
Rader, "DARTs take aim at BiTEs," Blood (Apr. 28, 2011); 117(17):4403-4.
Rai et al., "Expression systems for production of heterologous proteins," Current Science 2001, vol. 80, No. 9, pp. 1121-1128.
"Recent patent applications in chimeric antigen receptors," Nature Biotechnology 32(3): 239 (2014), 1 page.
Receptors, NK Cell Lectin-Like MeSH Descriptor Data 2018, NIH U.S. National Library of Medicine, 2 pages (Jul. 25, 2018).
Reddy, M. P., et al., "Elimination of Fc receptor-dependent effector functions of a modified IgG4 monoclonal antibody to human CD4", The Journal of Immunology (2000); 164(4): 1925-1933.

(56) References Cited

OTHER PUBLICATIONS

Redmond et al., "The role of OX40-mediated co-stimulation in T cell activation and survival," Crit. Rev. Immunol. 2009, 29(3): 187-201.
Reichert, J. Day 1, Emerging Disruptive Technologies and Cutting-Edge Analytical Techniques, MAbs, 2009, 1:3:190-209; May/June.
Restifo, N.P. et al., "Adoptive immunotherapy for cancer: harnessing the T cell response", Nat Rev Immunol. (2012); 12(4):269-281.
Reubi, Jean Claude, "Peptide Receptors as Molecular Targets for Cancer Diagnosis and Therapy," Endocrine Reviews 24(4): 389-427 (2003).
Riha et al., "CD28 co-signaling in the adaptive immune response" Self/Nonself 1:3, 231-240; Jul./Aug./Sep. 2010.
Riley et al., "The CD28 family: aT-cell rheostat for therapeutic control of T-cell activation", Blood, Jan. 1, 2005, vol. 105, No. 1, pp. 13-21.
Rivière, I., "Retroviral-mediated gene transfer in primary murine and human T-lymphocytes," Mol. Biotechnol. 15 133-142 (2000).
Roberts, et al., "Antigen-specific cytolysis by neutrophils and NK cells expressing chimeric immune receptors bearing zeta or gamma signaling domains," J. Immunol. (1998); 161:375-84.
Roberts et al., "Chemistry for peptide and protein PEGylation," Advanced Drug Delivery Reviews (2002); 54:459-476.
Rodgers D.T., et al., "Switch-Mediated Activation and Retargeting of CAR-T Cells for B-cell Malignancies," Proceedings of the National Academy of Sciences, 2016, vol. 113(4), pp. E459-E468.
Romeo, C. at al., "Sequence requirements for induction of cytolysis by the T cell antigen/Fe receptor zeta chain," Cell (1992); 68:889-897.
Romeo, C., et al., "Cellular immunity to HIV activated by CD4 fused to T cell or Fe receptor polypeptides," Cell (1991 ); 64:1037-1046.
Rosenberg "Cell transfer immunotherapy for metastatic solid cancer—what clinicians need to know" (2011) Nat Rev Clin Oneal. 8(10):577-85).
Rosenberg, S. A. et al., "Adoptive cell therapy for the treatment of patients with metastatic melanoma," Current Opinion in Immunology, 2009, 21, 233-240.
Rosenberg, S.A. et al. (2008). "Adoptive cell transfer: a clinical path to effective cancerImmunotherapy," Nature Reviews Cancer 8:299-308.
Rossi, et al., "2730 Phase 1 Biomarker Analysis of the ZUMA-1 (KTE-Cl9-1 01) Study: A Phase 1-2 Multi-Center Study Evaluating the Safety and Efficacy of Anti-CD19 CART Cells (KTEC19) in Subjects with Refractory Aggressive Non-Hodgkin Lymphoma (NHL)," American Society of Hematology (2015) (https://ash.confex.com/ash/20 15/webprogramscheduler/Paper80339. html) (2 pages) (presentation date Dec. 6, 2015).
Rotz Seth J. et al. "Severe cytokine release syndrome in a patient receiving PO-I-directed therapy" Pediatr Blood Cancer. Dec. 2017;64(12). Epub May 24, 2017 (4 pages).
Rueckert S, et al., "A monoclonal antibody as an effective therapeutic agent in breast cancer: trastuzumab" Expert Opin Bioi Ther. Jun. 2005;5(6):853-66.
Sadelain et al., "Targeting Tumours with Genetically Enhanced T Lymphocytes," Nat Rev Cancer (Jan. 2003); 3(1): 35-45.
Sadelain et al., "The basic principles of chimeric antigen receptor design." Cancer Discov., Apr. 2013, vol. 3, No. 4, pp. 388-398.
Sadelain, M. et al. (2009). "The promise and potential pitfalls of chimeric antigen receptors," Curr. Opin. Immunol, 21:215-223.
Sambrook, et al., Molecular Cloning: A Laboratory Manual, 3rd Edition, Cold Spring Harbor Laboratory Press, Cold Spring Harbor, New York, 2001, 9.47-9.55.
Samudrala et al., "Ab Initio Protein Structure Prediction Using a Combined Hierarchical Approach," Proteins, Structure, Function and Genetics Suppl., 3:194-198 (1999).
Saolli, C, et al., "CD28-independent, TRAF2-dependent Costimulation of Resting T Cells by 4-IBB Ligand," Department of Immunology University of Toronto (1998); 1-67.

Saraswat et al., "DNA as Therapeutics; an Update," Indian J Ph arm Sci. Sep.-Oct. 2009; 71 (5): 488-498.
Scholler, J., et al., "Decade-long safety and function of retroviral-modified chimeric antigen receptor T cells," Sci Transl Med (May 2, 2012); 4(132): 132ra53 (7 pages).
Schonfeld, K, et al., "Selective Inhibition of Tumor Growth by Clonal NK Cells Expressing an Erb82/HER2-Specific Chimeric Antigen Receptor", Mol. Ther., vol. 23 No. 2, 330-338 Feb. 2015.
Schreiber, S.L., "Organic synthesis toward small-molecule probes and drugs" PNAS, vol. 108, No. 17, Apr. 26, 2011, pp. 6699-6702.
Schutsky, K, et al., "Rigorous optimization and validation of potent RNA CAR T cell therapy for the treatment of common epithelial cancers expressing folate receptor," Oncotarget (Oct. 6, 2015); 6(30):28911-28.
Schwesinger et al., "Unbinding forces of single antibody-antigen complexes correlate with their thermal dissociation rates," PNAS (2000) 97(18), 9972-9977.
Scott, D., et al., "Immunogenicity of biotinylated hapten-avidin complexes," MolImmunol (1984); 21 (1 1 ): 10 55-60.
Sega E. et al.. Tumor detection using fola1 e receptor-targeted imaging agents. •• Cancer Me1 astasis Rev., 2008, 27, 655-664.
Sentman "Challenges of creating effective chimeric antigen receptors for cancer therapy" Immunotherapy. Aug. 2013;5(8):783-5.
Serghides et al., "Evaluation of OX40 Ligand as a Costimulator of Human Antiviral Memory CDS T Cell Responses: Comparison with B7.1 and 4-IBBL," The Journal of Immunology 175:6368-6377 (2005).
Shields, R. L., et al., "High resolution mapping of the binding site on human IgG1 for FcγRI, FcγRII, FcγRIII, and FcRn and design of IgG1 variants with improved binding to the FcγR", Journal of Biological Chemistry (2001); 276(9): 6591-6604.
Shirasu et al., "Construction and Molecular Characterization of Human Chimeric T-Cell Antigen Receptors Specific for Carcinoembryonic Antigen," Anticancer Research 30: 2731-2738 (2010).
Shishkin A.M., Development of a method of adoptive immunotherapy of cancer-embryonic antigen positive human tumors, Moscow, FGBU "Russian Scientific Center of radiology and nuclear medicine," 2015, 23 pages including English Summary.
Sobota et al., "Binding of IgG-Opsonized Particles to FcyR Is an Active Stage of Phagocytosis That Involves Receptor Clustering and Phosphorylation," The Journal of Immunology 2005; 175:4450-4457.
Song, DG, et al., "A fully human chimeric antigen receptor with potent activity against cancer cells but reduced risk for off-tumor toxicity," Oncotarget (Aug. 28, 2015);6(25):21533-46.
Song, DG, et al., "CD27 costimulation augments the survival and antitumor activity of redirected human T cells in vivo," Blood (Jan. 19, 2012); 119(3):696-706 (Epub Nov. 23, 2011).
Song et al., "In vivo persistence, tumor localization and anti-tumor activity of CAR engineered T cells is enhanced by costimulatory signaling through CD137 (4-IBB)," Cancer Research (2011); 71:4617-27.
Stancovski et al., "Targeting of T lymphocytes to Neu/HER2-expressing cells using chimeric single chain Fv receptors," J. Immunol 1993; 151: 6577-6582.
Stein et al., "The Cytoplasmic Domain of CD28 Is both Necessary and Sufficient for Costimulation of Interleukin-2 Secretion and Association with Phosphatidylinositoi3'-Kinase," Molecular And Cellular Biology, (May 1994) 14(5): 3392-3402.
Stephan, M. et al., "T cell-encoded CD80 and 4-1BBL induce auto- and transcostimulation, resulting in potent tumor rejection", Nat Med. (2007); 13(12): 1440-1449.
Stevens et al., "Generation of Tumor-Specific CTLs from Melanoma Patients by Using Peripheral Blood Stimulated with Allogeneic Melanoma Tumor Cell Lines," J. Immunol (1995); 154:762-771.
Stone, J.D., et al., "A sensitivity scale for targeting T cells with chimeric antigen receptors (CARs) and bispecific T-cell Engagers (BiTEs)," Oncoimmunology (Sep. 2012); 1(6): 863-873.
Suhoski et al., "Engineering artificial antigen-presenting cells to express a diverse array of co-stimulatory molecules," Mol. Ther. 15, 981-88, 2007.

(56) References Cited

OTHER PUBLICATIONS

Sun et al., "Immunotherapy with CAR-Modified T cells: toxicities and overcoming strategies," Journal of Immunology Research, 2018:1-10 (2018).
Swanson et al., "The coordination of signaling during Fc receptor-mediated phagocytosis," Journal of Leukocyte Biology, vol. 76, Dec. 2004, pp. 1093-1103.
Tam et al., "Functional, Biophysical, and Structural Characterization of Human IgG1 and IgG4 Fc Variants with Ablated Immune Functionality," Antibodies. Sep. 1, 2017, 6, 12, 34 pages.
Tamada et al., Correction Feb. 14, 2013, 2 pages, "Redirecting Gene-Modified T Cells Toward Various Cancer Types Using Tagged Antibodies," Clinical Cancer Research 2012:18(23)6436-6445.
Tamada K., et al., "Redirecting Gene-Modified T cells Toward Various Cancer Types using Tagged Antibodies," Clinical Cancer Research, 2012, vol. 18(23), pp. 6436-6445.
Tan, L.K. et al., "Influence of the hinge region on complement activation, C1q binding, and segmental flexibility in chimeric human immunoglobulins," Proc. Natl. Acad. Sci. USA 87:162-166, (1990).
Tanaka, Toshio et al. "Immunotherapeutic implications of IL-6 blockade for cytokine storm." Immunotherapy. Jul. 2016;8(8) :959-70.
Teachey D. T. et al Cytokine release syndrome after blinatumomab treatment related to abnormal macrophage activation and ameliorated with cytokine-directed therapy Blood. Jun. 27, 2013;121(26)5154-7. doi 10.1182/blood-2013-02-485623. Epub May 15, 2013.
Terakura et al., "Generation of CD19-chimeric antigen receptor modified CD8+ T cells derived from virus-specific central memory T cells," Blood 119(1):72-82 (2012) e-pub Oct. 26, 2011.
The LTR Retroviral Promoter; Long Terminal Repeats: The Retroviral Promoter. https://web.stanford.edu/group/nolan/_OldWebsite/tutorials/retcl_3_1trs.html retrieved Jul. 26, 2018, 2 pages.
Themeli, M., et al., "Generation of tumor-targeted human T lymphocytes from induced pluripotent stem cells for cancer therapy," Nat Biotechnol (2013); 31(10):928-33 (Epub Aug. 11, 2013 ).
Till et al., "Adoptive immunotherapy for indolent non-Hodgkin lymphoma and mantle cell lymphoma using genetically modified autologous CD20-specific T cells," Blood 112(6): 2261-2271 (2008).
"TNF Superfamily Pathway," ThermoFinder Scientific, 4 pages, undated.
Traversari et al., "The potential immunogenicity of the TK suicide gene does not prevent full clinical benefit associated with the use of TK-transduced donor lymphocytes in HSCT for hematologic malignancies," Blood 109(11):4708-4715 (2007).
Tsukahara et al. "CD19 target-engineered T-cells accumulate at tumor lesions in human B-cell lymphoma xenograft mouse models" (2013) Biochem Biophys Res Commun 438(1): 84-9. Epub Jul. 17, 2013.
"Tumor necrosis factor receptor superfamily," HUGO Gene Nomenclature Committee, 2 pages, undated.
Turatti et al., "Redirected activity of human antitumor chimeric immune receptors is governed by antigen and receptor expression levels and affinity of interaction," Journal of Immunotherapy 30(7):684-693 (2007).
Turtle et al., "Engineered T cells for anti-cancer therapy" Curr. Opin. Immunol., Oct. 2012; 24(5): 633-39. Epub Jul. 18, 2012.
Uherek, C, et al., "Chimeric antigen receptors for the retargeting of cytotoxic effector cells," J. Hematother. Stem Cell Res. (2001); 10: 523-534.
Uherek, C, et al., "Retargeting of natural killer-cell cytolytic activity to ErbB2 expressing cancer cells results in efficient and selective tumor cell destruction," Blood (2002); 100: 1265-1273.
UniProtKB—P01732 (CDSA_HUMAN). T-cell surface glycoprotein CDS alpha chain; 11 pages; retrieved on May 13, 2016 from http://www.uniprot.org/uniproUPOI732.
UniProtKB—P10747 (CD28_HUMAN), 15 pages, dated Jul. 1, 1989.
UniProtKB—P10966 (CD8B_HUMAN), 14 pages, dated Jul. 1, 1989.
UniProtKB—P20963 (CD3Z_HUMAN). T-cell surface glycoprotein CD3 zeta chain; 12 pages; retrieved on May 13, 2016 from http://www.uniprot.org/uniproUP20963.
UniProtKB—043914, "Tyro protein tyrosine kinase-binding protein", pp. 1-15, dated May 30, 2000.
UniProtKB—P02701 (AVID_CHICK), 8 pages, AVO—Avidin precursor,dated Jul. 21, 1986.
"UniProtKB—P24161 (CD3Z_MOUSE)" (12 pages), retrieved from http://www.uniprot.org/uniproVP24161 on Oct. 14, 2016.
UniProtKB—Q07011 (TNR9_HUMAN). Tumor necrosis factor receptor superfamily member 9; 14 pages; retrieved on May 13, 2016 from http://www.uniprot.org/uniproUQ07011.
Urba et al., "Redirecting T cells," New Engl. J. Med., 2011, 365, 754-757.
Urbanska, K., et al., "A Universal Immune Receptor Expressed by T Cells for the Targeting of Diverse and Multiple Tumor Associated Antigens" IN Abstracts for the 26th Annual Scientific Meeting of the Society for Immunotherapy of Cancer (SITC), J Immunother, vol. 34, No. 9, Nov.-Dec. 2011 (62 pages), p. 381.
Urbanska, K., et al., A universal strategy for adoptive immunotherapy of cancer through use of a novel T-cell antigen receptor, Cancer Research 72(7):1844-1852 (2012).
Urbanska, K. et al., "Development of a novel universal immune receptor for antigen targeting: To Infinity and beyond," Oncoimmunology (Aug. 2012 I); 1(5): p. 777-779.
U.S. Appl. No. 61/473,409, inventor Morgan; Richard, filed Apr. 8, 2011.
U.S. Appl. No. 61/701,056, inventor Robbins; Paul, filed Sep. 14, 2012.
U.S. Appl. No. 61/891,347, inventor Cao:Yu, filed Oct. 15, 2013.
U.S. Appl. No. 61/895,704, inventor Cao:Yu, filed Oct. 25, 2013.
U.S. Appl. No. 62/009,054, inventor Young:Travis, filed Jun. 6, 2014.
U.S. Appl. No. 62/009,056, inventor Cao:Yu, filed Jun. 6, 2014.
U.S. Appl. No. 62/030,514, inventor Wang; Feng, filed Jul. 29, 2014.
U.S. Appl. No. 62/030,526, inventor Wang; Feng, filed Jul. 29, 2014.
U.S. Appl. No. 62/059,752, inventor Kim:Chanhyuk, filed Oct. 3, 2014.
U.S. Appl. No. 62/108,947, inventor Kim:Chanhyuk, filed Jan. 28, 2015.
U.S. Appl. No. 62/148,063, inventor Young:Travis, filed Apr. 15, 2015.
U.S. Appl. No. 62/148,070, inventor Kim: Chanhyuk, filed Apr. 15, 2015.
U.S. Appl. No. 62/253,465, inventor Kim:Chanhyuk, filed Nov. 10, 2015.
U.S. Appl. No. 62/253,467, inventor Young:Travis, filed Nov. 10, 2015.
Uttenthal et al., "Challenges in T cell receptor gene therapy," Journal of Gene Med 14(6):386-399 (2012).
Van Blitterswijk et al., "Anticancer mechanisms and clinical application of alkylphopholipids," Biochimica et Biophysica Acta (2013) 1831(3)663-674.
Van Dam et al., "Intraoperative tumor-specific fluorescence imaging in ovarian cancer by folate receptor-alpha targeting: first in-human results," Nature Medicine 17(10):1315-1319 (2011).
Van Der Luit et al., "A new class of anticancer alkylphospholipids uses lipid rafts as membrane gateways to induce apoptosis in lymphoma cells," Mol Cancer Ther (2007) 6(8)2337-2345.
Van Der Stegen et al., "The pharmacology of second-generation chimeric antigen receptors." Nature reviews Drug Discovery 14(7):499-509 (2015).
Van Rhijn I. V., et al., "Human Autoreactive T Cells Recognize CD1band Phospholipids," Proceedings of the National Academy of Sciences, Nov. 30, 2015, vol. 113(2), pp. 380-385.
Vaughan et al., "Human antibodies with sub-nanomolar affinities isolated from a large non-immunized phage display library," Nature Biotechnology, Mar. 1996, 14(3), pp. 309-314.
Verdine et al., "The Challenge of Drugging Undruggable Targets in Cancer: Lessons Learned from Targeting BCL-2 Family Members" Clin. Cancer Res. Vol. 13, No. 24, Dec. 15, 2007, pp. 7264-7270.

(56) References Cited

OTHER PUBLICATIONS

Verhoeyen et al., "Lentiviral Vector Gene Transfer Into Human T Cells," Methods in Molecular Biology, Methods and Protocols, 2009, vol. 506, pp. 97-114.
Wang et al., "Current status and perspectives of chimeric antigen receptor modified T cells for cancer treatment," Protein Cell2017, 8(12):896-925.
Wang et al., "Phenotypic and functional attributes of lentivirus-modified CD19-specific human CD8+ central memory T cells manufactured at clinical scale," J. Immunol Ther 35(9):689-701 (2012).
Wayua et al., "Evaluation of a Cholecystokinin 2 Receptor-Targeted Near-Infrared Dye for Fluorescence-Guided Surgery of Cancer," Molecular Pharmaceutics 11:468-476 (2014).
Webpage, COVID-19 Treatment Guidelines—Interleukin-6 Inhibitors, dated Sep. 26, 2022, 5 pages, retrieved online on Oct. 7, 2022 at https://www.covid19treatmentguidelines.nih.gov/therapies/immunomodulators/interleukin-6-inhibitors/.
Weijtenset al., "Single chain Ig/gamma gene-redirected human T lymphocytes produce cytokines, specifically lyse tumor cells, and recycle lytic capacity.," J. Immunol. (Jul. 15, 1996); 157(2):836-43.
Weissman et al., "Molecular cloning and chromosomal localization of the human T-cell receptor zeta chain: Distinction from the molecular CD3 complex" Proc. Natl. Acad. Sci. Vol. 85, Dec. 1988, pp. 9709-9713.
Weissman et al., "Role of the zeta chain in the expression of the T cell antigen receptor: genetic reconstitution studies" The EMBO Journal, vol. 8, No. 12, 1989, pp. 3651-3656.
Wen, T. et al., "4-1BB Ligand-Mediated Costimulation of Human T Cells Induces CD4 and CD8 T Cell Expansion, Cytokine Production, and the Development of Cytolytic Effector Function," The Journal of Immunology, 168:4897-4906 (2002).
Wesolowski, J, et al., "Single domain antibodies: promising experimental and therapeutic tools in infection and immunity", Med MicrobiolImmunol (2009) 198:157-174.
Wikipedia, Amino acid, https://en.wikipedia.org/wiki/Amino_acid, downloaded Jul. 30, 2018,13 pages, undated.
Wikipedia, Antibody, https://en.wikipedia.org/w/index.php?title=Antibody&oldid=851456273, downloaded Jul. 22, 2018, 29 pages, undated.
Wikipedia, Avidin, https://en.wikipedia.org/wiki/Avidin, downloaded Aug. 24, 2018, 8 pages, undated.
Wikipedia, CD137, https://en.wikipedia.org/w/index.php?title=CD137&oldid=788581779, downloaded Jul. 2, 2017, 8 pages, undated.
Wikipedia, CD28, https://en.wikipedia.org/w/index.php?title=CD28&oldid=831459950, downloaded Mar. 20, 2018, 9 pages, undated.
Wikipedia, CD3 (immunology), https://en.wikipedia.org/wiki/CD3_(immunology), downloaded Jul. 24, 2018, 3 pages, undated.
Wikipedia, CD8, https://en.wikipedia.org/w/index.php?title=CD8&oldid=840166968, downloaded May 8, 2018, 3 pages, undated.
Wikipedia, "Chimeric antigen receptor"; 9 pages; retrieved on Nov. 13, 2014 from http://en.wikipedia.org/wiki/Chimeric antigen receptor.
Wikipedia, Cholecystokinin B receptor, https://en.wikipedia.org/w/index.php?title=Cholecystokinin_B_receptor&oldid=837355377, downloaded Apr. 20, 2018, 9 pages, undated.
Wikipedia, C-type lectin, https://en.wikipedia.org/wiki/C-type_lectin, downloaded Jul. 25, 2018, 4 pages, undated.
Wikipedia, Cytokine, https://en.wikipedia.org/w/index.php?title=Cytokine&oldid=847147607, downloaded Jun. 23, 2018, 8 pages, undated.
Wikipedia, Fc receptor, https://en.wikipedia.org/w/index.php?title=Fc_receptor&oldid=845940301. downloaded Jun. 15, 2018, 13 pages, undated.
Wikipedia, Folate, https://en.wikipedia.org/w/index.php?title=Folate&oldid=851466622, downloaded Jun. 22, 2018, 12 pages, undated.
Wikipedia, Folate receptor 1, https://en.wikipedia.org/w/index.php?title=Folate_receptor_I &oldid=845790606, downloaded Jun. 14, 2018, 8 pages.
Wikipedia, Folate receptor gamma, https://en.wikipedia.org/w/index.php?title=Folate receptor gamma&oldid=621589158, downloaded Aug. 17, 2014, 1 page.
Wikipedia, Folate receptor, https://en.wikipedia.org/w/index.php?title=Folate receptor&oldid=834246297, downloaded Apr. 4, 2018, 1 page.
Wikipedia, FOLR2, https://en.wikipedia.org/w/index.php?title=FOLR2&oldid=798129670, downloaded Aug. 31, 2017, 6 pages, undated.
Wikipedia, Glutamate carboxypeptidase II, https://en.wikipedia.org/w/index.php?title=Giutamate carboxypeptidase _II &oldid=845231234, downloaded Jun. 10, 2018, 17 pages, undated.
Wikipedia, Glycosylation, https://en.wikipedia.org/wiki/Giycosylation, downloaded Jul. 31, 2018, 3 pages.
Wikipedia, IL-2 receptor, https://en.wikipedia.org/w/index.php?title=IL-2_receptor&oldid=8471 73411, downloaded Jun. 23, 2018, 4 pages, undated.
Wikipedia, Interferon, https://en.wikipedia.org/w/index.php?title=Interferon&oldid=848844304, downloaded Jul. 4, 2018, 15 pages, undated.
Wikipedia, Interleukin 10, https://en.wikipedia.org/w/index.php?title=Interleukin_10&oldid=835415026, downloaded Apr. 8, 2018, 16 pages, undated.
Wikipedia, Interleukin 2, https://en.wikipedia.org/w/index.php?title=Interleukin_2&oldid=838351 127, downloaded Apr. 26, 2018, 11 pages, undated.
Wikipedia, Killer-cell immunoglobulin-like receptor, https://en.wikipedia.org/wiki/Killer-cell immunoglobulin-like receptor, downloaded Jul. 25, 2018, 9 pages, undated.
Wikipedia, KLRAI, https://en.wikipedia.org/wiki/KLRAI, downloaded Jul. 25, 2018, 2 pages, undated.
Wikipedia, Interleukin-1 family, https://en.wikipedia.org/w/index.php?title=Interleukin- I family&oldid=84725301 O,downloaded Jun. 24, 2018, 10 pages, undated.
Wikipedia, NKG2D, https://en.wikipedia.org/wiki/NKG2D, downloaded Jul. 25, 2018, 8 pages, undated.
Wikipedia, Paratope, https://en.wikipedia.org/wiki/Paratope, downloaded Jul. 25, 2018, 1 page.
Wikipedia, Protein, https://en.wikipedia.org/w/index.php?title=Protein&oldid=861574349, downloaded Oct. 15, 2018, 26 pages, undated.
Wikipedia, Single-chain variable fragment, https://en.wikipedia.org/w/index.php?title=Single- chain variable fragment&oldid=841449115, downloaded May 15, 2018, 4 pages.
Wikipedia, Single-domain antibody, https://en.wikipedia.org/wiki/Single-domain_antibody, downloaded Jul. 27, 2018, 9 pages, undated.
Wikipedia, Small molecule, https://en.wikipedia.org/wiki/Small_molecule, downloaded Jul. 27, 2018, 3 pages.
Wikipedia, TNF receptor superfamily, https://en.wikipedia.org/w/index.php?title= TNF_receptor_superfamily&oldid=850804991, downloaded 07118/2018, 6 pages, undated.
Wikipedia, Transforming growth factor beta superfamily, https://en.wikipedia.org/w/index.php? title= Transforming growth factor beta superfamily&oldid=850390369, downloaded Jul. 15, 2018, 3 pages, undated.
Wilkie et al., "Retargeting of Human T Cells to Tumor-Associated MUCI: The Evolution of a Chimeric Antigen Receptor," The Journal of Immunology Apr. 2008, pp. 4901-4909.
Wilson, et al. "DAP12 and KAPIO (DAPIO)-novel transmembrane adapter proteins of the CD3zeta family," Immunol Res. (2000); 22(1):21-42.
WO2010025177—Sequence Listing (Mar. 4, 2010), 45 pages.
Wu, C-Y. et al. (Oct. 16, 2015) "Remote control of therapeutic T cells through a small molecule-gated chimeric receptor" Science, 350(6258); DOI: 10.1126/science.aab4077, 10 pages, with Summary, p. 293.
Wu et al., "Adoptive T -cell therapy using autologous tumor-infiltrating lymphocytes for metastatic melanoma: current status and future outlook" Cancer, Mar. 18, 2012(2): 160-75.
Wu, et al., "An activating immunoreceptor complex formed by NKG2D and DAPIO," Science (1999); 285:730-732.
Xu et al., "Cytokine release syndrome in cancer immunotherapy with chimeric antigen receptor engineered T cells" Cancer Lett. Feb. 28, 2014;343(2):172-8. Epub Oct. 16, 2013.

(56) References Cited

OTHER PUBLICATIONS

Xu et al., "Efficacy and safety of adoptive immunotherapy using anti-CD19 chimeric antigen receptor transduced T-cells: a systematic review of phase I clinical trials," Leuk Lymphoma 54(2):255-260 (2013).
Ye, H, et al., "The Structural Basis for the Recognition of Diverse Receptor Sequences by TRAF2," The Weill Medical College and Graduate School of Medical Sciences of Cornell University; v: 321-330 (1999).
Yee, C., et al., "Prospects for Adoptive T Cell Therapy," Current Opinion in Immunology (1997); 9(5):702-708.
Zacchetti, A, "Antitumor effects of a human dimeric antibody fragment 131I-AFRA-DFM5.3 in a mouse model for ovarian cancer," J Nucl Med (Dec. 2011); 52(12):1938-46 (Epub Nov. 8, 2011).
Zarour, "Reversing T-cell dysfunction and exhaustion in cancer," Clinical Cancer Research, 22(8):1856-1864 (2016).
Zhang, et al., "Chimeric NKG2D modified T cells inhibit systemic T-cell lymphoma growth in a manner involving multiple cytokines and cytotoxic pathways," Cancer Res. (2007); 67(22): 11029-36.
Zhang, et al., "Generation of antitumor responses by genetic modification of primary human T cells with a chimeric NKG2D receptor," Cancer Res. (2006); 66(11):5927-33.
Zhang et al., "Phase I Escalating-Dose Trial of CAR-T Therapy Targeting CEA+ Metastatic Colorectal Cancers," Molecular Therapy (2017), 25(5): 1248-1258.
Zhang, H., et al., 4-IBB is superior to CD28 costimulation for generating CD8+ cytotoxic lymphocytes for adoptive immunotherapy. J Immunol, 2007. 179(7): p. 4910-8.
Zhang, T. (2005). Chimeric NK-receptor-bearing T cells mediate antitumor immunotherapy. Blood 106, 1544-1551.
Zhao et al., "A Herceptin-Based Chimeric Antigen Receptor with Modified Signaling Domains Leads to Enhanced Survival of Transduced T Lymphocytes and Antitumor Activity", J Immunol (2009); 183: 5563-5574.
Zheng et al., "Arming Tumor-Reactive T Cells with Costimulator 87-1 Enhances Therapeutic Efficacy of the T Cells," Cancer Research, 2006, vol. 66, No. 13, pp. 6793-6799.
Zheng, F. et al., "Relationship between levels of serum folate and inflammatory cytokines in hypertension cases". Zhongguo Redai Yixue (2015), 15(5), 521-524.
Zhong, et al., "Integrated CD28 and 4-IBB Signals Strongly Potentiate CDS+ T Cell Mediated Eradication of Metastatic Prostate Cancer," Molecular Therapy (Jan. 1, 2006); 13: p. SI03, Abstract.
Zhong X., et al., "Chimeric Antigen Receptors Combining 4-1BB and CD28 Signaling Domains Augment PI3kinase/AKT/Bcl-XL Activation and CD8+ T Cell-mediated Tumor Eradication," Molecular Therapy, 2010, vol. 18(2), pp. 413-420.
"Chinese Application Serial No. 201980027953.8, Office Action mailed Nov. 10, 2023", w English translation, 20 pgs.
"International Application Serial No. PCT US2019 019191, International Preliminary Report on Patentability mailed Sep. 3, 2020", 9 pgs.
"Japanese Application Serial No. 2020-544671, Decision of Rejection mailed Feb. 6, 2024", w English Translation, 4 pgs.
"Canadian Application Serial No. 3,091,674, Voluntary Amendment Filed Feb. 21, 2024", 12 pgs.
"Chinese Application Serial No. 201980027953.8, Response filed May 24, 2024 to Office Action mailed Nov. 10, 2023", w English claims, 20 pgs.
"Japanese Application Serial No. 2020-544671, Response filed Jun. 5, 2024 to Decision of Rejection mailed Feb. 6, 2024", w English claims, 12 pgs.
"Japanese Application Serial No. 2020-544671, Office Action mailed Jun. 18, 2024", W English Claims, 7 pgs.
"Taiwanese Application Serial No. 108106131, Office Action mailed Oct. 24, 2023", 28 pgs.
"Japanese Application Serial No. 2020-544671, Response filed Jul. 12, 2024 to Office Action mailed Jun. 18, 2024", W English Claims (not amended), 30 pgs.
"Chinese Application Serial No. 201980027953.8, Voluntary Amendment filed Jun. 17, 2021", w English Claims, 18 pgs.
"Taiwanese Application Serial No. 108106131, Decision of Reexamination mailed Apr. 30, 2024", w English translation, 12 pgs.
Eugenia, Zah, "T cells expressing CD19 CD20 bi-specific chimeric antigen receptors prevent antigen escape by malignant B cells", Cancer Immunol Res, vol. 4, No. 6, (Apr. 8, 2016), 498-508.
Jennifer, S Y. Ma, "Versatile strategy for controlling the specificity and activity of engineered T cells", vol. 113, No. 4, [Online] Retrieved from the internet:https: doi.org 10.1073 pnas. 1524193113, (Jan. 12, 2016), E450-E458.

* cited by examiner

Days post CAR-T cell injection

*Antitumor activity (N = 5)*

SEQUENCING METHOD FOR CAR T CELL THERAPY

CROSS REFERENCE TO RELATED APPLICATIONS

This application is a U.S. national stage application under 35 U.S.C. § 371(b) of International Application No. PCT/US2019/019191 filed Feb. 22, 2019, which claims priority to U.S. Provisional Patent Application No. 62/634,573 filed on Feb. 23, 2018, U.S. Provisional Patent Application No. 62/656,265 filed on Apr. 11, 2018, U.S. Provisional Patent Application No. 62/724,345 filed on Aug. 29, 2018, and U.S. Provisional Patent Application No. 62/736,730 filed on Sep. 26, 2018, the disclosures of all of which are hereby expressly incorporated by reference in their entirety.

TECHNICAL FIELD

The present disclosure relates to methods of treating a patient with a cancer by administering to the patient a composition comprising CAR T cells and administering to the patient a small molecule linked to a targeting moiety by a linker. The disclosure also relates to compositions for use in such methods.

BACKGROUND

Immunotherapy based on adoptive transfer of lymphocytes (e.g., T cells) into a patient is a valuable therapy in the treatment of cancer and other diseases. Important advancements have been made in the development of immunotherapies based on adoptive transfer of lymphocytes. Among the many different types of immunotherapeutic agents, one of the most promising of the immunotherapeutic agents being developed is T cells expressing chimeric antigen receptors (CAR T cells). The chimeric antigen receptor (CAR) is a genetically engineered receptor that is designed to target a specific antigen, for example, a tumor antigen. This targeting can result in cytotoxicity against the tumor, for example, such that CAR T cells expressing CARs can target and kill tumors via the specific tumor antigens.

First generation CARs are composed of a recognition region, e.g., a single chain fragment variable (scFv) region derived from an antibody for recognition and binding to the antigen expressed by the tumor, and an activation signaling domain, e.g., the CD3ζ chain of T cells can serve as a T cell activation signal in CARs. Although CAR T cells have shown positive results in vitro, they have had limited success in eliminating disease (e.g., cancer) in clinical trials. One problem has been the inability to prolong activation and expand the CAR T cell population in vivo.

To address this problem, a co-stimulation domain (e.g., CD137, CD28 or CD134) has been included in second generation CARs to achieve prolonged activation of T cells in vivo. Addition of a co-stimulation domain enhances the in vivo proliferation and survival of T cells containing CARs, and initial clinical data have shown that such constructs are promising therapeutic agents in the treatment of diseases, such as cancer.

Although improvements have been made in CAR T cell therapies, several problems remain. First, 'off-target' toxicity may occur due to normal cells that express the antigen targeted by the CAR T cells (e.g., a tumor-associated antigen). Second, unregulated CAR T cell activation may be found where the rapid and uncontrolled elimination of diseased cells (e.g., cancer cells) by CAR T cells induces a constellation of metabolic disturbances, called tumor lysis syndrome, or cytokine release syndrome (CRS), which can be fatal to patients. Tumor lysis syndrome and CRS can result due to administered CAR T cells that cannot be easily regulated, and are activated uncontrollably. Accordingly, although CAR T cells show great promise as a tool in the treatment of diseases, such as cancer, additional CAR T cell therapeutic protocols are needed that provide reduced off-target toxicity, and more precise control of CAR T cell activation.

SUMMARY OF THE INVENTION

In the various embodiments described herein, a small molecule ligand linked to a targeting moiety by a linker is used as a bridge between the cancer and the CAR T cells directing the CAR T cells to the cancer for amelioration of the cancer. In one embodiment, the "small molecule ligand" can be, for example, a folate, DUPA, an NK-1R ligand, a CAIX ligand, a ligand of gamma glutamyl transpeptidase, an NKG2D ligand, or a CCK2R ligand, each of which is a small molecule ligand that binds specifically to cancer cells (i.e., the receptor for these ligands is overexpressed on cancers compared to normal tissues).

In one embodiment, the "small molecule ligand" is linked to a "targeting moiety" that binds to the CAR expressed by CAR T cells. In various embodiments, the "targeting moiety" can be selected, for example, from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.

The "targeting moiety" binds to the recognition region of the genetically engineered CAR expressed by CAR T cells. Accordingly, the recognition region of the CAR (e.g., a single chain fragment variable region (scFv) of an antibody, an Fab, Fv, Fc, (Fab')$_2$ fragment, and the like) is directed to the "targeting moiety." Thus, the small molecule ligand linked to a targeting moiety by a linker acts as a bridge between the cancer and the CAR T cells, directing the CAR T cells to the cancer for amelioration of the cancer.

In one embodiment, a method of treatment of a cancer is provided. The method comprises i) administering to a patient at least one dose of a CAR T cell composition comprising CAR T cells wherein the CAR T cells comprise a CAR directed to a targeting moiety; ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in at least a first dose escalation sequence and a second dose escalation sequence.

In another embodiment, a method of treatment of a cancer is provided. The method comprises i) administering to a patient at least one dose of a CAR T cell composition comprising CAR T cells wherein the CAR T cells comprise a CAR directed to a targeting moiety; ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in a first dose escalation sequence wherein, if serious CRS occurs in the first dose escalation sequence, the compound, or the pharmaceutically acceptable salt thereof, is administered using a lower dose escalation sequence wherein the first dose of the compound, or the pharmaceutically acceptable salt thereof, in the lower dose escalation sequence is lower than the first dose of the compound, or the pharmaceutically acceptable salt thereof, administered in the first dose escalation sequence. In one embodiment, in the lower dose escalation sequence, the compound, or the pharmaceutically acceptable salt thereof, can be administered at about 0.5 percent, about 5 percent, and about 50 percent of a full dose of the compound, or the pharmaceutically acceptable salt thereof, on three separate days.

Additional embodiments are also described by the following enumerated clauses. Any of the following embodiments in combination with any applicable embodiments described in the Summary section, the Detailed Description of the Illustrative Embodiments section, the Examples section, or the claims of this patent application, are also contemplated.

1. A method of treatment of a cancer, the method comprising
  i) administering to a patient at least one dose of a CAR T cell composition comprising CAR T cells wherein the CAR T cells comprise a CAR directed to a targeting moiety;
  ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in at least a first dose escalation sequence and a second dose escalation sequence.

2. The method of clause 1 wherein the compound, or the pharmaceutically acceptable salt thereof, is administered in at least a first dose escalation sequence, a second dose escalation sequence, and a third dose escalation sequence.

3. The method of clause 1 wherein the compound, or the pharmaceutically acceptable salt thereof, is administered in at least a first dose escalation sequence, a second dose escalation sequence, a third dose escalation sequence, and a fourth dose escalation sequence.

4. The method of clause 1 wherein the compound, or the pharmaceutically acceptable salt thereof, is administered is administered in at least a first dose escalation sequence, a second dose escalation sequence, a third dose escalation sequence, a fourth dose escalation sequence, and a fifth dose escalation sequence.

5. The method of clause 1 wherein the compound, or the pharmaceutically acceptable salt thereof, is administered in at least a first dose escalation sequence, a second dose escalation sequence, a third dose escalation sequence, a fourth dose escalation sequence, a fifth dose escalation sequence, and a sixth dose escalation sequence.

6. The method of any one of clauses 1 to 5 wherein a first dose of the CAR T cells and a second dose of the CAR T cells are administered to the patient.

7. The method of clause 6 wherein the first dose of the CAR T cells is a test dose to monitor the patient for tolerability to the CAR T cells.

8. The method of clause 6 wherein the second dose of the CAR T cells comprises a higher dose of the CAR T cells than the first dose of the CAR T cells.

9. The method of any one of clauses 6 to 8 wherein the first dose of the CAR T cells comprises about $0.5 \times 10^5$ of the CAR T cells per kg of patient body weight to about $1.5 \times 10^6$ of the CAR T cells per kg of patient body weight.

10. The method of any one of clauses 6 to 9 wherein the second dose of the CAR T cells comprises about $0.8 \times 10^6$ of the CAR T cells per kg of patient body weight to about $2 \times 10^7$ of the CAR T cells per kg of patient body weight.

11. The method of any one of clauses 1 to 10 wherein the first dose escalation sequence is followed by a period of time during which the compound, or the pharmaceutically acceptable salt thereof, is not administered.

12. The method of any one of clauses 1 to 11 wherein the second dose escalation sequence is followed by a period of time during which the compound, or the pharmaceutically acceptable salt thereof, is not administered.

13. The method of any one of clauses 2 to 12 wherein the third dose escalation sequence is followed by a period of time during which the compound, or the pharmaceutically acceptable salt thereof, is not administered.

14. The method of any one of clauses 3 to 13 wherein the fourth dose escalation sequence is followed by a period of time during which the compound, or the pharmaceutically acceptable salt thereof, is not administered.

15. The method of any one of clauses 4 to 14 wherein the fifth dose escalation sequence is followed by a period of time during which the compound, or the pharmaceutically acceptable salt thereof, is not administered.

16. The method of any one of clauses 5 to 15 wherein the sixth dose escalation sequence is followed by a period of time during which the compound, or the pharmaceutically acceptable salt thereof, is not administered.

17. The method of any one of clauses 11 to 16 wherein the period of time is about 7 days.

18. The method of any one of clauses 1 to 17 wherein the first dose escalation sequence comprises administering to the patient about 1 percent, about 10 percent, and about 100 percent of a full dose of the compound, or the pharmaceutically acceptable salt thereof, on three separate days.

19. The method of any one of clauses 1 to 18 wherein the second dose escalation sequence comprises administering to the patient about 1 percent, about 30 percent, and about 300 percent of a full dose of the compound, or the pharmaceutically acceptable salt thereof, on three separate days.

20. The method of any one of clauses 2 to 19 wherein the third dose escalation sequence comprises administering to the patient about 1 percent, about 50 percent, and about 500 percent of a full dose of the compound, or the pharmaceutically acceptable salt thereof, on three separate days.

21. The method of any one of clauses 3 to 20 wherein the fourth dose escalation sequence comprises administering to the patient about 1 percent, about 10 percent, and about 100 percent of a full dose of the compound, or the pharmaceutically acceptable salt thereof, on three separate days.

22. The method of any one of clauses 4 to 21 wherein the fifth dose escalation sequence comprises administering to the patient about 1 percent, about 30 percent, and about 300 percent of a full dose of the compound, or the pharmaceutically acceptable salt thereof, on three separate days.

23. The method of any one of clauses 5 to 22 wherein the sixth dose escalation sequence comprises administering to the patient about 1 percent, about 50 percent, and about 500 percent of a full dose of the compound, or the pharmaceutically acceptable salt thereof, on three separate days.

24. The method of any one of clauses 18 to 23 wherein the full dose of the compound, or the pharmaceutically acceptable salt thereof, is about 10 µg/kg to about 50 µg/kg of the compound, or the pharmaceutically acceptable salt thereof.

25. The method of any one of clauses 18 to 24 wherein the full dose of the compound, or the pharmaceutically acceptable salt thereof, is about 20 µg/kg to about 40 µg/kg of the compound, or the pharmaceutically acceptable salt thereof.

26. The method of any one of clauses 18 to 25 wherein the full dose of the compound, or the pharmaceutically acceptable salt thereof, is about 25 µg/kg to about 35 µg/kg of the compound, or the pharmaceutically acceptable salt thereof.

27. The method of any one of clauses 18 to 26 wherein the full dose of the compound, or the pharmaceutically acceptable salt thereof, is about 30 µg/kg of the compound, or the pharmaceutically acceptable salt thereof.

28. The method of any one of clauses 6 to 27 wherein the first dose of the CAR T cells and the second dose of the CAR T cells are administered to the patient during week 1.

29. The method of any one of clauses 6 to 28 wherein the first dose of the CAR T cells and the second dose of the CAR T cells are administered to the patient during week 1 on Monday and Thursday.

30. The method of any one of clauses 1 to 29 wherein the first dose escalation sequence for the compound, or the pharmaceutically acceptable salt thereof, occurs during weeks 2 and 3.

31. The method of any one of clauses 1 to 30 wherein the second dose escalation sequence for the compound, or the pharmaceutically acceptable salt thereof, occurs during weeks 4 and 5.

32. The method of any one of clauses 2 to 31 wherein the third dose escalation sequence for the compound, or the pharmaceutically acceptable salt thereof, occurs during weeks 6 and 7.

33. The method of clause 30 wherein the compound, or the pharmaceutically acceptable salt thereof, is administered on three separate days and the three separate days are Monday and Thursday of week 2 and Monday of week 3.

34. The method of clause 31 wherein the compound, or the pharmaceutically acceptable salt thereof, is administered on three separate days and the three separate days are Monday and Thursday of week 4 and Monday of week 5.

35. The method of clause 32 wherein the compound, or the pharmaceutically acceptable salt thereof, is administered on three separate days and the three separate days are Monday and Thursday of week 6 and Monday of week 7.

36. The method of any one of clauses 1 to 35 wherein lymphocytes are depleted in the patient before administration of the CAR T cell composition to the patient.

37. The method of any one of clauses 1 to 36 further comprising administering platelets to the patient, administering packed red blood cells to the patient, administering cryoprecipitate to the patient, administering intravenous immunoglobulin to the patient, and/or providing antimicrobial therapy to the patient.

38. The method of any one of clauses 1 to 37 wherein, if no CRS or neurotoxicity is observed in the patient during the first dose escalation sequence, the method is advanced to the second dose escalation sequence.

39. The method of any one of clauses 2 to 38 wherein, if no CRS or neurotoxicity is observed in the patient during the second dose escalation sequence, the method is advanced to the third dose escalation sequence.

40. The method of any one of clauses 3 to 39 wherein, if no CRS or neurotoxicity is observed in the patient during the third dose escalation sequence, the method is advanced to the fourth dose escalation sequence.

41. The method of any one of clauses 4 to 40 wherein, if no CRS or neurotoxicity is observed in the patient during the fourth dose escalation sequence, the method is advanced to the fifth dose escalation sequence.

42. The method of any one of clauses 5 to 41 wherein, if no CRS or neurotoxicity is observed in the patient during the fifth dose escalation sequence, the method is advanced to the sixth dose escalation sequence.

43. The method of any one of clauses 1 to 42 wherein if fever without hypotension is observed in the patient and no neurotoxicity is observed in the patient during any one of the dose escalation sequences, all subsequent doses of the compound, or the pharmaceutically acceptable salt thereof, are administered to the patient at the dose escalation sequence level that caused the fever without hypotension.

44. The method of any one of clauses 1 to 43 wherein, if serious CRS or neurotoxicity occurs in the patient in any dose escalation sequence, all subsequent doses of the compound, or the pharmaceutically acceptable salt thereof, are administered to the patient at the dose escalation sequence level below the dose escalation sequence level that caused the serious CRS or neurotoxicity in the patient.

45. A method of treatment of a cancer, the method comprising
  i) administering to a patient at least one dose of a CAR T cell composition comprising CAR T cells wherein the CAR T cells comprise a CAR directed to a targeting moiety;
  ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in a first dose escalation sequence wherein, if serious CRS occurs in the first dose escalation sequence, the compound, or the pharmaceutically acceptable salt thereof, is administered using a lower dose escalation sequence wherein the first dose of the compound, or the pharmaceutically acceptable salt thereof, in the lower dose escalation sequence is lower than the first dose of the compound, or the pharmaceutically acceptable salt thereof, administered in the first dose escalation sequence.

46. The method of clause 45 wherein in the lower dose escalation sequence, the compound, or the pharmaceutically acceptable salt thereof, is administered at about 0.5 percent, about 5 percent, and about 50 percent of a full dose of the compound, or the pharmaceutically acceptable salt thereof, on three separate days.

47. The method of clause 46 wherein the full dose of the compound, or the pharmaceutically acceptable salt thereof, is about the full dose of the compound, or the pharmaceutically acceptable salt thereof, is about 10 µg/kg to about 50 µg/kg of the compound, or the pharmaceutically acceptable salt thereof.

48. The method of any one of clauses 46 to 47 wherein the full dose of the compound, or the pharmaceutically acceptable salt thereof, is about 25 µg/kg to about 35 µg/kg of the compound, or the pharmaceutically acceptable salt thereof.

49. The method of any one of clauses 46 to 48 wherein the full dose of the compound, or the pharmaceutically acceptable salt thereof, is about 30 µg/kg of the compound, or the pharmaceutically acceptable salt thereof.

50. The method of any one of clauses 1 to 49 wherein the ligand is selected from the group consisting of a folate, DUPA, an NK-1R ligand, a CAIX ligand, a ligand of gamma glutamyl transpeptidase, an NKG2D ligand, and a CCK2R ligand.

51. The method of any one of clauses 1 to 50 wherein the ligand is a folate.

52. The method of any one of clauses 1 to 50 wherein the ligand is an NK-1R ligand.

53. The method of any one of clauses 1 to 50 wherein the ligand is DUPA.

54. The method of any one of clauses 1 to 50 wherein the ligand is a CCK2R ligand.

55. The method of any one of clauses 1 to 50 wherein the ligand is a ligand of gamma glutamyl transpeptidase.

56. The method of any one of clauses 1 to 55 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

57. The method of any one of clauses 1 to 56 wherein the targeting moiety is FITC.

58. The method of any one of clauses 1 to 56 wherein the targeting moiety is DNP.

59. The method of any one of clauses 1 to 56 wherein the targeting moiety is TNP.

60. The method of any one of clauses 1 to 59 wherein the linker comprises polyethylene glycol (PEG), polyproline, a hydrophilic amino acid, a sugar, an unnatural peptidoglycan, a polyvinylpyrrolidone, pluronic F-127, or a combination thereof.

61. The method of any one of clauses 1 to 60 wherein the linker comprises PEG.

62. The method of any one of clauses 1 to 61 wherein the compound, or the pharmaceutically acceptable salt thereof, has the formula

B-L-T, wherein B represents the small molecule ligand, L represents the linker, and T represents the targeting moiety, and wherein L comprises a structure having the formula

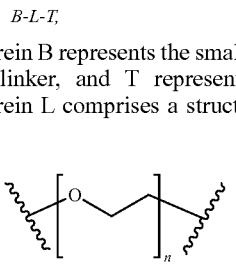

wherein n is an integer from 0 to 200.

63. The method of clause 62 wherein n is an integer from 0 to 150.

64. The method of clause 62 wherein n is an integer from 0 to 110.

65. The method of clause 62 wherein n is an integer from 0 to 20.

66. The method of clause 62 wherein n is an integer from 15 to 20.

67. The method of clause 62 wherein n is an integer from 15 to 110.

68. The method of any one of clauses 1 to 67 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, including pediatric or non-pediatric osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

69. The method of any one of clauses 1 to 51 or 56 to 68 wherein the cancer is a folate receptor expressing cancer.

70. The method of any one of clauses 1 to 69 wherein the cancer is an osteosarcoma.

71. The method of any one of clauses 1 to 70 wherein the CAR has a recognition region and the recognition region is a single chain fragment variable (scFv) region of an antibody.

72. The method of any one of clauses 1 to 57 or 60 to 71 wherein the CAR has a recognition region and the recognition region of the CAR is a single chain fragment variable (scFv) region of an anti-FITC antibody.

73. The method of any one of clauses 1 to 72 wherein the CAR has a co-stimulation domain and the co-stimulation domain is selected from the group consisting of CD28, CD137 (4-1BB), CD134 (OX40), and CD278 (ICOS).

74. The method of any one of clauses 1 to 73 wherein the CAR has an activation signaling domain and the activation signaling domain is a T cell CD3ζ chain or an Fc receptor γ.

75. The method of any one of clauses 1 to 57 or 60 to 74 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

76. The method of any one of clauses 1 to 75 wherein the patient is imaged prior to administration of the compound, or the pharmaceutically acceptable salt thereof, or prior to administration of the CAR T cell composition.

77. The method of any one of clauses 1 to 76 wherein the compound, or the pharmaceutically acceptable salt thereof, is not an antibody, and does not comprise a fragment of an antibody.

78. The method of any one of clauses 1 to 77 wherein the targeting moiety does not comprise a peptide epitope.

79. The method of any one of clauses 1 to 78 wherein cytokine release resulting in off-target toxicity in the patient does not occur and wherein CAR T cell toxicity to the cancer occurs.

80. The method of any one of clauses 1 to 78 wherein off-target tissue toxicity does not occur in the patient and wherein CAR T cell toxicity to the cancer occurs.

81. The method of any one of clauses 1 to 78 wherein the cancer comprises a tumor, wherein tumor size is reduced in the patient, and wherein off-target toxicity does not occur.

82. The method of any one of clauses 1 to 81 wherein the CAR T cells comprise a nucleic acid comprising SEQ ID NO:1.

83. The method of any one of clauses 1 to 82 wherein the CAR T cells comprise a polypeptide comprising SEQ ID NO:2.

84. The method of clause 82 wherein the nucleic acid encodes a chimeric antigen receptor.

85. The method of any one of clauses 1 to 81 wherein the CAR T cells comprise a nucleic acid comprising SEQ ID NO:4.

86. The method of any one of clauses 1 to 81 or 85 wherein the CAR T cells comprise a polypeptide comprising SEQ ID NO:5.

87. The method of clause 85 wherein the nucleic acid encodes a chimeric antigen receptor.

88. The method of any one of clauses 1 to 87 wherein the CAR comprises humanized amino acid sequences.

89. The method of any one of clauses 1 to 87 wherein the CAR consists of humanized amino acid sequences.

90. The method of any one of clauses 1 to 89 further comprising administering to the patient a folate, a conjugate comprising a folate wherein the conjugate comprising a folate does not comprise a targeting moiety, or an agent that inhibits activation of the CAR T cells.

91. The method of clause 90 wherein a folate is administered.

92. The method of clause 90 wherein folic acid or leucovorin is administered.

93. The method of clause 90 wherein the conjugate comprising a folate is administered.

94. The method of clause 93 wherein the conjugate comprising a folate comprises a folate linked to one or more amino acids.

95. The method of clause 93 wherein the conjugate comprising a folate has the formula

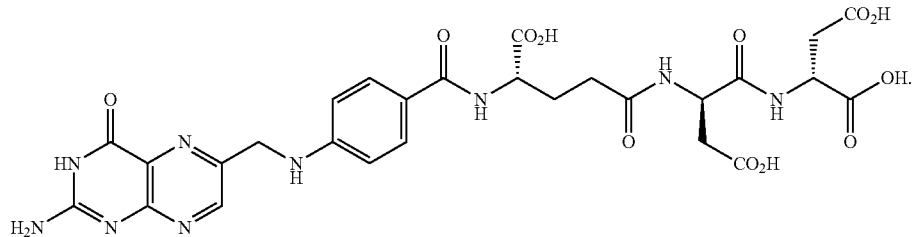 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

96. The method of clause 91 wherein the folate has the formula

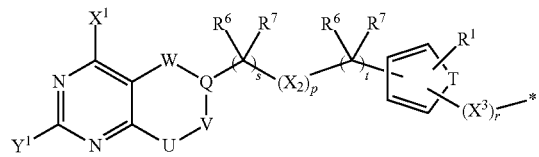

wherein $X^1$ and $Y^1$ are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyneoxy, where Z is oxygen or sulfur;

$R^1$ is selected from the group consisting of hydrogen, halo, $C_1$-$C_{12}$ alkyl, and $C_1$-$C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;

$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

97. The method of clause 90 wherein the agent that inhibits activation of the CAR T cells is selected from the group consisting of a lymphocyte-specific protein tyrosine kinase inhibitor, a PI3 kinase inhibitor, an inhibitor of an IL-2 inducible T cell kinase, a JAK inhibitor, a BTK inhibitor, EC2319, and an agent that blocks CAR T cell binding to the compound, or the pharmaceutically acceptable salt thereof, but does not bind to the cancer.

98. The method of clause 90 wherein the agent that inhibits activation of the CAR T cells is administered and the agent is a lymphocyte-specific protein tyrosine kinase inhibitor.

99. The method of clause 98 wherein the lymphocyte-specific protein tyrosine kinase inhibitor is Dasatinib.

100. The method of clause 90 wherein the agent that inhibits activation of the CAR T cells is administered and the agent is a PI3 kinase inhibitor.

101. The method of clause 100 wherein the PI3 kinase inhibitor is GDC0980.

102. The method of clause 90 wherein the agent that inhibits activation of the CAR T cells is administered and the agent is an IL-2 inducible T cell kinase inhibitor.

103. The method of clause 102 wherein the IL-2 inducible T cell kinase inhibitor is BMS-509744.

104. The method of clause 90 wherein the agent that inhibits activation of the CAR T cells is administered and is an agent that blocks CAR T cell binding to the compound, or the pharmaceutically acceptable salt thereof, but does not bind to the cancer.

105. The method of clause 104 wherein the agent is fluoresceinamine, FITC, or sodium fluorescein.

106. The method of clause 105 wherein the agent is sodium fluorescein.

107. The method of any one of clauses 90 to 106 wherein administration of the folate, the conjugate comprising a folate wherein the conjugate comprising a folate does not comprise a targeting moiety, or the agent that inhibits activation of the CAR T cells causes reduction in cytokine levels in the patient.

108. The method of clause 107 wherein the reduction in cytokine levels is a reduction to about the cytokine levels in an untreated patient.

109. The method of any one of clauses 90 to 108 wherein the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient.

110. The method of any one of clauses 104 to 106 wherein the agent that inhibits activation of the CAR T cells is administered to the patient when the CRS grade reaches 1, 2, 3, or 4.

111. The method of clause 110 wherein the agent that inhibits activation of the CAR T cells is administered to the patient when the CRS grade reaches 3 or 4.

112. The method of any one of clauses 104 to 106 wherein the agent that inhibits activation of the CAR T cells is administered at a dose of about 0.01 to about 300 umoles/kg of body weight of the patient.

113. The method of any one of clauses 1 to 112 wherein CRS is reduced or prevented in the patient and the method results in a decrease in tumor volume in the patient.

114. The method of any one of clauses 1 to 113 wherein body weight loss due to CRS is reduced or prevented.

115. The method of any one of clauses 90 to 114 further comprising re-administering the compound, or the pharmaceutically acceptable salt thereof, to the patient.

116. The method of clause 115 wherein the subsequent administration of the compound, or the pharmaceutically acceptable salt thereof, causes CAR T cell activation and an increase in cytokine levels in the patient.

117. The method of any one of clauses 1 to 116 wherein the CAR T cell composition is administered before the compound, or the pharmaceutically acceptable salt thereof.

118. The method of any one of clauses 1 to 117 wherein the CAR T cells are autologous.

119. The method of any one of clauses 2 to 17 wherein the first dose escalation sequence comprises administering to the patient about 1 percent, about 2 percent, and about 20 percent of a full dose of the compound, or the pharmaceutically acceptable salt thereof, on three separate days, wherein the second dose escalation sequence comprises administering to the patient about 1 percent, about 6 percent, and about 60 percent of a full dose of the compound, or the pharmaceutically acceptable salt thereof, on three separate days, and wherein the third dose escalation sequence comprises administering to the patient about 1 percent, about 10 percent, and about 100 percent of a full dose of the compound, or the pharmaceutically acceptable salt thereof, on three separate days.

120. The method of any one of clauses 2 to 17 wherein the first dose escalation sequence comprises administering to the patient about 1 percent, about 10 percent, and about 100 percent of a full dose of the compound, or the pharmaceutically acceptable salt thereof, on three separate days, and wherein the second dose escalation sequence comprises administering to the patient about 1 percent, about 20 percent, and about 200 percent of a full dose of the compound, or the pharmaceutically acceptable salt thereof, on three separate days.

121. The method of any one of clauses 2 to 17 wherein the first dose escalation sequence comprises administering to the patient about 1 percent, about 10 percent, and about 100 percent of a full dose of the compound, or the pharmaceutically acceptable salt thereof, on three separate days, and wherein the second dose escalation sequence comprises administering to the patient about 1 percent, about 10 percent, and about 100 percent of a full dose of the compound, or the pharmaceutically acceptable salt thereof, on three separate days.

122. The method of any one of clauses 2 to 17 wherein the first dose escalation sequence comprises administering to the patient about 1 percent, about 20 percent, and about 200 percent of a full dose of the compound, or the pharmaceutically acceptable salt thereof, on three separate days, and wherein the second dose escalation sequence comprises administering to the patient about 1 percent, about 20 percent, and about 200 percent of a full dose of the compound, or the pharmaceutically acceptable salt thereof, on three separate days.

123. The method of any one of clauses 119 to 122 wherein the full dose of the compound, or the pharmaceutically acceptable salt thereof, is about 500 nmoles/kg.

Figures 1, 2:
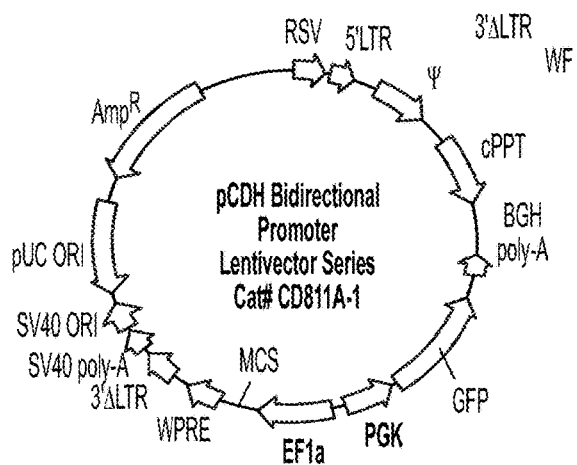
FIG. 1 shows a diagram of an exemplary dosing scheme according to the claimed method. In this exemplary scheme, E2 CAR T cell (CAR T cell expressing SEQ ID NO:4) administration occurs in week 1 on Monday and Thursday prior to administration of the small molecule ligand linked to the targeting moiety by a linker (e.g., EC17) beginning in week 2.

In week 2, the small molecule ligand linked to the targeting moiety by a linker (e.g., EC17) is administered on Monday and Thursday, and then in week 3 on Monday using a dose escalation sequence (i.e., Sequence 1). There is no administration of the small molecule ligand linked to the targeting moiety by a linker (e.g., EC17) during week 3 on Tuesday to Sunday. Weeks 2 to 3 are referred to as "Cycle 1".

In week 4, the small molecule ligand linked to the targeting moiety by a linker (e.g., EC17) is administered on Monday and Thursday, and then in week 5 on Monday using a dose escalation sequence (i.e., Sequence 2). There is no administration of the small molecule ligand linked to the targeting moiety by a linker (e.g., EC17) during week 5 on Tuesday to Sunday. Weeks 4 to 5 are referred to as "Cycle 2".

In week 6, the small molecule ligand linked to the targeting moiety by a linker (e.g., EC17) is administered on Monday and Thursday, and then in week 7 on Monday using a dose escalation sequence (i.e., Sequence 3). There is no administration of the small molecule ligand linked to the targeting moiety by a linker (e.g., EC17) during week 7 on Tuesday to Sunday. Weeks 6 to 7 are referred to as "Cycle 3". Weeks 2 to 7 are referred to as "Course 1".

During Sequence 1, the small molecule ligand linked to the targeting moiety by a linker (e.g., EC17) is administered in week 2 on Monday and Thursday, and then in week 3 on Monday with doses of the small molecule ligand linked to the targeting moiety by a linker (e.g., EC17) that are 1, 10, and 100 percent of a full dose (e.g., 31 µg/kg), respectively, of the small molecule ligand linked to the targeting moiety (e.g., EC17).

During Sequence 2, the small molecule ligand linked to the targeting moiety by a linker (e.g., EC17) is administered in week 4 on Monday and Thursday, and then in week 5 on Monday with doses of the small molecule ligand linked to the targeting moiety by a linker (e.g., EC17) that are 1, 30, and 300 percent of a full dose (e.g., 31 µg/kg), respectively, of the small molecule ligand linked to the targeting moiety (e.g., EC17).

During Sequence 3, the small molecule ligand linked to the targeting moiety by a linker (e.g., EC17) is administered in week 6 on Monday and Thursday, and then in week 7 on Monday with doses of the small molecule ligand linked to the targeting moiety by a linker (e.g., EC17) that are 1, 50, and 500 percent of a full dose (e.g., 31 µg/kg), respectively, of the small molecule ligand linked to the targeting moiety (e.g., EC17). Course 1 is then repeated assuming clinical benefit and tolerable toxicity.

FIG. 2 shows a general diagram of a construct used for CAR T transduction.

Figure 3:
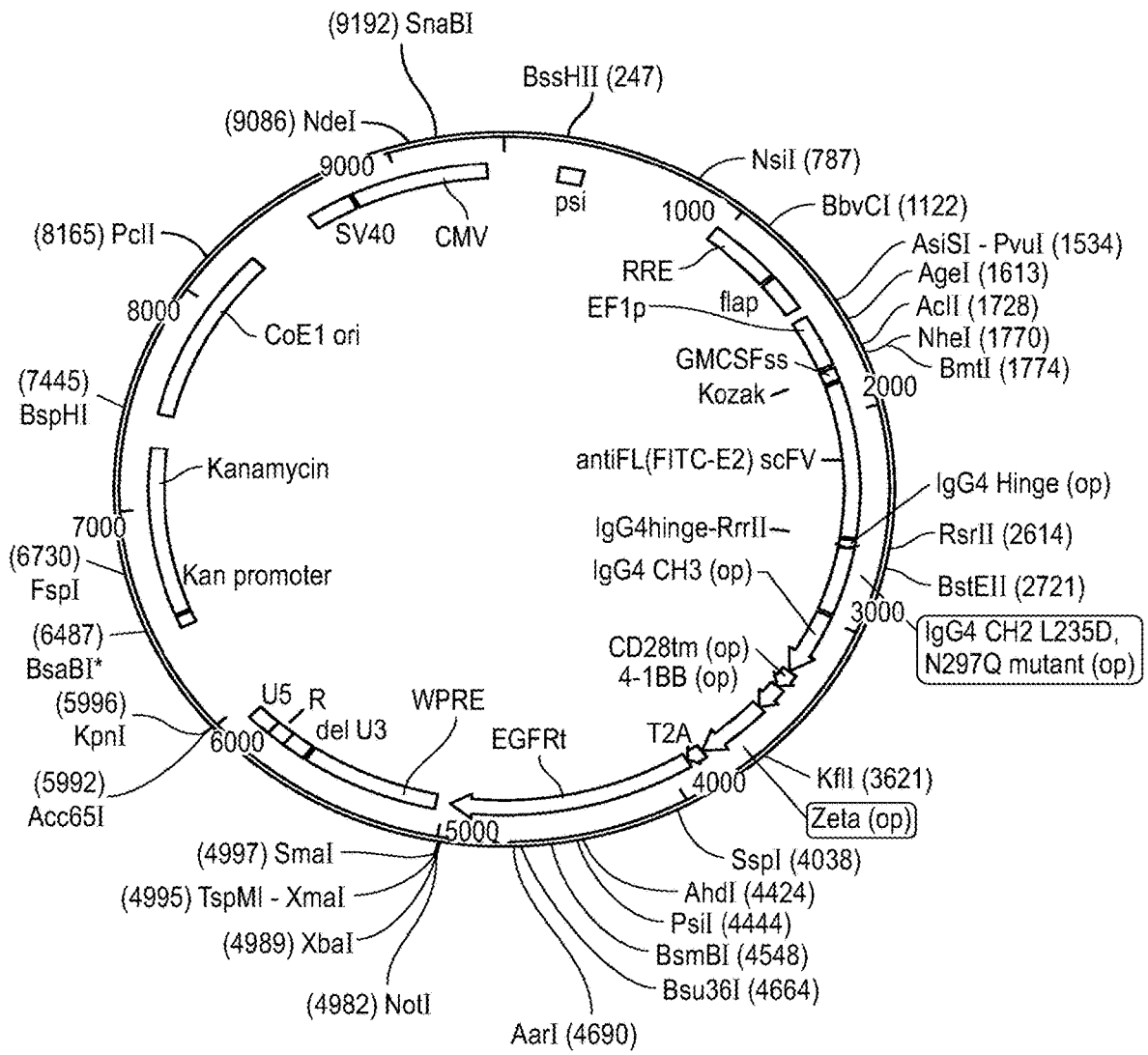

FIG. 3 shows an E2 construct vs. a 4M5.3 construct diagrammatically and shows a map of the E2 construct.

Figure 4:
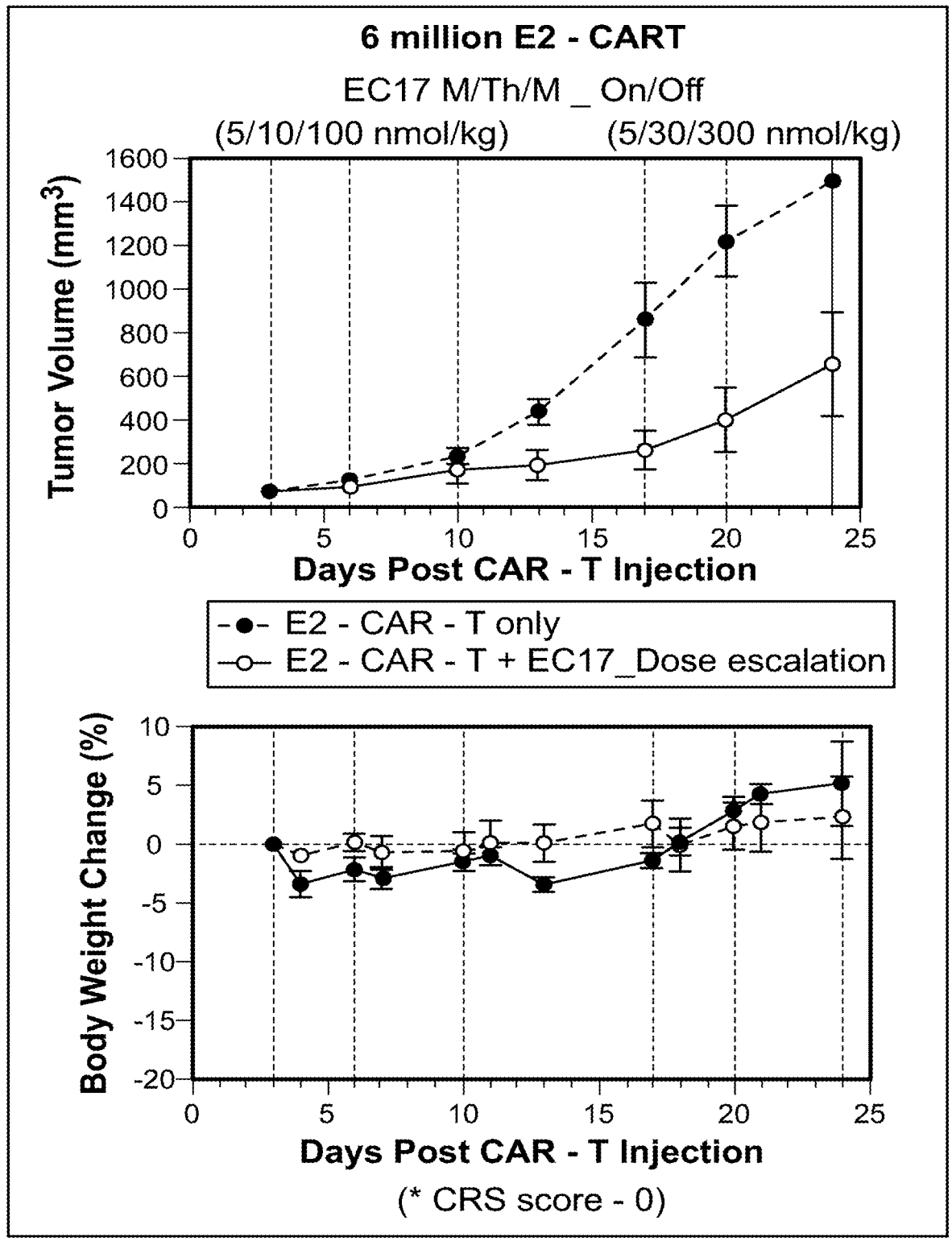

FIG. 4 (top panel) is a chart showing tumor volumes of HOS-FRα tumors when treated with E2 Car-T cells only (●) and E2 Car-T cells+EC-17 (○). FIG. 4 (bottom panel) is a chart showing the body weight change in mice bearing HOS-FRα tumors when treated with E2 Car-T cells only (●) and E2 Car-T cells+EC-17 (○).

Figure 5:
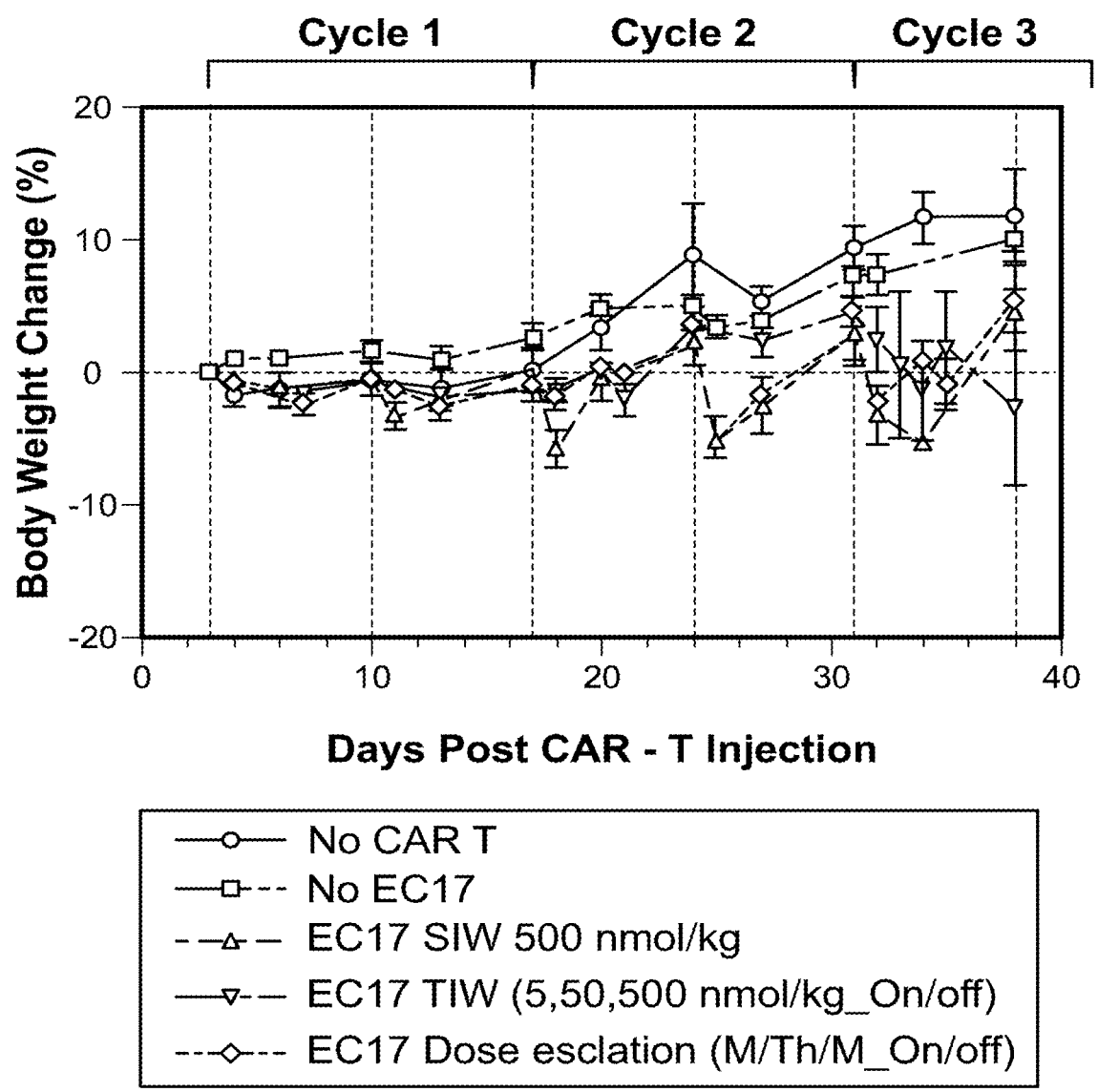

FIG. 5 is a chart showing the body weight change in mice bearing THP-1-FRβ AML when treated with no Car-T (●); no EC-17 (■); EC-17 SIW 500 nmol/kg (▲); EC-17 TIW (5, 50, 500 nmol/kg on/off); (♦) EC-17 dose escalation (M/Th/M on/off).

Figure 6:
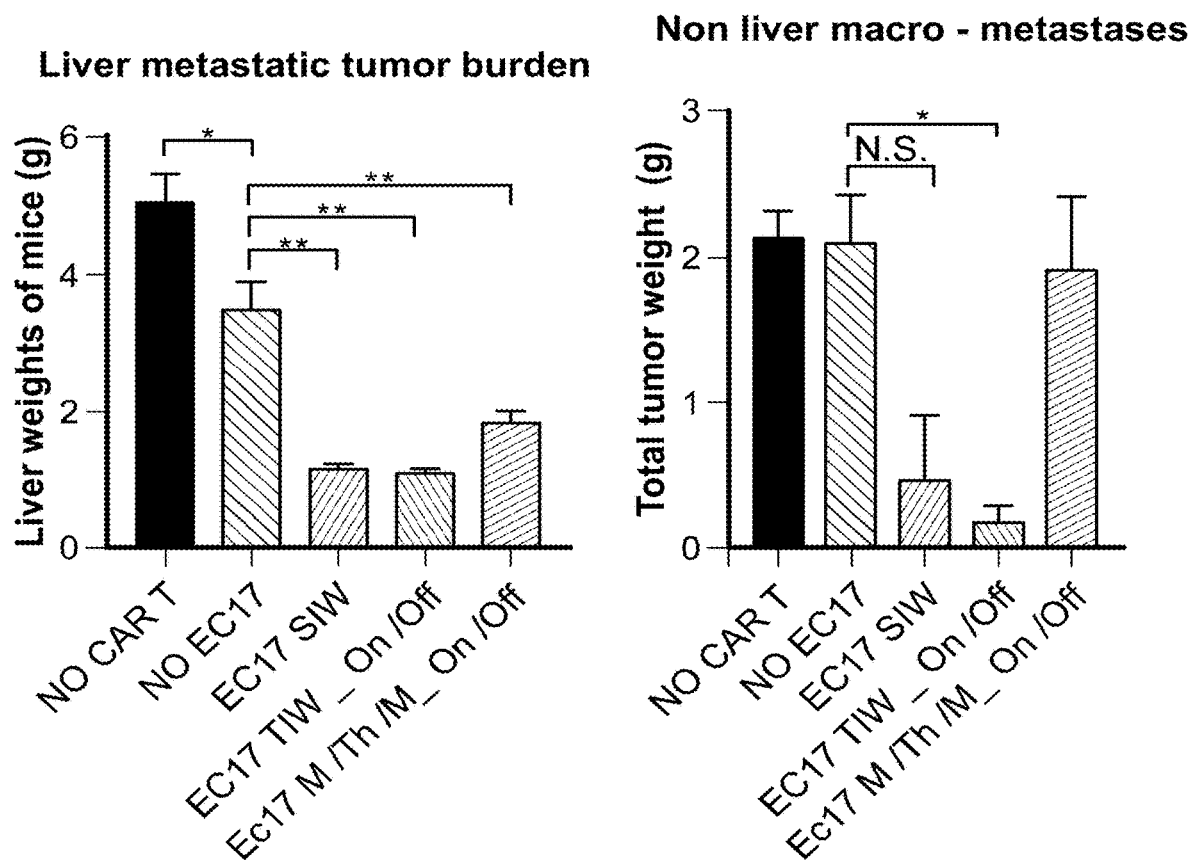

FIG. 6 (left panel) is a chart showing liver metastatic tumor burden. FIG. 6 (right panel) is a chart showing non-liver metastatic tumor burden.

Figure 7:
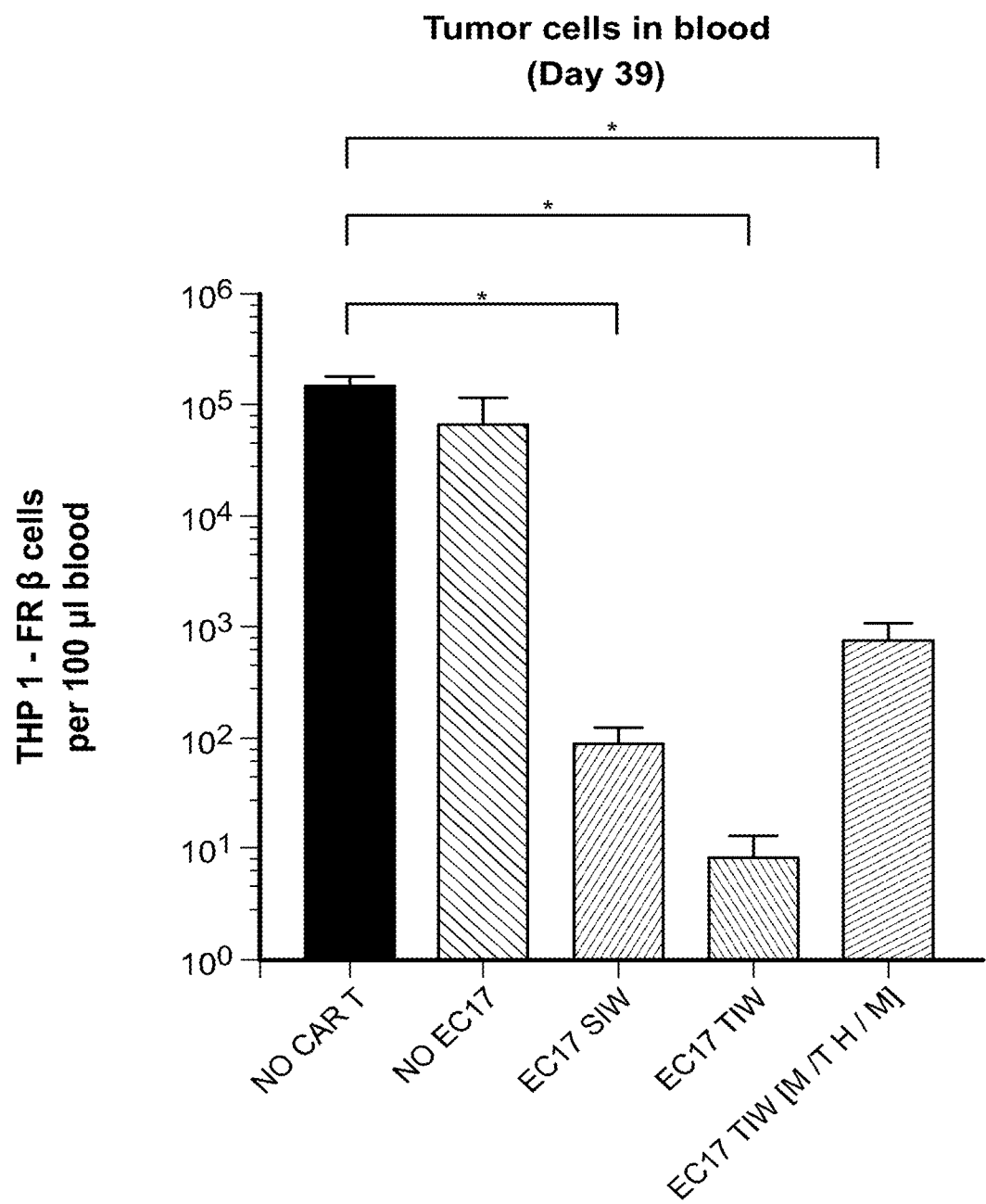

FIG. 7 is a chart showing counts of circulating THP1-FRβ cells per 100 µL blood at day 39 on a logarithmic scale.

Figure 8:
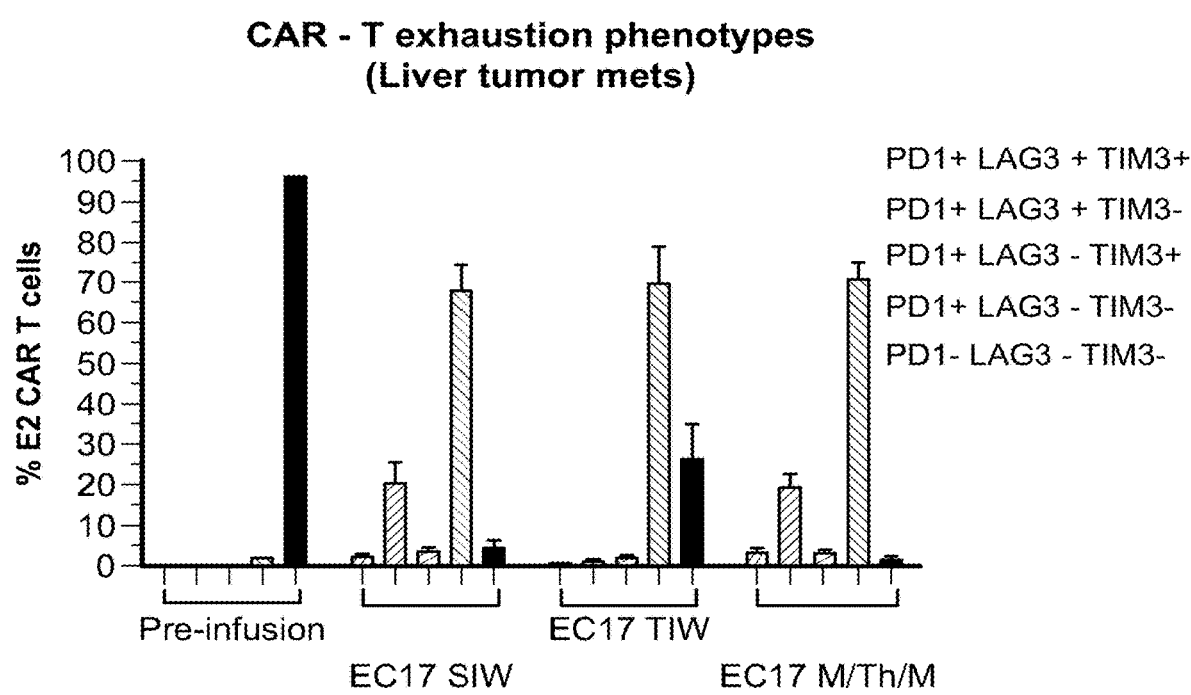

FIG. 8 is a chart showing percentage of the total E2 CAR T cells isolated from the solid liver tumors (y axis) at different EC-17 dosing regimens. For each dosing regimen, far left bar is PD1+ LAG3+ TIM3+, second left bar is PD1+ LAG3+ TIM3−, middle bar is PD1+ LAG3− TIM3+; second right bar is PD1+ LAG3− TIM3−; far right bar is PD1− LAG3− TIM3−.

Figure 9:
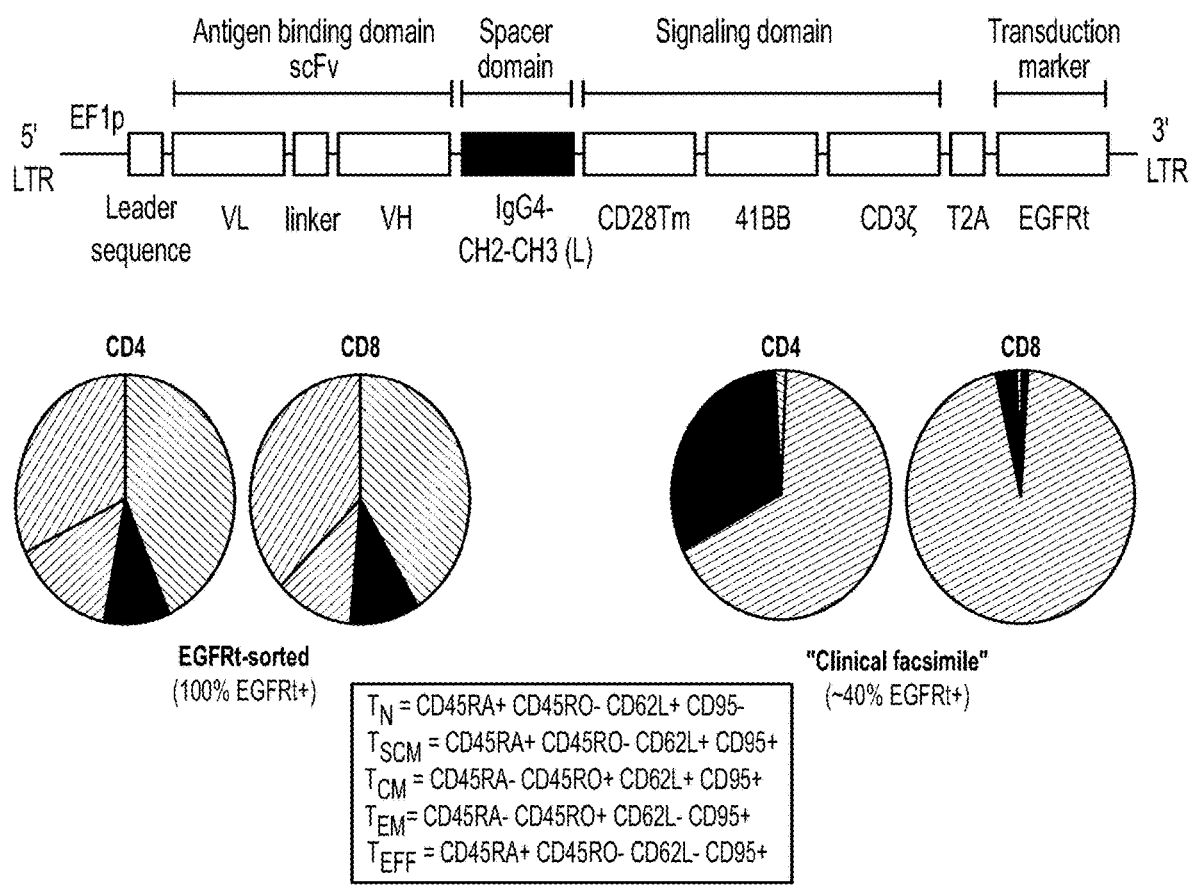

FIG. 9 shows a fully human CAR construct including anti-FITC scFv (clone E2), a full-length IgG4 spacer (Fc derived hinge-CH2(L235D, N297Q)-CH3), CD28tm transmembrane domain, 4-1BB/CD3ζ cytoplasmic activation domains, and a non-functional truncated cell surface polypeptide of epidermal growth factor receptor (EGFRt). Bottom: Examples of CD4/CD8 T cell phenotyping performed by flow cytometry on an EGFRt-sorted (left pie charts) CAR-T cell preparation and an unsorted "clinical facsimile" (right pie charts). The color keys are as shown.

Figure 10A:
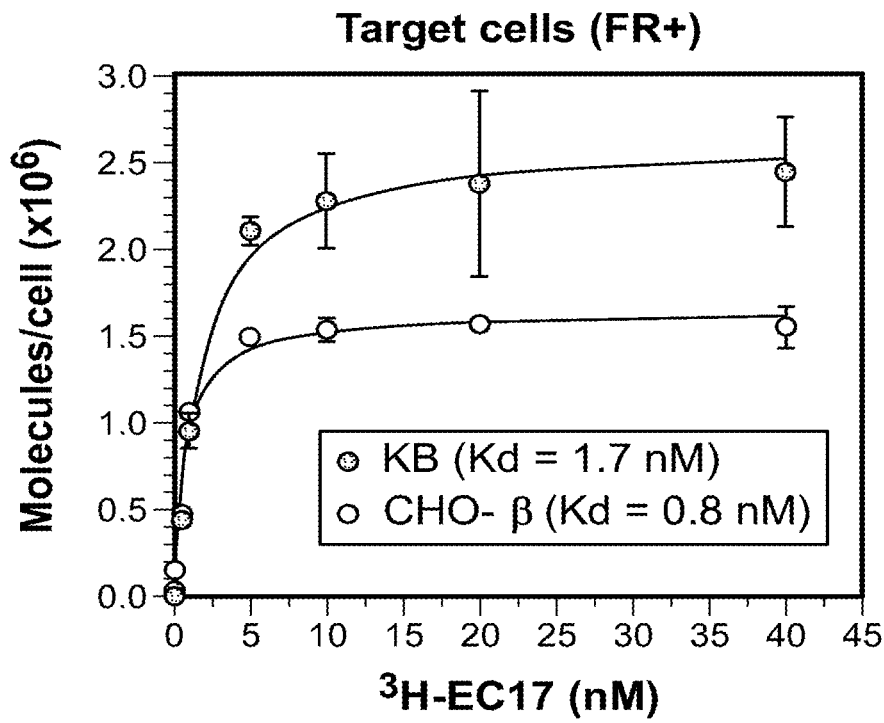
Figure 10B:
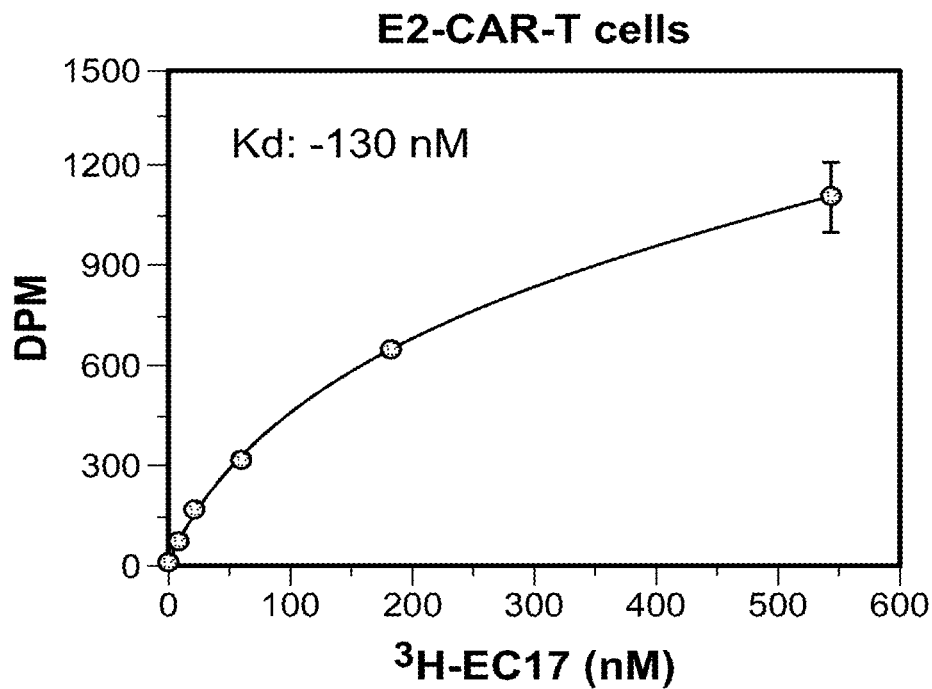

FIG. 10, Panel A: Kd values of $^3$H-EC17 uptake by FR+ target cells after a 2 hour incubation at 37° C. (calculated from the numbers of molecules bound per cell). Panel B: Kd value of $^3$H⁻EC17 uptake by E2-CAR-T cells (~24% EGFRt+, ~95:5 CD8/CD4 ratio) after a 2 hour incubation at room temperate (calculated from total cell-associated radioactivity, DPM).

Figure 11:
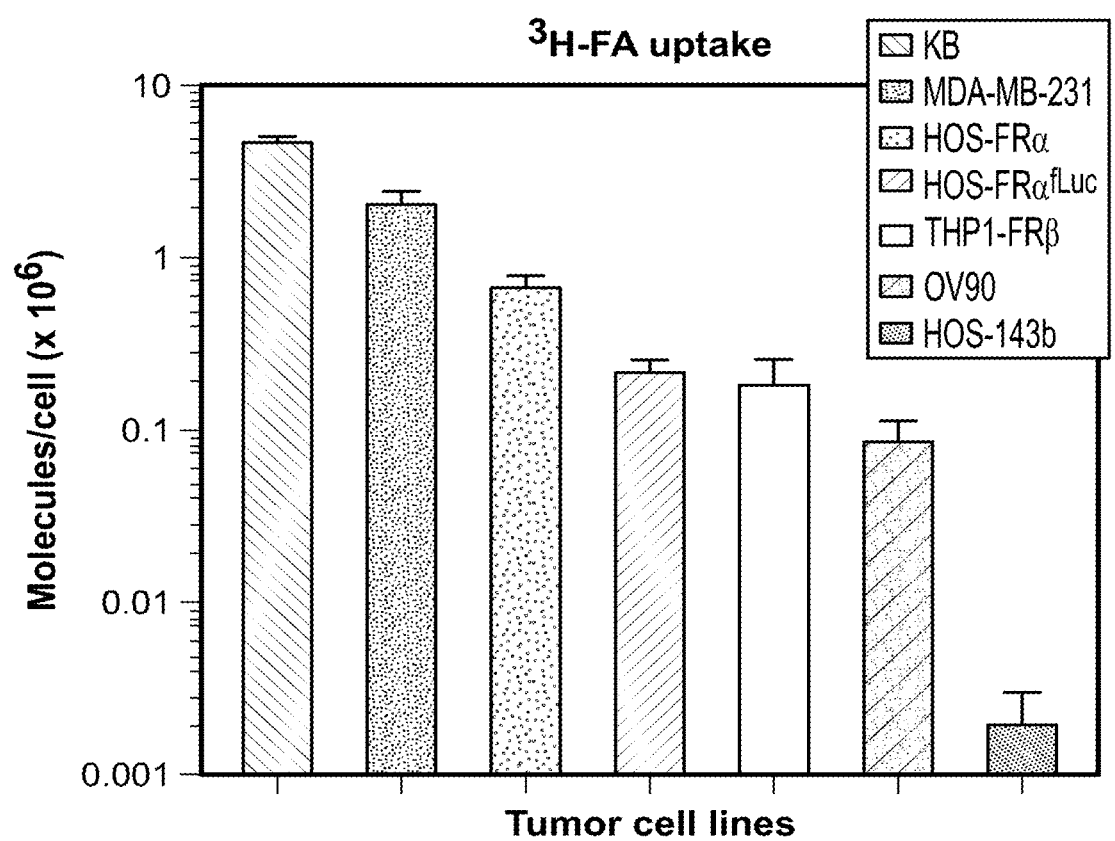
Figure 12A:
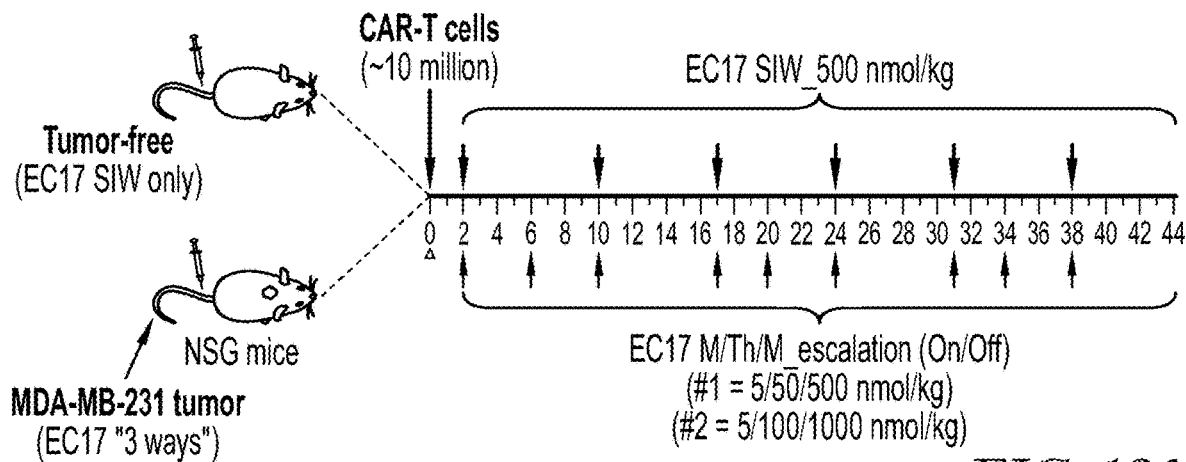
Figure 12B:
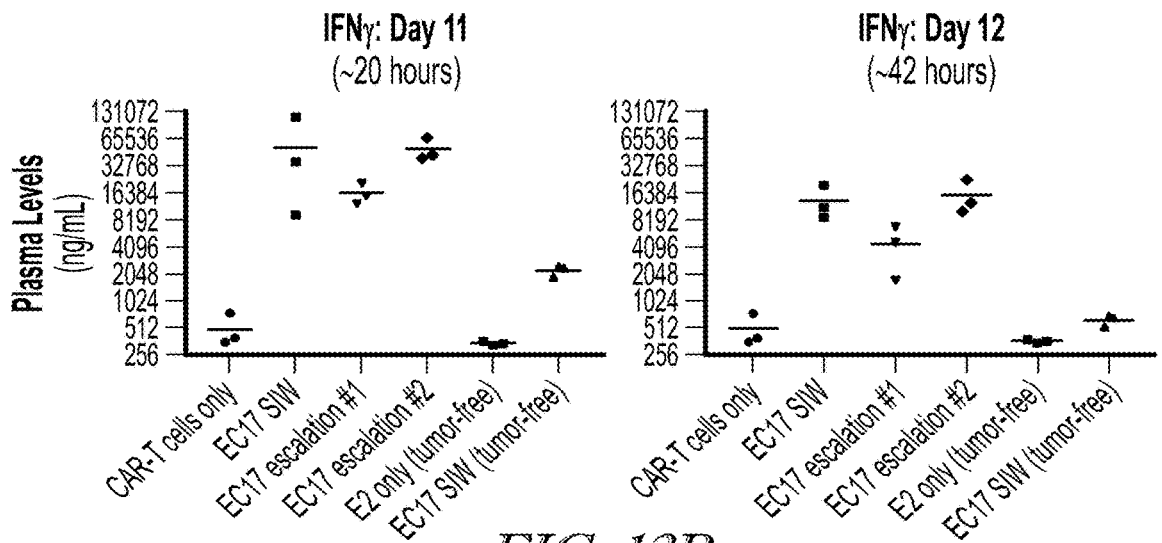
Figure 12C:
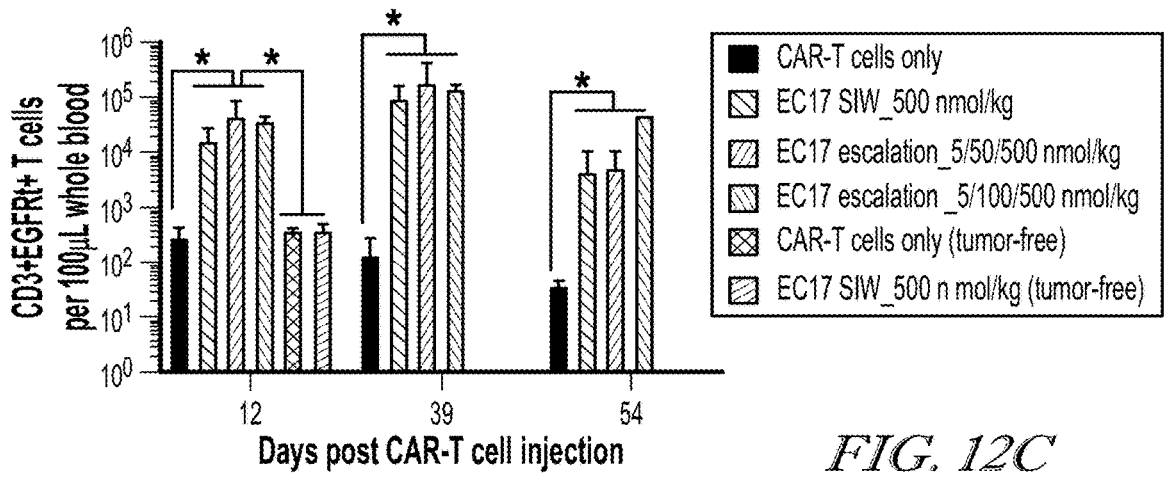
Figure 12D:
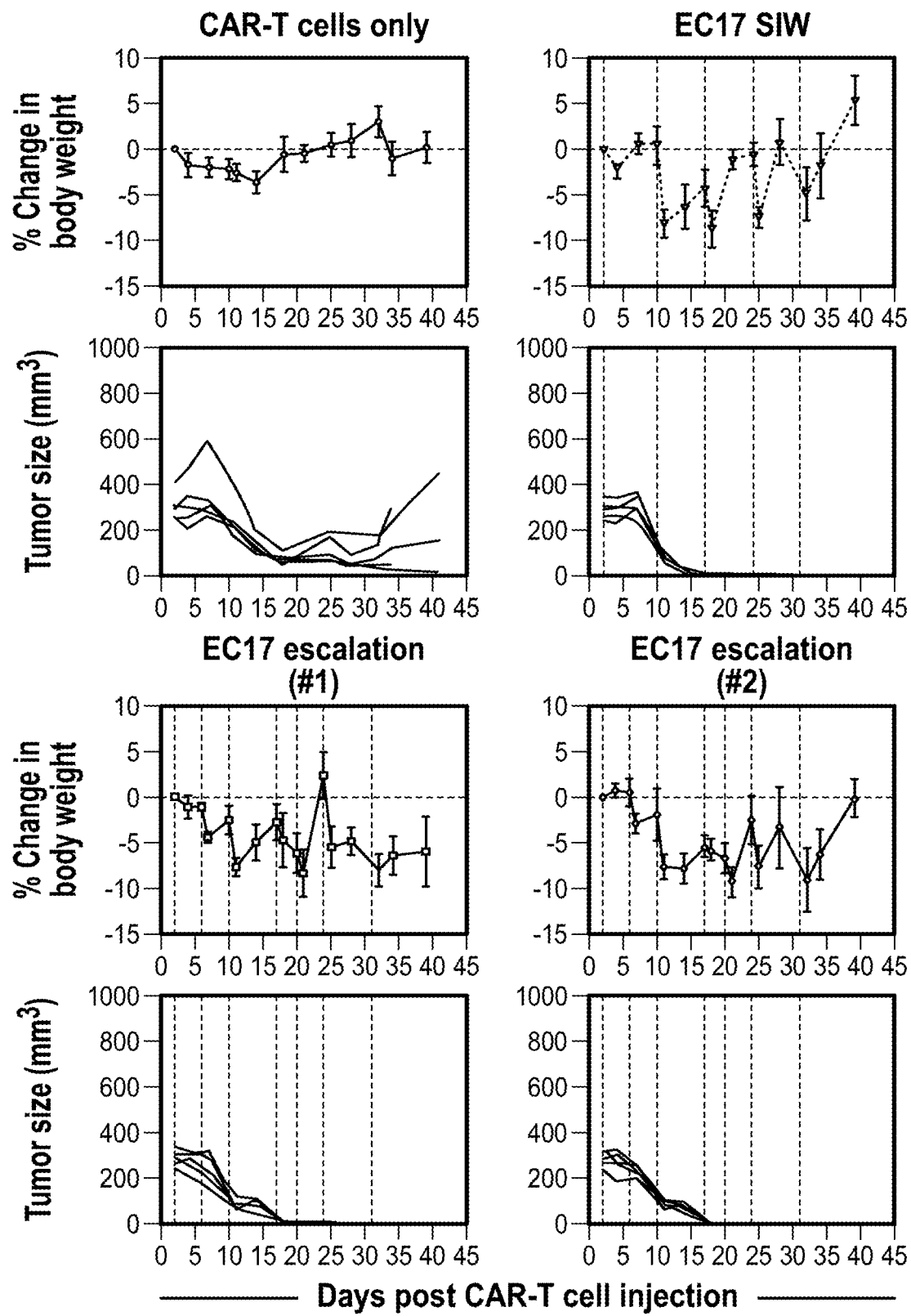
Figure 13A:
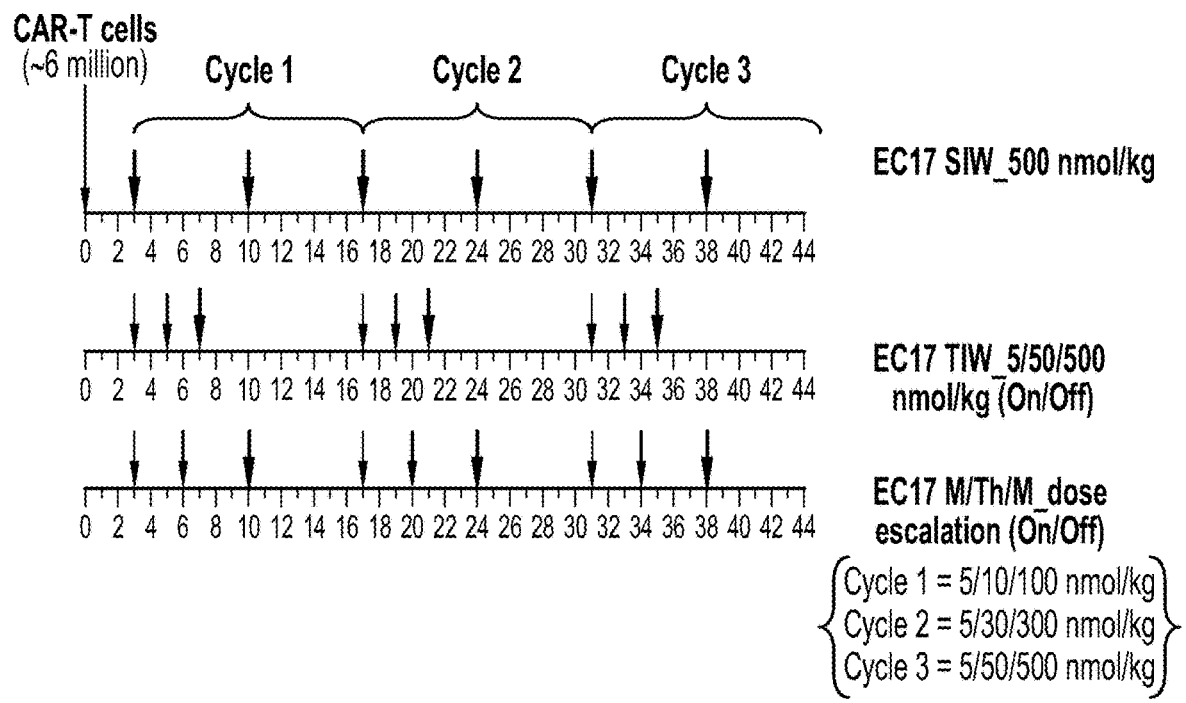
Figure 13B:
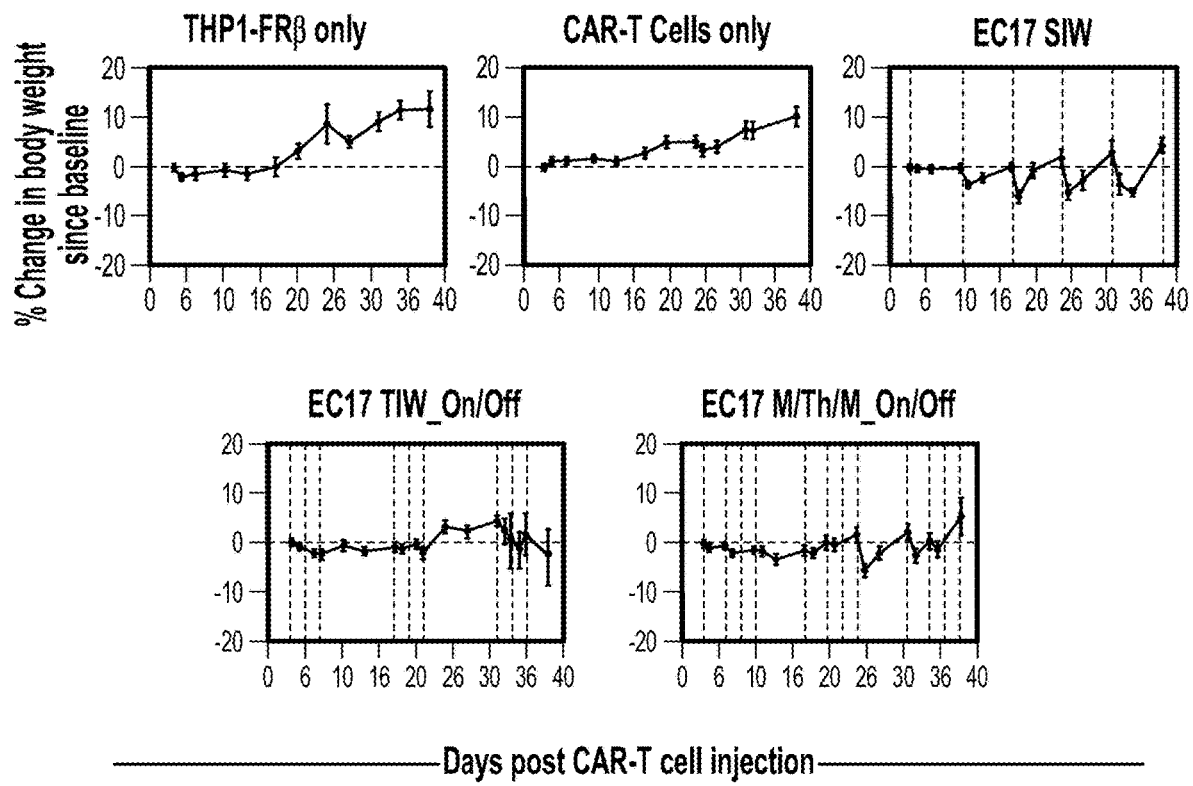
Figure 13C:
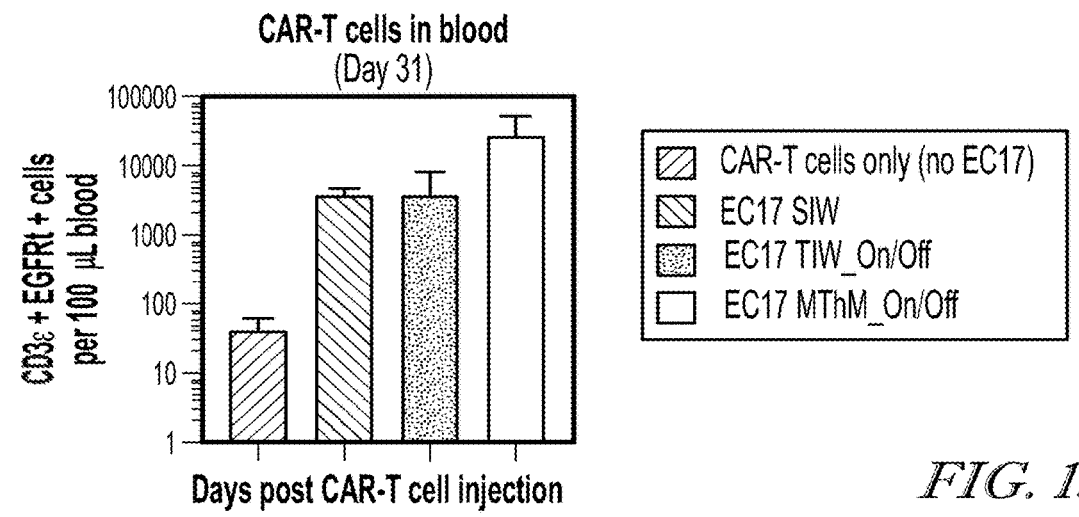
Figure 13D:
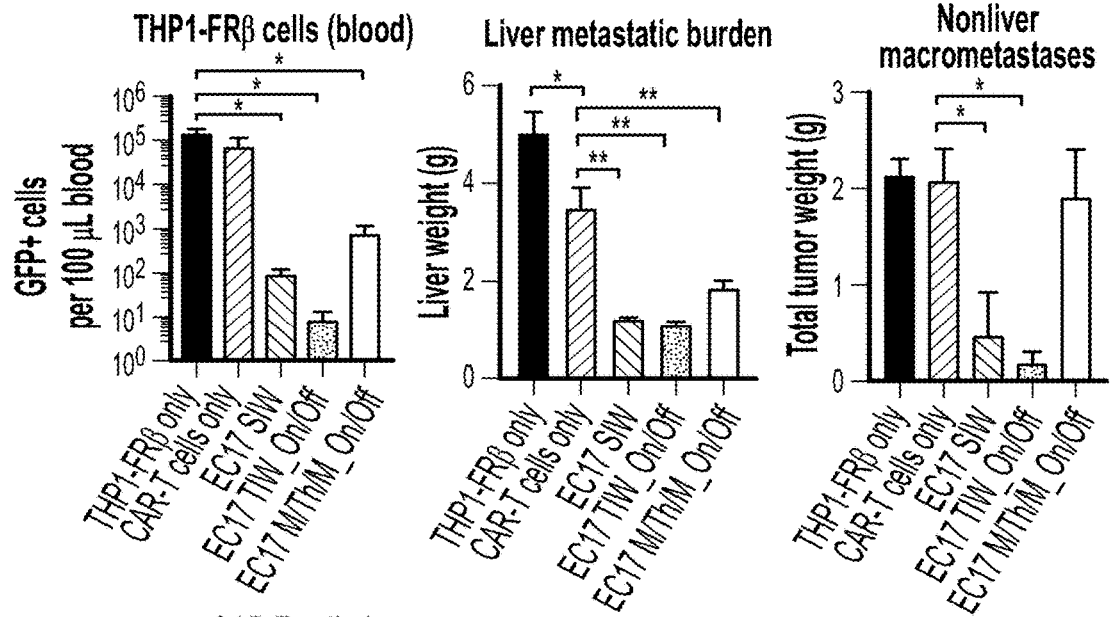
Figure 13E:
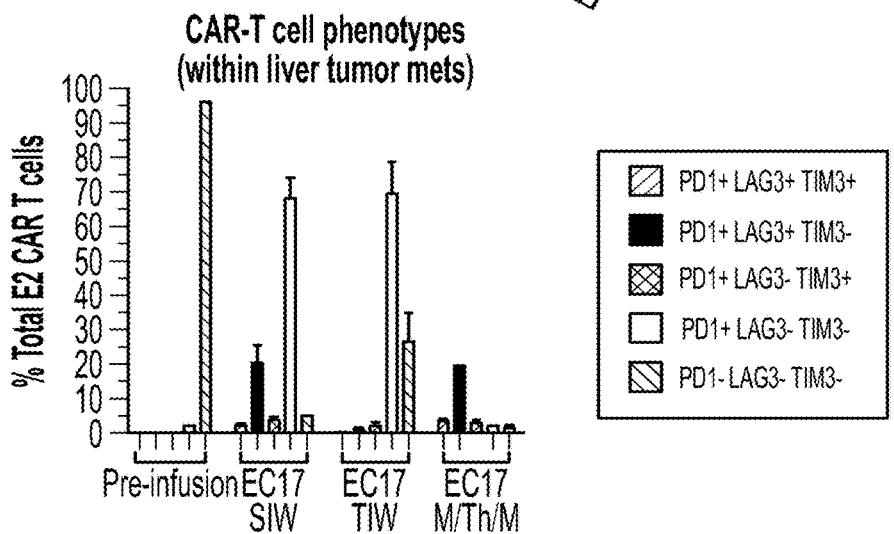

FIG. 11 shows functional FR levels on tumor cells measured by a $^3$H-FA-based binding assay (100 nM, 1 hour at 37° C.).

FIG. 12 shows EC17 dose finding and CRS assessment in tumor versus tumor-free mice. Panel A: Schematic diagram to show dose scheduling of CAR-T cells (~10 million "clinical facsimile") plus EC17 dosed 3 different ways in NSG mice without or with pre-established MDA-MB-231 xenografts. Tumor-free mice received EC17 SIW 500 nmol/kg (2 doses on days 2 and 10). Tumor-bearing mice received EC17 as follows: EC17 SIW 500 nmol/kg (5 doses on days 2, 10, 17, 24, and 31), EC17 M/Th/M_Escalation-1 (repeats of 5/50/500 nmol/kg on Monday/Thursday/Monday followed by 1-week break, i.e. on days 2, 6, 10, 17, 20, 24, and 31), or EC17 M/Th/M_Escalation-2 (repeats of 5/100/1000 nmol/kg on Monday/Thursday/Monday followed by 1-week break, i.e. days 2, 6, 10, 17, 20, 24, and 31). Panel B: Systemic levels of human IFNγ on a log 2 scale detected in mouse plasma on days 11 and 12 after CAR-T cell injection in tumor-bearing versus tumor-free mice (i.e., ~20 and 42 hours after the previous EC17 dose in all treated cohorts). Panel C: Circulating CAR-T cells in mouse blood identified as human CD3ε+ EGFRt+ events by flow cytometry and enumerated per 100 µL of whole blood. Panel D: Measurements of change in body weight and tumor volume in tumor-bearing mice that received CAR-T cells only or CAR-T cells plus EC17 dosed 3 different ways (dashed lines indicated each EC17 dose). n=5 mice per group. All data represent mean±s.e.m. * p<0.05 by one-way ANOVA test.

FIG. 13 shows EC17 dose escalation in safety and antileukemic activity in-vivo. Panel A: Schematic diagrams to show dose scheduling of EC17 plus unsorted EGFRt CAR-T cells (~6 million, day 0) in NSG mice with 1-day-old intravenous THP1-FRβ xenografts. Starting 3 days after CAR-T cell injection, EC17 was dosed in 3 different ways: EC17 SIW 500 nmol/kg (5 doses on days 3, 10, 17, 24, 31, and 38), EC17 TIW 5/50/500 nmol/kg (3 repeats of 5/50/500 nmol/kg on Monday/Wednesday/Friday followed by a 9-day break, i.e. on days 3/5/7, 17/19/21 and 31/33/35), or EC17 M/Th/M_dose escalation on Monday/Thursday/Monday (3 escalation cycles at 5/10/100 nmol/kg in Cycle 1, 5/30/300 nmol/kg in Cycle 2, and 5/50/500 nmol/kg in Cycle 3, i.e. on days 3/6/10, 17/20/24, and 31/34/38). Panel B: Measurements of change in body weight (n=5). Panel C: Circulating CAR-T cells as human CD3ε+ EGFRt+ events found per 100 µL of mouse whole blood on a logarithmic scale on day 31. Panel D: Left bar graph: circulating tumor cells (GFP+) per 100 µL of whole blood in all cohorts measured at the end of study (day 39); Middle bar graph: THP1-FRβ infiltrated liver weights representing liver metastatic burden; Right bar graph: total tumor weights of all non-liver macrometastases. Panel E: Flow cytometric analysis of T-cell exhaustion markers, PD1, LAG3, TIM3, on preinfusion CAR-T cell product (triple-negative) and tumor-infiltrating CAR-T cells isolated from liver metastases. A cardinal feature of fully exhausted T cells is co-expression of multiple inhibitory receptor markers (i.e. triple-positive).

Figure 14A:
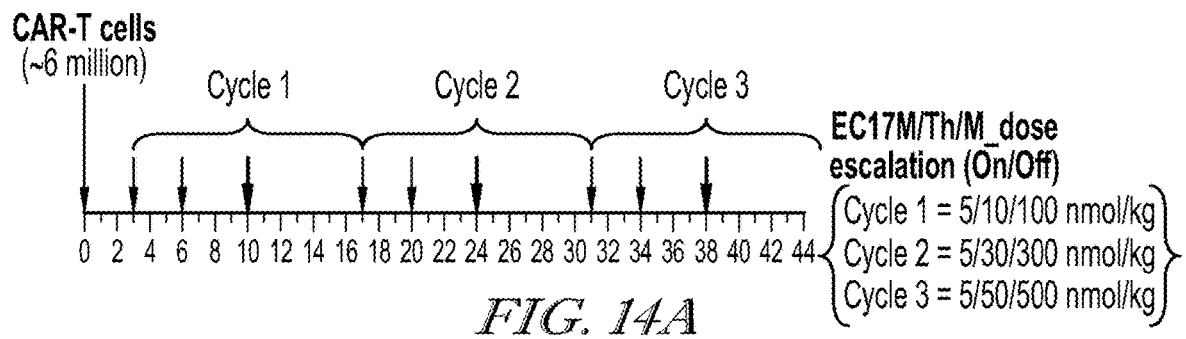
Figure 14B:
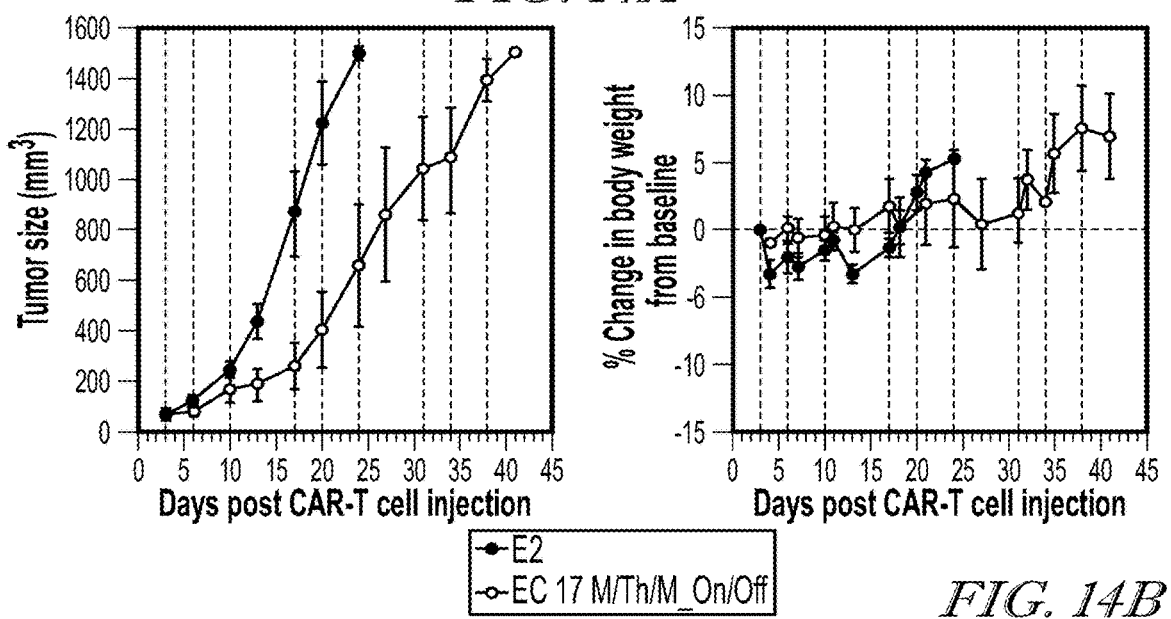
Figure 14C:
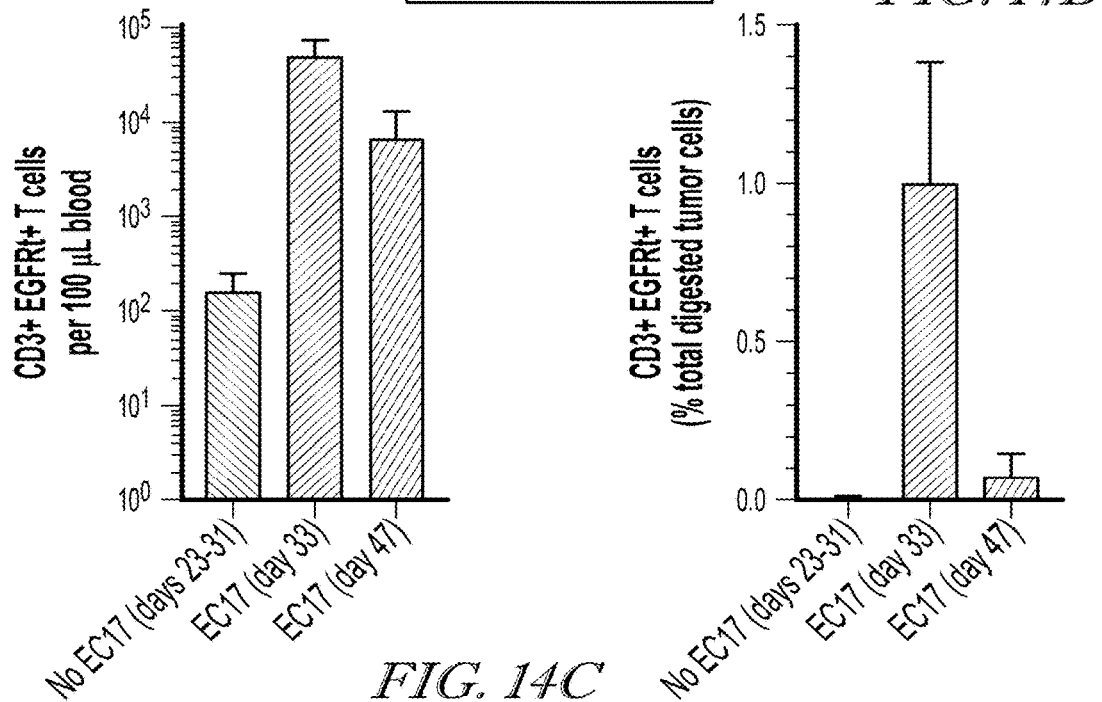

FIG. 14 shows antitumor activity and CRS rescue in an aggressive model of pediatric osteosarcoma. Panel A: Schematic diagram to show dose scheduling of CAR-T cells (~6 million, day 0) plus EC17 in NSG mice with 3-day-old subcutaneous HOS-FRα xenografts (n=5). Starting 3 days after CAR-T cell injection (6 days after tumor implant), 3 cycles of EC17 M/Th/M "intra-patient" dose escalation on Monday/Thursday/Monday at 5/10/100 nmol/kg in Cycle 1, 5/30/300 nmol/kg in Cycle 2, and 5/50/500 nmol/kg in Cycle 3, i.e. on days 3/6/10, 17/20/24, and 31/34/38. Panel B: Measurements of tumor volumes and change in body weights. Due to tumor progression, five mice received CAR-T cells only (no EC17) were euthanized on days 23-31, and five EC17 treated mice were euthanized on days 33 (2 mice) and 47 (3 mice), respectively. Panel C: Flow cytometric analysis of CAR-T cells (human CD3ε+EGFRT+) PER 100 µL OF WHOLE BLOOD PLOTTED ON A LOGARITHMIC SCALE (LEFT) AND TUMOR-infiltrating CAR-T cells at the time of euthanasia (right).

Figure 15:
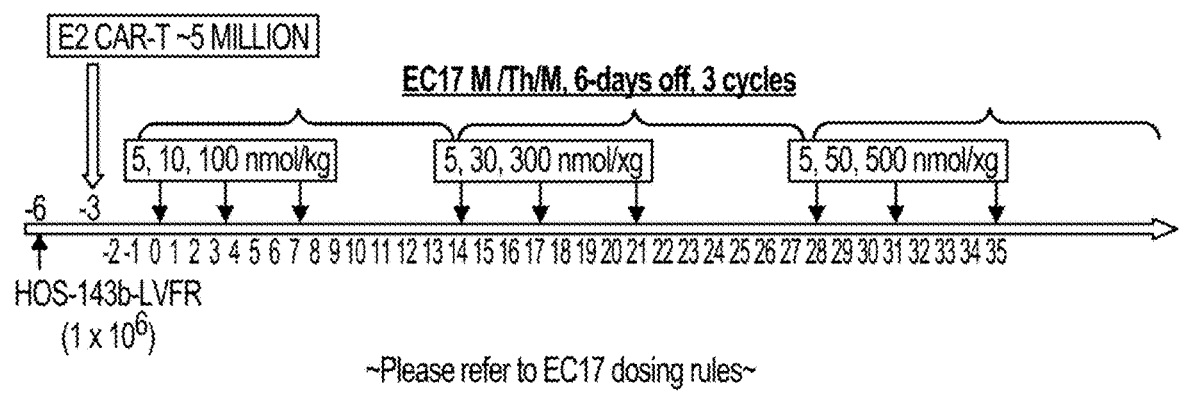

FIG. 15 shows a dose escalation regimen according to Example 18.

Figure 16:
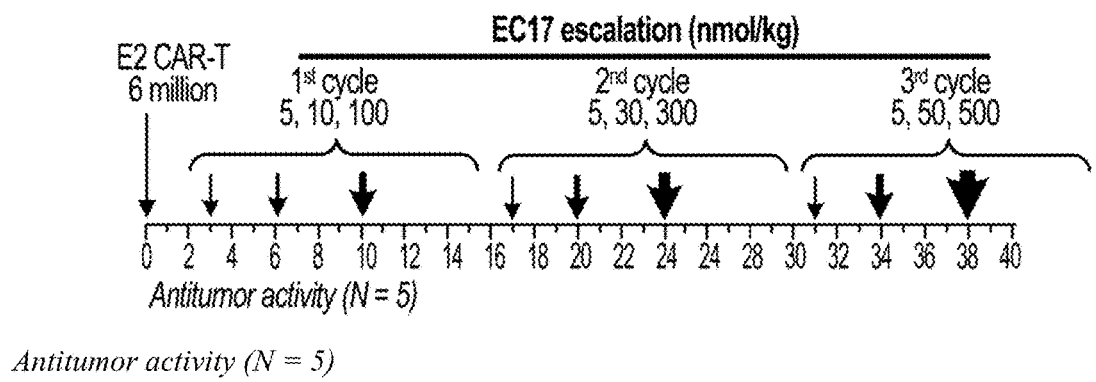

FIG. 16 shows an EC17 intra-host dose escalation treatment (3 cycles) according to Example 18.

FIGS. 17-20 are study schema for groups 2-5 according to Example 18.

FIGS. 21-26 show dosing schedules for Cohorts 3-5 according to Example 18.

DEFINITIONS

As used herein, "a" or "an" may mean one or more. As used herein, "about" in reference to a numeric value, including, for example, whole numbers, fractions, and percentages, generally refers to a range of numerical values (e.g., +/−5% to 10% of the recited value) that one of ordinary skill in the art would consider equivalent to the recited value (e.g., having the same function or result).

As used herein, the terms "treat," "treating," "treated," or "treatment" refer to both therapeutic treatment and prophylactic or preventative treatment.

As used herein, the terms "ameliorate," "ameliorating," "amelioration," or "ameliorated" in reference to cancer can mean reducing the symptoms of the cancer, reducing the size of a tumor, completely or partially removing the tumor (e.g., a complete or partial response), causing stable disease, preventing progression of the cancer (e.g., progression free survival), or any other effect on the cancer that would be considered by a physician to be a therapeutic, prophylactic, or preventative treatment of the cancer.

As used herein, the terms "administer," administering," or "administered" mean all means of introducing the compound, or pharmaceutically acceptable salt thereof, or CAR T cell composition described herein to the patient, including, but not limited to, oral, intravenous, intramuscular, subcutaneous, and transdermal.

As used herein, the term "off-target toxicity" means organ damage or a reduction in the patient's weight that is unacceptable to the physician treating the patient, or any other effect on the patient that is unacceptable to the physician treating the patient, for example, B cell aplasia, a fever, a drop in blood pressure, or pulmonary edema.

As used herein, the terms "transduction" and "transfection" are used equivalently and the terms mean introducing a nucleic acid into a cell by any artificial method, including viral and non-viral methods.

As used herein, the term "dose escalation sequence" means that increasing doses of the compound, or the pharmaceutically acceptable salt thereof, are administered over time. As used herein, references to "first dose escalation sequence" for use in combination with a "second dose escalation sequence", a "third dose escalation sequence", a "fourth dose escalation sequence", a "fifth dose escalation sequence", and a "sixth dose escalation sequence", etc. mean that multiple dose escalation sequences occur, and that for each separate dose escalation sequence, after the first dose escalation sequence, the first dose of the compound, or the pharmaceutically acceptable salt thereof, in the subsequent dose escalation sequence, is lower than the last dose of the compound, or the pharmaceutically acceptable salt thereof, in the prior dose escalation sequence (see, for example, FIG. 1 and the explanation of FIG. 1 in the Brief Description of the Drawings).

DETAILED DESCRIPTION OF THE ILLUSTRATIVE EMBODIMENTS

In the various embodiments described herein, a small molecule ligand linked to a targeting moiety by a linker is used as a bridge between a cancer and CAR T cells (i.e, T cells expressing a chimeric antigen receptor). The bridge directs the CAR T cells to the cancer for amelioration of the cancer. In one embodiment, the "small molecule ligand" can be a folate, a CAIX ligand, DUPA, an NK-1R ligand, a ligand of gamma glutamyl transpeptidase, an NKG2D ligand, or a CCK2R ligand, each of which is a small molecule ligand that binds specifically to a cancer cell type (i.e., the receptor for each of these ligands is overexpressed on cancers compared to normal tissues).

The "targeting moiety" linked to the small molecule ligand binds to the recognition region of the genetically engineered CAR expressed by the CAR T cells. Accordingly, the recognition region of the CAR (e.g., a single chain fragment variable region (scFv) of an antibody, an Fab, Fv, Fc, or (Fab')$_2$ fragment, and the like) is directed to the "targeting moiety." Thus, the small molecule ligand linked to a targeting moiety by a linker acts as a bridge between the cancer and the CAR T cells directing the CAR T cells to the cancer for amelioration of the cancer. In various embodiments, the bridge between the cancer and the CAR T cells can be any of the applicable conjugates shown in the Examples.

The bridge is a small organic molecule so clearance from the bloodstream can be rapidly achieved (e.g., about 20 minutes or less). In one aspect, the CAR T cell response can be targeted to only those cancer cells expressing a receptor for the small molecule ligand portion of the 'bridge,' thereby reducing off-target toxicity to normal tissues. Additionally, this system can be 'universal' because one type of CAR T cell construct can be used to target a wide variety of cancers using different 'bridges'. Illustratively, the targeting moiety recognized by the CAR T cells may remain constant so that one type of CAR T cell construct can be used, while the small molecule ligand that binds to the cancer can be altered to allow targeting of a wide variety of cancers.

In one embodiment, a method of treatment of a cancer is provided. The method comprises i) administering to a patient at least one dose of a CAR T cell composition comprising CAR T cells wherein the CAR T cells comprise a CAR directed to a targeting moiety; ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in at least a first dose escalation sequence and a second dose escalation sequence.

In another embodiment, a method of treatment of a cancer is provided. The method comprises i) administering to a patient at least one dose of a CAR T cell composition comprising CAR T cells wherein the CAR T cells comprise a CAR directed to a targeting moiety; ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in a first dose escalation sequence wherein, if serious CRS occurs in the first dose escalation sequence, the compound, or the pharmaceutically acceptable salt thereof, is administered using a lower dose escalation sequence wherein the first dose of the compound, or the pharmaceutically acceptable salt thereof, in the lower dose escalation sequence is lower than the first dose of the compound, or the pharmaceutically acceptable salt thereof, administered in the first dose escalation sequence. In another embodiment, in the lower dose escalation sequence, the compound, or the pharmaceutically acceptable salt thereof, can be administered at about 0.5 percent, about 5 percent, and about 50 percent of a full dose of the compound, or the pharmaceutically acceptable salt thereof, on three separate days.

In various embodiments described in the clause list below and in the claims and throughout the application, the small molecule ligand linked to a targeting moiety by a linker is referred to as a "compound." Several embodiments are described by the following enumerated clauses. Any of the following embodiments in combination with any applicable embodiments described in the Summary section of this patent application, in the Detailed Description of the Illustrative Embodiments section, the Examples section, or the claims of this patent application, are also contemplated.

1. A method of treatment of a cancer, the method comprising
   i) administering to a patient at least one dose of a CAR T cell composition comprising CAR T cells wherein the CAR T cells comprise a CAR directed to a targeting moiety;
   ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in at least a first dose escalation sequence and a second dose escalation sequence.

2. The method of clause 1 wherein the compound, or the pharmaceutically acceptable salt thereof, is administered in at least a first dose escalation sequence, a second dose escalation sequence, and a third dose escalation sequence.

3. The method of clause 1 wherein the compound, or the pharmaceutically acceptable salt thereof, is administered in at least a first dose escalation sequence, a second dose escalation sequence, a third dose escalation sequence, and a fourth dose escalation sequence.

4. The method of clause 1 wherein the compound, or the pharmaceutically acceptable salt thereof, is administered is administered in at least a first dose escalation sequence, a second dose escalation sequence, a third dose escalation sequence, a fourth dose escalation sequence, and a fifth dose escalation sequence.

5. The method of clause 1 wherein the compound, or the pharmaceutically acceptable salt thereof, is administered in at least a first dose escalation sequence, a second dose escalation sequence, a third dose escalation sequence, a fourth dose escalation sequence, a fifth dose escalation sequence, and a sixth dose escalation sequence.

6. The method of any one of clauses 1 to 5 wherein a first dose of the CAR T cells and a second dose of the CAR T cells are administered to the patient.

7. The method of clause 6 wherein the first dose of the CAR T cells is a test dose to monitor the patient for tolerability to the CAR T cells.

8. The method of clause 6 wherein the second dose of the CAR T cells comprises a higher dose of the CAR T cells than the first dose of the CAR T cells.

9. The method of any one of clauses 6 to 8 wherein the first dose of the CAR T cells comprises about $0.5 \times 10^5$ of the CAR T cells per kg of patient body weight to about $1.5 \times 10^6$ of the CAR T cells per kg of patient body weight.

10. The method of any one of clauses 6 to 9 wherein the second dose of the CAR T cells comprises about $0.8 \times 10^6$ of the CAR T cells per kg of patient body weight to about $2 \times 10^7$ of the CAR T cells per kg of patient body weight.

11. The method of any one of clauses 1 to 10 wherein the first dose escalation sequence is followed by a period of time during which the compound, or the pharmaceutically acceptable salt thereof, is not administered.

12. The method of any one of clauses 1 to 11 wherein the second dose escalation sequence is followed by a period of time during which the compound, or the pharmaceutically acceptable salt thereof, is not administered.

13. The method of any one of clauses 2 to 12 wherein the third dose escalation sequence is followed by a period of time during which the compound, or the pharmaceutically acceptable salt thereof, is not administered.

14. The method of any one of clauses 3 to 13 wherein the fourth dose escalation sequence is followed by a period of time during which the compound, or the pharmaceutically acceptable salt thereof, is not administered.

15. The method of any one of clauses 4 to 14 wherein the fifth dose escalation sequence is followed by a period of time during which the compound, or the pharmaceutically acceptable salt thereof, is not administered.

16. The method of any one of clauses 5 to 15 wherein the sixth dose escalation sequence is followed by a period of time during which the compound, or the pharmaceutically acceptable salt thereof, is not administered.

17. The method of any one of clauses 11 to 16 wherein the period of time is about 7 days.

18. The method of any one of clauses 1 to 17 wherein the first dose escalation sequence comprises administering to the patient about 1 percent, about 10 percent, and about 100 percent of a full dose of the compound, or the pharmaceutically acceptable salt thereof, on three separate days.

19. The method of any one of clauses 1 to 18 wherein the second dose escalation sequence comprises administering to the patient about 1 percent, about 30 percent, and about 300 percent of a full dose of the compound, or the pharmaceutically acceptable salt thereof, on three separate days.

20. The method of any one of clauses 2 to 19 wherein the third dose escalation sequence comprises administering to the patient about 1 percent, about 50 percent, and about 500 percent of a full dose of the compound, or the pharmaceutically acceptable salt thereof, on three separate days.

21. The method of any one of clauses 3 to 20 wherein the fourth dose escalation sequence comprises administering to the patient about 1 percent, about 10 percent, and about 100 percent of a full dose of the compound, or the pharmaceutically acceptable salt thereof, on three separate days.

22. The method of any one of clauses 4 to 21 wherein the fifth dose escalation sequence comprises administering to the patient about 1 percent, about 30 percent, and about 300 percent of a full dose of the compound, or the pharmaceutically acceptable salt thereof, on three separate days.

23. The method of any one of clauses 5 to 22 wherein the sixth dose escalation sequence comprises administering to the patient about 1 percent, about 50 percent, and about 500 percent of a full dose of the compound, or the pharmaceutically acceptable salt thereof, on three separate days.

24. The method of any one of clauses 18 to 23 wherein the full dose of the compound, or the pharmaceutically acceptable salt thereof, is about 10 µg/kg to about 50 µg/kg of the compound, or the pharmaceutically acceptable salt thereof.

25. The method of any one of clauses 18 to 24 wherein the full dose of the compound, or the pharmaceutically acceptable salt thereof, is about 20 µg/kg to about 40 µg/kg of the compound, or the pharmaceutically acceptable salt thereof.

26. The method of any one of clauses 18 to 25 wherein the full dose of the compound, or the pharmaceutically acceptable salt thereof, is about 25 µg/kg to about 35 µg/kg of the compound, or the pharmaceutically acceptable salt thereof.

27. The method of any one of clauses 18 to 26 wherein the full dose of the compound, or the pharmaceutically acceptable salt thereof, is about 30 μg/kg of the compound, or the pharmaceutically acceptable salt thereof.

28. The method of any one of clauses 6 to 27 wherein the first dose of the CAR T cells and the second dose of the CAR T cells are administered to the patient during week 1.

29. The method of any one of clauses 6 to 28 wherein the first dose of the CAR T cells and the second dose of the CAR T cells are administered to the patient during week 1 on Monday and Thursday.

30. The method of any one of clauses 1 to 29 wherein the first dose escalation sequence for the compound, or the pharmaceutically acceptable salt thereof, occurs during weeks 2 and 3.

31. The method of any one of clauses 1 to 30 wherein the second dose escalation sequence for the compound, or the pharmaceutically acceptable salt thereof, occurs during weeks 4 and 5.

32. The method of any one of clauses 2 to 31 wherein the third dose escalation sequence for the compound, or the pharmaceutically acceptable salt thereof, occurs during weeks 6 and 7.

33. The method of clause 30 wherein the compound, or the pharmaceutically acceptable salt thereof, is administered on three separate days and the three separate days are Monday and Thursday of week 2 and Monday of week 3.

34. The method of clause 31 wherein the compound, or the pharmaceutically acceptable salt thereof, is administered on three separate days and the three separate days are Monday and Thursday of week 4 and Monday of week 5.

35. The method of clause 32 wherein the compound, or the pharmaceutically acceptable salt thereof, is administered on three separate days and the three separate days are Monday and Thursday of week 6 and Monday of week 7.

36. The method of any one of clauses 1 to 35 wherein lymphocytes are depleted in the patient before administration of the CAR T cell composition to the patient.

37. The method of any one of clauses 1 to 36 further comprising administering platelets to the patient, administering packed red blood cells to the patient, administering cryoprecipitate to the patient, administering intravenous immunoglobulin to the patient, and/or providing antimicrobial therapy to the patient.

38. The method of any one of clauses 1 to 37 wherein, if no CRS or neurotoxicity is observed in the patient during the first dose escalation sequence, the method is advanced to the second dose escalation sequence.

39. The method of any one of clauses 2 to 38 wherein, if no CRS or neurotoxicity is observed in the patient during the second dose escalation sequence, the method is advanced to the third dose escalation sequence.

40. The method of any one of clauses 3 to 39 wherein, if no CRS or neurotoxicity is observed in the patient during the third dose escalation sequence, the method is advanced to the fourth dose escalation sequence.

41. The method of any one of clauses 4 to 40 wherein, if no CRS or neurotoxicity is observed in the patient during the fourth dose escalation sequence, the method is advanced to the fifth dose escalation sequence.

42. The method of any one of clauses 5 to 41 wherein, if no CRS or neurotoxicity is observed in the patient during the fifth dose escalation sequence, the method is advanced to the sixth dose escalation sequence.

43. The method of any one of clauses 1 to 42 wherein if fever without hypotension is observed in the patient and no neurotoxicity is observed in the patient during any one of the dose escalation sequences, all subsequent doses of the compound, or the pharmaceutically acceptable salt thereof, are administered to the patient at the dose escalation sequence level that caused the fever without hypotension.

44. The method of any one of clauses 1 to 43 wherein, if serious CRS or neurotoxicity occurs in the patient in any dose escalation sequence, all subsequent doses of the compound, or the pharmaceutically acceptable salt thereof, are administered to the patient at the dose escalation sequence level below the dose escalation sequence level that caused the serious CRS or neurotoxicity in the patient.

45. A method of treatment of a cancer, the method comprising
  i) administering to a patient at least one dose of a CAR T cell composition comprising CAR T cells wherein the CAR T cells comprise a CAR directed to a targeting moiety;
  ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in a first dose escalation sequence wherein, if serious CRS occurs in the first dose escalation sequence, the compound, or the pharmaceutically acceptable salt thereof, is administered using a lower dose escalation sequence wherein the first dose of the compound, or the pharmaceutically acceptable salt thereof, in the lower dose escalation sequence is lower than the first dose of the compound, or the pharmaceutically acceptable salt thereof, administered in the first dose escalation sequence.

46. The method of clause 45 wherein in the lower dose escalation sequence, the compound, or the pharmaceutically acceptable salt thereof, is administered at about 0.5 percent, about 5 percent, and about 50 percent of a full dose of the compound, or the pharmaceutically acceptable salt thereof, on three separate days.

47. The method of clause 46 wherein the full dose of the compound, or the pharmaceutically acceptable salt thereof, is about the full dose of the compound, or the pharmaceutically acceptable salt thereof, is about 10 μg/kg to about 50 μg/kg of the compound, or the pharmaceutically acceptable salt thereof.

48. The method of any one of clauses 46 to 47 wherein the full dose of the compound, or the pharmaceutically acceptable salt thereof, is about 25 μg/kg to about 35 μg/kg of the compound, or the pharmaceutically acceptable salt thereof.

49. The method of any one of clauses 46 to 48 wherein the full dose of the compound, or the pharmaceutically acceptable salt thereof, is about 30 μg/kg of the compound, or the pharmaceutically acceptable salt thereof.

50. The method of any one of clauses 1 to 49 wherein the ligand is selected from the group consisting of a folate, DUPA, an NK-1R ligand, a CAIX ligand, a ligand of gamma glutamyl transpeptidase, an NKG2D ligand, and a CCK2R ligand.

51. The method of any one of clauses 1 to 50 wherein the ligand is a folate.

52. The method of any one of clauses 1 to 50 wherein the ligand is an NK-1R ligand.

53. The method of any one of clauses 1 to 50 wherein the ligand is DUPA.

54. The method of any one of clauses 1 to 50 wherein the ligand is a CCK2R ligand.

55. The method of any one of clauses 1 to 50 wherein the ligand is a ligand of gamma glutamyl transpeptidase.

56. The method of any one of clauses 1 to 55 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

57. The method of any one of clauses 1 to 56 wherein the targeting moiety is FITC.

58. The method of any one of clauses 1 to 56 wherein the targeting moiety is DNP.

59. The method of any one of clauses 1 to 56 wherein the targeting moiety is TNP.

60. The method of any one of clauses 1 to 59 wherein the linker comprises polyethylene glycol (PEG), polyproline, a hydrophilic amino acid, a sugar, an unnatural peptidoglycan, a polyvinylpyrrolidone, pluronic F-127, or a combination thereof.

61. The method of any one of clauses 1 to 60 wherein the linker comprises PEG.

62. The method of any one of clauses 1 to 61 wherein the compound, or the pharmaceutically acceptable salt thereof, has the formula

B-L-T, wherein B represents the small molecule ligand, L represents the linker, and T represents the targeting moiety, and wherein L comprises a structure having the formula

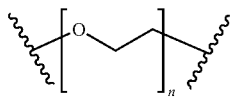

wherein n is an integer from 0 to 200.

63. The method of clause 62 wherein n is an integer from 0 to 150.

64. The method of clause 62 wherein n is an integer from 0 to 110.

65. The method of clause 62 wherein n is an integer from 0 to 20.

66. The method of clause 62 wherein n is an integer from 15 to 20.

67. The method of clause 62 wherein n is an integer from 15 to 110.

68. The method of any one of clauses 1 to 67 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, including pediatric or non-pediatric osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

69. The method of any one of clauses 1 to 51 or 56 to 68 wherein the cancer is a folate receptor expressing cancer.

70. The method of any one of clauses 1 to 69 wherein the cancer is an osteosarcoma.

71. The method of any one of clauses 1 to 70 wherein the CAR has a recognition region and the recognition region is a single chain fragment variable (scFv) region of an antibody.

72. The method of any one of clauses 1 to 57 or 60 to 71 wherein the CAR has a recognition region and the recognition region of the CAR is a single chain fragment variable (scFv) region of an anti-FITC antibody.

73. The method of any one of clauses 1 to 72 wherein the CAR has a co-stimulation domain and the co-stimulation domain is selected from the group consisting of CD28, CD137 (4-1BB), CD134 (OX40), and CD278 (ICOS).

74. The method of any one of clauses 1 to 73 wherein the CAR has an activation signaling domain and the activation signaling domain is a T cell CD3ζ chain or an Fc receptor γ.

75. The method of any one of clauses 1 to 57 or 60 to 74 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

76. The method of any one of clauses 1 to 75 wherein the patient is imaged prior to administration of the compound, or the pharmaceutically acceptable salt thereof, or prior to administration of the CAR T cell composition.

77. The method of any one of clauses 1 to 76 wherein the compound, or the pharmaceutically acceptable salt thereof, is not an antibody, and does not comprise a fragment of an antibody.

78. The method of any one of clauses 1 to 77 wherein the targeting moiety does not comprise a peptide epitope.

79. The method of any one of clauses 1 to 78 wherein cytokine release resulting in off-target toxicity in the patient does not occur and wherein CAR T cell toxicity to the cancer occurs.

80. The method of any one of clauses 1 to 78 wherein off-target tissue toxicity does not occur in the patient and wherein CAR T cell toxicity to the cancer occurs.

81. The method of any one of clauses 1 to 78 wherein the cancer comprises a tumor, wherein tumor size is reduced in the patient, and wherein off-target toxicity does not occur.

82. The method of any one of clauses 1 to 81 wherein the CAR T cells comprise a nucleic acid comprising SEQ ID NO:1.

83. The method of any one of clauses 1 to 82 wherein the CAR T cells comprise a polypeptide comprising SEQ ID NO:2.

84. The method of clause 82 wherein the nucleic acid encodes a chimeric antigen receptor.

85. The method of any one of clauses 1 to 81 wherein the CAR T cells comprise a nucleic acid comprising SEQ ID NO:4.

86. The method of any one of clauses 1 to 81 or 85 wherein the CAR T cells comprise a polypeptide comprising SEQ ID NO:5.

87. The method of clause 85 wherein the nucleic acid encodes a chimeric antigen receptor.

88. The method of any one of clauses 1 to 87 wherein the CAR comprises humanized amino acid sequences.

89. The method of any one of clauses 1 to 87 wherein the CAR consists of humanized amino acid sequences.

90. The method of any one of clauses 1 to 89 further comprising administering to the patient a folate, a conjugate comprising a folate wherein the conjugate comprising a folate does not comprise a targeting moiety, or an agent that inhibits activation of the CAR T cells.

91. The method of clause 90 wherein a folate is administered.

92. The method of clause 90 wherein folic acid or leucovorin is administered.

93. The method of clause 90 wherein the conjugate comprising a folate is administered.

94. The method of clause 93 wherein the conjugate comprising a folate comprises a folate linked to one or more amino acids.

95. The method of clause 93 wherein the conjugate comprising a folate has the formula

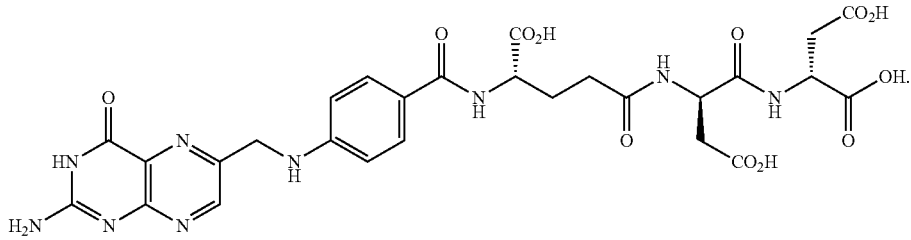 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

96. The method of clause 91 wherein the folate has the formula

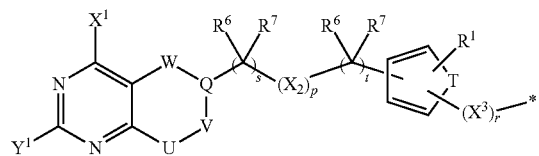

wherein $X^1$ and $Y^1$ are each-independently selected from the group consisting of halo, $R^2$, $OR^2$, $SR^3$, and $NR^4R^5$;

U, V, and W represent divalent moieties each independently selected from the group consisting of —($R^{6a}$)C═, —N═, —($R^{6a}$)C($R^{7a}$)—, and —N($R^{4a}$)—; Q is selected from the group consisting of C and CH; T is selected from the group consisting of S, O, N, and —C═C—;

$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyleneoxy, where Z is oxygen or sulfur;

$R^1$ is selected from the group consisting of hydrogen, halo, $C_1$-$C_{12}$ alkyl, and $C_1$-$C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;

$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

97. The method of clause 90 wherein the agent that inhibits activation of the CAR T cells is selected from the group consisting of a lymphocyte-specific protein tyrosine kinase inhibitor, a PI3 kinase inhibitor, an inhibitor of an IL-2 inducible T cell kinase, a JAK inhibitor, a BTK inhibitor, EC2319, and an agent that blocks CAR T cell binding to the compound, or the pharmaceutically acceptable salt thereof, but does not bind to the cancer.

98. The method of clause 90 wherein the agent that inhibits activation of the CAR T cells is administered and the agent is a lymphocyte-specific protein tyrosine kinase inhibitor.

99. The method of clause 98 wherein the lymphocyte-specific protein tyrosine kinase inhibitor is Dasatinib.

100. The method of clause 90 wherein the agent that inhibits activation of the CAR T cells is administered and the agent is a PI3 kinase inhibitor.

101. The method of clause 100 wherein the PI3 kinase inhibitor is GDC0980.

102. The method of clause 90 wherein the agent that inhibits activation of the CAR T cells is administered and the agent is an IL-2 inducible T cell kinase inhibitor.

103. The method of clause 102 wherein the IL-2 inducible T cell kinase inhibitor is BMS-509744.

104. The method of clause 90 wherein the agent that inhibits activation of the CAR T cells is administered and is an agent that blocks CAR T cell binding to the compound, or the pharmaceutically acceptable salt thereof, but does not bind to the cancer.

105. The method of clause 104 wherein the agent is fluoresceinamine, FITC, or sodium fluorescein.

106. The method of clause 105 wherein the agent is sodium fluorescein.

107. The method of any one of clauses 90 to 106 wherein administration of the folate, the conjugate comprising a folate wherein the conjugate comprising a folate does not comprise a targeting moiety, or the agent that inhibits activation of the CAR T cells causes reduction in cytokine levels in the patient.

108. The method of clause 107 wherein the reduction in cytokine levels is a reduction to about the cytokine levels in an untreated patient.

109. The method of any one of clauses 90 to 108 wherein the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient.

110. The method of any one of clauses 104 to 106 wherein the agent that inhibits activation of the CAR T cells is administered to the patient when the CRS grade reaches 1, 2, 3, or 4.

111. The method of clause 110 wherein the agent that inhibits activation of the CAR T cells is administered to the patient when the CRS grade reaches 3 or 4.

112. The method of any one of clauses 104 to 106 wherein the agent that inhibits activation of the CAR T cells is administered at a dose of about 0.01 to about 300 umoles/kg of body weight of the patient.

113. The method of any one of clauses 1 to 112 wherein CRS is reduced or prevented in the patient and the method results in a decrease in tumor volume in the patient.

114. The method of any one of clauses 1 to 113 wherein body weight loss due to CRS is reduced or prevented.

115. The method of any one of clauses 90 to 114 further comprising re-administering the compound, or the pharmaceutically acceptable salt thereof, to the patient.

116. The method of clause 115 wherein the subsequent administration of the compound, or the pharmaceutically acceptable salt thereof, causes CAR T cell activation and an increase in cytokine levels in the patient.

117. The method of any one of clauses 1 to 116 wherein the CAR T cell composition is administered before the compound, or the pharmaceutically acceptable salt thereof.

118. The method of any one of clauses 1 to 117 wherein the CAR T cells are autologous.

119. The method of any one of clauses 2 to 17 wherein the first dose escalation sequence comprises administering to the patient about 1 percent, about 2 percent, and about 20 percent of a full dose of the compound, or the pharmaceutically acceptable salt thereof, on three separate days, wherein the second dose escalation sequence comprises administering to the patient about 1 percent, about 6 percent, and about 60 percent of a full dose of the compound, or the pharmaceutically acceptable salt thereof, on three separate days, and wherein the third dose escalation sequence comprises administering to the patient about 1 percent, about 10 percent, and about 100 percent of a full dose of the compound, or the pharmaceutically acceptable salt thereof, on three separate days.

120. The method of any one of clauses 2 to 17 wherein the first dose escalation sequence comprises administering to the patient about 1 percent, about 10 percent, and about 100 percent of a full dose of the compound, or the pharmaceutically acceptable salt thereof, on three separate days, and wherein the second dose escalation sequence comprises administering to the patient about 1 percent, about 20 percent, and about 200 percent of a full dose of the compound, or the pharmaceutically acceptable salt thereof, on three separate days.

121. The method of any one of clauses 2 to 17 wherein the first dose escalation sequence comprises administering to the patient about 1 percent, about 10 percent, and about 100 percent of a full dose of the compound, or the pharmaceutically acceptable salt thereof, on three separate days, and wherein the second dose escalation sequence comprises administering to the patient about 1 percent, about 10 percent, and about 100 percent of a full dose of the compound, or the pharmaceutically acceptable salt thereof, on three separate days.

122. The method of any one of clauses 2 to 17 wherein the first dose escalation sequence comprises administering to the patient about 1 percent, about 20 percent, and about 200 percent of a full dose of the compound, or the pharmaceutically acceptable salt thereof, on three separate days, and wherein the second dose escalation sequence comprises administering to the patient about 1 percent, about 20 percent, and about 200 percent of a full dose of the compound, or the pharmaceutically acceptable salt thereof, on three separate days.

123. The method of any one of clauses 119 to 122 wherein the full dose of the compound, or the pharmaceutically acceptable salt thereof, is about 500 nmoles/kg.

Accordingly, various embodiments are provided in the preceding paragraphs and in the clause list above, and all applicable embodiments described in this "Detailed Description of Illustrative Embodiments," the "Summary" section, the Examples, and the claims apply to the these embodiments.

As described herein, a "patient" can be a human or, in the case of veterinary applications, the patient can be a laboratory, an agricultural, a domestic, or a wild animal. In various aspects, the patient can be a laboratory animal such as a rodent (e.g., mouse, rat, hamster, etc.), a rabbit, a monkey, a chimpanzee, a domestic animal such as a dog, a cat, or a rabbit, an agricultural animal such as a cow, a horse, a pig, a sheep, a goat, or a wild animal in captivity such as a bear, a panda, a lion, a tiger, a leopard, an elephant, a zebra, a giraffe, a gorilla, a dolphin, or a whale.

In various embodiments, the cancer to be treated can be selected from a carcinoma, a sarcoma, a lymphoma, a melanoma, a mesothelioma, a nasopharyngeal carcinoma, a leukemia, an adenocarcinoma, or a myeloma. In other embodiments, the cancer may be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, including pediatric or non-pediatric osteosarcoma, cancer of the urethra, prostate cancer, chronic leukemia, acute leukemia, including acute myelocytic leukemia, a lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, a neoplasm of the central nervous system (CNS), primary CNS lymphoma, a spinal axis tumor, a brain stem glioma, a pituitary adenoma, and an adenocarcinoma of the gastroesophageal junction.

In some aspects of these embodiments, the cancer is a folate receptor expressing cancer. In another embodiment, the cancer is a folate receptor α-expressing cancer. In yet another embodiment, the cancer is a folate receptor β-expressing cancer. In some aspects of these embodiments, the cancer is an endometrial cancer, a non-small cell lung cancer, an ovarian cancer, an osteosarcoma, including pediatric or non-pediatric osteosarcoma, or a triple-negative breast cancer. In another embodiment, the cancer being treated is a tumor. In another embodiment, the cancer is malignant. In another embodiment, the cancer is an osteosarcoma including pediatric or non-pediatric osteosarcoma.

In one embodiment, the "small molecule ligand" can be a folate, DUPA (a ligand bound by PSMA-positive human prostate cancer cells and other cancer cell types), an NK-1R ligand (receptors for the NK-1R ligand are found, for example, on cancers of the colon and pancreas), a CAIX ligand (receptors for the CAIX ligand are found, for example, on renal, ovarian, vulvar, and breast cancers), a ligand of gamma glutamyl transpeptidase (the transpeptidase is overexpressed, for example, in ovarian cancer, colon cancer, liver cancer, astrocytic gliomas, melanomas, and leukemias), an NKG2D ligand (receptors for the NKG2D ligand are found, for example, on cancers of the lung, colon, kidney, prostate, and on T and B cell lymphomas), or a CCK2R ligand (receptors for the CCK2R ligand are found on cancers of the thyroid, lung, pancreas, ovary, brain, stomach, gastrointestinal stroma, and colon, among others), each of which is a small molecule ligand that binds specifically to a cancer cell type (i.e., the receptor for each of these ligands can be overexpressed on cancers compared to normal tissues).

In one embodiment, the small molecule ligand may have a mass of less than about 10,000 Daltons, less than about 9000 Daltons, less than about 8,000 Daltons, less than about 7000 Daltons, less than about 6000 Daltons, less than about 5000 Daltons, less than about 4500 Daltons, less than about 4000 Daltons, less than about 3500 Daltons, less than about 3000 Daltons, less than about 2500 Daltons, less than about 2000 Daltons, less than about 1500 Daltons, less than about 1000 Daltons, or less than about 500 Daltons. In another embodiment, the small molecule ligand may have a mass of about 1 to about 10,000 Daltons, about 1 to about 9000 Daltons, about 1 to about 8,000 Daltons, about 1 to about 7000 Daltons, about 1 to about 6000 Daltons, about 1 to about 5000 Daltons, about 1 to about 4500 Daltons, about 1 to about 4000 Daltons, about 1 to about 3500 Daltons, about 1 to about 3000 Daltons, about 1 to about 2500 Daltons, about 1 to about 2000 Daltons, about 1 to about 1500 Daltons, about 1 to about 1000 Daltons, or about 1 to about 500 Daltons.

In one embodiment, a DUPA derivative can be the ligand of the small molecule ligand linked to a targeting moiety, and DUPA derivatives are described in WO 2015/057852, incorporated herein by reference.

In one embodiment, the small molecule ligand in the context of the "small molecule ligand linked to a linker" is a folate. In various embodiments, the folate can be folic acid, a folic acid analog, or another folate receptor-binding molecule. In various embodiments, analogs of folate that can be used include folinic acid (e.g., leucovorin), pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In another embodiment, the small molecule ligand in the context of the "small molecule ligand linked to a linker" can have the formula

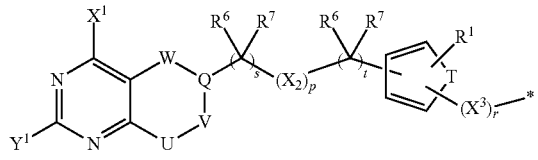

wherein $X^1$ and $Y^1$ are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;

$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

In one aspect, the "targeting moiety" that binds to the CAR expressed by CAR T cells can be selected, for example, from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, a DARPin, an affibody, an affilin, an anticalin, an atrimer, an avimer, a bicyclic peptide, an FN3 scaffold, a cys-knot, a fynomer, a Kunitz domain, or an Obody. The identity of the targeting moiety is limited only in that it should be recognized and bound by the CAR, preferably with specificity, and that it has a relatively low molecular weight. In various aspects, exemplary targeting moieties are haptens, including small molecular weight organic molecules.

In one illustrative embodiment, the targeting moiety can have the following illustrative structure:

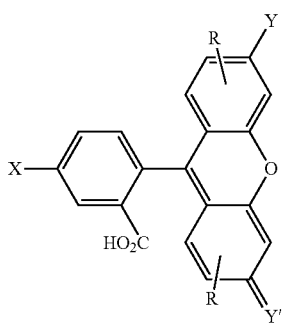

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from H, fluoro, sulfonic acid, sulfonate, and salts thereof, and the like; and $R^a$ is hydrogen or alkyl.

In one illustrative aspect, the linker can comprise polyethylene glycol (PEG), polyproline, a hydrophilic amino acid, a sugar, an unnatural peptidoglycan, a polyvinylpyrrolidone, pluronic F-127, or a combination thereof.

In another illustrative aspect, the linker in the compound, or pharmaceutically acceptable salt thereof, described herein can comprise a direct linkage (e.g., a reaction between the isothiocyanate group of FITC and a free amine group of a small molecule ligand) or the linkage can be through an intermediary linker. In one embodiment, if present, an intermediary linker can be any biocompatible linker known in the art, such as a divalent linker. In one illustrative embodiment, the divalent linker can comprise about 1 to about 30 carbon atoms. In another illustrative embodiment, the divalent linker can comprise about 2 to about 20 carbon atoms. In other embodiments, lower molecular weight divalent linkers (i.e., those having an approximate molecular weight of about 30 to about 300 Daltons) are employed. In another embodiment, linker lengths that are suitable include, but are not limited to, linkers having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, or more atoms.

In various embodiments, the small molecule ligand linked to a targeting moiety can be of the formula

B-L-T, wherein B represents the small molecule ligand, L represents the linker, and T represents the targeting moiety, and wherein L comprises a structure having the formula

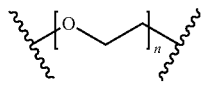

wherein n is an integer from 0 to 200. In another embodiment, n can be an integer from 0 to 150, 0 to 110, 0 to 100, 0 to 90, 0 to 80, 0 to 70, 0 to 60, 0 to 50, 0 to 40, 0 to 30, 0 to 20, 0 to 15, 0 to 14, 0 to 13, 0 to 12, 0 to 11, 0 to 10, 0 to 9, 0 to 8, 0 to 7, 0 to 6, 0 to 5, 0 to 4, 0 to 3, 0 to 2, 0 to 1, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 15 to 31, 15 to 32, 15 to 33, 15 to 34, 15 to 35, 15 to 36, 15 to 37, 15 to 38, 15 to 39, 15 to 40, 15 to 50, 15 to 60, 15 to 70, 15 to 80, 15 to 90, 15 to 100, 15 to 110, 15 to 120, 15 to 130, 15 to 140, 15 to 150, or n can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 108, 110, 120, 130, 140, or 150.

In another embodiment, the linker may be a divalent linker that may include one or more spacers. Illustrative spacers are shown in the following table. The following non-limiting, illustrative spacers are described where * indicates the point of attachment to the small molecule ligand or to the targeting moiety, or to other divalent linker portions.

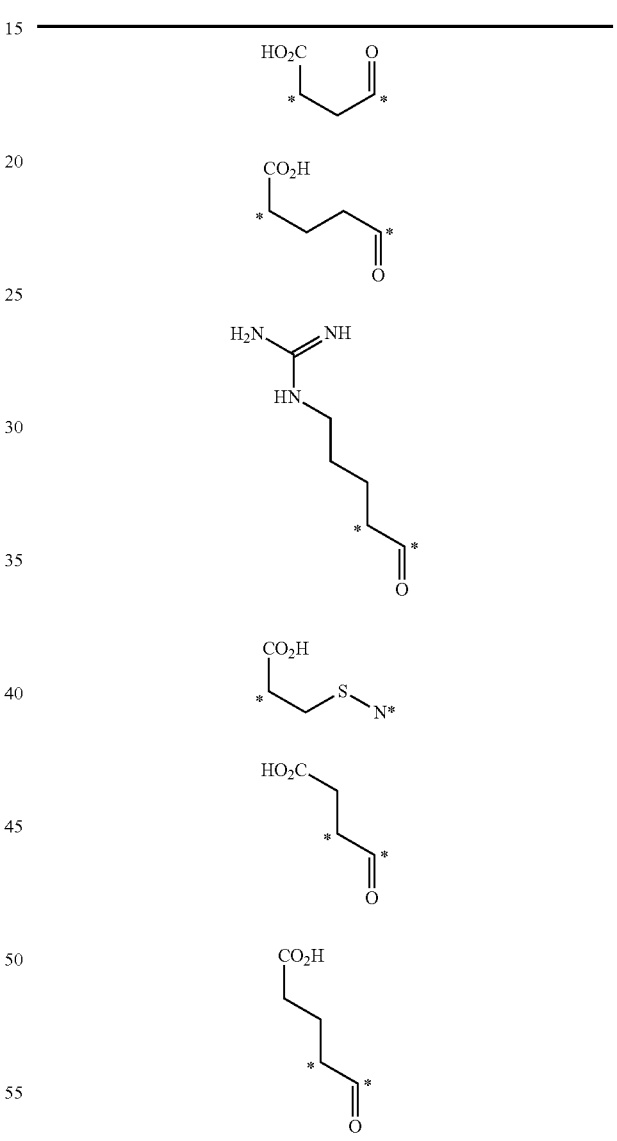

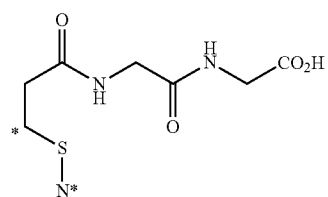

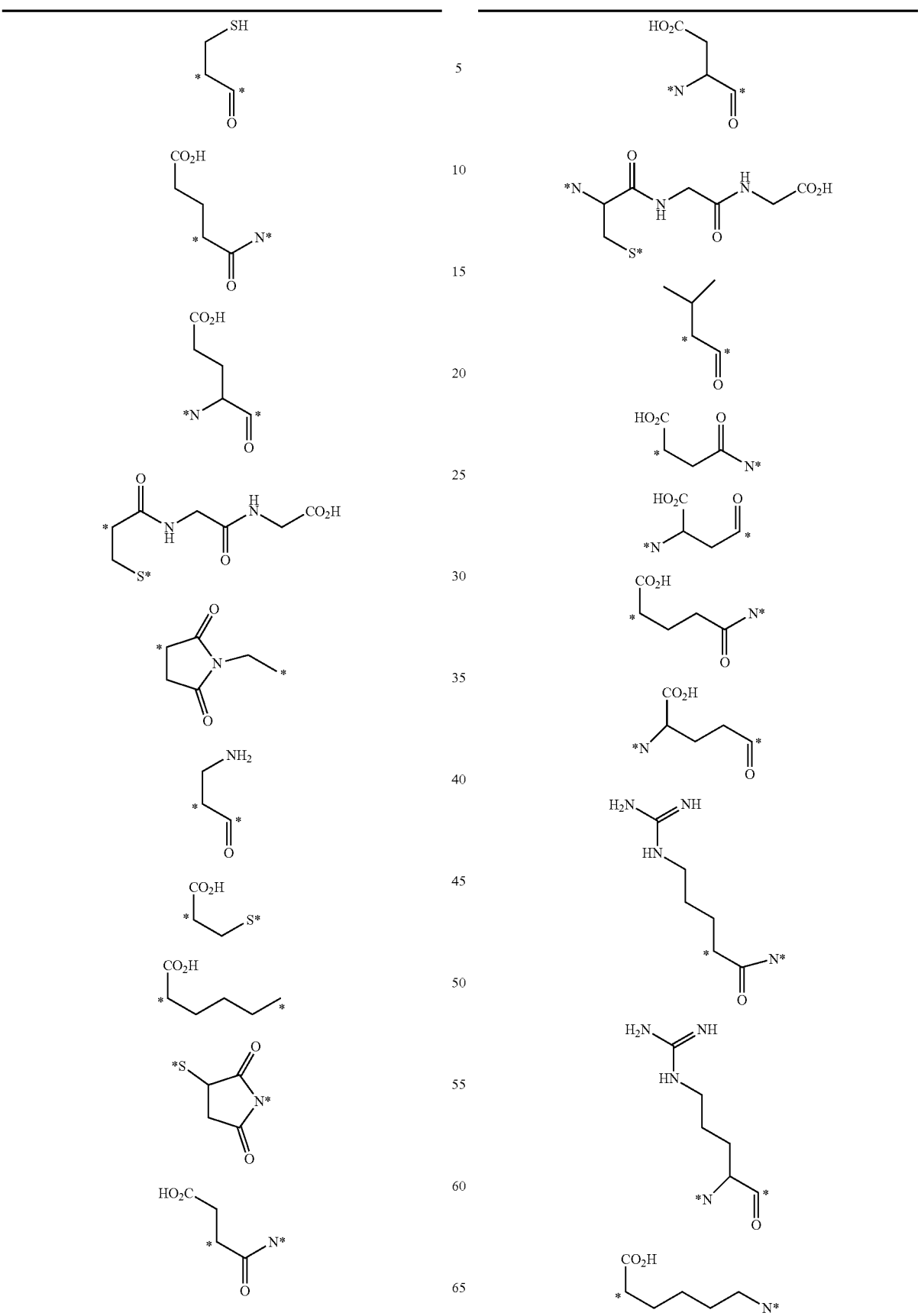

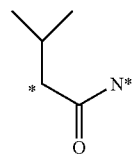
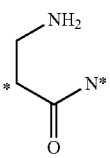
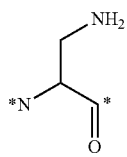
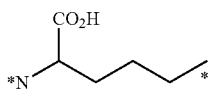
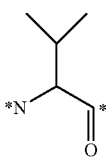
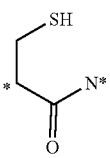
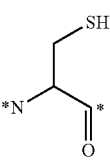
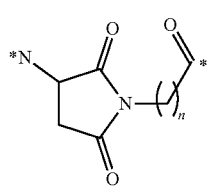
n = 1-3
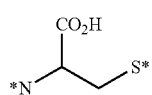
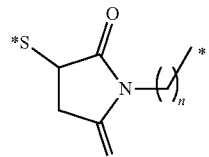
n = 0-3
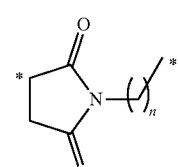
n = 0-3
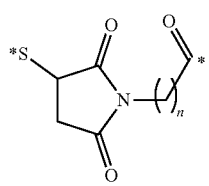
n = 1-3
In other embodiments, the small molecule ligand linked to a targeting moiety (bridge) can have any of the following structures.
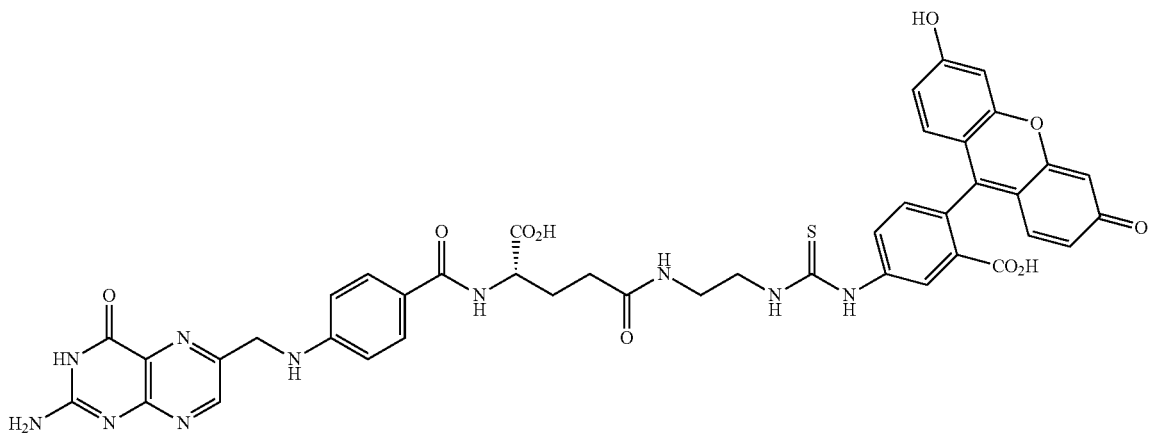

-continued
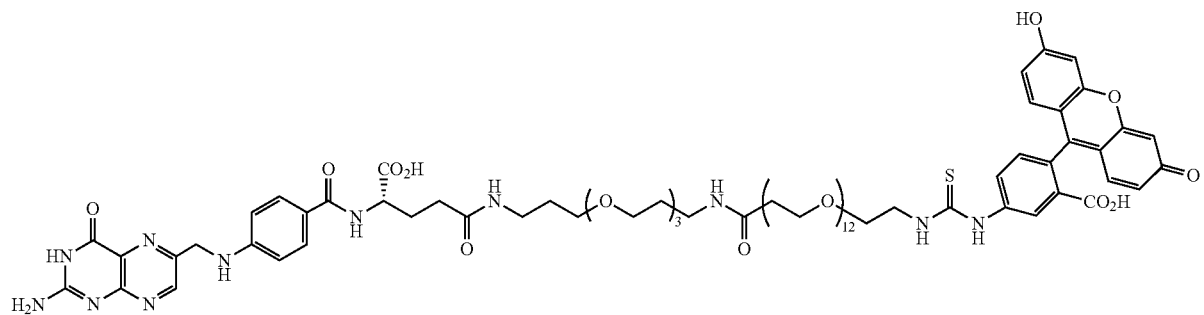
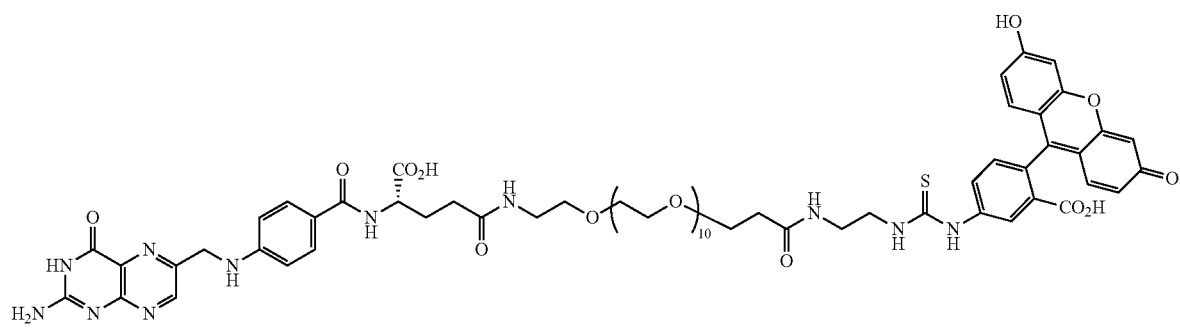
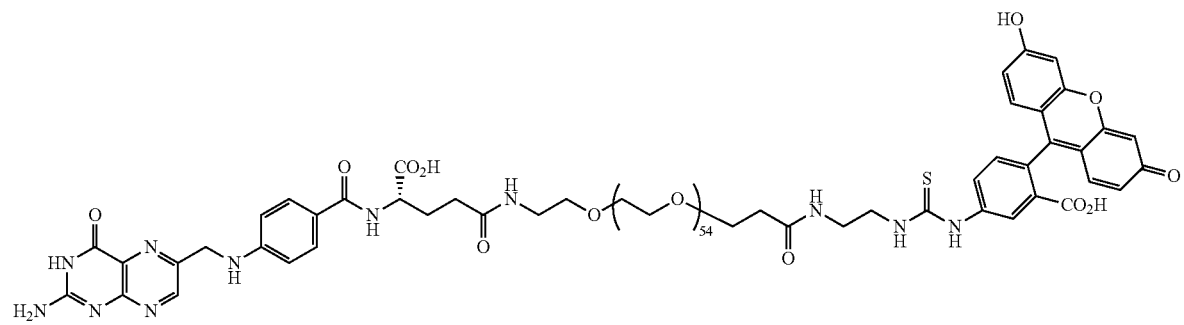
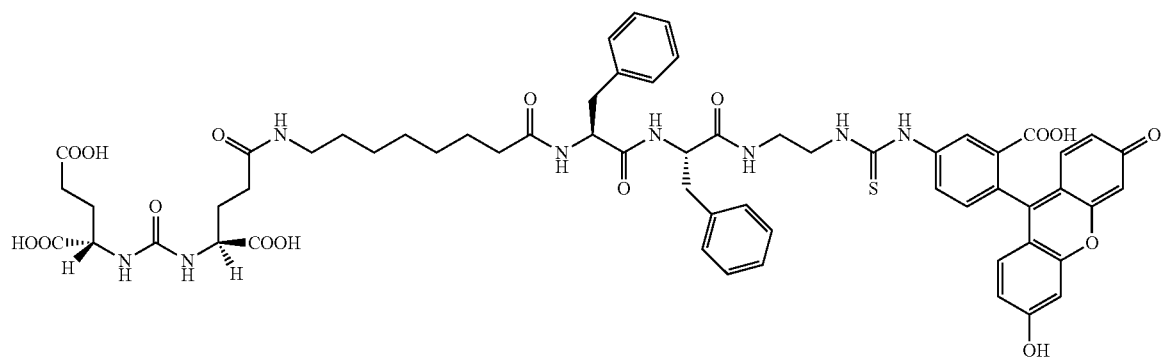
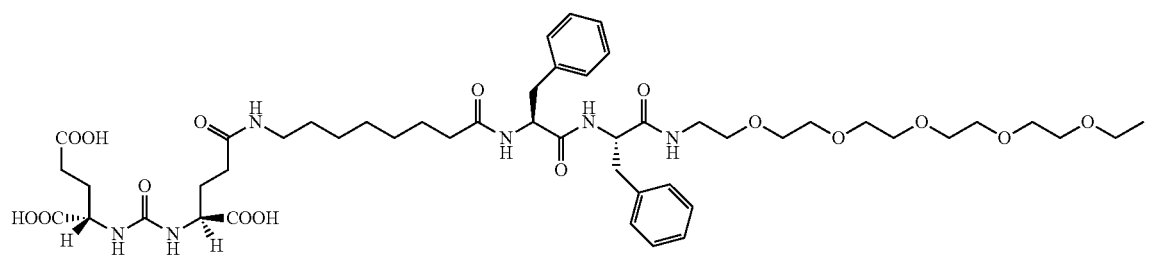

37
-continued
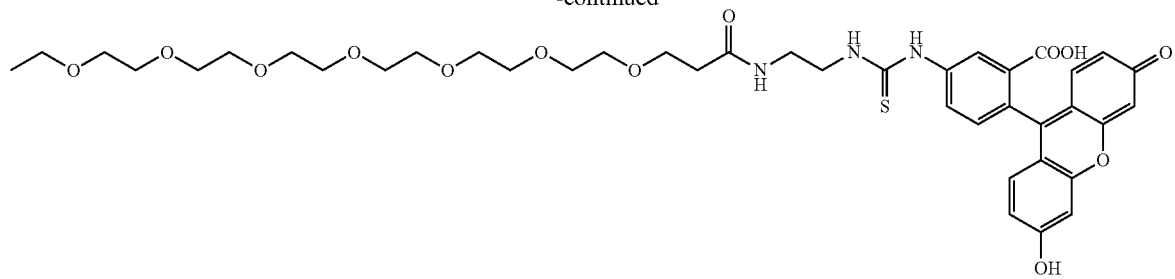
38
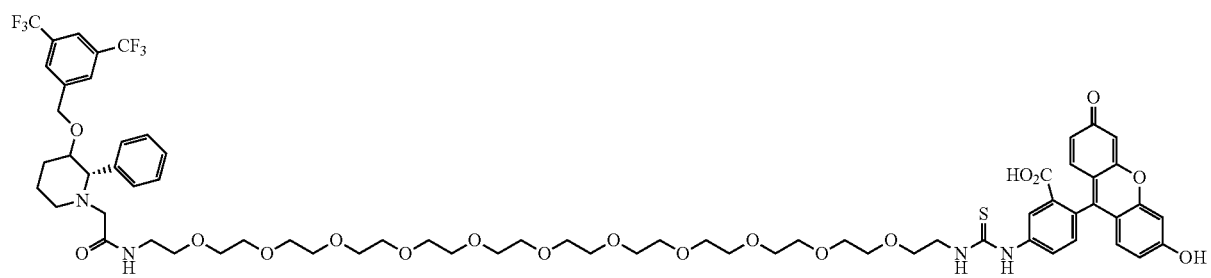
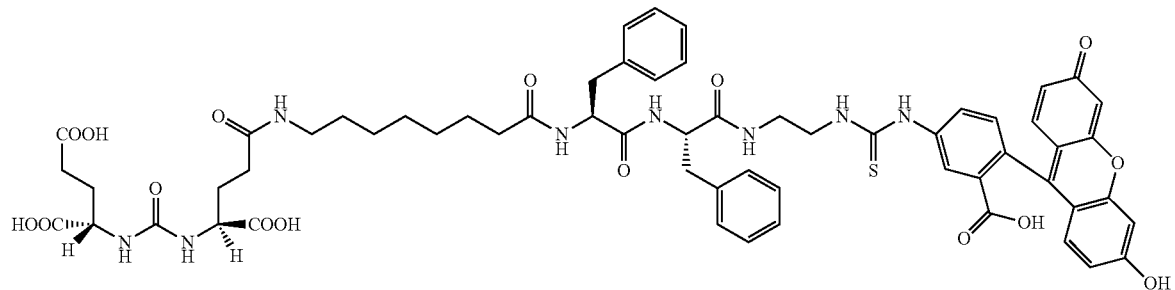
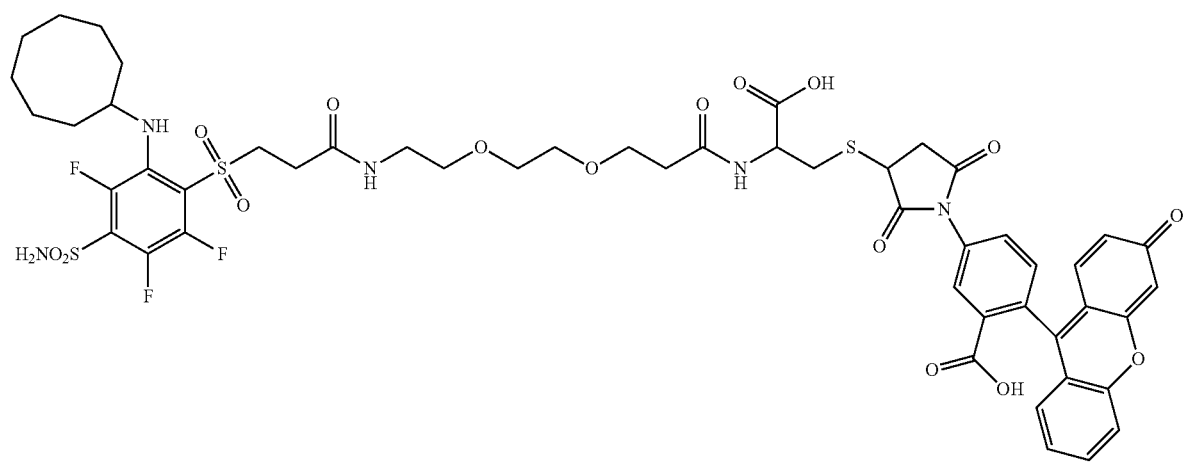

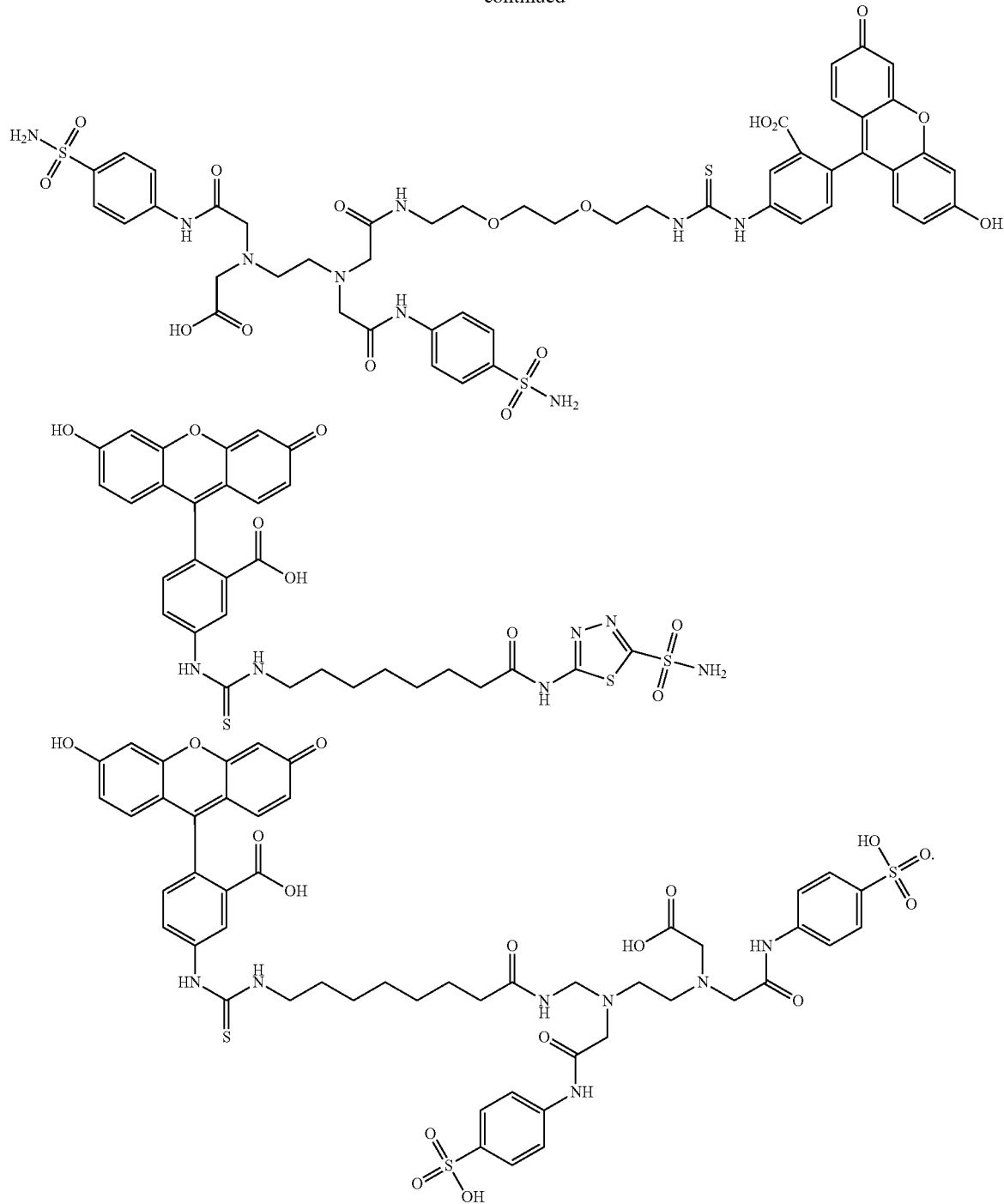

In other embodiments, the compound, or the pharmaceutically acceptable salt thereof, is not an antibody, and does not comprise a fragment of an antibody. In yet another embodiment, the targeting moiety does not comprise a peptide epitope.

In one illustrative embodiment, the small molecule ligand linked to a targeting moiety by a linker (the bridge) comprises fluorescein isothiocyanate (FITC) linked to the small molecule ligand. In one aspect, the cancer may overexpress a receptor for the small molecule ligand. In another aspect, for example, cytotoxic T cells, or another type of T cell, can be transformed to express a CAR that comprises anti-FITC scFv. In this aspect, the CAR may target FITC wherein the cancer is decorated with FITC molecules as a result of binding of the small molecule ligand to the cancer. Thus, toxicity to normal, non-target cells can be avoided or reduced. In this embodiment, when the anti-FITC CAR-expressing T cells bind FITC, the CAR T cells are activated and the cancer is ameliorated.

A "pharmaceutically acceptable salt" of a small molecule ligand linked to a targeting moiety by a linker is contemplated. As used herein, the term "pharmaceutically acceptable salt" refers to those salts whose counter ions may be used in pharmaceuticals. In various embodiments, such salts include, but are not limited to 1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or 2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like. Pharmaceutically acceptable salts are well-known to those skilled in the art, and any such pharmaceutically acceptable salt is contemplated in connection with the embodiments described herein.

In various embodiments, suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

In various embodiments, suitable base salts are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one illustrative aspect, the compound, or a pharmaceutically salt thereof, described herein may contain one or more chiral centers, or may otherwise be capable of existing as multiple stereoisomers. Accordingly, various embodiments may include pure stereoisomers as well as mixtures of stereoisomers, such as enantiomers, diastereomers, and enantiomerically or diastereomerically enriched mixtures. In one aspect, the compound, or pharmaceutically acceptable salt thereof, described herein may be capable of existing as geometric isomers. Accordingly, various embodiments may include pure geometric isomers or mixtures of geometric isomers.

In some aspects, the compound, or pharmaceutically acceptable salt thereof, described herein may exist in unsolvated forms as well as solvated forms, including hydrated forms. In general, the solvated forms are equivalent to unsolvated forms and are encompassed within the scope of the present invention.

The methods described herein also utilize T lymphocytes (e.g., cytotoxic T lymphocytes) engineered to express a chimeric antigen receptor (CAR) that recognizes and binds to the targeting moiety (e.g., FITC, DNP, or TNP) of the bridge. In one embodiment, the CARs described herein comprise three domains including 1) a recognition region (e.g., a single chain fragment variable (scFv) region of an antibody, a Fab fragment, and the like) which recognizes and binds to the targeting moiety with specificity, 2) a co-stimulation domain which enhances the proliferation and survival of the T lymphocytes, and 3) an activation signaling domain which generates a T lymphocyte activation signal.

In various aspects, as non-limiting examples, scFv regions of antibodies that bind 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, a DARPin, an affibody, an affilin, an anticalin, an atrimer, an avimer, a bicyclic peptide, an FN3 scaffold, a cys-knot, a fynomer, a Kunitz domain, or an Obody can be used. In illustrative non-limiting embodiments, the scFv regions can be prepared from (i) an antibody known in the art that binds a targeting moiety, (ii) an antibody newly prepared using a selected targeting moiety, such as a hapten, and (iii) sequence variants derived from the scFv regions of such antibodies, e.g., scFv regions having at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity with the amino acid sequence of the scFv region from which they are derived.

In one aspect, the co-stimulation domain serves to enhance the proliferation and survival of the cytotoxic T lymphocytes upon binding of the CAR to a targeting moiety. Suitable co-stimulation domains include, but are not limited to, CD28, CD137 (4-1BB), a member of the tumor necrosis factor (TNF) receptor family, CD134 (OX40), a member of the TNFR-superfamily of receptors, CD27, CD30, CD150, DAP10, NKG2D, and CD278 (ICOS), a CD28-superfamily co-stimulatory molecule expressed on activated T cells, or combinations thereof. A skilled artisan will understand that sequence variants of these co-stimulation domains can be used without adversely impacting the invention, where the variants have the same or similar activity as the domain upon which they are modeled. In various embodiments, such variants can have at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the domain from which they are derived.

In an illustrative embodiment, the activation signaling domain serves to activate T lymphocytes (e.g., cytotoxic T lymphocytes) upon binding of the CAR to a targeting moiety. In various embodiments, suitable activation signaling domains include the T cell CD3ζ chain, CD3 delta receptor protein, mbl receptor protein, B29 receptor protein, and the Fc receptor γ. The skilled artisan will understand that sequence variants of these activation signaling domains can be used where the variants have the same or similar activity as the domain upon which they are modeled. In various embodiments, the variants have at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity with the amino acid sequence of the domain from which they are derived.

In one aspect, constructs encoding the CARs are prepared using genetic engineering techniques. Such techniques are described in detail in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference.

As examples, a plasmid or viral expression vector (e.g., a lentiviral vector, a retrovirus vector, sleeping beauty, and piggyback (transposon/transposase systems that include a non-viral mediated CAR gene delivery system)) can be prepared that encodes a fusion protein comprising a recognition region, one or more co-stimulation domains, and an activation signaling domain, in frame and linked in a 5' to 3' direction. In other embodiments, other arrangements are acceptable and include a recognition region, an activation signaling domain, and one or more co-stimulation domains. In one embodiment, the placement of the recognition region in the fusion protein will generally be such that display of the region on the exterior of the CAR T cell is achieved. In one embodiment, the CARs may include additional elements, such as a signal peptide (e.g., CD8α signal peptide) to ensure proper export of the fusion protein to the cell surface, a transmembrane domain to ensure the fusion protein is maintained as an integral membrane protein (e.g., CD8α transmembrane domain, CD28 transmembrane domain, or CD3ζ transmembrane domain), and a hinge domain (e.g., CD8α hinge) that imparts flexibility to the recognition region and allows strong binding to the targeting moiety.

Diagrams of exemplary CARs are shown in FIGS. 2 and 3. For FIG. 2, the fusion protein sequence can be incorporated into a lentivirus expression vector where "SP" is a signal peptide, the CAR is an anti-FITC CAR, a CD8α hinge and a CD8α transmembrane domain are present, the co-stimulation domain is 4-1BB, and the activation signaling domain is CD3ζ. Exemplary nucleic acid sequences of a CAR insert are provided as SEQ ID NOS:1 and 3 and the encoded amino acid sequence is provided as SEQ ID NO:2. In yet another embodiment, SEQ ID NO:2 can comprise or consist of humanized, or human amino acid sequences.

For FIG. 3, a diagram of an exemplary CAR construct wherein the expressed CAR comprises an E2 anti-fluorescein antibody fragment is shown where the fusion protein sequence can be incorporated into an expression vector and where the CAR comprises an E2 anti-fluorescein antibody fragment, an IgG4 hinge domain, a CD28 transmembrane domain, and where the co-stimulation domain is CD137 (4-1BB), and the activation signaling domain is CD3ζ. The CAR can comprise additional suitable domains. An exemplary nucleic acid sequence of such a CAR insert is provided as SEQ ID NO:4 and the exemplary encoded amino acid sequence is provided as SEQ ID NO:5. As used herein, "SEQ ID NO:4" means the sequence beginning at the underlined "agc" codon and ending with the underlined "ggc" codon. This portion of the longer sequence, encodes the CAR that is inserted into the T cell membrane. The other portions of the longer sequence include coding sequence for signal peptides, the EGFRt domain, etc. which are not part of the CAR that is inserted into the membrane and which functions as the chimeric antigen receptor. As used herein, "SEQ ID NO:5" means the sequence beginning at the underlined "S" and ending with the underlined "G". This portion of the longer sequence is the amino acid sequence for the CAR that is inserted into the T cell membrane. The other portions of the longer sequence include amino acid sequences for signal peptides, the EGFRt domain, etc. which are not part of the CAR inserted into the membrane and which functions as the chimeric antigen receptor. In yet another embodiment, SEQ ID NO:5 can comprise or consist of humanized, or human amino acid sequences. SEQ ID NOS:4 and 5 are as described above and which are shown below. The start and stop codons in the longer nucleic acid sequence are underlined and the longer sequence is an exemplary sequence that can be used for transduction of T cells for use in the methods as described herein.

(E2 anti-fluorescein antibody fragment CAR nucleic acid sequence (insert))

SEQ ID NO: 4

<u>atg</u>cttctcctggtgacaagccttctgctctgtgagttaccacacccagc attcctcctgatcccaagcgtgctgacacagcctagctccgtgtctgccg cccctggccagaaagtgaccatcagctgtagcggcagcaccagcaacatc ggcaacaactacgtgtcctggtatcagcagcaccccggcaaggcccccaa gctgatgatctacgacgtgtccaagcggcccagcggcgtgcccgatagat tttccggcagcaagagcggcaacagcgccagcctggatatcagcggcctg cagtctgaggacgaggccgactactattgcgccgcctgggacgatagcct gagcgagttcctgtttggcaccggcaccaagctgacagtgctgggcggag gcggaggatctggcggcggaggaagtggcggaggggggatctcaggtgcag ctggtggaaagcggcggcaacctggtgcagcctggcggatctctgagact gagctgtgccgccagcggcttcaccttcggcagcttcagcatgagctggg tgcgccaggctcctggggggaggactggaatgggtggcaggactgagcgcc agaagcagcctgacccactacgccgatagcgtgaaggccgcggttcaccat cagccgggacaacgccaagaacagcgtgtacctgcagatgaacagcctgc gggtggaagataccgccgtgtactactgcgcgcagacggtcctacgacagc agcggctactggggccacttctacagctacatggacgtgtggggccaggg cacccttcgtgacagtgtctgagagcaagtacggaccgccctgccccctt gccctgccccgagttcgacggcggacccagcgtgttcctgttccccccc aagcccaaggacaccctgatgatcagccggaccccgaggtgacctgcgt ggtggtggacgtgagccaggaagatcccgaggtccagttcaattggtacg tggacggcgtggaagtgcacaacgccaagaccaagcccagagaggaacag ttccagagcacctaccgggtggtgtctgtgctgaccgtgctgcaccagga ctggctgaacggcaaagaatacaagtgcaaggtgtccaacaagggcctgc ccagcagcatcgaaaagaccatcagcaaggccaagggccagcctcgcgag ccccaggtgtacaccctgcctccctcccaggaagagatgaccaagaacca ggtgtccctgacctgcctggtgaagggcttctaccccagcgacatcgccg tggagtgggagagcaacggccagcctgagaacaactacaagaccacccct cccgtgctggacagcgacggcagcttcttcctgtacagccggctgaccgt ggacaagagccggtggcaggaaggcaacgtctttagctgcagcgtgatgc acgaggccctgcacaaccactacacccagaagagcctgagcctgtccctg ggcaagatgttctgggtgctggtggtggtgggcggggtgctggcctgcta cagcctgctggtgacagtggccttcatcatcttttgggtgaaacggggca gaaagaaactcctgtatatattcaaacaaccatttatgagaccagtacaa actactcaagaggaagatggctgtagctgccgatttccagaagaagaaga aggaggatgtgaactgcgggtgaagttcagcagaagcgccgacgcccctg cctaccagcagggccagaatcagctgtacaacgagctgaacctgggcaga

```
agggaagagtacgacgtcctggataagcggagaggccgggaccctgagat
gggcggcaagcctcggcggaagaaccccaggaaggcctgtataacgaac
tgcagaaagacaagatggccgaggcctacagcgagatcggcatgaagggc
gagcggaggcggggcaagggccacgacggcctgtatcagggcctgtccac
cgccaccaaggatacctacgacgccctgcacatgcaggccctgccccca
ggctcgaggcggcggagagggcagaggaagtcttctaacatgcggtgac
gtggaggagaatcccggccctaggatgcttctcctggtgacaagccttct
gctctgtgagttaccacacccagcattcctcctgatcccacgcaaagtgt
gtaacggaataggtattggtgaatttaaagactcactctccataaatgct
acgaatattaaacacttcaaaaactgcacctccatcagtggcgatctcca
catcctgccggtggcatttagggggtgactccttcacacatactcctcctc
tggatccacaggaactggatattctgaaaaccgtaaaggaaatcacaggg
ttttttgctgattcaggcttggcctgaaaacaggacggacctccatgcctt
tgagaacctagaaatcatacgcggcaggaccaagcaacatggtcagtttt
ctcttgcagtcgtcagcctgaacataacatccttgggattacgctccctc
aaggagataagtgatggagatgtgataatttcaggaaacaaaaatttgtg
ctatgcaaatacaataaactggaaaaaactgtttgggacctccggtcaga
aaaccaaaattataagcaacagaggtgaaaacagctgcaaggccacaggc
caggtctgccatgccttgtgctcccccgagggctgctggggcccggagcc
cagggactgcgtctcttgccggaatgtcagccgaggcagggaatgcgtgg
acaagtgcaaccttctggagggtgagccaagggagtttgtggagaactct
gagtgcatacagtgccacccagagtgcctgcctcaggccatgaacatcac
ctgcacaggacggggaccagacaactgtatccagtgtgcccactacattg
acggcccccactgcgtcaagacctgcccggcaggagtcatgggagaaaac
aacacectggtctggaagtacgcagacgccggccatgtgtgccacctgtg
ccatccaaactgcacctacggatgcactgggccaggtcttgaaggctgtc
caacgaatgggcctaagatcccgtccatcgccactgggatggtggggggcc
ctcctcttgctgctggtggtggccctggggatcggcctcttcatgtga
```

(E2 anti-fluorescein antibody fragment CAR amino acid sequence (insert))

SEQ ID NO: 5
```
M L L L V T S L L L C E L P H P A F L L I P S V L
T Q P S S V S A A P G Q K V T I S C S G S T S N I
G N N Y V S W Y Q Q H P G K A P K L M I Y D V S K
R P S G V P D R F S G S K S G N S A S L D I S G L
Q S E D E A D Y Y C A A W D D S L S E F L F G T G
T K L T V L G G G G S G G G G S G G G G S Q V Q
L V E S G G N L V Q P G G S L R L S C A A S G F T
F G S F S M S W V R Q A P G G G L E W V A G L S A
R S S L T H Y A D S V K G R F T I S R D N A K N S
V Y L Q M N S L R V E D T A V Y Y C A R R S Y D S
S G Y W G H F Y S Y M D V W G Q G T L V T V S E S
K Y G P P C P P C P A P E F D G G P S V F L F P P
K P K D T L M I S R T P E V T C V V V D V S Q E D
P E V Q F N W Y V D G V E V H N A K T K P R E E Q
F Q S T Y R V V S V L T V L H Q D W L N G K E Y K
C K V S N K G L P S S I E K T I S K A K G Q P R E
P Q V Y T L P P S Q E E M T K N Q V S L T C L V K
G F Y P S D I A V E W E S N G Q P E N N Y K T T P
P V L D S D G S F F L Y S R L T V D K S R W Q E G
N V F S C S V M H E A L H N H Y T Q K S L S L S L
G K M F W V L V V V G G V L A C Y S L L V T V A F
I I F W V K R G R K K L L Y I F K Q P F M R P V Q
T T Q E E D G C S C R F P E E E E G G C E L R V K
F S R S A D A P A Y Q Q G Q N Q L Y N E L N L G R
R E E Y D V L D K R R G R D P E M G G K P R R K N
P Q E G L Y N E L Q K D K M A E A Y S E I G M K G
E R R R G K G H D G L Y Q G L S T A T K D T Y D A
L H M Q A L P P R L E G G G E G R G S L L T C G D
V E E N P G R M L L L V T S L L L C E L P H P A
F L L I P R K V C N G I G I G E F K D S L S I N A
T N I K H F K N C T S I S G D L H I L P V A F R G
D S F T H T P P L D P Q E L D I L K T V K E I T G
F L L I Q A W P E N R T D L H A F E N L E I I R G
R T K Q H G Q F S L A V V S L N I T S L G L R S L
K E I S D G D V I I S G N K N L C Y A N T I N W K
K L F G T S G Q K T K I I S N R G E N S C K A T G
Q V C H A L C S P E G C W G P E P R D C V S C R N
V S R G R E C V D K C N L L E G E P R E F V E N S
E C I Q C H P E C L P Q A M N I T C T G R G P D N
C I Q C A H Y I D G P H C V K T C P A G V M G E N
N T L V W K Y A D A G H V C H L C H P N C T Y G C
T G P G L E G C P T N G P K I P S I A T G M V G A
L L L L L V V A L G I G L F M
```

Another exemplary CAR construct is the 4M5.3 CAR shown diagrammatically in FIG. 3. As used herein, "SEQ ID NO:6" means the sequence shown below beginning at the underlined "gac" codon and ending with the underlined "ggc" codon. This portion of the longer sequence, encodes the exemplary 4M5.3 CAR. The CAR is inserted into the T cell membrane. The other portions of the longer sequence include coding sequence for signal peptides, the EGFRt domain, etc. which are not part of the CAR that is inserted into the membrane and which functions as the chimeric antigen receptor. As used herein, "SEQ ID NO:7" means the sequence beginning at the underlined "D" and ending with the underlined "G". This portion of the longer sequence is the amino acid sequence for the CAR that is inserted into the T cell membrane. The other portions of the longer sequence include amino acid sequences for signal peptides, the EGFRt domain, etc. which are not part of the CAR inserted into the membrane and which functions as the chimeric antigen receptor. In yet another embodiment, SEQ ID NO:7 can comprise or consist of humanized, or human amino acid sequences. SEQ ID NOS:6 and 7 are as described above and which are shown below. The start and stop codons in the longer nucleic acid sequence are underlined and the longer sequence is an exemplary sequence that can be used for transduction of T cells to prepare the 4M5.3 CAR.

SEQ ID NO: 7 [4M5.3-CAR Amino Acid Sequence (Insert)]
MLLLVTSLLLCELPHPAFLLIPDVVMTQTPLSLPVSL-
GDQASISCRSSQSLVHSNGNTYL RWYLQKPGQSP-
KVLIYKVSNRVSGVPDRFSGSGSGTDFTLKINRVEAE-
DLGVYFCSQST HVPWTFGGGTKLEIKSSADDAKK-
DAAKKDDAKKDDAKKDGGVKLDETGGGLVQPG
GAMKLSCVTSGFTFGHYWMNWVRQSPEKGLE-
WVAQFRNKPYNYETYYSDSVKGRFT ISRDD-
SKSSVYLQMNNLRVEDTGIYYCTGASYGMEY-
LGQGTSVTVSESKYGPPCPPCP APEFDGGPSVFLF-
PPKPKDTLMISRTPEVTCVVVDVSQEDPE-
VQFNWYVDGVEVHNAK TKPREEQFQSTYRVVSV-
LTVLHQDWLNGKEYKCKVSNKGLPSSIEKTISKAK-
GQPREP QVYTLPPSQEEMTKNQVSLTCLVKGFYPS-
DIAVEWESNGQPENNYKTTPPVLDSDGSFF LYSRL-
TVDKSRWQEGNVFSCSVMHEALHNHYTQKSLS-
LSLGKMFWVLVVVGGVLAC YSLLVTVAFIIFWVKR-
GRKKLLYIFKQPFMRPVQTTQEEDGCSCRFPEEEE-
GGCELRVK FSRSADAPAYQQGQNQLYNELNLGR-
REEYDVLDKRRGRDPEMGGKPRRKNPQEGLY
NELQKDKMAEAYSEIGMKGERRRGKGHDGLYQGL-
STATKDTYDALHMQALPPRLEG GGEGRGSLLTCGD-
VEENPGPRMLLLVTSLLLCELPHPAFLLIPRKVCNGI-
GIGEFKDSLSI NATNIKHFKNCTSISGDLHILPVAFR-
GDSFTHTPPLDPQELDILKTVKEITGFLLIQAWPE
NRTDLHAFENLEIIRGRTKQHGQFSLAVVSLNIT-
SLGLRSLKEISDGDVIISGNKNLCYA NTINW-
KKLFGTSGQKTKIISNRGENSCKATGQVCHAL-
CSPEGCWGPEPRDCVSCRNVS RGRECVDKCNL-
LEGEPREFVENSECIQCHPECLPQAMNITCTGRGPDN-
CIQCAHYIDGP HCVKTCPAGVMGENNTLV-
WKYADAGHVCHLCHPNCTYGCTGPGLEGCPTNGP-
KIPSI ATGMVGALLLLLVVALGIGLFM

[4M5.3-CAR amino acid sequence (insert)]
SEQ ID NO: 7
MLLLVTSLLLCELPHPAFLLIPDVVMTQTPLSLPVSLGDQASISCRSSQS

LVHSNGNTYLRWYLQKPGQSPKVLIYKVSNRVSGVPDRFSGSGSGTDFTL

KINRVEAEDLGVYFCSQSTHVPWTFGGGTKLEIKSSADDAKKDAAKKDDA

KKDDAKKDGGVKLDETGGGLVQPGGAMKLSCVTSGFTFGHYWMNWVRQSP

EKGLEWVAQFRNKPYNYETYYSDSVKGRFTISRDDSKSSVYLQMNNLRVE

DTGIYYCTGASYGMEYLGQGTSVTVSESKYGPPCPPCPAPEFDGGPSVFL

FPPKPKDTLMISRTPEVTCVVVDVSQEDPEVQFNWYVDGVEVHNAKTKPR

EEQFQSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLS

LSLGKMFWVLVVVGGVLACYSLLVTVAFIIFWVKRGRKKLLYIFKQPFMR

PVQTTQEEDGCSCRFPEEEEGGCELRVKFSRSADAPAYQQGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPRLEGGGEGRGSLLT

CGDVEENPGPRMLLLVTSLLLCELPHPAFLLIPRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFM

[4M5.3-CAR nucleotide acid sequence (insert)]
SEQ ID NO: 6
ATG(START)cttctcctggtgacaagccttctgctctgtgagttaccac acccagcattcctcctgatcccagacttgtaatgacccagacccctctgt ctctccccgtaagcttgggcgaccaggcgagcatctcttgtcggtcttcc cagtccctggtccattcaaacggcaatacttacttgcggtggtacttgca gaagcccggtcaatccccaaaagtgctgatatacaaggttagcaatcggg tcagtggagtgcccgaccgcttcagcggaagcggatccgggactgacttc actctgaagatcaaccgggtagaagctgaagacctgggggtgtacttctg ctctcagtcaacacacgtgccatggacctttggaggtggcaccaagctgg aaatcaaatcatcagcggacgatgccaaaaaagacgcggccaagaaggac gatgccaagaaggatgatgctaaaaaggatggcggagtcaaattggacga gacaggcggggactggtgcagcccggcggtgccatgaaactgtcttgtg tgaccagcggctttaccttcgggcattattggatgaactgggtgcgacag tctccagagaaagggctcgagtgggtggcccagtttcgaaataaaccgta caattatgagacctactattcagattctgtgaaagggcgcttcactattt cacgcgacgacagcaaaagttccgtctaccttcagatgaacaaccttaga gtggaggataccggaatatactactgcacgggtgccagttatggcatgga gtacttggggcaggggacatctgtgaccgtttctgagagcaagtacggac cgccctgcccccttgccctgccccgagttcgacggcggaccagcgtg ttcctgttcccccccaagcccaaggacaccctgatgatcagccggacccc cgaggtgacctgcgtggtggtggacgtgagccaggaagatcccgaggtcc agttcaattggtacgtggacggcgtggaagtgcacaacgccaagaccaag cccagagaggaacagaccagagcacctacccgggtggtgtctgtgctgacc gtgctgcaccaggactggctgaacggcaaagaatacaagtgcaaggtgtc caacaagggcctgcccagcagcatcgaaaagaccatcagcaaggccaagg gccagcctcgcgagccccaggtgtacaccctgcctccctcccaggaagag atgaccaagaaccaggtgtccctgacctgcctggtgaagggcttctaccc -continued

```
cagcgacatcgccgtggagtgggagagcaacggccagcctgagaacaact
acaagaccacccctcccgtgctggacagcgacggcagcttcttcctgtac
agccggctgaccgtggacaagagccggtggcaggaaggcaacgtctttag
ctgcagcgtgatgcacgaggccctgcacaaccactacacccagaagagcc
tgagcctgtccctgggcaagatgttctgggtgctggtggtggtgggcggg
gtgctggcctgctacagcctgctggtgacagtggccttcatcatcatttt
gggtgaaacggggcagaagaaactcctgtatatattcaaacaaccatttt
atgagaccagtacaaactactcaagaggaagatggctgtagctgccgatt
tccagaagaagaagaaggaggatgtgaactgcgggtgaagttcagcagaa
gcgccgacgcccctgcctaccagcagggcagaatcagctgtacaacgag
ctgaacctgggcagaagggaagagtacgacgtcctggataagcggagagg
ccgggaccctgagatgggcggcaagcctcggcggaagaaccccaggaag
gcctgtataacgaactgcagaaagacaagatggccgaggcctacagcgag
atcggcatgaagggcgagcggaggcggggcaaggccacgacggcctgta
tcagggcctgtccaccgccaccaaggatacctacgacgccctgcacatgc
aggccctgccccaaggctcgaggcggcggagagggcagaggaagtctt
ctaacatgcggtgacgtggaggagaatcccggccctaggatgcttctcct
ggtgacaagccttctgctctgtgagttaccacacccagcattcctcctga
tcccacgcaaagtgtgtaacggaataggtattggtgaatttaaagactca
ctctccataaatgctacgaatattaaacacttcaaaaactgcacctccat
cagtggcgatctccacatcctgccggtggcatttagggggtgactccttca
cacatactcctcctctggatccacaggaactggatattctgaaaaccgta
aaggaaatcacagggttttttgctgattcaggcttggcctgaaaacaggac
ggacctccatgcctttgagaacctagaaatcatacgcggcaggaccaagc
aacatggtcagttttctcttgcagtcgtcagcctgaacataacatccttg
ggattacgctccctcaaggagataagtgatggagatgtgataatttcagg
aaacaaaaatttgtgctatgcaaatacaataaactggaaaaaactgtttg
ggacctccggtcagaaaaccaaaattataagcaacagaggtgaaaacagc
tgcaaggccacaggccaggtctgccatgccttgtgctccccgagggctg
ctggggcccggagcccagggactgcgtctcttgccggaatgtcagccgag
gcagggaatgcgtggacaagtgcaaccttctggagggtgagccaagggag
tttgtggagaactctgagtgcatacagtgccaccccagagtgcctgcctca
ggccatgaacatcacctgcacaggacggggaccagacaactgtatccagt
gtgcccactacattgacggccccactgcgtcaagacctgcccggcagga
gtcatggagaaaacaacaccctggtctggaagtacgcagacgccggcca
tgtgtgccacctgtgccatccaaactgcacctacggatgcactgggccag
gtcttgaaggctgtccaacgaatgggcctaagatcccgtccatcgccact
gggatggtggggccctcctcttgctgctggtggtggccctggggatcgg
cctcttcatgTGA (STOP CODON)
```

In one embodiment, the CAR has a recognition region and the recognition region is a single chain fragment variable (scFv) region of an anti-FITC antibody, a co-stimulation domain and the co-stimulation domain is CD137 (4-1BB), and an activation signaling domain and the activation signaling domain is a T cell CD3ζ chain. It is well-known to the skilled artisan that an anti-FITC scFv and an anti-fluorescein scFv are equivalent terms.

In one embodiment, T lymphocytes (e.g., cytotoxic T lymphocytes) can be genetically engineered to express CAR constructs by transfecting a population of the T lymphocytes with an expression vector encoding the CAR construct. Suitable methods for preparing a transduced population of T lymphocytes expressing a selected CAR construct are well-known to the skilled artisan, and are described in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference.

In one embodiment, CAR T cells comprising a nucleic acid of SEQ ID NO:1, 3, 4, or 6 are provided. In another embodiment, CAR T cells comprising a polypeptide of SEQ ID NO:2, 5, or 7 are provided. In another illustrative aspect, a nucleic acid (e.g., an isolated nucleic acid) comprising SEQ ID NO:1, 3, 4, or 6 and encoding a chimeric antigen receptor is provided. In yet another embodiment, a chimeric antigen receptor polypeptide comprising SEQ ID NO:2, 5, or 7 is provided. In another embodiment, a vector is provided comprising SEQ ID NO:1, 3, 4 or 6. In another aspect, a lentiviral vector is provided comprising SEQ ID NO:1, 3, 4, or 6. In yet another embodiment, SEQ ID NO:2, 5, or 7 can comprise or consist of humanized, or human amino acid sequences.

In each of these embodiments, variant nucleic acid sequences or amino acid sequences having at least about 80%, at least about 90%, at least about 95%, at least about 97%, at least about 98%, at least about 99%, or at least about 99.5% sequence identity to SEQ ID NOS: 1 to 7 are contemplated. In another embodiment, the nucleic acid sequence can be a variant nucleic acid sequence having at least about 80%, at least about 90%, at least about 95%, at least about 97%, at least about 98%, at least about 99%, or at least about 99.5% sequence identity to SEQ ID NO:1, 3, 4, or 6 as long as the variant sequence encodes a polypeptide of SEQ ID NO:2 (for SEQ ID NOS: 1 and 3), 5 (for SEQ ID NO:4), or 7 (for SEQ ID NO:6). In another embodiment, the nucleic acid sequence or the amino acid sequence can be a variant nucleic acid or amino acid sequence having at least about 80%, at least about 90%, at least about 95%, at least about 97%, at least about 98%, at least about 99%, or at least about 99.5% sequence identity to SEQ ID NO:1, 3, 4, or 6 along a stretch of 200 nucleic acids or, for SEQ ID NO:2, 5, or 7 along a stretch of 200 amino acids. In one embodiment, determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid or amino acid sequence of interest. Algorithms for database searching are typically based on the BLAST software (Altschul et al., 1990). In some embodiments, the percent identity can be determined along the full-length of the nucleic acid or amino acid sequence.

Also within the scope of the invention are nucleic acids complementary to the nucleic acids represented by SEQ ID NO:1, 3, 4, or 6 and those that hybridize to the nucleic acids represented by SEQ ID NO:1, 3, 4, or 6 or those that hybridize to their complements under highly stringent conditions. In accordance with the invention "highly stringent conditions" means hybridization at 65° C. in 5×SSPE and 50% formamide, and washing at 65° C. in 0.5×SSPE. Conditions for high stringency, low stringency and moderately stringent hybridization are described in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference. In some illustrative aspects, hybridization occurs along the full-length of the nucleic acid.

In one embodiment, the T lymphocytes (e.g., cytotoxic T lymphocytes used to prepare CAR T cells), used in the methods described herein, can be autologous cells, although heterologous cells can also be used, such as when the patient being treated has received high-dose chemotherapy or radiation treatment to destroy the patient's immune system. In one embodiment, allogenic cells can be used.

In one aspect, the T lymphocytes can be obtained from a patient by means well-known in the art. For example, T cells (e.g., cytotoxic T cells) can be obtained by collecting peripheral blood from the patient, subjecting the blood to Ficoll density gradient centrifugation, and then using a negative T cell isolation kit (such as EasySep™ T Cell Isolation Kit) to isolate a population of T cells from the peripheral blood. In one illustrative embodiment, the population of T lymphocytes (e.g., cytotoxic T cells) need not be pure and may contain other cells such as other types of T cells (in the case of cytotoxic T cells, for example), monocytes, macrophages, natural killer cells, and B cells. In one aspect, the population being collected can comprise at least about 90% of the selected cell type, at least about 91%, 92%, 93%, 94%, 95%, 96%, 97%, 98%, 99%, or 100% of the selected cell type.

In one embodiment, after the T lymphocytes (e.g., cytotoxic T cells used to prepare CAR T cells) are obtained, the cells are cultured under conditions that promote the activation of the cells. In this embodiment, the culture conditions may be such that the cells can be administered to a patient without concern for reactivity against components of the culture medium. For example, the culture conditions may not include bovine serum products, such as bovine serum albumin. In one illustrative aspect, the activation can be achieved by introducing known activators into the culture medium, such as anti-CD3 antibodies in the case of cytotoxic T cells. Other suitable activators include anti-CD28 antibodies. In one aspect, the population of lymphocytes can be cultured under conditions promoting activation for about 1 to about 4 days. In one embodiment, the appropriate level of activation can be determined by cell size, proliferation rate, or activation markers determined by flow cytometry.

In one illustrative embodiment, after the population of T lymphocytes (e.g., cytotoxic T lymphocytes used to prepare CAR T cells) has been cultured under conditions promoting activation, the cells can be transfected with an expression vector encoding a CAR. Suitable vectors and transfection methods for use in various embodiments are described above. In one aspect, after transfection, the cells can be immediately administered to the patient or the cells can be cultured for at least about 1, 2, 3, 4, 5, 6, 7, 8, 9, 10, 11, 12, 13, 14, 15, 16, 17, 18 or more days, or between about 5 and about 12 days, between about 6 and about 13 days, between about 7 and about 14 days, or between about 8 and about 15 days, for example, to allow time for the cells to recover from the transfection. In one aspect, suitable culture conditions can be similar to the conditions under which the cells were cultured for activation either with or without the agent that was used to promote activation.

Thus, as described above, in one illustrative aspect, the methods of treatment described herein can further comprise 1) obtaining a population of autologous or heterologous T lymphocytes (e.g., cytotoxic T lymphocytes used to prepare CAR T cells), 2) culturing the T lymphocytes under conditions that promote the activation of the cells, and 3) transfecting the lymphocytes with an expression vector encoding a CAR to form CAR T cells.

In one embodiment, culture media that lacks any animal products, such as bovine serum, can be used to culture the CAR T cells. In another embodiment, tissue culture conditions typically used by the skilled artisan to avoid contamination with bacteria, fungi and mycoplasma can be used. In an exemplary embodiment, prior to being administered to a patient, the cells (e.g., CAR T cells) are pelleted, washed, and are resuspended in a pharmaceutically acceptable carrier or diluent. Exemplary compositions comprising CAR-expressing T lymphocytes (e.g., cytotoxic T lymphocytes) include compositions comprising the cells in sterile 290 mOsm saline, in infusible cryomedia (containing Plasma-Lyte A, dextrose, sodium chloride injection, human serum albumin and DMSO), in 0.9% NaCl with 2% human serum albumin, or in any other sterile 290 mOsm infusible materials. Alternatively, in another embodiment, depending on the identity of the culture medium, the CAR T cells can be administered in the culture media as the composition, or concentrated and resuspended in the culture medium before administration. In various embodiments, the CAR T cell composition can be administered to the patient via any suitable means, such as parenteral administration, e.g., intradermally, subcutaneously, intramuscularly, intraperitoneally, intravenously, or intrathecally.

In one aspect, the total number of CAR T cells and the concentration of the cells in the composition administered to the patient will vary depending on a number of factors including the type of T lymphocytes (e.g., cytotoxic T lymphocytes) being used, the binding specificity of the CAR, the identity of the targeting moiety and the small molecule ligand, the identity of the cancer, the location of the cancer in the patient, the means used to administer the compositions to the patient, and the health, age and weight of the patient being treated. In various embodiments, suitable compositions comprising transduced CAR T cells include those having a volume of about 0.1 ml to about 200 ml and about 0.1 ml to about 125 ml.

In various embodiments, the transduced CAR T cells administered to the patient can comprise from about $1 \times 10^5$ to about $1 \times 10^{15}$ or $1 \times 10^6$ to about $1 \times 10^{15}$ transduced CAR T cells. In various embodiments about $1 \times 10^5$ to about $1 \times 10^{10}$, about $1 \times 10^6$ to about $1 \times 10^{10}$, about $1 \times 10^6$ to about $1 \times 10^9$, about $1 \times 10^6$ to about $1 \times 10^8$, about $1 \times 10^6$ to about $2 \times 10^7$, about $1 \times 10^6$ to about $3 \times 10^7$, about $1 \times 10^6$ to about $1.5 \times 10^7$, about $1 \times 10^6$ to about $1 \times 10^7$, about $1 \times 10^6$ to about $9 \times 10^6$, about $1 \times 10^6$ to about $8 \times 10^6$, about $1 \times 10^6$ to about $7 \times 10^6$, about $1 \times 10^6$ to about $6 \times 10^6$, about $1 \times 10^6$ to about $5 \times 10^6$, about $1 \times 10^6$ to about $4 \times 10^6$, about $1 \times 10^6$ to about $3 \times 10^6$, about $1 \times 10^6$ to about $2 \times 10^6$, about $2 \times 10^6$ to about $6 \times 10^6$, about $2 \times 10^6$ to about $5 \times 10^6$, about $3 \times 10^6$ to about $6 \times 10^6$, about $4 \times 10^6$ to about $6 \times 10^6$, about $4 \times 10^6$ to about $1 \times 10^7$, about $1 \times 10^6$ to about $1 \times 10^7$, about $1.5 \times 10^7$, about $1 \times 10^6$ to about $2 \times 10^7$, about $0.2 \times 10^6$ to about $1 \times 10^7$, about $0.2 \times 10^6$ to about $1.5 \times 10^7$, about $0.2 \times 10^6$ to about $2 \times 10^7$, about $0.2 \times 10^6$ to about $3 \times 10^7$, about $0.2 \times 10^6$ to about $4 \times 10^7$, about $0.2 \times 10^6$ to about $5 \times 10^7$, about $0.2 \times 10^5$ to about $1.5×10^6$, about $0.5×10^5$ to about $1.5×10^6$, about $0.2×10^5$ to about $1.4×10^6$, about $0.2×10^5$ to about $1.3×10^6$, about $0.5×10^5$ to about $1.3×10^6$, about $0.8×10^6$ to about $2×10^7$, about $0.8×10^6$ to about $1.5×10^7$, about $0.9×10^6$ to about $1.2×10^7$, or about $0.5×10^6$, $1×10^6$, $5×10^6$, $6×10^6$, $7×10^6$, $8×10^6$, $9×10^6$, $1×10^7$, $1.5×10^7$, $2×10^7$, $3×10^7$, $4×10^7$ or $5×10^7$ CAR T cells can be administered to the patient. These amounts can be per kg of patient body weight.

In other embodiments, the dose of the CAR T cells administered to the patient in the CAR T cell composition is selected from the group consisting of about 1 million, about 2 million, about 3 million, about 4 million, about 5 million, about 6 million, about 7 million, about 8 million, about 9 million, about 10 million, about 11 million, about 12 million, about 12.5 million, about 13 million, about 14 million, and about 15 million of the CAR T cells. These amounts can be per kg of patient body weight.

In any of the embodiments described in this paragraph, the CAR T cell dose can be in numbers of CAR T cells per kg of patient body weight. In one aspect, in any embodiment described herein, a single dose or multiple doses of the CAR T cells can be administered to the patient. In one illustrative embodiment, a first dose of the CAR T cells and a second dose of the CAR T cells can be administered to the patient. In one aspect, the first dose of the CAR T cells can be a test dose to monitor the patient for tolerability to the CAR T cells, and the second dose of the CAR T cells can comprise a higher dose of the CAR T cells than the first dose of the CAR T cells. In one embodiment, the first dose of the CAR T cells can comprise about $0.5×10^7$ of the CAR T cells to about $1.5×10^6$ of the CAR T cells. In another embodiment, the second dose of the CAR T cells can comprise about $0.8×10^6$ of the CAR T cells to about $2×10^7$ of the CAR T cells. In these embodiments involving a first and second dose of CAR T cells, any dose of CAR T cells described herein can be administered.

In any embodiment described herein, the CAR T cells can be administered before or after the compound, or the pharmaceutically acceptable salt thereof. As would be understood, the designations i), ii), and iii), etc. for steps of any method described herein do not indicate an order unless otherwise stated.

The compound, or pharmaceutically acceptable salt thereof, or CAR T cell composition described herein can be administered to the patient using any suitable method known in the art. As described herein, the term "administering" or "administered" includes all means of introducing the compound, or pharmaceutically acceptable salt thereof, or CAR T cell composition to the patient, including, but not limited to, oral, intravenous, intramuscular, subcutaneous, transdermal, and the like. In one aspect, the compound, or pharmaceutically acceptable salt thereof, described herein may be administered in a unit dosage form and/or formulations containing conventional nontoxic pharmaceutically acceptable carriers, adjuvants, and vehicles.

In one aspect, the compound, or pharmaceutically acceptable salt thereof, or CAR T cell composition as described herein may be administered directly into the blood stream, into muscle, or into an internal organ. In various embodiments, suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but they may be more suitably formulated as a sterile non-aqueous solution or as a dried form to be used in conjunction with a suitable vehicle such as sterile, pyrogen-free water or sterile saline. In other embodiments, any of the liquid formulations described herein may be adapted for parenteral administration as described herein.

The preparation under sterile conditions, by lyophilization to produce a sterile lyophilized powder for a parenteral formulation, may readily be accomplished using standard pharmaceutical techniques well-known to those skilled in the art. In one embodiment, the solubility of the compound, or pharmaceutically acceptable salt thereof, used in the preparation of a parenteral formulation may be increased by the use of appropriate formulation techniques, such as the incorporation of solubility-enhancing agents.

In one embodiment, the amount of the compound, or pharmaceutically acceptable salt thereof, to be administered to the patient can vary significantly depending on the cancer being treated, the route of administration of the compound, or pharmaceutically acceptable salt thereof, and the tissue distribution. In one aspect, the amount to be administered to a patient can be based on body surface area, mass, and physician assessment.

In various embodiments, the compound, or the pharmaceutically acceptable salt thereof, can be administered in 1) at least a first dose escalation sequence and a second dose escalation sequence, 2) at least a first dose escalation sequence, a second dose escalation sequence, and a third dose escalation sequence, 3) at least a first dose escalation sequence, a second dose escalation sequence, a third dose escalation sequence, and a fourth dose escalation sequence, 4) at least a first dose escalation sequence, a second dose escalation sequence, a third dose escalation sequence, a fourth dose escalation sequence, and a fifth dose escalation sequence, 5) at least a first dose escalation sequence, a second dose escalation sequence, a third dose escalation sequence, a fourth dose escalation sequence, a fifth dose escalation sequence, and a sixth dose escalation sequence, or 6) one or more additional dose escalation sequences can be included.

In various embodiments, for the first, second, third, fourth, fifth, or sixth, etc. dose escalation sequence, the amount of the compound, or the pharmaceutically acceptable salt thereof, to be administered to the patient can be about 0.1 µg/kg to about 2000 µg/kg, 0.1 µg/kg to about 1500 µg/kg, 0.1 µg/kg to about 1000 µg/kg, 0.1 µg/kg to about 500 µg/kg, about 0.1 µg/kg to about 100 µg/kg, about 0.1 µg/kg to about 80 µg/kg, about 0.1 µg/kg to about 70 µg/kg, about 0.1 µg/kg to about 50 µg/kg, about 0.1 µg/kg to about 40 µg/kg, about 0.1 µg/kg to about 30 µg/kg, about 0.3 µg/kg to about 500 µg/kg, about 0.3 µg/kg to about 400 µg/kg, about 0.3 µg/kg to about 300 µg/kg, about 0.3 µg/kg to about 200 µg/kg, about 0.3 µg/kg to about 100 µg/kg, about 0.3 µg/kg to about 90 µg/kg, about 0.1 µg/kg to about 400 µg/kg, about 0.1 µg/kg to about 350 µg/kg, about 0.1 µg/kg to about 300 µg/kg, about 0.1 µg/kg to about 250 µg/kg, about 0.1 µg/kg to about 200 µg/kg, about 0.1 µg/kg to about 150 µg/kg, or about 0.3 µg/kg to about 150 µg/kg, or 5 µg/kg to about 2000 µg/kg, 5 µg/kg to about 1500 µg/kg, 5 µg/kg to about 1000 µg/kg, 5 µg/kg to about 500 µg/kg, about 5 µg/kg to about 100 µg/kg, about 5 µg/kg to about 80 µg/kg, about 5 µg/kg to about 70 µg/kg, about 5 µg/kg to about 50 µg/kg, about 5 µg/kg to about 40 µg/kg, or about 5 µg/kg to about 30 µg/kg.

In another embodiment, for the first and fourth dose escalation sequences, the amount of the compound, or the pharmaceutically acceptable salt thereof, to be administered to the patient can be about 0.1 µg/kg to about 100 µg/kg, about 0.1 µg/kg to about 80 µg/kg, about 0.1 µg/kg to about 70 µg/kg, about 0.1 µg/kg to about 50 µg/kg, about 0.1 µg/kg to about 40 µg/kg, about 0.1 µg/kg to about 30 µg/kg, or about 0.3 µg/kg to about 30 µg/kg, about 5 µg/kg to about 100 µg/kg, about 5 µg/kg to about 80 µg/kg, about 5 µg/kg to about 70 µg/kg, about 5 µg/kg to about 50 µg/kg, about 5 µg/kg to about 40 µg/kg, about 5 µg/kg to about 30 µg/kg, or about 5 µg/kg to about 2000 µg/kg, or about 5 µg/kg to about 1500 µg/kg, or about 5 µg/kg to about 1000 µg/kg, or about 5 µg/kg to about 500 µg/kg. In another embodiment, for the second and fifth dose escalation sequences, the amount of the compound, or the pharmaceutically acceptable salt thereof, to be administered to the patient can be about 0.3 µg/kg to about 500 µg/kg, about 0.3 µg/kg to about 400 µg/kg, about 0.3 µg/kg to about 300 µg/kg, about 0.3 µg/kg to about 200 µg/kg, about 0.3 µg/kg to about 100 µg/kg, or about 0.3 µg/kg to about 90 µg/kg, or about 5 µg/kg to about 100 µg/kg, about 5 µg/kg to about 80 µg/kg, about 5 µg/kg to about 70 µg/kg, about 5 µg/kg to about 50 µg/kg, about 5 µg/kg to about 40 µg/kg, about 5 µg/kg to about 30 µg/kg, or about 5 µg/kg to about 2000 µg/kg, or about 5 µg/kg to about 1500 µg/kg, or about 5 µg/kg to about 1000 µg/kg, or about 5 µg/kg to about 500 µg/kg. In yet another embodiment, for the third and sixth dose escalation sequences, the amount of the compound, or the pharmaceutically acceptable salt thereof, to be administered to the patient can be 0.1 µg/kg to about 400 µg/kg, about 0.1 µg/kg to about 350 µg/kg, about 0.1 µg/kg to about 300 µg/kg, about 0.1 µg/kg to about 250 µg/kg, about 0.1 µg/kg to about 200 µg/kg, about 0.1 µg/kg to about 150 µg/kg, or about 0.3 µg/kg to about 150 µg/kg, or about 5 µg/kg to about 100 µg/kg, about 5 µg/kg to about 80 µg/kg, about 5 µg/kg to about 70 µg/kg, about 5 µg/kg to about 50 µg/kg, about 5 µg/kg to about 40 µg/kg, about 5 µg/kg to about 30 µg/kg, or about 5 µg/kg to about 2000 µg/kg, or about 5 µg/kg to about 1500 µg/kg, or about 5 µg/kg to about 1000 µg/kg, or about 5 µg/kg to about 500 µg/kg. In these embodiments, "kg" is kilograms of body weight of the patient.

In any of these embodiments, the range of amounts of the compound, or the pharmaceutically acceptable salt thereof, can be a range based on calculating percentages of a "full dose" of the compound, or the pharmaceutically acceptable salt thereof, wherein a "full dose" of the compound, or the pharmaceutically acceptable salt thereof, can be about 30 µg/kg, and wherein the percentages are about 1 percent to about 100 percent (see Sequence 1 in FIG. 1), about 1 percent to about 300 percent (see Sequence 2 in FIG. 1), and about 1 percent to about 500 percent (see Sequence 3 in FIG. 1) of the "full dose" of the compound, or the pharmaceutically acceptable salt thereof. In other embodiments, the percentages of the "full dose" of the compound, or the pharmaceutically acceptable salt thereof, administered in a dose escalation sequence can be about 1 percent, about 2 percent, about 3 percent, about 4 percent, about 5 percent, about 6 percent, about 7 percent, about 8 percent, about 9 percent, about 10 percent, about 20 percent, about 30 percent, about 40 percent, about 50 percent, about 60 percent, about 70 percent, about 80 percent, about 90 percent, about 100 percent, about 200 percent, about 300 percent, about 400 percent, or about 500 percent, and the amounts administered can be about 0.3 µg/kg, about 3 µg/kg, about 9 µg/kg, about 15 µg/kg, about 30 µg/kg, about 90 µg/kg, or about 150 µg/kg, respectively or about 17 percent, about 333 percent, about 1666 percent, or about 3333 percent, and the amounts administered can be about 5 µg/kg, about 100 µg/kg, about 500 µg/kg, or about 1000 µg/kg, respectively. In these embodiments, "kg" is kilograms of body weight of the patient.

In another embodiment, the percentages of the "full dose" of the compound, or the pharmaceutically acceptable salt thereof, administered in a dose escalation sequence can be about 1 percent, about 2 percent, and about 20 percent for the first dose escalation sequence, about 1 percent, about 6 percent, and about 60 percent for the second dose escalation sequence, and about 1 percent, about 10 percent, and about 100 percent for the third dose escalation sequence, and the "full dose" of the compound, or the pharmaceutically acceptable salt thereof, can be 500 nmoles/kg. In this embodiment, "kg" is kilograms of body weight of the patient. In this embodiment, the compound, or the pharmaceutically acceptable salt thereof, can be administered on Monday, Thursday, and Monday with about 6 days between each dose escalation cycle.

In another embodiment, the percentages of the "full dose" of the compound, or the pharmaceutically acceptable salt thereof, administered in a dose escalation sequence can be about 1 percent, about 10 percent, and about 100 percent for the first dose escalation sequence, and about 1 percent, about 20 percent, and about 200 percent for the second dose escalation sequence, and the "full dose" of the compound, or the pharmaceutically acceptable salt thereof, can be 500 nmoles/kg. In this embodiment, "kg" is kilograms of body weight of the patient. In this embodiment, the compound, or the pharmaceutically acceptable salt thereof, can be administered on Monday, Thursday, and Monday with about 6 days between each dose escalation cycle.

In another embodiment, the percentages of the "full dose" of the compound, or the pharmaceutically acceptable salt thereof, administered in a dose escalation sequence can be about 1 percent, about 10 percent, and about 100 percent for the first dose escalation sequence, and about 1 percent, about 10 percent, and about 100 percent for the second dose escalation sequence, and the "full dose" of the compound, or the pharmaceutically acceptable salt thereof, can be 500 nmoles/kg. In this embodiment, "kg" is kilograms of body weight of the patient. In this embodiment, the compound, or the pharmaceutically acceptable salt thereof, can be administered on Monday, Thursday, and Monday with about 6 days between each dose escalation cycle. In another embodiment, the compound, or the pharmaceutically acceptable salt thereof, can be administered on Monday, Thursday, and Monday with about 9 days between each dose escalation cycle. In other embodiments, the dose escalations can be repeated one, two, three, four, five, six, seven, eight, nine, or ten times or any appropriate number of times.

In yet another embodiment, the percentages of the "full dose" of the compound, or the pharmaceutically acceptable salt thereof, administered in a dose escalation sequence can be about 1 percent, about 20 percent, and about 200 percent for the first dose escalation sequence, and about 1 percent, about 20 percent, and about 200 percent for the second escalation sequence, and the "full dose" of the compound, or the pharmaceutically acceptable salt thereof, can be 500 nmoles/kg. In this embodiment, "kg" is kilograms of body weight of the patient. In this embodiment, the compound, or the pharmaceutically acceptable salt thereof, can be administered on Monday, Thursday, and Monday with about 6 days between each dose escalation cycle. In other embodiments, the dose escalations can be repeated one, two, three, four, five, six, seven, eight, nine, or ten times or any appropriate number of times.

In another embodiment, the percentages of the "full dose" of the compound, or the pharmaceutically acceptable salt thereof, administered in the first or fourth dose escalation sequence can be about 1 percent, about 10 percent, and about 100 percent of the "full dose" of the compound, or the pharmaceutically acceptable salt thereof, (about 10 to about 50, about 20 to about 40, about 25 to about 35, or about 30 μg/kg) in escalating amounts, and the amounts of the compound, or the pharmaceutically acceptable salt thereof, administered can be about 0.3 μg/kg, about 3 μg/kg, and about 30 μg/kg, respectively. In yet another embodiment, the percentages of the "full dose" of the compound, or the pharmaceutically acceptable salt thereof, administered in the second or fifth dose escalation sequence can be about 1 percent, about 30 percent, and about 300 percent of the "full dose" of the compound, or the pharmaceutically acceptable salt thereof, (about 10 to about 50, about 20 to about 40, about 25 to about 35, or about 30 μg/kg) in escalating amounts, and the amounts of the compound, or the pharmaceutically acceptable salt thereof, administered can be about 0.3 μg/kg, about 9 μg/kg, and about 90 μg/kg, respectively. In still another embodiment, the percentages of the "full dose" of the compound, or the pharmaceutically acceptable salt thereof, administered in the third or sixth dose escalation sequence can be about 1 percent, about 50 percent, and about 500 percent of the "full dose" of the compound, or the pharmaceutically acceptable salt thereof, (about 10 to about 50, about 20 to about 40, about 25 to about 35, or about 30 μg/kg) in escalating amounts, and the amounts of the compound, or the pharmaceutically acceptable salt thereof, administered can be about 0.3 μg/kg, about 15 μg/kg, and about 150 μg/kg, respectively. In these embodiments, "kg" is kilograms of body weight of the patient.

In various other embodiments, amounts to be administered to the patient can range, for example, from about 0.05 mg to about 30 mg, 0.05 mg to about 25.0 mg, about 0.05 mg to about 20.0 mg, about 0.05 mg to about 15.0 mg, about 0.05 mg to about 10.0 mg, about 0.05 mg to about 9.0 mg, about 0.05 mg to about 8.0 mg, about 0.05 mg to about 7.0 mg, about 0.05 mg to about 6.0 mg, about 0.05 mg to about 5.0 mg, about 0.05 mg to about 4.0 mg, about 0.05 mg to about 3.0 mg, about 0.05 mg to about 2.0 mg, about 0.05 mg to about 1.0 mg, about 0.05 mg to about 0.5 mg, about 0.05 mg to about 0.4 mg, about 0.05 mg to about 0.3 mg, about 0.05 mg to about 0.2 mg, about 0.05 mg to about 0.1 mg, about 0.01 mg to about 2 mg, about 0.3 mg to about 10 mg, about 0.1 mg to about 20 mg, or about 0.8 to about 3 mg.

In other embodiments, the dose of the compound, or pharmaceutically acceptable salt thereof, can range, for example, from about 50 nmoles/kg to about 3000 nmoles/kg of patient body weight, about 50 nmoles/kg to about 2000 nmoles/kg, about 50 nmoles/kg to about 1000 nmoles/kg, about 50 nmoles/kg to about 900 nmoles/kg, about 50 nmoles/kg to about 800 nmoles/kg, about 50 nmoles/kg to about 700 nmoles/kg, about 50 nmoles/kg to about 600 nmoles/kg, about 50 nmoles/kg to about 500 nmoles/kg, about 50 nmoles/kg to about 400 nmoles/kg, about 50 nmoles/kg to about 300 nmoles/kg, about 50 nmoles/kg to about 200 nmoles/kg, about 50 nmoles/kg to about 100 nmoles/kg, about 100 nmoles/kg to about 300 nmoles/kg, about 100 nmoles/kg to about 500 nmoles/kg, about 100 nmoles/kg to about 1000 nmoles/kg, about 100 nmoles/kg to about 2000 nmoles/kg of patient body weight. In other embodiments, the dose may be about 1 nmoles/kg, about 5 nmoles/kg, about 10 nmoles/kg, about 20 nmoles kg, about 25 nmoles/kg, about 30 nmoles/kg, about 40 nmoles/kg, about 50 nmoles/kg, about 60 nmoles/kg, about 70 nmoles/kg, about 80 nmoles/kg, about 90 nmoles/kg, about 100 nmoles/kg, about 150 nmoles/kg, about 200 nmoles/kg, about 250 nmoles/kg, about 300 nmoles/kg, about 350 nmoles/kg, about 400 nmoles/kg, about 450 nmoles/kg, about 500 nmoles/kg, about 600 nmoles/kg, about 700 nmoles/kg, about 800 nmoles/kg, about 900 nmoles/kg, about 1000 nmoles/kg, about 2000 nmoles/kg, about 2500 nmoles/kg or about 3000 nmoles/kg of body weight of the patient. In yet other embodiments, the dose may be about 0.1 nmoles/kg, about 0.2 nmoles/kg, about 0.3 nmoles/kg, about 0.4 nmoles kg, or about 0.5 nmoles/kg, about 0.1 nmoles/kg to about 1000 nmoles/kg, about 0.1 nmoles/kg to about 900 nmoles/kg, about 0.1 nmoles/kg to about 850 nmoles/kg, about 0.1 nmoles/kg to about 800 nmoles/kg, about 0.1 nmoles/kg to about 700 nmoles/kg, about 0.1 nmoles/kg to about 600 nmoles/kg, about 0.1 nmoles/kg to about 500 nmoles/kg, about 0.1 nmoles/kg to about 400 nmoles/kg, about 0.1 nmoles/kg to about 300 nmoles/kg, about 0.1 nmoles/kg to about 200 nmoles/kg, about 0.1 nmoles/kg to about 100 nmoles/kg, about 0.1 nmoles/kg to about 50 nmoles/kg, about 0.1 nmoles/kg to about 10 nmoles/kg, or about 0.1 nmoles/kg to about 1 nmoles/kg of body weight of the patient. In other embodiments, the dose may be about 0.3 nmoles/kg to about 1000 nmoles/kg, about 0.3 nmoles/kg to about 900 nmoles/kg, about 0.3 nmoles/kg to about 850 nmoles/kg, about 0.3 nmoles/kg to about 800 nmoles/kg, about 0.3 nmoles/kg to about 700 nmoles/kg, about 0.3 nmoles/kg to about 600 nmoles/kg, about 0.3 nmoles/kg to about 500 nmoles/kg, about 0.3 nmoles/kg to about 400 nmoles/kg, about 0.3 nmoles/kg to about 300 nmoles/kg, about 0.3 nmoles/kg to about 200 nmoles/kg, about 0.3 nmoles/kg to about 100 nmoles/kg, about 0.3 nmoles/kg to about 50 nmoles/kg, about 0.3 nmoles/kg to about 10 nmoles/kg, or about 0.3 nmoles/kg to about 1 nmoles/kg of body weight of the patient. In these embodiments, "kg" is kilograms of body weight of the patient.

In another embodiment, a first dose escalation step and a second dose escalation step with the compound (e.g., where each dose escalation step is 50 nmol/kg and then 500 nmol/kg), or a pharmaceutically acceptable salt thereof, are performed after administration of CAR-T cells (e.g., in any of the amounts described herein). In this embodiment, after the first and second dose escalation steps in, for example, weeks one and two, the level of the compound, or a pharmaceutically acceptable salt thereof, can be kept constant in week three relative to the last dose administered in week two (e.g., kept constant at 500 nmol/kg). In any embodiment described herein, the level of the compound, or a pharmaceutically acceptable salt thereof, can be kept constant in the succeeding week relative to the last dose administered in the prior week.

In various other embodiments, the dose of the compound, or the pharmaceutically acceptable salt thereof, may range from, for example, about 10 nmoles/kg to about 10000 nmoles/kg, from about 10 nmoles/kg to about 5000 nmoles/kg, from about 10 nmoles/kg to about 3000 nmoles/kg, about 10 nmoles/kg to about 2500 nmoles/kg, about 10 nmoles/kg to about 2000 nmoles/kg, about 10 nmoles/kg to about 1000 nmoles/kg, about 10 nmoles/kg to about 900 nmoles/kg, about 10 nmoles/kg to about 800 nmoles/kg, about 10 nmoles/kg to about 700 nmoles/kg, about 10 nmoles/kg to about 600 nmoles/kg, about 10 nmoles/kg to about 500 nmoles/kg, about 10 nmoles/kg to about 400 nmoles/kg, about 10 nmoles/kg to about 300 nmoles/kg, about 10 nmoles/kg to about 200 nmoles/kg, about 10 nmoles/kg to about 150 nmoles/kg, about 10 nmoles/kg to about 100 nmoles/kg, about 10 nmoles/kg to about 90 nmoles/kg, about 10 nmoles/kg to about 80 nmoles/kg, about 10 nmoles/kg to about 70 nmoles/kg, about 10 nmoles/kg to about 60 nmoles/kg, about 10 nmoles/kg to about 50 nmoles/kg, about 10 nmoles/kg to about 40 nmoles/kg, about 10 nmoles/kg to about 30 nmoles/kg, about 10 nmoles/kg to about 20 nmoles/kg, about 200 nmoles/kg to about 900 nmoles/kg, about 200 nmoles/kg to about 800 nmoles/kg, about 200 nmoles/kg to about 700 nmoles/kg, about 200 nmoles/kg to about 600 nmoles/kg, about 200 nmoles/kg to about 500 nmoles/kg, about 250 nmoles/kg to about 600 nmoles/kg, about 300 nmoles/kg to about 600 nmoles/kg, about 300 nmoles/kg to about 500 nmoles/kg, or about 400 nmoles/kg to about 600 nmoles/kg, of body weight of the patient. In these embodiments, "kg" is kilograms of body weight of the patient.

In all of the dose embodiments described above, the percentages of the "full dose" of the compound, or the pharmaceutically acceptable salt thereof, administered at any step in a dose escalation sequence can be about 1 percent, about 2 percent, about 3 percent, about 4 percent, about 5 percent, about 6 percent, about 7 percent, about 8 percent, about 9 percent, about 10 percent, about 20 percent, about 30 percent, about 40 percent, about 50 percent, about 60 percent, about 70 percent, about 80 percent, about 90 percent, about 100 percent, about 200 percent, about 300 percent, about 400 percent, or about 500 percent of the "full dose" of the compound, or the pharmaceutically acceptable salt thereof. The "full dose" of the compound, or the pharmaceutically acceptable salt thereof, can be any of the doses of the compound, or the pharmaceutically acceptable salt thereof, described in the preceding paragraphs as being doses administered in a dose escalation sequence.

In various other embodiments, the dose of the compound, or the pharmaceutically acceptable salt thereof, may range from, for example, about 1 nmoles/kg to about 10000 nmoles/kg, from about 1 nmoles/kg to about 5000 nmoles/kg, from about 1 nmoles/kg to about 3000 nmoles/kg, about 1 nmoles/kg to about 2500 nmoles/kg, about 1 nmoles/kg to about 2000 nmoles/kg, about 1 nmoles/kg to about 1000 nmoles/kg, about 1 nmoles/kg to about 900 nmoles/kg, about 1 nmoles/kg to about 800 nmoles/kg, about 1 nmoles/kg to about 700 nmoles/kg, about 1 nmoles/kg to about 600 nmoles/kg, about 1 nmoles/kg to about 500 nmoles/kg, about 1 nmoles/kg to about 400 nmoles/kg, about 1 nmoles/kg to about 300 nmoles/kg, about 1 nmoles/kg to about 200 nmoles/kg, about 1 nmoles/kg to about 150 nmoles/kg, about 1 nmoles/kg to about 100 nmoles/kg, about 1 nmoles/kg to about 90 nmoles/kg, about 1 nmoles/kg to about 80 nmoles/kg, about 1 nmoles/kg to about 70 nmoles/kg, about 1 nmoles/kg to about 60 nmoles/kg, about 1 nmoles/kg to about 50 nmoles/kg, about 1 nmoles/kg to about 40 nmoles/kg, about 1 nmoles/kg to about 30 nmoles/kg, or about 1 nmoles/kg to about 20 nmoles/kg, In these embodiments, "kg" is kilograms of body weight of the patient.

In another embodiment, from about 20 ug/kg of body weight of the patient to about 3 mg/kg of body weight of the patient of the compound, or the pharmaceutically acceptable salt thereof, can be administered to the patient. In another aspect, amounts can be from about 0.2 mg/kg of body weight of the patient to about 0.4 mg/kg of body weight of the patient.

In any of the above-described dose embodiments, a single dose or multiple doses of the compound, or pharmaceutically acceptable salt thereof, may be administered to the patient.

In one embodiment, the small molecule ligand linked to the targeting moiety can be administered to the patient before the CAR T cell composition. In another embodiment, the small molecule ligand linked to the targeting moiety can be administered to the patient at the same time as the CAR T cell composition, but in different formulations, or in the same formulation. In yet another embodiment, the small molecule ligand linked to the targeting moiety can be administered to the patient after the CAR T cell composition.

In one illustrative aspect, the timing between the administration of CAR T cells and the small molecule linked to the targeting moiety may vary widely depending on factors that include the type of CAR T cells being used, the binding specificity of the CAR, the identity of the targeting moiety and the small molecule ligand, the identity of the cancer, the location in the patient of the cancer, the means used to administer to the patient the CAR T cells and the small molecule ligand linked to the targeting moiety, and the health, age, and weight of the patient. In one aspect, the small molecule ligand linked to the targeting moiety can be administered before or after the CAR T cells, such as within about 3, 6, 9, 12, 15, 18, 21, 24, 27, 30, 33, 36, 39, 42, 45, 48, or 51 hours, or within about 0.5, 1, 1.5, 2, 2.5, 3, 4 5, 6, 7, 8, 9, 10 or more days.

In one embodiment, any applicable dosing schedule known in the art can be used for administration of the compound, or the pharmaceutically acceptable salt thereof, or for the CAR T cell composition. In one aspect, the dosing schedule selected for the compound, or the pharmaceutically acceptable salt thereof, and the CAR T cell composition can take into consideration the concentration of the compound, or the pharmaceutically acceptable salt thereof, and the number of CAR T cells administered, to regulate the cytotoxicity of the CAR T cell composition and to control CRS.

In one exemplary embodiment, the first dose escalation sequence, the second dose escalation sequence, the third dose escalation sequence, the fourth dose escalation sequence, the fifth dose escalation sequence, the sixth dose escalation sequence, or any additional dose escalation sequence can be followed by a period of time during which the compound, or the pharmaceutically acceptable salt thereof, is not administered. In various illustrative embodiments, the period of time that the compound, or the pharmaceutically acceptable salt thereof, is not administered can be 1, 2, 3, 4, 5, 6, 7, 8, 9, or 10 days. In another embodiment, the period of time that the compound, or the pharmaceutically acceptable salt thereof, is not administered can be 6, 7, or 8 days. In yet another embodiment, the period of time that the compound, or the pharmaceutically acceptable salt thereof, is not administered can be 7 days.

In one aspect, a first dose of the CAR T cells and a second dose of the CAR T cells are administered to the patient during week 1, for example, on Monday and Thursday. In this embodiment, the first dose escalation sequence for the compound, or the pharmaceutically acceptable salt thereof, can then occur during weeks 2 and 3. For example, the compound, or the pharmaceutically acceptable salt thereof, can be administered on three separate days and the three separate days can be Monday and Thursday of week 2 and Monday of week 3 (see Sequence 1 in FIG. 1). In this embodiment, the second dose escalation sequence for the compound, or the pharmaceutically acceptable salt thereof, can then occur during weeks 4 and 5 (see Sequence 2 in FIG.

1). For example, the compound, or the pharmaceutically acceptable salt thereof, can be administered on three separate days and the three separate days can be Monday and Thursday of week 4 and Monday of week 5. In this embodiment, the third dose escalation sequence for the compound, or the pharmaceutically acceptable salt thereof, can then occur during weeks 6 and 7 (see Sequence 3 in FIG. 1). For example, the compound, or the pharmaceutically acceptable salt thereof, can be administered on three separate days and the three separate days can be Monday and Thursday of week 6 and Monday of week 7. In other embodiments, subsequent dose escalation sequences can follow a similar sequence, or Sequence 3 can be repeated about 7 days after Sequence 3 ends as "Course 2" and no additional treatments with the compound, or the pharmaceutically acceptable salt thereof, occur until the beginning of "Course 3" (the length of "Course 2" being based on the length of time shown in FIG. 1 for "Course" 1). In one embodiment, the patient can receive four Courses of therapy.

In another illustrative embodiment, a method of treatment of a cancer is provided. The method comprises i) administering to a patient at least one dose of a CAR T cell composition comprising CAR T cells wherein the CAR T cells comprise a CAR directed to a targeting moiety, ii) administering to the patient a compound, or a pharmaceutically acceptable salt thereof, wherein the compound comprises a small molecule ligand linked to a targeting moiety by a linker and wherein the compound, or the pharmaceutically acceptable salt thereof, is administered in a first dose escalation sequence wherein, if serious CRS occurs in the first dose escalation sequence, the compound, or the pharmaceutically acceptable salt thereof, is administered using a lower dose escalation sequence wherein the first dose of the compound, or the pharmaceutically acceptable salt thereof, in the lower dose escalation sequence is lower than the first dose of the compound, or the pharmaceutically acceptable salt thereof, administered in the first dose escalation sequence. In this embodiment, in the lower dose escalation sequence, the compound, or the pharmaceutically acceptable salt thereof, is administered at about 0.5 percent, about 5 percent, and about 50 percent of a full dose of the compound, or the pharmaceutically acceptable salt thereof, on three separate days. In this embodiment, the full dose of the compound, or the pharmaceutically acceptable salt thereof, can be about 10 µg/kg to about 50 µg/kg, about 20 µg/kg to about 40 µg/kg, about 25 µg/kg to about 35 µg/kg, or about 30 µg/kg. In these embodiments, "kg" is kilograms of body weight of the patient.

In various related embodiments, lymphocytes can be depleted in the patient before administration of the CAR T cell composition to the patient using, for example, cytoxan, fludarabine, and/or etopside, and the method can further comprise additional steps including, but not limited to, administering platelets to the patient, administering packed red blood cells to the patient, administering cryoprecipitate to the patient, administering intravenous immunoglobulin to the patient, treating with calcium supplements, acid-citrate-dextrose, and/or heparin, and/or providing antimicrobial therapy to the patient. In one embodiment, lymphodepletion occurs at least about 24 hours prior to CAR T cell administration.

In another aspect, the method can comprise CRS monitoring steps. In one illustrative aspect, if no CRS or neurotoxicity is observed in the patient during the first dose escalation sequence, the method can be advanced to the second dose escalation sequence. If no CRS or neurotoxicity is observed in the patient during the second dose escalation sequence, the method can be advanced to the third dose escalation sequence. If no CRS or neurotoxicity is observed in the patient during the third dose escalation sequence, the method can be advanced to the fourth dose escalation sequence. If no CRS or neurotoxicity is observed in the patient during the fourth dose escalation sequence, the method can be advanced to the fifth dose escalation sequence. If no CRS or neurotoxicity is observed in the patient during the fifth dose escalation sequence, the method can be advanced to the sixth dose escalation sequence, and so on.

In another illustrative embodiment, if fever without hypotension (i.e., non-serious CRS) is observed in the patient and no neurotoxicity is observed in the patient during any one of the dose escalation sequences, all subsequent doses of the compound, or the pharmaceutically acceptable salt thereof, can be administered to the patient at the dose escalation sequence level that caused the fever without hypotension. In another aspect, if CRS (i.e., serious CRS) or neurotoxicity occurs in the patient in any dose escalation sequence, all subsequent doses of the compound, or the pharmaceutically acceptable salt thereof, can be administered to the patient at the dose escalation sequence level below the dose escalation sequence level that caused the serious CRS or neurotoxicity in the patient.

In one aspect serious CRS may include any toxicity requiring the use of cetuximab, any ≥grade 3 autoimmune toxicity, any ≥grade 3 toxicity that may be attributed to CAR T cell administration or administration of the compound, or the pharmaceutically acceptable salt thereof, and that occurs within 28 days following initiation of treatment except ≤grade 4 fever lasting for less than 48 hours after initiation of treatment, ≤grade 3 chills lasting for less than 24 hours after initiation of treatment, ≤grade 3 cough lasting for less than 24 hours after initiation of treatment, ≤grade 3 transaminases lasting for less than 7 days after initiation of treatment, ≤grade 3 hypotension lasting for less than 48 hours after initiation of treatment, ≤grade 3 CRS lasting for less than 48 hours after initiation of treatment, ≤grade 3 anaphylaxis related to DMSO resolvable with Benadryl and/or epinephrine, or ≤grade 3 pain controlled with oral or IV narcotic therapy, or, in addition, except for toxicities occurring about 3 weeks after the CAR T cell infusion including ≤grade 3 chills lasting up to 5 days, ≤grade 3 transaminases lasting up to 2 weeks, ≤grade 3 CRS lasting up to 2 weeks, ≤grade 4 lymphopenia, ≤grade 4 leukopenia, or ≤grade 3 pain lasting for up to 2 weeks controlled with oral or IV narcotic therapy.

In one embodiment, to prevent or inhibit CRS in the patient, the method can further comprise the step of administering to the patient a folate, a conjugate comprising a folate wherein the conjugate comprising a folate does not comprise a targeting moiety, or a drug that inhibits activation of the CAR T cells. In this embodiment, any of a folate, a conjugate comprising a folate wherein the conjugate comprising a folate does not comprise a targeting moiety, or a drug that inhibits activation of the CAR T cells can be referred to herein as "a rescue agent". In one embodiment, a folate, such as folic acid, can be administered to prevent or inhibit CRS in the patient. In this embodiment, the folate inhibits interaction of the bridge (i.e., the small molecule ligand linked to the targeting moiety by a linker) with the receptors for the bridge on the tumor inhibiting tumor lysis and preventing or inhibiting CRS in the patient.

In one embodiment, the folate administered as an inhibitor of binding of the bridge to the tumor can be, for example, folic acid, a folic acid analog, or another folate receptor-binding molecule. In various embodiments, analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In another embodiment, the folate administered as an inhibitor of binding of the bridge to the tumor has the formula

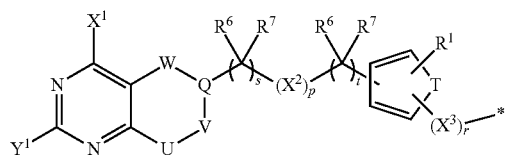

wherein $X^1$ and $Y^1$ are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;

$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

In yet another embodiment, a conjugate comprising a folate can be administered to prevent or inhibit cytokine release syndrome (CRS) in the patient. CRS can cause detrimental effects to the patient, including, but not limited to weight loss, high fever, pulmonary edema, and a dangerous drop in blood pressure.

In this embodiment, the conjugate comprising a folate does not comprise a targeting moiety, and, thus, the conjugate inhibits interaction of the bridge with the tumor to prevent tumor lysis and reduce CRS in the patient. In this embodiment, the folate moiety in the conjugate comprising a folate can comprise any of the folates described in the preceding paragraphs linked to a chemical moiety that does not comprise a targeting moiety. In one aspect, the conjugate comprising a folate can comprise a folate linked to one or more amino acids that do not comprise a targeting moiety. Illustratively, the conjugate comprising a folate can have the formula

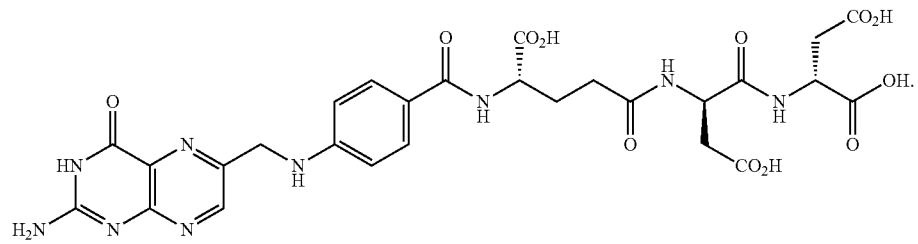 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

This compound can also be referred to as "EC923". In these embodiments, the folate or the conjugate comprising a folate can be administered to the patient in molar excess relative to the bridge (i.e., the small molecule ligand linked to a targeting moiety by a linker), such as a 10-fold excess, a 100-fold excess, a 200-fold excess a 300-fold excess a 400-fold excess a 500-fold excess a 600-fold excess a 700-fold excess a 800-fold excess a 900-fold excess, a 1000-fold excess, or a 10,000-fold excess of the folate or the conjugate comprising a folate relative to the small molecule ligand linked to a targeting moiety by a linker. The amount of the folate or the conjugate comprising a folate relative to the amount of the small molecule ligand linked to a targeting moiety by a linker needed to inhibit interaction of the bridge with the tumor can be determined by the skilled artisan.

In another embodiment, an agent that inhibits activation of the CAR T cells can be administered to the patient to inhibit CAR T cell activation and to inhibit or prevent CRS in the patient. In one aspect the agent can be selected from the group consisting of a lymphocyte-specific protein tyrosine kinase inhibitor (e.g., Dasatinib), a PI3 kinase inhibitor (e.g., GDC0980), Tociluzumab, an inhibitor of an IL-2 inducible T cell kinase (e.g., BMS-509744), JAK inhibitors, BTK inhibitors, SIP agonists (e.g. Siponimod and Ozanimod), and an agent that blocks CAR T cell binding to the bridge, but does not bind to the cancer (e.g., fluoresceinamine, FITC, or sodium fluorescein). It is understood by the skilled artisan that FITC (i.e., fluorescein) can be in the form of a salt (e.g., sodium fluorescein), or in its unsalted form, under physiological conditions or, for example, in a buffer at physiological pH. Accordingly, in one embodiment, when fluorescein is administered to a patient it may be in equilibrium between its salted form (e.g., sodium fluorescein) and its unsalted form. In another embodiment, a rescue agent that inhibits activation of CAR T cells can be a compound of the formula 30-fold excess, about a 40-fold excess, about a 50-fold excess, about a 60-fold excess, about a 70-fold excess, about a 80-fold excess, about a 90-fold excess, about a 100-fold excess, about a 200-fold excess, about a 300-fold excess, about a 400-fold excess, about a 500-fold excess, about a 600-fold excess, about a 700-fold excess, about a 800-fold excess, about a 900-fold excess, about a 1000-fold excess, or about a 10,000-fold excess of the rescue agent relative to the small molecule ligand linked to a targeting moiety by a linker. The amount of the rescue agent relative to the amount of the small molecule ligand linked to a targeting moiety by a linker needed to inhibit interaction of the compound, or its pharmaceutically acceptable salt, with the tumor and/or the CAR T cells can be determined by the skilled artisan.

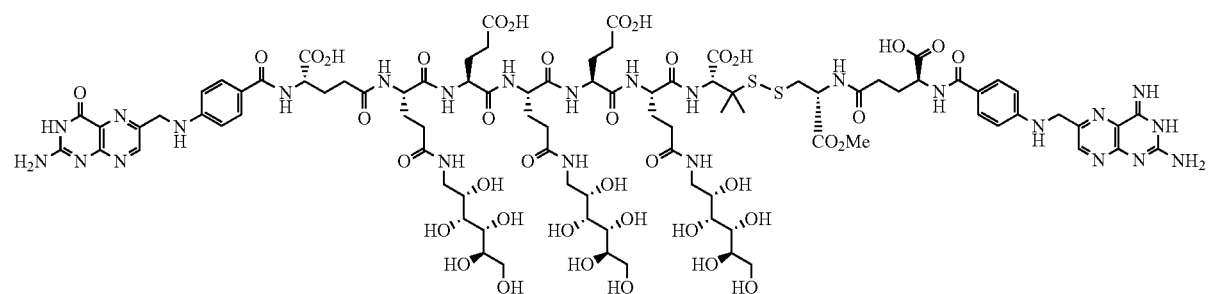 [SMILES: COC(=O)[C@H](CSSC(C)(C)[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c1ccc(NCc2cnc3nc(N)[nH]c(=O)c3n2)cc1)C(=O)O)C(=O)O)NC(=O)CC[C@H](NC(=O)c1ccc(NCc2cnc3nc(N)[nH]c(=N)c3n2)cc1)C(=O)O]

This compound can also be referred to as "EC2319".

In various embodiments, the rescue agent can be administered at a concentration of from about 0.001 nM to about 100 mM, about 0.01 nM to about 100 mM, about 1 nM to about 100 mM, about 10 nM to about 100 mM, about 50 nM to about 100 mM, or from about 100 nM to about 100 mM in any appropriate volume, including, for example, 0.1 ml, 0.2 ml, 0.3 ml, 0.4 ml, 0.5 ml, 0.6 ml, 0.7 ml, 0.8 ml, 0.9 ml, 1 ml, 2 ml, 3 ml, 4 ml, 5 ml, 10 ml, 100 ml, or 1000 ml. In other embodiments, the rescue agent can be administered at a dose of about 0.01 to about 300 umoles/kg of body weight of the patient, about 0.06 to about 100 umoles/kg of body weight of the patient, about 0.06 to about 90 umoles/kg of body weight of the patient, about 0.06 to about 80 umoles/kg of body weight of the patient, about 0.06 to about 70 umoles/kg of body weight of the patient, about 0.06 to about 60 umoles/kg of body weight of the patient, about 0.06 to about 50 umoles/kg of body weight of the patient, about 0.06 to about 40 umoles/kg of body weight of the patient, about 0.06 to about 30 umoles/kg of body weight of the patient, about 0.06 to about 20 umoles/kg of body weight of the patient, about 0.06 to about 10 umoles/kg of body weight of the patient, about 0.06 to about 8 umoles/kg of body weight of the patient, or about 0.06 to about 6 umoles/kg of body weight of the patient.

In these embodiments, the rescue agent can be administered to the patient in molar excess relative to the compound, or its pharmaceutically acceptable salt (i.e., the small molecule ligand linked to a targeting moiety by a linker), such as about a 10-fold excess, about a 20-fold excess, about a In another embodiment, more than one dose can be administered to the patient of the folate, the conjugate comprising a folate wherein the conjugate comprising a folate does not comprise a targeting moiety, or the agent that inhibits activation of the CAR T cells.

In the 'rescue agent' embodiments described herein, the folate, the conjugate comprising a folate wherein the conjugate comprising a folate does not comprise a targeting moiety, or the agent that inhibits activation of the CAR T cells can be administered to the patient before and/or after the compound, or the pharmaceutically acceptable salt thereof. In another aspect, the compound, or the pharmaceutically acceptable salt thereof, can be administered before and subsequent to administration of the folate, the conjugate comprising a folate wherein the conjugate comprising a folate does not comprise a targeting moiety, or the agent that inhibits activation of the CAR T cells. In this embodiment, the subsequent administration of the compound, or the pharmaceutically acceptable salt thereof, can cause CAR T cell activation and an increase in cytokine levels in the patient.

In another embodiment, administration of the folate, the conjugate comprising a folate wherein the conjugate comprising a folate does not comprise a targeting moiety, or the agent that inhibits activation of the CAR T cells can cause reduction in cytokine levels in the patient. In another embodiment, the reduction in cytokine levels is a reduction to about the cytokine levels in an untreated patient. In other embodiments, the agent that inhibits activation of the CAR T cells is administered to the patient when the CRS grade reaches 1, 2, 3, or 4 or when the CRS grade reaches 3 or 4.

In any of the embodiments described herein where a folate is the ligand linked to the targeting moiety by a linker, the patient can be put on a folate deficient diet prior to treatment with the methods described herein, or the patient can be administered a folate in the diet. In the embodiment where the patient is administered folate, the dose can range, for example, from about 50 nmol/kg to about 3000 nmol/kg of patient body weight, about 50 nmol/kg to about 2000 nmol/kg, about 50 nmol/kg to about 1000 nmol/kg, about 50 nmol/kg to about 900 nmol/kg, about 50 nmol/kg to about 800 nmol/kg, about 50 nmol/kg to about 700 nmol/kg, about 50 nmol/kg to about 600 nmol/kg, about 50 nmol/kg to about 500 nmol/kg, about 50 nmol/kg to about 400 nmol/kg, about 50 nmol/kg to about 300 nmol/kg, about 50 nmol/kg to about 200 nmol/kg, about 50 nmol/kg to about 100 nmol/kg, about 100 nmol/kg to about 300 nmol/kg, about 100 nmol/kg to about 500 nmol/kg, about 100 nmol/kg to about 1000 nmol/kg, about 100 nmol/kg to about 2000 nmol/kg of patient body weight. In other embodiments, the dose may be about 100 nmol/kg, about 150 nmol/kg, about 200 nmol/kg, about 250 nmol/kg, about 300 nmol/kg, about 350 nmol/kg, about 400 nmol/kg, about 450 nmol/kg, about 500 nmol/kg, about 600 nmol/kg, about 700 nmol/kg, about 800 nmol/kg, about 900 nmol/kg, about 1000 nmol/kg, about 2000 nmol/kg, or about 3000 nmol/kg of patient body weight. In these embodiments, "kg" is kilograms of patient body weight. In one aspect, the folate can be administered, for example, daily, weekly, biweekly, three times a week, or using any suitable regimen for administration of the folate.

In various embodiments described herein, the CAR T cells can persist in elevated numbers of circulating CAR T cells for as long as about 10 days, as long as about 15 days, as long as about 20 days, as long as about 25 days, as long as about 30 days, as long as about 35 days, as long as about 40 days, as long as about 45 days, as long as about 50 days, as long as about 55 days, as long as about 60 days, as long as about 65 days, as long as about 70 days, as long as about 75 days, or as long as about 80 days post CAR T cell administration.

In various embodiments described herein, half-maximal effective concentrations ($EC_{50}$) for the compound, or the pharmaceutically acceptable salt thereof, can be about 1 pM to about 2 nM, about 1 pM to about 5 nM, about 1 pM to about 10 nM, about 1 pM to about 20 nM, about 1 pM to about 30 nM, about 1 pM to about 40 nM, about 1 pM to about 50 nM, about 1 pM to about 60 nM, about 1 pM to about 70 nM, about 1 pM to about 80 nM, about 1 pM to about 90 nM, about 1 pM to about 100 nM, about 1 pM to about 200 nM, about 1 pM to about 300 nM, about 1 pM to about 400 nM, about 1 pM to about 500 nM, about 1 pM to about 600 nM, about 1 pM to about 700 nM, about 1 pM to about 800 nM, about 1 pM to about 900 nM, about 1 nM, about 1 pM to about 900 pM, about 1 pM to about 800 pM, about 1 pM to about 700 pM, about 1 pM to about 600 pM, about 1 pM to about 500 pM, about 1 pM to about 400 pM, about 1 pM to about 300 pM, about 1 pM to about 200 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, or about 1 pM to about 5 pM.

In various embodiments described herein, the Kd for binding of the compound, or the pharmaceutically acceptable salt thereof, to the CAR T cells can be about 1 nM to about 100 nM, about 1 nM to about 200 nM, about 1 nM to about 300 nM, about 1 nM to about 400 nM, about 1 nM to about 500 nM, about 1 nM to about 600 nM, about 1 nM to about 700 nM, about 1 nM to about 800 nM, about 1 nM to about 900 nM, about 100 nM to about 500 nM, about 100 nM to about 400 nM, about 100 nM to about 300 nM, about 100 nM to about 200 nM, about 100 nM to about 150 nM, or about 130 nM.

In the various embodiments described herein, EGFRt-sorted or unsorted CAR T cells can be used. In another embodiment, a "clinical facsimile" batch of CAR T cells can be used with a low differentiation profile. In another embodiment, a "research batch" of CAR T cells can be used. The "clinical facsimile" batch (~39% EGFRt+) can comprise CD4+ subsets at about 66% $T_{SCM}$ and about 32% $T_{CM}$ and CD8 subsets at about 95% $T_{SCM}$ and about 3% $T_{CM}$. The research batch (~23% EGFRt+) can comprise CD4 subsets at about 32% $T_{SCM}$, about 53% $T_{CM}$, about 11% $T_{EM}$ and about 3.7% $T_{EFF}$ and CD8 subsets at about 44% $T_{SCM}$, about 0.28% $T_{CM}$, about 3.4% $T_{EM}$ and about 52% $T_{EFF}$.

In various illustrative embodiments described herein, the compound, or the pharmaceutically acceptable salt thereof, can be first administered to the patient about 1, about 2, about 3, about 4, about 5, about 6, about 7, about 8, about 9, or about 10 days before or after the CAR T cells, or on any appropriate day before or after the CAR T cells.

In one embodiment of the methods described herein, the cancer is imaged prior to administration to the patient of the compound, or the pharmaceutically acceptable salt thereof, or prior to administration of the CAR T cell composition to the patient. In one illustrative embodiment, imaging occurs by PET imaging. In other illustrative embodiments imaging occurs by MRI imaging or SPECT/CT imaging. The imaging method can be any suitable imaging method known in the art. In one embodiment, the imaging method can involve the use of the small molecule ligand described herein, but linked to an imaging agent suitable for the types of imaging described herein to determine if the patient is positive for folate receptor expression. In another embodiment, immunohistochemical analysis can be used for this purpose.

In any of the embodiments described herein, cytokine release resulting in off-target toxicity in the patient may not occur even though CAR T cell toxicity to the cancer occurs. In any embodiment described herein, off-target tissue toxicity may not occur in the patient even though CAR T cell toxicity to the cancer occurs. In any embodiment described herein, the cancer may comprise a tumor, and tumor size may be reduced in the patient, even though off-target toxicity does not occur. In any of the embodiments described herein, CRS can be reduced or prevented and the method can result in a decrease in tumor volume in the patient.

In any embodiment described herein, body weight loss due to CRS, and CAR T cell exhaustion can be reduced or prevented. In any embodiment described herein, the cancer can comprise a tumor and a complete response for the tumor may be obtained.

Example 1

Synthesis of FITC-Folate

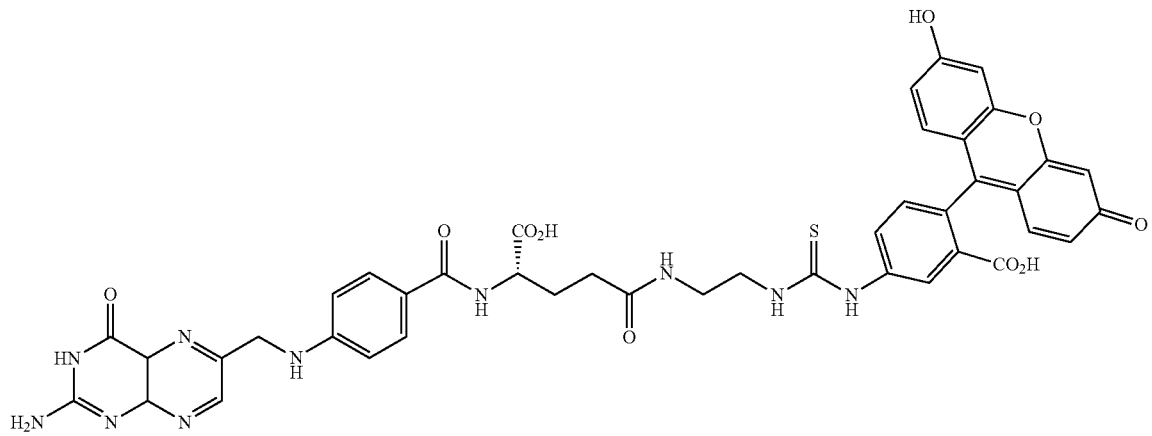 [SMILES: NC1=NC2N=CC(CNc3ccc(C(=O)N[C@@H](CCC(=O)NCCNC(=S)Nc4ccc(-c5c6ccc(=O)cc-6oc6cc(O)ccc56)c(C(=O)O)c4)C(=O)O)cc3)=NC2C(=O)N1]

Folate-γ-ethylenediamine was coupled to fluorescein isothiocyanate (FITC) isomer I (Sigma-Aldrich) in anhydrous dimethylsulfoxide (DMSO) in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, pH 7.4) and 1% acetonitrile (mobile phase B) and reaching 90% A and 10% B in 10 min at a flow rate of 20 mL/min. Under these conditions, the FITC-folate main peak typically eluted at 27-50 min. The quality of the FITC-folate fraction was monitored by analytical reverse-phase HPLC with a UV detector. Fractions with greater than 98.0% purity (LCMS) were lyophilized to obtain the final FITC-folate product. As known in the art, the compound with this structure is also referred to as EC17.

Example 2

Synthesis of FITC-PEG12-Folate

Universal polyethylene glycol (PEG) Nova Tag™ resin (0.2 g) was loaded into a peptide synthesis vessel and washed with isopropyl alcohol (i-PrOH) (3×10 mL) and dimethylformamide (DMF, 3×10 mL). 9-fluorenylmethoxycarbonyl (Fmoc) deprotection was carried out using 20% piperidine in DMF (3×10 mL). Kaiser tests were performed to assess reaction progress. To the vessel was then introduced a solution of Fmoc-L-glutamic acid 5-tert-butyl ester (Fmoc-Glu-(O-t-Bu)-OH) (23.5 mg) in DMF, N,N-diisopropylethylamine (i-Pr₂NEt) (4 equiv), and benzotriazol-1-yloxytripyrrolidinophosphonium hexafluorophosphate (PyBOP) (2 equiv). Fmoc deprotection was carried out using 20% piperidine in DMF (3×10 mL). To the vessel was then introduced a solution of $N^{10}$-TFA-Pte-OH (22.5 mg), DMF, i-Pr₂NEt (4 equiv), and PyBOP (2 equiv). Argon was bubbled for 2 h, and the resin was washed with DMF (3×3 mL) and i-PrOH (3×3 mL). After swelling the resin in dichloromethane (DCM), a solution of 1M hydroxybenzotriazole (HOBT) in DCM/trifluoroethane (TFE) (1:1) (2×3 mL) was added. Argon was bubbled for 1 h, the solvent was removed, and the resin was washed with DMF (3×3 mL) and i-PrOH (3×3 mL). After swelling the resin in DMF, a solution of Fmoc-NH-(PEG)₁₂-COOH (46.3 mg) in DMF, i-Pr₂NEt (4 equiv), and PyBOP (2 equiv) was added. Argon was bubbled for 2 h, and the resin was washed with DMF (3×3 mL) and i-PrOH (3×3 mL). Fmoc deprotection was carried out using 20% piperidine in DMF (3×10 mL).

Kaiser tests were performed to assess reaction progress. To the vessel was then introduced a solution of FITC (Life Technologies 21.4 mg) in DMF and i-Pr₂NEt (4 equiv), then

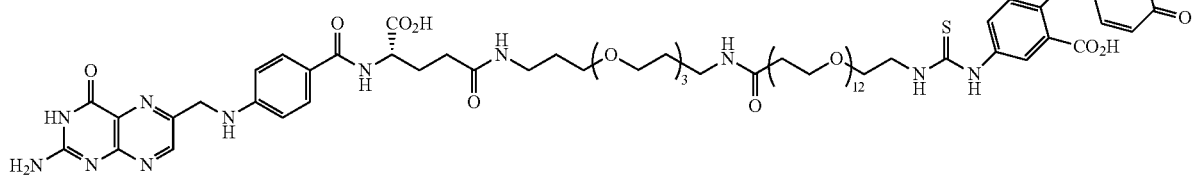

Argon was bubbled for 2 h, and the resin was washed with DMF (3×3 mL) and i-PrOH (3×3 mL). Then to the vessel was added 2% NH₂NH₂ in DMF (2×2 mL). The final compound was cleaved from the resin using a TFA:H₂O:triisopropylsilane (TIS) (95:2.5:2.5) (Cleavage Solution) and concentrated under vacuum. The concentrated product was precipitated in Et₂O and dried under vacuum. The crude product was purified using preparative RP-HPLC (mobile phase: A=10 mM ammonium acetate pH=7, B=ACN; method: 0% B to 30% B in 30 min at 13 mL/min). The pure fractions were pooled and freeze-dried, providing the FITC-PEG12-Folate.

Example 3

Synthesis of FITC-PEG20-Folate

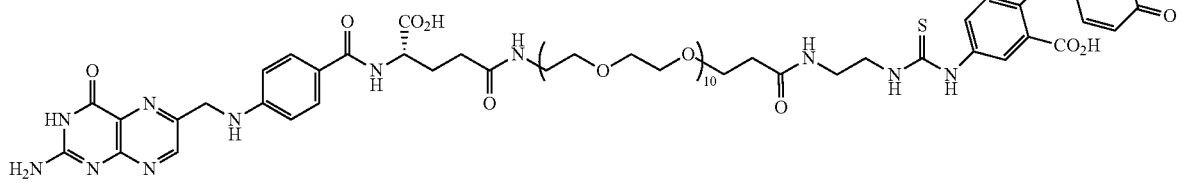

Ethylenediamine, polymer-bound (200-400 mesh)-resin (50 mg) was loaded into a peptide synthesis vessel and swollen with DCM (3 mL) followed by DMF (3 mL). To the vessel was then introduced the Fmoc-PEG$_{20}$-COOH solution (131 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete the reaction with Fmoc-Glu-OtBu (72 mg, 2.0 equiv) and Tfa·Pteroic-acid (41 mg, 1.2 equiv) coupling steps. The resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. The folate-peptide was cleaved from the resin using the Cleavage Solution. 10 mL of the cleavage mixture was introduced and argon was bubbled for 1.5 h. The cleavage mixture was drained into a clean flask. The resin was washed 3 times with more cleavage mixture. The combined mixture was concentrated under reduced pressure to a smaller volume (~5 mL) and precipitated in ethyl ether.

The precipitate was collected by centrifugation, washed with ethyl ether (3 times) and dried under high vacuum. The dried Folate-PEG$_{20}$-EDA (1.0 equiv) was treated with FITC (50 mg, 1.5 equiv) in DMSO and DIPEA at room temperature. Progress of the reaction monitored by LCMS. After 8 h the starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG20-Folate in 60% yield.

Example 4

Synthesis of FITC-PEG108-Folate

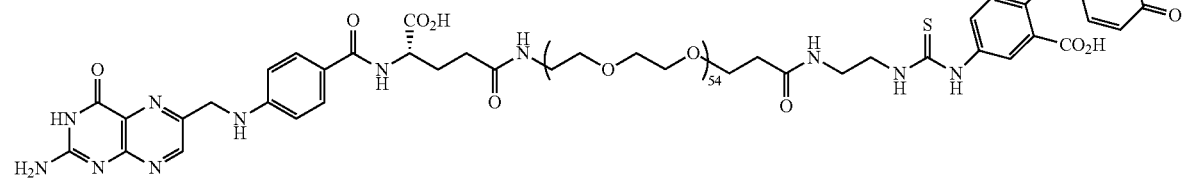

Ethylenediamine, polymer-bound (200-400 mesh)-resin (50 mg) was loaded in a peptide synthesis vessel and swollen with DCM (3 mL) followed by DMF (3 mL). To the vessel was then introduced the Fmoc-PEG$_{36}$-COOH solution (161 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete reaction with 2× Fmoc-PEG$_{36}$-COOH (161 mg, 1.0 equiv), Fmoc-Glu-OtBu (72 mg, 2.0 equiv) and Tfa·Pteroic-acid (41.0 mg, 1.2 equiv) coupling steps. At the end the resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. Folate-peptide was cleaved from the resin using the Cleavage Solution. 10 mL of the cleavage mixture was introduced and argon was bubbled for 1.5 h. The cleavage mixture was drained into a clean flask. The resin was washed 3× with more Cleavage Solution. The combined mixture was concentrated under reduced pressure to a smaller volume (~5 mL) and precipitated in ethyl ether.

The precipitate was collected by centrifugation, washed with ethyl ether (3×) and dried under high vacuum. The dried Folate-PEG$_{108}$-EDA (1.0 equiv) was treated with FITC (50 mg, 1.5 equiv) in DMSO and DIPEA at room temperature. Reaction progress was monitored by LCMS. After 10 h starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG108-Folate in 64% yield.

mL) and i-PrOH (3×3 mL). After swelling the resin in DCM, a solution of 1 M HOBt in DCM/TFE (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and the resin was washed with DMF (3×3 mL) and i-PrOH (3×3 mL). The above sequence was repeated for 2 more coupling steps for addition of 8-aminooctanoic acid and fluorescein isothiocyanate or rhodamine B isothiocyanate. The final compound was cleaved from the resin using the Cleavage Solution and concentrated under vacuum. The concentrated product was precipitated in diethyl ether and dried under vacuum. The crude product was purified using preparative RP-HPLC [λ=488 nm; solvent gradient: 1% B to 80% B in 25 min, 80% B wash 30 min run; A=10 mM NH$_4$OAc, pH=7; B=acetonitrile (ACN)]. ACN was removed under vacuum, and purified fractions were freeze-dried to yield FITC-DUPA as a brownish-orange solid. RP-HPLC: tR=8.0 min (A=10 mM NH4OAc, pH=7.0; B=ACN, solvent gradient: 1% B to 50% B in 10 min, 80% B wash 15 min run). $^1$H NMR (DMSO-d6/D$_2$O): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H), 6.61 (dd,

Example 5

Synthesis of FITC-DUPA

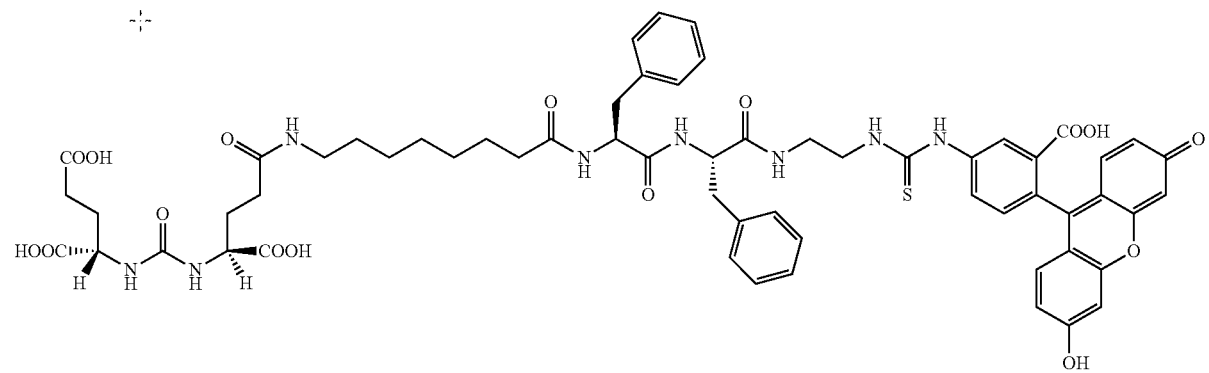 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

DUPA-FITC was synthesized by solid phase methodology as follows. Universal Nova Tag™ resin (50 mg, 0.53 mM) was swollen with DCM (3 mL) followed by DMF 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)-OH (1.5 equiv), HATU (2.5 equiv), and i-Pr$_2$NEt (4.0 equiv) in DMF was added. Argon was bubbled for 2 h, and resin was washed with DMF (3×3

J=5.3, 3.5 Hz, 2H); 6.64 (s, 2H); 7.05 (d, J=8.2 Hz, 2H), 7.19 (m, 5H); 7.76 (d, J=8.0 Hz, 1H); 8.38 (s, 1H). HRMS (ESI) (m/z): (M+H)$^+$ calcd for C$_{51}$H$_{59}$N$_7$O$_{15}$S, 1040.3712, found, 1040.3702. UV/vis: λ max=491 nm.

Example 6

Synthesis of FITC-PEG12-DUPA

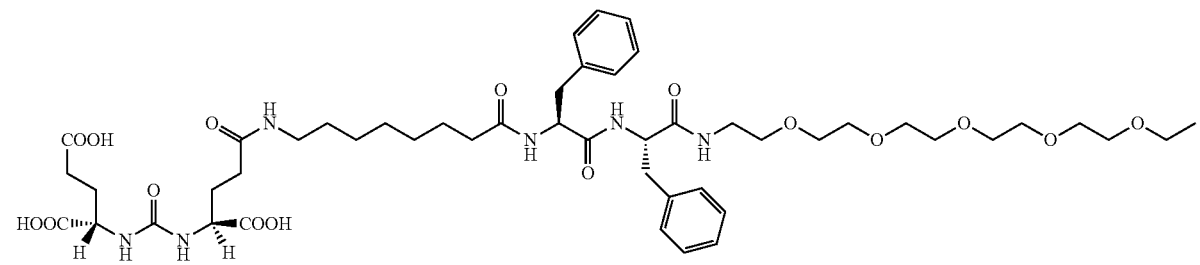

-continued

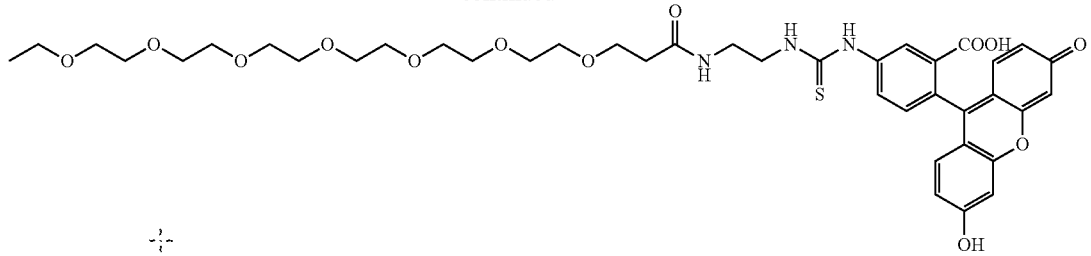

1,2-Diaminoethane trityl-resin (0.025 g) was loaded into a peptide synthesis vessel and washed with i-PrOH (3×10 mL), followed by DMF (3×10 mL). To the vessel was then introduced a solution of Fmoc-NH-(PEG)$_{12}$-COOH (42.8 mg) in DMF, i-Pr$_2$NEt (2.5 equiv), and PyBOP (2.5 equiv). The resulting solution was bubbled with Ar for 1 h, the coupling solution was drained, and the resin washed with DMF (3×10 mL) and i-PrOH (3×10 mL). Kaiser tests were performed to assess reaction progress. Fmoc deprotection was carried out using 20% piperidine in DMF (3×10 mL). This procedure was repeated to complete the all coupling steps (2×1.5 equiv of Fmoc-Phe-OH and 1.5 equiv of 8-aminooctanoic acid and 1.2 equiv of DUPA were used on each of their respective coupling steps). After the DUPA coupling, the resin was washed with DMF (3×10 mL) and i-PrOH (3×10 mL) and dried under reduced pressure. The peptide was cleaved from the resin in the peptide synthesis vessel using the Cleavage Solution. 15 mL of the Cleavage Solution was added to the peptide synthesis vessel, and the reaction was bubbled under Ar for 15 min. The resin was treated with two additional 10 mL quantities of the Cleavage Solution for 5 min each. The cleavage mixture was concentrated to about 5 mL and precipitated with ethyl ether. The precipitate was collected by centrifugation, washed with ethyl ether (3×), and dried under high vacuum, resulting in the recovery of crude material. To a stirred solution of the crude DUPA-(PEG)$_{12}$-EDA (10 mg) and FITC (5.6 mg) in dimethylsulfoxide (DMSO, 1 mL) was added i-Pr$_2$NEt (5 equiv) at room temperature and stirred for 6 h under argon. The reaction was monitored by LCMS and purified by preparative HPLC (mobile phase: A=10 mM ammonium acetate pH=7, B=ACN; method: 0% B to 50% B in 30 min at 13 mL/min). The purified fractions were pooled and freeze-dried, providing the FITC-PEG12-DUPA.

Example 7

Synthesis of FITC-PEG11-NK1 ene glycol (BocNH-PEG$_{11}$-NH$_2$) (Sigma, 0.0336 g, 0.0521 mmol, 1.2 eq.), Benzotriazol-1-yl-oxytripyrrolidinophosphonium hexafluorophosphate (PyBOP) (0.027 g, 0.0521 mmol, 1.2 eq.) in dry CH$_2$Cl$_2$ was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=220 nm, 254 nm). The pure fractions were collected, all organic solvents were evaporated and the sample was lyophilized for 48 h to provide the NK1-PEG$_{11}$-NHBoc. Yield: 40.13 mg (97%). To the NK1-PEG$_{11}$-NHBoc (0.0165 g, 0.015 mmol) in dry DCM was added trifluoroacetic acid (TFA, 20 eq.) and the reaction mixture was stirred for 4 h at r.t. The excess TFA was removed, and the remaining solution was diluted with water and extracted using CH$_2$C$_{12}$ (3×5 mL). The combined organic layers were washed with brine, dried (Na$_2$SO$_4$) and concentrated. The residue obtained was dried under vacuum and used for the next-step without further purification. A stirred solution of NK1-PEG$_{11}$-NH$_2$ (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added to diisopropylethyl amine (0.0028 mL, 0.0162 mmol, 2.0 eq.) at room temperature under argon. The reaction progress was monitored by LCMS and the product was purified by preparative RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=280 nm). The pure fractions were collected, all organic solvents were evaporated and the sample was lyophilized for 48 h to provide the FITC-PEG11-NK1 in a yield of 8.54 mg (77%).

*Note: The NK-1 compound was synthesized by a two-step procedure starting from the base ligand, which was prepared by using a procedure in the literature. (Ref: DESIGN AND DEVELOPMENT OF NEUROKI-

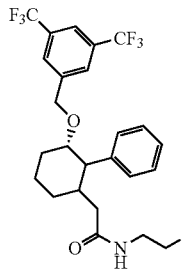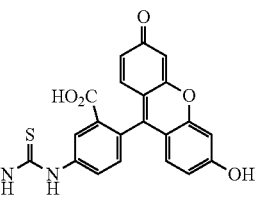

To a stirred solution of NK-1 (0.02 g, 0.0433 mmol, 1.0 eq.), O-(2-Aminoethyl)-O'-[2-(Boc-amino)ethyl]decaethyl- NIN-1 RECEPTOR-BINDING AGENT DELIVERY CONJUGATES, Application Number: PCT/US2015/44229; incorporated herein by reference.

Example 8

Synthesis of FITC-PEG2-CA9

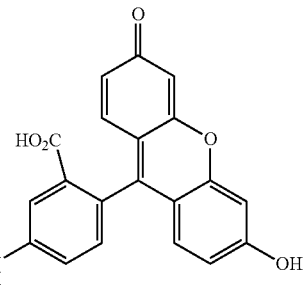
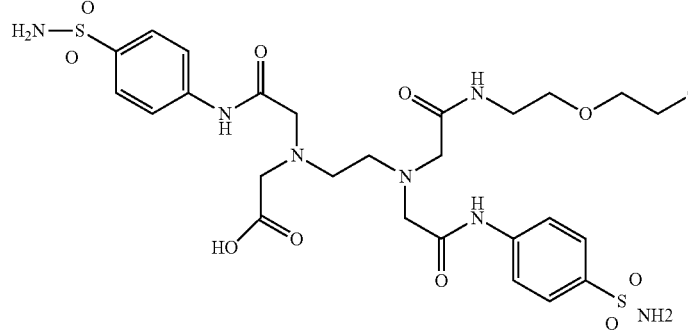

CA9 ligand (53.6 mg) was dissolved in DMF (2-3 mL) in a 50 mL round bottom flask using a Teflon magnetic stir bar. Ambient air was removed using a vacuum and replaced with nitrogen gas, this was done in three cycles. The round bottom flask was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 µL of Boc-PEG$_2$-NH$_2$ (Sigma Aldrich). 5.4 µL of triethylamine (TEA) was added and the reaction was stirred overnight. The reaction mixture was purified using HPLC and confirmed with UHPLC-MS (target m/z of 831). Acetonitrile was removed using high vacuum rotary evaporation and the product lyopholized. The compound was mixed with 1:1 TFA:DCM for 30 minutes. The TFA/DCM was removed using high vacuum rotary evaporation followed by 30 minutes on high vacuum. The compound was then dissolved in DMF and combined with 5 molar equivalents of i-Pr$_2$NEt, 16 mg of fluorescein isothiocyanate (Life Technologies) and stirred for 1 h. The reaction mixture was purified by HPLC and the target compound was confirmed with UHPLC-MS (target m/z of 1120). The samples were lyophilized and stored at −20° C.

Example 9

T Cell Preparation

Human peripheral blood mononuclear cells (PBMCs) were isolated from whole blood of healthy donors by using Ficoll density gradient centrifugation (GE Healthcare Lifesciences). T cells were then isolated from PBMCs by using an EasySep™ Human T Cell Isolation Kit (STEM CELL technologies). T cells were cultured in TexMACS medium (Miltenyi Biotech Inc) with 40-100 IU/mL human IL-2 (Miltenyi Biotech), 2% human AB type serum, and 1% penicillin/streptomycin sulfate. Dynabeads Human T-Activator CD3/CD28 (ThermoFisher Scientific) were added to T cells at 1:1 ratio to activate T cells. 12-24 hours after activation, T cells were transduced with FITC-CAR lentiviral particles in the presence of 8 µg/mL polybrine (Santa Cruiz Biotech) by spinfection at 1,200 g for 90 minutes at 22-32° C. T cell mixture containing those with CAR modification (CAR-Ts) and those without CAR modification (non-transformed Ts) was cultured in the presence of activation beads for 6 days before the removal of activation beads. Fluorescence-Activated Cell Sorting was used to sort out CAR-T cells (GFP positive) and non-transformed T cells (GFP negative) based on their GFP expression. The sorted T cells were cultured for 7-15 days before injection into mice. When a T cell mixture was used, CAR-T cells and non-transformed T cells were mixed at the desired ratio before mouse injection.

Example 10

Generation of Lentiviral Vector Encoding CAR Gene

An overlap PCR method was used to generate CAR constructs comprising scFv against fluorescein. scFV against fluorescein, 4M5.3 (Kd=270 fM, 762 bp) derived from anti-fluorescein (4-4-20) antibody was synthesized. Sequence encoding the human CD8α signal peptide (SP, 63 bp), the hinge, and transmembrane region (249 bp), the cytoplasmic domain of 4-1BB (CD137, 141 bp) and the CD3ζ chain (336 bp), as shown in FIG. 2, were fused with the anti-fluorescein scFV by overlapping PCR. The resulting CAR construct (1551 bp) was inserted into EcoRI/NotI cleaved lentiviral expression vector pCDH-EF1-MCS-(PGK-GFP) (FIG. 2, System Biosciences). The sequence of the CAR construct in lentiviral vector was confirmed by DNA sequencing.

An exemplary CAR nucleic acid coding sequence may comprise:

(SEQ ID NO: 1)
ATGGCCTTACCAGTGACCGCCTTGCTCCTGCCGCTGGCCTTGCTGCTCCA

CGCCGCCAGGCCGGATGTCGTGATGACCCAGACCCCCCTCAGCCTCCCAG

```
TGTCCCTCGGTGACCAGGCTTCTATTAGTTGCAGATCCAGCCAGTCCCTC

GTGCACTCTAACGGTAATACCTACCTGAGATGGTATCTCCAGAAGCCCGG

ACAGAGCCCTAAGGTGCTGATCTACAAAGTCTCCAACCGGGTGTCTGGAG

TCCCTGACCGCTTCTCAGGGAGCGGTTCCGGCACCGACTTCACCCTGAAG

ATCAACCGGGTGGAGGCCGAAGACCTCGGCGTCTATTTCTGCTCTCAGAG

TACACATGTGCCCTGGACCTTCGGCGGAGGGACCAAGCTGGAGATCAAAA

GCTCCGCAGACGATGCCAAGAAAGATGCCGCTAAGAAAGACGATGCTAAG

AAAGACGATGCAAAGAAAGACGGTGGCGTGAAGCTGGATGAAACGGAGG

AGGTCTCGTCCAGCCAGGAGGAGCCATGAAGCTGAGTTGCGTGACCAGCG

GATTCACCTTTGGGCACTACTGGATGAACTGGGTGCGACAGTCCCCAGAG

AAGGGGCTCGAATGGGTCGCTCAGTTCAGGAACAAACCCTACAATTATGA

GACATACTATTCAGACAGCGTGAAGGGCAGGTTTACTATCAGTAGAGACG

ATTCCAAATCTAGCGTGTACCTGCAGATGAACAATCTCAGGGTCGAAGAT

ACAGGCATCTACTATTGCACAGGGGCATCCTATGGTATGGAGTATCTCGG

TCAGGGGACAAGCGTCACAGTCAGTTTCGTGCCGGTCTTCCTGCCAGCGA

AGCCCACCACGACGCCAGCGCCGCGACCACCAACACCGGCGCCCACCATC

GCGTCGCAGCCCCTGTCCCTGCGCCCAGAGGCGTGCCGGCCAGCGGCGGG

GGGCGCAGTGCACACGAGGGGGCTGGACTTCGCCTGTGATATCTACATCT

GGGCGCCCTTGGCCGGGACTTGTGGGGTCCTTCTCCTGTCACTGGTTATC

ACCCTTTACTGCAACCACAGGAACCGTTTCTCTGTTGTTAAACGGGGCAG

AAAGAAACTCCTGTATATATTCAAACAACCATTTATGAGACCAGTACAAA

CTACTCAAGAGGAAGATGGCTGTAGCTGCCGATTTCCAGAAGAAGAAGAA

GGAGGATGTGAACTGAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCCCCTCG

CTAA.
```

In the exemplary nucleic acid sequence shown above (SEQ ID NO:1) the first ATG is the start codon. An exemplary CAR amino acid sequence may comprise:

(SEQ ID NO: 2)
MALPVTALLLPLALLLHAARPDVVMTQTPLSLPVSLGDQASISCRSSQSL

VHSNGNTYLRWYLQKPGQSPKVLIYKVSNRVSGVPDRFSGSGSGTDFTLK

INRVEAEDLGVYFCSQSTHVPWTFGGGTKLEIKSSADDAKKDAAKKDDAK

KDDAKKDGGVKLDETGGGLVQPGGAMKLSCVTSGFTFGHYWMNWVRQSPE

KGLEWVAQFRNKPYNYETYYSDSVKGRFTISRDDSKSSVYLQMNNLRVED

TGIYYCTGASYGMEYLGQGTSVTVSFVPVFLPAKPTTTPAPRPPTPAPTI

ASQPLSLRPEACRPAAGGAVHTRGLDFACDIYIWAPLAGTCGVLLLSLVI

TLYCNHRNRFSVVKRGRKKLLYIFKQPFMRPVQTTQEEDGCSCRFPEEEE

GGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR

An exemplary insert may comprise:

```
                                           (SEQ ID NO: 3)
GCCACCATGGCCTTACCAGTGACCGCCTTGCTCCTGCCGCTGGCCTTGCT

GCTCCACGCCGCCAGGCCGGATGTCGTGATGACCCAGACCCCCCTCAGCC

TCCCAGTGTCCCTCGGTGACCAGGCTTCTATTAGTTGCAGATCCAGCCAG

TCCCTCGTGCACTCTAACGGTAATACCTACCTGAGATGGTATCTCCAGAA

GCCCGGACAGAGCCCTAAGGTGCTGATCTACAAAGTCTCCAACCGGGTGT

CTGGAGTCCCTGACCGCTTCTCAGGGAGCGGTTCCGGCACCGACTTCACC

CTGAAGATCAACCGGGTGGAGGCCGAAGACCTCGGCGTCTATTTCTGCTC

TCAGAGTACACATGTGCCCTGGACCTTCGGCGGAGGGACCAAGCTGGAGA

TCAAAAGCTCCGCAGACGATGCCAAGAAAGATGCCGCTAAGAAAGACGAT

GCTAAGAAAGACGATGCAAAGAAAGACGGTGGCGTGAAGCTGGATGAAAC

CGGAGGAGGTCTCGTCCAGCCAGGAGGAGCCATGAAGCTGAGTTGCGTGA

CCAGCGGATTCACCTTTGGGCACTACTGGATGAACTGGGTGCGACAGTCC

CCAGAGAAGGGGCTCGAATGGGTCGCTCAGTTCAGGAACAAACCCTACAA

TTATGAGACATACTATTCAGACAGCGTGAAGGGCAGGTTTACTATCAGTA

GAGACGATTCCAAATCTAGCGTGTACCTGCAGATGAACAATCTCAGGGTC

GAAGATACAGGCATCTACTATTGCACAGGGGCATCCTATGGTATGGAGTA

TCTCGGTCAGGGGACAAGCGTCACAGTCAGTTTCGTGCCGGTCTTCCTGC

CAGCGAAGCCCACCACGACGCCAGCGCCGCGACCACCAACACCGGCGCCC

ACCATCGCGTCGCAGCCCCTGTCCCTGCGCCCAGAGGCGTGCCGGCCAGC

GGCGGGGGCGCAGTGCACACGAGGGGGCTGGACTTCGCCTGTGATATCT

ACATCTGGGCGCCCTTGGCCGGGACTTGTGGGGTCCTTCTCCTGTCACTG

GTTATCACCCTTTACTGCAACCACAGGAACCGTTTCTCTGTTGTTAAACG

GGGCAGAAAGAAACTCCTGTATATATTCAAACAACCATTTATGAGACCAG

TACAAACTACTCAAGAGGAAGATGGCTGTAGCTGCCGATTTCCAGAAGAA

GAAGAAGGAGGATGTGAACTGAGAGTGAAGTTCAGCAGGAGCGCAGACGC

CCCCGCGTACCAGCAGGGCCAGAACCAGCTCTATAACGAGCTCAATCTAG

GACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAA

TGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTC

AGTACAGCCACCAAGGACACCTACGACGCCCTTCACATGCAGGCCCTGCC

CCCTCGCTAA
```

In the exemplary insert described above (SEQ ID NO:3), the first GCCACC sequence may comprise a restriction enzyme cleavage site, followed by the ATG start codon. The encoded amino acid sequence may comprise:

81

(SEQ ID NO: 2)
MALPVTALLLPLALLLHAARPDVVMTQTPLSLPVSLGDQASISCRSSQSL

VHSNGNTYLRWYLQKPGQSPKVLIYKVSNRVSGVPDRFSGSGSGTDFTLK

INRVEAEDLGVYFCSQSTHVPWTFGGGTKLEIKSSADDAKKDAAKKDDAK

KDDAKKDGGVKLDETGGGLVQPGGAMKLSCVTSGFTFGHYWMNWVRQSPE

KGLEWVAQFRNKPYNYETYYSDSVKGRFTISRDDSKSSVYLQMNNLRVED

TGIYYCTGASYGMEYLGQGTSVTVSFVPVFLPAKPTTTPAPRPPTPAPTI

ASQPLSLRPEACRPAAGGAVHTRGLDFACDIYIWAPLAGTCGVLLLSLVI

TLYCNHRNRFSVVKRGRKKLLYIFKQPFMRPVQTTQEEDGCSCRFPEEEE

GGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR

Example 11

Production of Lentivirus Containing CAR Gene for Human T Cell Transduction

To prepare lentiviral virus containing an anti-fluorescein (i.e., anti-FITC) single chain fragment variable (scFv) CAR, a HEK-293TN packaging cell line was co-transfected with the lentiviral vector encoding anti-fluorescein scFv CAR and a 2nd generation of a lentiviral packaging plasmid mix (Cellecta) or ViraPower Lentivrial Packaging Mix (ThermoFisher). After 24 and 48 hours of transfection, supernatants containing the lentivirus with the CAR gene were harvested and virus particles were concentrated by the standard polyethylene glycol virus concentration method (Clontech) for future transduction with human T cells.

Example 12

Isolation of Human T Cells from Human PBMC

T cells were isolated from human peripheral blood mononuclear cells (PBMC) by Ficoll density gradient centrifugation (GE Healthcare Lifesciences). After washing away remaining Ficoll solution, T cells were isolated by using an EasySep™ Human T Cell Isolation Kit (STEM CELL technologies). Purified T cells were cultured in TexMACS™ medium (Miltenyi Biotech Inc) with 1% penicillin and streptomycin sulfate in the presence of human IL-2 (100 IU/mL, Miltenyi Biotech Inc). T cells were cultured at density of $1 \times 10^6$ cells/mL in multi-well plates. T cells were split and re-feed every 2-3 days.

Example 13

Transduction of Human T Cells

Isolated T cells were activated with Dynabeads coupled with anti-CD3/CD28 antibodies (Life Technologies) for 12-24 hours in the presence of human IL-2 (100 IU/mL), then transduced with lentivirus encoding an anti-fluorescein CAR gene. Cells were harvested after 72 hours and the expression of CAR on transduced T cells was identified by measuring GFP fluorescent cells using flow cytometry.

Example 14

Synthesis of FITC-Folate

Folate-γ-ethylenediamine was coupled to fluorescein isothiocyanate (FITC) isomer I (Sigma-Aldrich) in anhydrous dimethylsulfoxide (DMF) in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, pH7.4) and 1% acetonitrile (mobile phase B) and reaching 90% A and 10% B in 10 min at a flow rate of 20 mL/min. Under these conditions, the FITC-folate main peak typically eluted at 27-50 min. The quality of the FITC-folate fraction was monitored by analytical reverse-phase HPLC with a UV detector. Fractions with greater than 98.0% purity (LCMS) were lyophilized to obtain the final FITC-folate product.

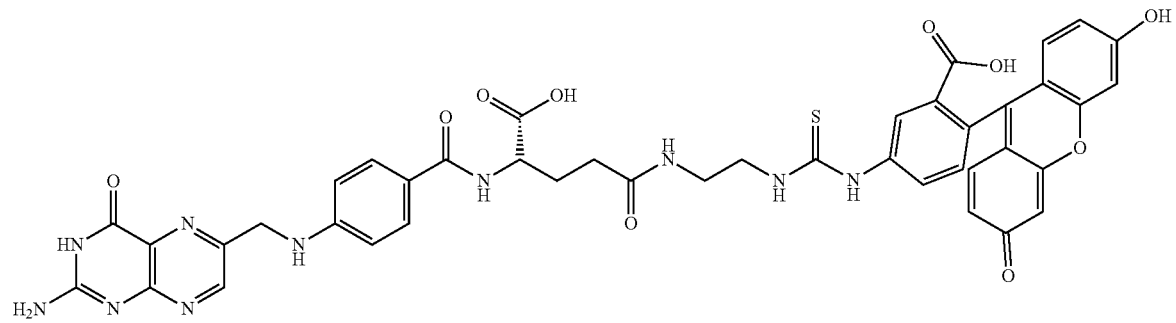

Example 15

Synthesis of FITC-DUPA

DUPA-FITC was synthesized by solid phase methodology as follows. Universal NovaTag resin (50 mg, 0.53 mM) was swollen with dichloromethane (DCM) (3 mL) followed by dimethylformamide (DMF, 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)-OH (1.5 equiv), HATU (2.5 equiv) and DIPEA (4.0 equiv) in DMF was added. Argon was bubbled for 2 h, and resin was washed with DMF (3×3 mL) and i-PrOH (3×3 mL). After swelling the resin in DCM, a solution of 1 M HOBt in DCM/trifluoroethane (TFE) (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and resin was washed with DMF (3×3 mL) and i-PrOH (3××3 mL). The above sequence was repeated for 2 more coupling steps for addition of 8-aminooctanoic acid and fluorescein isothiocyanate or rhodamine B isothiocyanate. Final compound was cleaved from the resin using a trifluoroacetic acid (TFA):H2O: triisopropylsilane:cocktail (95:2.5:2.5) and concentrated under vacuum. The concentrated product was precipitated in diethyl ether and dried under vacuum. The crude product was purified using preparative RP-HPLC [λ=488 nm; solvent gradient: 1% B to 80% B in 25 min, 80% B wash 30 min run; A=10 mM $NH_4OAc$, pH=7; B=acetonitrile (ACN)]. ACN was removed under vacuum, and pure fractions were freeze-dried to yield DUPA-FITC as a brownish-orange solid. RP-HPLC: tR=8.0 min (A=10 mM $NH_4OAc$, pH=7.0; B=ACN, solvent gradient: 1% B to 50% B in 10 min, 80% B wash 15 min run). 1H NMR (DMSO-d6/$D_2O$): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H); 6.61 (dd, J=5.3, 3.5 Hz, 2H); 6.64 (s, 2H); 7.05 (d, J=8.2 Hz, 2H); 7.19 (m, 5H); 7.76 (d, J=8.0 Hz, 1H); 8.38 (s, 1H). HRMS (ESI) (m/z): (M+H)+ caled for C51H59N7O15S, 1040.3712, found, 1040.3702. UV/vis: λ max=491 nm.

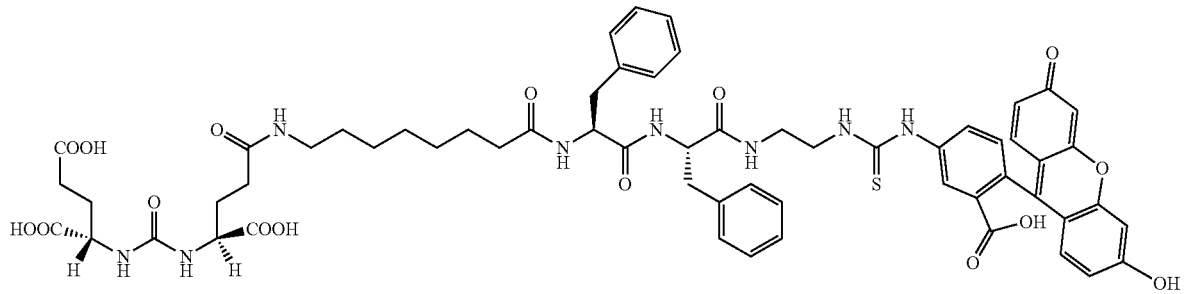 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

Example 16

Synthesis of FITC-CA9

In a 50 mL round bottom flask CA9 ligand (53.6 mg, synthesized in lab) was dissolved in a desired amount of N,N-Dimethylformamide (DMF) (2-3 mL) using a Teflon magnetic stir bar. Ambient air was removed using vacuum and replaced with nitrogen gas, this was done in three cycles. Then the round bottom was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 μL of Boc-PEG2-NH2 (purchased from Sigma Aldrich). 5.4 μL of triethylamine (TEA) was added last and the reaction was allowed to stir overnight. The reaction mixture was purified using HPLC and confirm with UHPLC-MS (target m/z of 831). Acetonitrile was removed using high vacuum rotary evaporation and place on lyophilizer for 48 hours. Deprotection of Boc was done with with 1:1 TFA:DCM for 30 minutes. TFA/DCM was removed using high vacuum rotary evaporation followed by 30 minutes on high vacuum. The compound was then dissolved in DMF and combined with 5 molar equivalents of N,N-Diisopropylethylamine (DIPEA). 16 mg of fluorescein isothiocyanate (purchased from Life Technologies) was added to the solution and stirred for 1 hour. Reaction mixture was purified by HPLC and target compound was confirmed with UHPLC-MS (target m/z of 1120). The samples was placed on lyophilizer for 48 hours and store compound at −20° C.

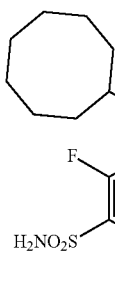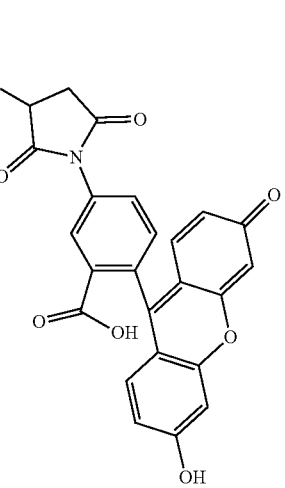

Example 17

Synthesis of FITC-NK1R

To a stirred solution of NK-1 (0.02 g, 0.0433 mmol, 1.0 eq.), O-(2-Aminoethyl)-O'-[2-(Boc-amino)ethyl]decaethylene glycol (BocNH-PEG11-NH2) (Sigma, 0.0336 g, 0.0521 mmol, 1.2 eq.), Benzotriazol-1-yl-oxytripyrrolidinophosphonium hexafluorophosphate (PYBOP) (0.027 g, 0.0521 mmol, 1.2 eq.) in dry $CH_2Cl_2$ was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 µm; 19×100 mm column, mobile phase A=20 mM ammonium acetate buffer, pH 7, B=acetonitrile, gradient 10-100% B in 30 min, 13 mL/min, λ=220 nm, 254 nm). The pure fractions were collected, evaporated all organic solvents and lyophilized the sample for 48 h to furnish the NK1-PEG11-NHBoc. Yield: 40.13 mg (97%). To the NK1-PEG11-NHBoc (0.0165 g, 0.015 mmol) in dry CH2Cl2 was added trifluoroacetic acid (TFA, 20 eq.) and reaction mixture was stirred for 4 h at r.t. The excess of TFA was removed, diluted with water and extracted using CH2Cl2 (3×5 mL). The combined organic layers were washed with brine, dried (Na2SO4) and concentrated. The residue obtained was dried under vacuum and used for next-step without further purification. A stirred solution of NK1-PEG11-NH2 (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added diisopropylethyl amine (0.0028 mL, 0.0162 mmol, 2.0 eq.) at room temperature under argon. The reaction progress was monitored by LCMS and purified by preparative RP-HPLC (Waters, XBridge™ Prep C18, 5 µm; 19×100 mm column, mobile phase A=20 mM ammonium acetate buffer, pH 7, B=acetonitrile, gradient 10-100% B in 30 min, 13 mL/min, λ=280 nm). The pure fractions were collected, evaporated all organic solvents and lyophilized the sample for 48 h to furnish the NK1-PEG11-FITC (5). Yield: 8.54 mg (77%).

The NK-1 compound was synthesized by a two-step procedure starting from base ligand, which was prepared by using a literature procedure. (Ref: DESIGN AND DEVELOPMENT OF NEUROKININ-1 RECEPTOR-BINDING AGENT DELIVERY CONJUGATES, Application Number: PCT/US2015/44229, incorporated herein by reference in its entirety).

Example 18

HOS-FR-α and AML Study Schema

Sequential escalating doses of EC17 will be administered under the following rules:
- If no CRS or neurotoxicity, advance through EC17 dose escalation as planned.
- If CRS grade ≤2, administer all subsequent EC17 doses at the Sequence level that provoked the non-serious CRS in the same cycle.
- If CRS grade >2, cancel further EC17 doses in the current Cycle, and commence all subsequent Cycles at the next highest Sequence below that which provoked the sCRS.

See FIG. 15.

A. Tumor Implantation

HOS-FRα (i.e. HOS-143b-LV-FRα) is a subclone of HOS-143B (ATCC CRL-8303) stably transfected with human FRα. HOS-143B was originally derived from a 13-year-old Caucasian female with osteosarcoma. The tumor cells were grown in folate-deficient RPMI 1640 with 5% FBS at 37° C. in a 5% CO2 humidified atmosphere. For the in-vivo study, tumor cells were inoculated subcutaneously at $1×10^6$ cells per animal.

B. CAR-T Cell Administration

EGFRt-sorted anti-FITC E2 scFv-CAR T cells were frozen in a T-cell freezing medium. Upon arrival, vials of frozen CAR-T cells were immediately stored at −80° C. The CAR-T cells were quickly thawed at 37° C., washed twice with PBS, and used for animal injection at 6 million viable EGFRt+ E2 CAR-T cells (CD4/CD8 at ~1:1) per animal. A small aliquot was taken on the day infusion for flow cytometric analysis of E2-CAR T-cell phenotypes.

C. Preparation of Dosing Drug Solutions

EC17 dosing solutions were prepared when dosing began by weighing appropriate amounts of each compound, reconstituting in PBS, pH 7.4, sterile filtering the drug solution through a 0.22 μm PVDF syringe filter, and freezing aliquots for each day of dosing at −20° C.

D. Compound Administration

All EC17 doses were given towards the end of day (3-4 PM) to allow potential CRS (cytokine release syndrome) to develop overnight. On the following morning, animals were scored according to a CRS grading system (see below).

E. Evaluation

CRS Grading System

| | | CRS Grading Scale | | | |
|---|---|---|---|---|---|
| 0 | 1 | 2 | 3 | 4 | 5 |
| Normal | ~pilo ~greasy still active | pilo greasy less active | pilo, greasy bunched, thin not active, unless stimulated | moribund bunched, pale lethargic | Death |

Tumor growth, body weight, and overall assessment: Tumor sizes were monitored 2-3 times/week and body weight measured 2-3 times/week. On the days immediately after any EC17 dose, body weight measurement was taken daily and attention was given to gross animal morphology and behavior.

Euthanasia: Euthanasia was performed when mice had lost ≥20% of their weight, when tumors reached ≥1500 mm³. Euthanasia was also performed if mice lost a lot of weight in a short duration (e.g., due to severe head-tilt), or when they approached moribund conditions per CRS grading system.

EC17 intra-host dose escalation treatment (3 cycles). See FIG. 16.

Antitumor activity (N=5)

As seen in FIG. 4:

Cohort 1 (E2-CAR T-cells only) showed HOS-FRα grew aggressively without EC17 treatment.

Cohort 2 (EC17 5/100/1000 nmol/kg, M/Th/M) showed significant tumor regression without body weight loss or CRS through this study.

The slow EC17 dose escalation (M/Th/M) regimen was safe. No body weight loss or symptoms of cytokine release syndrome (CRS) were observed in the HOS-FRα tumor-bearing mice.

One objective of this E2-CAR T-cell study was to test EC17/E2 CAR-T cell activity and related toxicity (e.g. sCRS) using multiple dosing regimens starting 3 days after CAR-T infusion. Three different EC17 dosing regimens include (a) once-a-week (SIW) at 500 nmol/kg, (b) "TIW-like" at 5, 50, and 500 nmol/kg on Monday/Wednesday/Friday with 9-day intervals, and (c) "TIW-like" at 5, 100, and 1000 nmol/kg on Monday/Thursday/Monday with 7-day intervals.

Experimental Groups (C=Cycle):

| Cohort | Groups | T cells§ | C1 Wk1 (EC17) | C2 Wk1 (EC17) | C1 Wk1 (EC17) | N (Efficacy) | N (Satellite) |
|---|---|---|---|---|---|---|---|
| 1 | Tumor only | N/A | N/A | N/A | N/A | 5 | N/A |
| 2 | CAR-T only | 6 million CAR-T | N/A | N/A | N/A | 5 | 0/3/0/3/0/3 |
| 3 | EC17 SIW | 6 million CAR-T | 500 nmol/kg | 500 nmol/kg | 500 nmol/kg | N/A | 3/3/0/3/0/3 |
| 4* | EC17 TIW (On/Off) | 6 million CAR-T | 5 nmol/kg 50 nmol/kg 500 nmol/kg | 5 nmol/kg 50 nmol/kg 500 nmol/kg | 5 nmol/kg 50 nmol/kg 500 nmol/kg | N/A | 0/0/0/3/3/0/3 |
| 5* | EC17 "TIW" M/Th/M | 6 million CAR-T | 5 nmol/kg 50 nmol/kg 500 nmol/kg | 5 nmol/kg 50 nmol/kg 500 nmol/kg | 5 nmol/kg 50 nmol/kg 500 nmol/kg | 5 | 0/3/3/3/0/3/3 |

*Groups 4-5: Skip dosing for Week 2 of each cycle.

Study Schema

Group 1 (no treatment): only for efficacy comparison.

Figure 17:
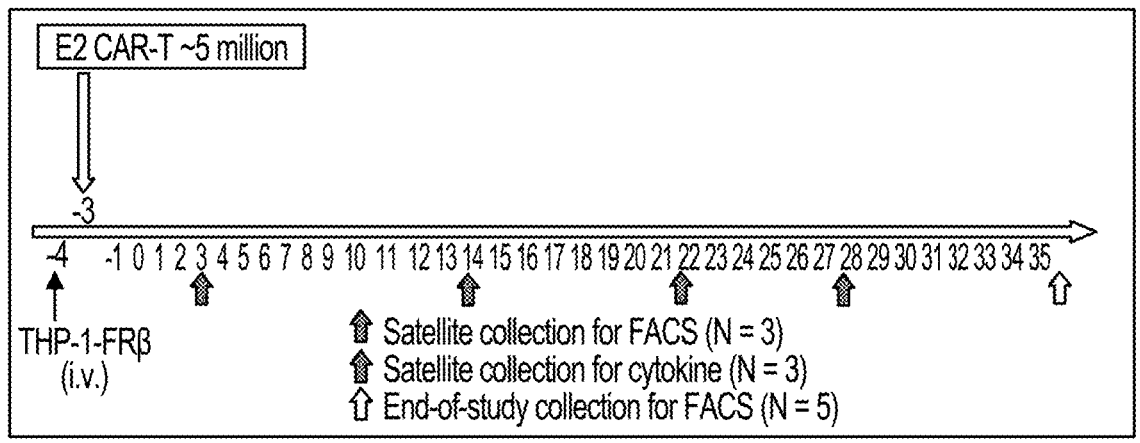

Group 2 (CAR-T only): see FIG. 17.

Figure 18:
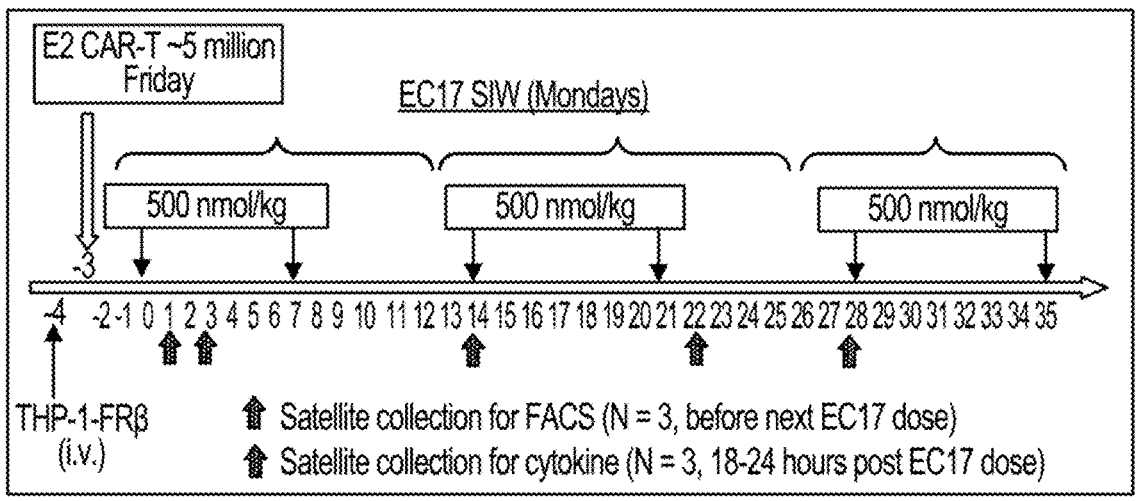

Group 3 (EC17 SIW): see FIG. 18.

Figure 19:
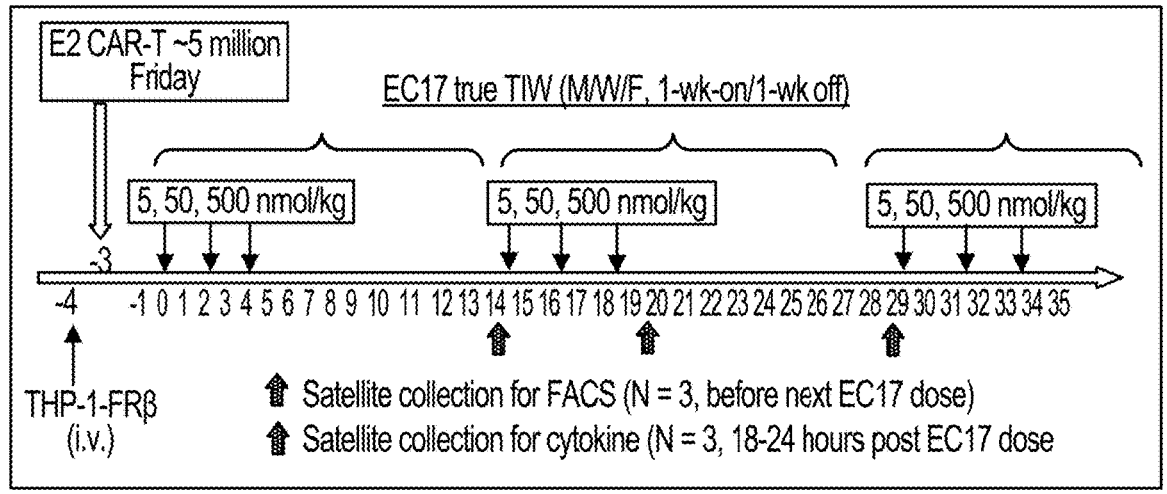

Group 4 (EC17 true TIW): see FIG. 19.

Figure 20:
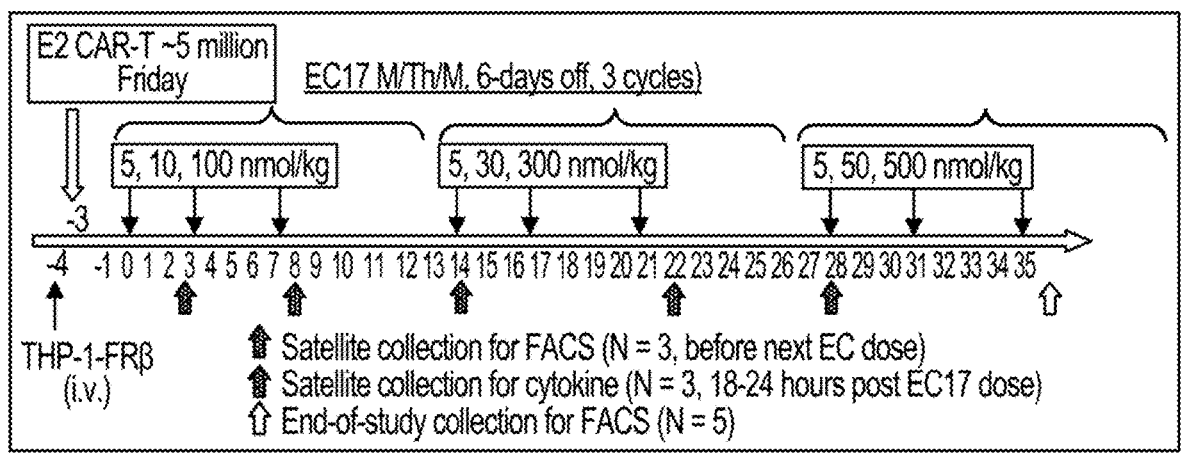

Groups 5—EC17 low-dose "TIW" (M/Th/M, 6-day off) with/efficacy: see FIG. 20.

A. Tumor Implantation

THP-1-FRβ AML tumor cells were grown in folate-deficient RPMI 1640 with 5-10% FBS at 37° C. in a 5% $CO_2$ humidified atmosphere. THP-1-FRβ tumor cells in serum-free folate-deficient RPMI1640 medium were i.v. injected at $5 \times 10^6$ cells per animal.

B. CAR-T Cell Administration

Anti-FITC E2 scFv-CAR T cells were frozen in a T-cell freezing medium. Upon arrival, vials of frozen CAR-T cells were immediately stored at −80° C. The CAR-T cells were quickly thawed at 37° C., washed twice with CAR-T cell culture medium, and used for animal injection at 6 million viable EGFRt+ E2 CAR-T cells (CD4/CD8 at ~1:1) per animal. A small aliquot was taken on the day infusion for flow cytometric analysis of E2-CAR T-cell phenotypes.

C. Preparation of Dosing Drug Solutions

EC17 and bis-EDA-FITC dosing solutions were prepared when dosing began by weighing appropriate amounts of each compound, reconstituting in PBS, pH 7.4, sterile filtering the drug solution through a 0.22 μm PVDF syringe filter, and freezing aliquots for each day of dosing at −20° C.

D. Compound Administration

All EC17 doses were given towards the end of day (3-4 PM) to allow potential CRS (cytokine release syndrome) to develop overnight. In the following morning, animals were scored according to a CRS grading system (see below).

EC17 Dose Schedule:

Cohorts 1-2: no EC17 dose given

Figure 21:
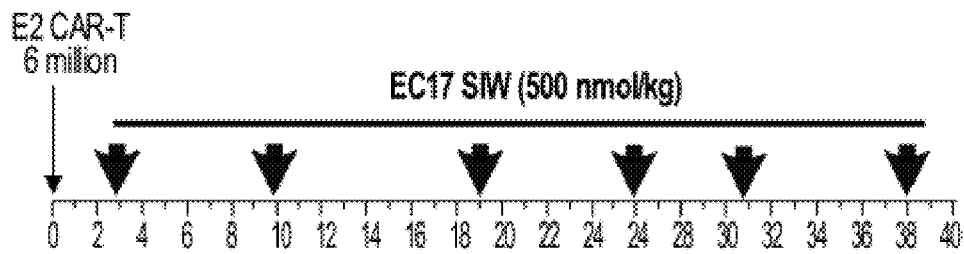

Cohort 3: see FIG. 21.

Figure 22:
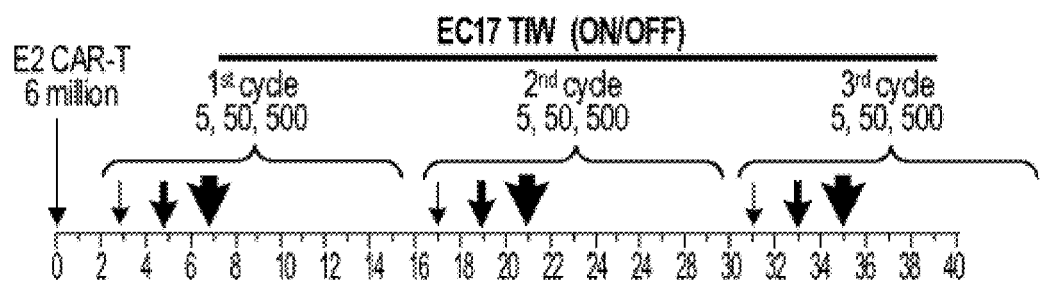

Cohort 4: see FIG. 22.

Figure 23:
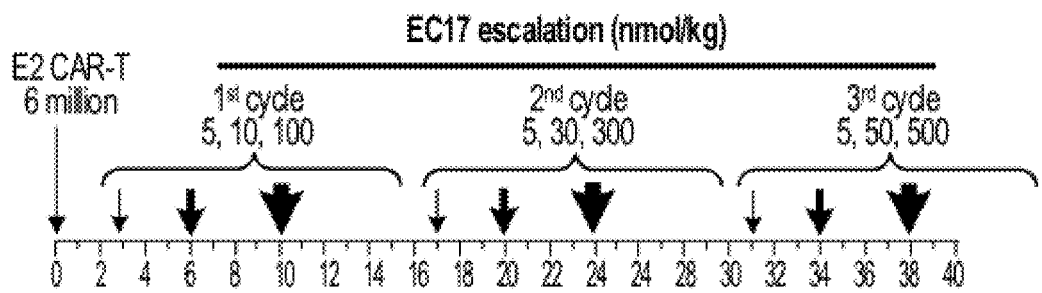

Cohort 5: see FIG. 23.

Monitoring/Efficacy:

Daily body weight measurement on the days after EC17 dose is required. Attention was given to gross animal morphology and behavior. Euthanasia was performed if mice lose a lot of weight in a short duration or when mice are approaching moribund conditions per CRS grading system or neurotoxicity.

CRS Grading System

| CRS Grading Scale | | | | | |
|---|---|---|---|---|---|
| 0 | 1 | 2 | 3 | 4 | 5 |
| Normal | ~pilo ~greasy still active | pilo greasy less active | pilo, greasy bunched, thin not active, unless stimulated | moribund bunched, pale lethargic | Death |

Tumor growth, body weight, and overall assessment: Body weight measured 2-3 times/week. On the days immediately after any EC17 dose, body weight measurement was taken daily and attentions were given to gross animal morphology and behavior.

Flow Cytometric Analysis

Whole blood cell analysis: Plasma was removed from predetermined volumes of whole EDTA treated blood and RBCs were lysed with RBC lysis solution. The leukocyte pellets were then resuspended in flow cytometry staining solution (1% bovine serum albumin, 50 mg/mL human IgG (Equitech Bio, cat #SLH56-0001), 0.9% sodium azide in a phosphate buffered saline, pH=7.4) and leukocyte surface marker staining was performed using the following antibodies: anti-human CD45 (clone HI30, eBioscience #47-0459-42 at 1:20 (v/v) dilution), anti-human CD137 (clone 4B4-1, BD Bioscience #564092 at 1:20 (v/v) dilution), anti-human CD8α [clone RPA-T8, BD Bioscience, catalog #557746 at 1:20 (v/v) dilution], anti-human CD4 [clone SK3, eBioscience catalog #46-0047-42 at 1:20 (v/v) dilution], anti-human EGFR [R&D systems, clone Hu1, catalog #FAB9577B @1:10 (v/v)], anti-human PD1 [BD Biosciences, clone EH12.1, catalog #562511 @1:20 (v/v)], anti-human LAG3 [BD Biosciences, clone T47-530, catalog #565616 @1:20 (v/v)], anti-human TIM3 [BD Biosciences, clone 7D3, catalog #565558 @1:20 (v/v)], anti-human CD3ε [BD Biosciences, clone SK7, catalog #557832 @1:20 (v/v)]. After leukocyte staining, cells were washed with PBS and resuspended in cold PBS containing 53,000 CountBright™ beads [Invitrogen catalog #C36950] and transferred to flow cytometry collection tubes. Flow cytometry data was collected on the Gallios flow cytometer (Beckman Coulter, Brea, CA). Determination of the concentration of CAR T cells in each blood sample was calculated according to Invitrogen's instructions. CAR T cells were identified as human CD3ε+ EGFRt+ events and easily distinguished and counted using the Kaluza™ flow cytometry software. The number of CAR T cells in the circulation of each infused mouse was then represented on the graphs as the total number of CAR T cells per 50 µL of whole blood analyzed. Statistical significance was determined by utilizing an unpaired, two-tailed, students t-test with significance set at $p<0.05$.

Tumor and tissue analysis: Solid tumors (100-1000 mm$^3$) were harvested, weighed, and minced into small pieces then transferred into 50 mL tubes containing 20 mL of a tumor digestion cocktail. The enzymatic tumor digestion cocktail consisted of 0.5 mg/mL Collagenase IV (Sigma-Aldrich, Catalog #C5138), 0.5 mg/mL Hyaluronidase (Sigma-Aldrich, Catalog #H3506) and 0.1 mg/mL DNase I (Sigma-Aldrich, Catalog #DN25) in serum-free and folate-deficient RPMI1640 medium supplemented with antibiotics. The tumor fragments were digested for one hour at 37° C. at 300 rpm on a horizontal shaker. Afterwards, the tumor digest was centrifuged at 400×g for 5 minutes and tumor cell pellet underwent a red blood cell lysis step, was then washed with cold phosphate-buffered saline (PBS, pH 7.4) and finally filtered through a 40 µm nylon cell strainer.

Results and Conclusions

A. Three Different Dose Schedules of EC17 Administration Showed Different Patterns of Body Weight Loss and Different Levels of CRS As seen in FIG. 5, Cohort 1 (no treatment) and Cohort 2 (CAR-T only) didn't show much body weight loss and had no CRS. Cohort 3 (EC17 SIW) showed EC17 dose-dependent body weight loss after each EC17 dose, and showed grade 1-2 CRS throughout the study. Cohort 5 (EC17 dose escalation) showed little body weight loss during the first two cycles, but started to show similar body weight loss as cohort 2 after the end of second cycle of EC17 dose. Cohort 4 (EC17 TIW ON/OFF) showed mildest body weight loss among three treatment groups. Neither Cohort 4 or 5 showed any CRS greater than 1.

Figure 24:
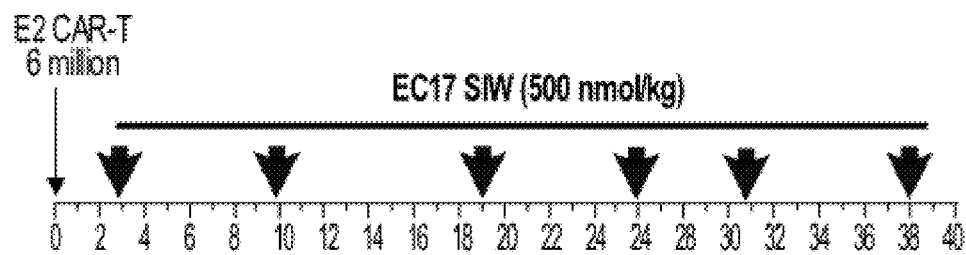
Figure 25:
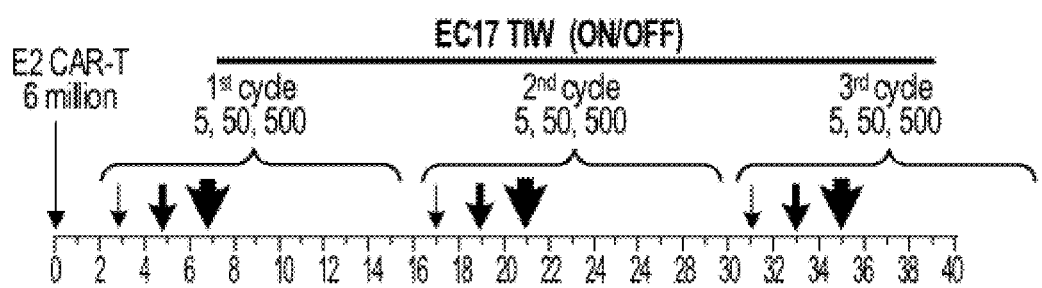
Figure 26:
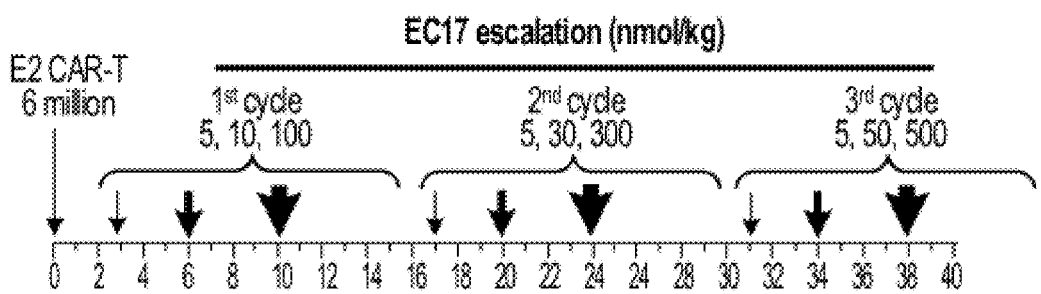

Cohort 3 See FIG. 24.
Cohort 4 See FIG. 25.
Cohort 5 See FIG. 26.

Three Different Dose Schedules of EC17 Administration Showed Different Anti-Tumor Activities.

As seen in FIG. 6, liver and non-liver tumor burden were assessed on Day 39 across all cohorts. Cohort 2 (CAR-T only) didn't show any difference comparing to Cohort 1 (no treatment). Cohort 4 showed the best anti-tumor activity among the three different EC17 dose schedules.

Elimination of Circulating AML Cell Line, THP1-FRβ

In studies using CD19 specific anti-ALL therapy, expansion and persistence of CAR T cells in the blood has been reported to correlate with elimination of circulating CD19+ ALL cells resulting in complete responses to therapy. In this experiment we perform a similar assay in our mouse AML model, to determine the anti-tumor activity of our adaptor controlled E2 CAR T cell by looking for the disappearance of our GFP labeled human AML cell line, THP1-FRβ, in response to different dosing regimens of the CAR T adaptor molecule, EC17. FIG. 7 displays the circulating THP1-FRβ cells with the y-axis showing the total number of GFP+ cells per 100 µL of whole blood on a logarithmic scale. The different bars represent the different treatment cohorts. It was demonstrated that a high AML cell burden existed in the circulation 40 days post infusion of AML cells into mice receiving neither CAR T cells nor EC17. No reduction of AML cells in the blood was seen in mice receiving an infusion of both AML cells and E2 CAR T cells, but no EC17 treatment. This demonstrates negligible anti-tumor activity by potential allogeneic reactivity of the human T cells with the allogeneic THP1 cells. Interestingly a significant reduction in circulating THP1 cell burden in all three cohorts of mice infused with E2 CAR T cells plus EC17 at different dosing regimens was seen, thus demonstrating the effectiveness of the CAR T therapy under three different adaptor dosing regimens.

E2-CAR-T Exhaustion Phenotypes

Under chronic antigen stimulation, for example in instances of chronic viral infections or cancer, T cells undergo a process of exhaustion where they are no longer able to proliferate, secrete inflammatory cytokines or kill antigen presenting target cells. CAR T cells also possess the potential for exhaustion under chronic stimulation of the CAR by constant presence of scFv stimulating antigen. Because our E2 CAR T cells only react to the presence of our bridge molecule, EC17, bound to the surface of FR+ tumor cells, we have the ability to prevent chronic antigen stimulation of the E2 CAR T cells by ceasing treatment with EC17 and hence removing the presence of surface bound antigen. The rest period characterized by the absence of surface antigen prevents chronic antigen exposure of E2 CAR T cells and prevents the resulting exhaustion that could result.

To confirm that our EC17 dosing regimens do not result in E2 CAR T cell exhaustion, flow cytometry analysis was performed on single cell preparations from THP1-FRβ liver metastases and surface markers which are expressed specifically on exhausted T cells. As T cells approach exhaustion, there is an increase in the co-expression of surface inhibitory receptors, PD1, LAG3 and TIM3. FIG. 8 shows a bar graph where the y-axis illustrates the percentage of the total E2 CAR T cells isolated from the solid liver tumors, which express the various combinations of the three surface markers which is represented by the different bars. Of note, fully exhausted T cells which simultaneously express all three markers are represented by the left-hand bar in each group. The left group shows the pre-infusion of E2 CAR T cells to the liver tumor CAR T cells isolated from the three different EC17 treated cohorts. The inhibitory receptor expression is almost zero in the preinfusion CAR T cell product as most of the T cells are negative for all three surface markers. Importantly, all three EC17 treated cohort E2 CAR T cells possessed the exhausted triple positive cells and interestingly, cohort 4 (EC17 TIW) expresses the fewest number of double and triple positive events and further consisted of a significant number of triple negative CAR T cells. These data suggest that all three EC17 dosing regimens utilized in this mouse experiment might be useful in the clinic in that there is significant anti-tumor activity and there is very little induction of CAR T exhaustion.

Examples 19 to 25—See FIGS. 9 to 14

Example 19

Cell Lines and Reagents

Unless otherwise noted, all FR+ and FR-negative cancer cell lines were maintained in RPMI-1640 medium (Gibco BRL) supplemented with 10% heat-inactivated fetal calf serum without (FFRPMI) or with (RPMI) 2.4 µM folic acid (FA). KB (FRα-expressing human cervical carcinoma with HeLa markers) and CHO-β (Chinese hamster ovary cells transfected with human FRβ) were used as the sources of FRα and FRβ for radioligand binding assays, respectively. MDA-MB-231 represents a FRα subclone of human TNBC (triple negative breast cancer) cell line. For AML studies, a green fluorescent protein (GFP)-expressing isogenic pairs of FRβ-positive (THP1-FRβ) and FR-negative (THP1-FG12) cell lines were provided. Both were established from THP-1 (ATCC, TIB-202), a commonly used cell model for researching pediatric AML which was originally derived from a 1-year-old male infant with acute monocytic leukemia. For osteosarcoma studies, HOS-FRα was established by lentiviral transduction of FR-negative HOS-143b (ATCC, CRL8303) with FOLR1 gene encoding the human FRα. HOS-143b is originally established from a primary tumor of a 13-year-old Caucasian female and is highly tumorigenic in NSG mice. The GFP-expressing bioluminescent pairs of FR+ HOS-FRα$^{fLuc}$ and FR-negative HOS-143b$^{fLuc}$ were transduced with lentiviral firefly luciferase.

LEGENDplex™ human cytokine panels were purchased from BioLegend (San Diego, CA). The lactate dehydrogenase (LDH) based CytoTox 96® non-radioactive cytotoxicity assay kit was purchased from Promega (Madison, WI). Commercially available anti-human antibodies used for multicolor flow cytometry were: CD45RA (clone HI100), CD45RO (clone UCHL1), CD4 (clone SK3), and CD69 (clone FN50) from Thermo Fisher Scientific (Waltham, MA); CD3ε (clone SK7), CD8α (clone RPA-T8), CD137/4-1BB (clone 4B4-1), CD25 (clone M-A251), PD1 (clone EH12.1), LAG3 (clone T47-530), and TIM3 (clone 7D3) from BD Bioscience (San Jose, CA); biotinylated anti-human EGFR (Cetuximab, clone Hu1) from R&D systems (Minneapolis, MN); and FRα (clone LK26) from BioLegend (San Diego, CA). A fluorophore-conjugated anti-biotin was also purchased from BioLegend. APC-conjugated anti-FITC mouse IgG2a/kappa antibody (clone NAWESLEE), CountBright™ beads (Invitrogen), Annexin V staining buffer, and AlexaFluor-647-conjugated Annexin V were purchased from Thermo Fisher Scientific. For enzymatic digestion of tumor tissues, collagenase IV, hyaluronidase and DNase I were all purchased from Sigma-Aldrich (St. Louis, MO).

EC17 or folate-FITC [FA-(γ)-ethylenediamine-FITC]was synthesized at Endocyte. $^3$H-EC17 was either purchased from Moravek biochemicals (Brea, CA) at a specific activity of ~0.952 Ci/mmol or prepared at Endocyte by conjugating FITC with $^3$H-FA-(γ)-ethylenediamine made by ViTrax (Placentia, CA) at a specific activity of ~1.2 Ci/mmol. $^3$H-FA was also purchased from ViTrax at a specific activity of 59 Ci/mmol. For CRS rescue, sodium fluorescein dosing solution was diluted from AK-FLUOR® 25% (fluorescein injection, USP) which was purchased from Purdue Pharmacy (NDC 17478-250-25).

Example 20

Humanized CAR Construct and CAR-Modified T Cells

Previous studies used a GFP+ second-generation anti-FITC scFv (clone 4M5.3) CAR containing the hinge and transmembrane sequences of CD8α and 4-1BB/CD3ζ signaling domains (i.e., FITC-4M5.3-scFv-CD8αhinge-CD8αtm-4-1BB/CD3ζ). For translation into first-in-human testing, the second-generation fully human FITC-specific (clone E2) CAR construct (herein referred to as E2) was developed (FIG. 9, top diagram). CAR-modified T cells are shown in FIG. 9, bottom pie charts.

The construct described herein is a FITC-specific CAR construct including (1) a fully human anti-FITC scFv (clone E2, Kd=0.75 nM), (2) an IgG4 hinge-CH2(L235D, N297Q)-CH3 spacer fused to a CD28-transmembrane domain, (3) a second-generation 4-1BB/CD3ζ-endodomain, and (4) a cell-surface human EGFRt tag (FIG. 9, top diagram) (SEQ ID NOS:4 and 5 are the nucleic acid and amino acid sequences, respectively). To generate CAR-modified T cells, lentivirus was produced in 293T cells co-transfected with CAR-encoding epHIV7 lentiviral vector. Donor CD4+ and CD8+ T cells were purified by immunomagnetic selection and transduced separately or at about a 50:50 ratio. In general, only one round of CD3/CD28 bead activation followed by one or two rounds of rapid in vitro expansion were carried out. For preclinical evaluations, several batches of EGFRt-sorted CD4, CD8 and unsorted CD4/CD8 CAR-T cells were used. All CAR-T cell preparations were analyzed prior to cryopreservation and after thawing to determine EGFRt expression and CD4/CD8 ratios by flow cytometry. Using combinations of surface markers, differentiation status of CD4+ and CD8+ CAR-T cell subsets on the day of infusion was analyzed and defined as $T_N$, CD45RA+ CD45RO− CD62L+ CD95− naïve T cells; $T_{SCM}$, CD45RA+ CD45RO− CD62L+ CD95+ stem cell memory T cells; $T_{CM}$, CD45RA− CD45RO+ CD62L+ CD95+ central memory T cells; $T_{EM}$, CD45RA− CD45RO+CD62L− CD95+ effector memory cells; and $T_{EFF}$, CD45RA+ CD45RO− CD62L− CD95+ effector T cells. For preclinical testing described below, studies included two batches of EGFRt-sorted pure CD4 and CD8 subsets (after mixing at 1:1 ratios) and several batches of unsorted ~1:1 EGFRt+ CD4/CD8 admixture including a "clinical facsimile" preparation with low differentiation profiles.

Amid a series of different CAR constructs synthesized and evaluated, the fully human anti-FITC scFv (FITC-E2) CAR was chosen for preclinical development (FIG. 9). This second-generation fully human CAR consisted of anti-FITC scFv (clone E2), an IgG4-Fc spacer/hinge with double mutations in the $CH_2$ region (L235D and N297Q) to reduce binding to FcγR, a CD28 transmembrane domain, and 4-1BB/CD3ζ signaling domains appended to a cell-surface EGFRt tag by a T2A ribosomal skip sequence (i.e., FITC-E2-scFv-IgG4hinge-CD28tm-4-1BB/CD3ζ-T2A-EGFRt). For preclinical studies, both EGFRt-sorted and unsorted E2 CAR-T cells were prepared at ~1:1 CD4/CD8 ratios, and T cell subtype phenotyping was routinely performed by flow cytometry at the time of CAR T cell infusion (day 0) for each in vivo experiment. A typical expression pattern of EGFRt-sorted CAR-T cells included both CD4 and CD8 subsets at approximately 42% $T_{SCM}$, 10% $T_{CM}$, 12% $T_{EM}$ and 34% $T_{EFF}$ (FIG. 9, pie charts on the left). Only EGFRt-sorted CAR-T cells were used for co-culture and pharmacokinetic studies. For tumor therapy, a "clinical facsimile" batch with a low differentiation profile (FIG. 9, pie charts on the right) for MDA-MB-231 was used, and a research batch was used for THP1-FRβ and HOS-FRα studies. The "clinical facsimile" batch (~39% EGFRt+) included CD4+ subsets at ~66% $T_{SCM}$ and ~32% $T_{CM}$ and CD8 subsets at ~95% $T_{SCM}$ and about 3% $T_{CM}$. The research batch (~23% EGFRt+) was more differentiated and included CD4 subsets at about 32% $T_{SCM}$, about 53% $T_{CM}$, about 11% $T_{EM}$ and about 3.7% $T_{EFF}$ and CD8 subsets at about 44% $T_{SCM}$, about 0.28% $T_{CM}$, about 3.4% $T_{EM}$ and about 52% $T_{EFF}$.

Example 21

EC17 CAM's Bispecific Affinity

The bispecific affinities of EC17 CAM (a CAM is equivalent to a "bridge" or the "compound" in this application) were assessed using $^3$H-EC17 in cell-based radioligand binding assays. For binding to FR+ targets, KB and CHO-β cells were pre-seeded overnight in 24-well tissue culture plates and incubated with 0.1, 0.5, 1, 5, 10, 20, and 40 nM of $^3$H-EC17 in FFRPMI for 2 h at 37° C. Afterwards, the cells were rinsed with phosphate-buffered saline (PBS, pH 7.4) and lysed with 1% sodium dodecylsulfate. The whole cell lysates were quantitated for the level of radioactivity and cellular protein content by standard Pierce BCA protein assay. The number of $^3$H-EC17 molecules bound per cell was calculated to determine the dissociation constants (Kd) for FRα (KB) and FRβ (CHO-β) respectively (FIG. 10).

The EC17 has already been tested in the clinic for immunotherapy and optical imaging purposes. To directly quantify its bispecific binding affinities, $^3$H-EC17 was synthesized and radioligand binding assays were carried out on KB and CHO-β cell lines representing FRα+ and FRβ+ target cells, respectively, and on unsorted EGFRt CAR-T cells representing the effector cells. When binding to its targets, EC17 demonstrated similar affinities towards both FRα and FRβ with low Kd values of 1.7 nM and 0.8 nM, respectively (FIG. 10, Panel A).). Upon binding to unsorted E2-CAR-T cells (~24% EGFRt+, ~95:5 CD8/CD4 ratio), the Kd value was estimated at ~130 nM (FIG. 10, Panel B).

Example 22

Tumor Models

All animal care and use were performed according to NIH guidelines and in compliance with protocols approved by the Purdue University Animal Use and Care Committee. Female 4 to 5-week-old NOD/SCID gamma (NSG™) mice (stock number: 005557) were purchased from The Jackson Laboratory (Bar Harbor, ME). Unless specifically indicated, all animals were maintained on a FA-deficient diet (TestDiet, St. Louis, MO) upon arrival and throughout the study. To establish subcutaneous xenografts, MDA-MB-231 and HOS-FRα were implanted in the right flank region at $2.5\times10^6$ and $1\times10^6$ cells per animal, respectively. For intravenous xenografts, THP1-FRβ cells were inoculated at $5\times10^6$ cells per animal. Subcutaneous tumors were measured 2-3 times per week with a caliper and calculated using the ellipsoidal formula (length×width$^2$)/2. Euthanasia was performed per study design or when (i) the animals had lost ≥20% of body weight or approached moribund conditions, (ii) subcutaneous tumors reached ≥1500 mm$^3$ in size, or (iii) animals displayed signs of swollen belly and severe distress (i.e., THP1-FRβ). All animal doses (CAR-T cells, EC17, sodium fluorescein) were given intravenously.

Example 23

Tumor Therapies

In a therapeutic setting, EC17 CAM can be given before or after CAR-T cell injection. As described herein, the first dose of EC17 was administered 2-3.5 days after CAR-T cells to allow for an observation period of human T cells in tumor-bearing mice. Two batches of unsorted E2-CAR-T cells (23% or 39% EGFRt+, 1:1 CD4/CD8) were used for in vivo studies. On the day of infusion for each experiment (day 0), frozen CAR-T cells were quickly thawed at 37° C., washed 2× with Dulbecco's 1×PBS (pH 7.4) and injected into the tail vein at desired EGFRt+ E2-CAR-T cell doses. In addition, a small aliquot of CAR-T cells was analyzed by flow cytometry for CD4 to CD8 ratio and differentiation status of CAR-T cells. On the first day of EC17 dose, tumor-bearing animals were randomly assigned into groups according to their tumor sizes or the same number of days post intravenous implantation (i.e., THP1-FRβ).

For MDA-MB-231 studies, mice received a high dose (~10 million) of a "clinical facsimile" of E2-CAR-T cells (~39% EGFRt+) with a low differentiation profile (FIG. 9). Two days later, 3 different treatment regimens of EC17 were started at an average tumor size of ~293±39 mm$^3$ (FIG. 12). The EC17 dosing was given once-a-week (SIW) at 500 nmol/kg on Mondays, or as escalating doses of 5, 50 or 100, and 500 or 1000 nmol/kg (i.e., 5/50/500 or 5/100/1000) on Monday, Thursday, and Monday with a 6-day break in-between cycles. Control mice were left untreated (received CAR-T cells but no EC17). For comparison, a cohort of tumor-free littermates also received the same number of CAR-T cells without or with EC17 SIW at 500 nmol/kg.

For AML studies (FIG. 13), mice were intravenously infused with THP1-FRβ tumor cells one day prior to receiving a low dose of ~6 million E2-CAR-T cells (~23% EGFRt+). At ~3.5 days post CAR-T cell infusion, EC17 was dosed in 3 different ways including i) SIW at 500 nmol/kg, ii) thrice at 5/50/500 nmol/kg on Monday/Wednesday/Friday followed by a 9-day break in between cycles (TIW On/Off), and iii) as escalating doses of 5/10/100 nmol/kg in Cycle 1, 5/30/300 nmol/kg in Cycle 2, and 5/50/500 nmol/kg in Cycle 3, all on Monday/Thursday/Monday with a 6-day break in between cycles (M/Th/M_On/Off). On day 31, satellite animals were harvested for quantification of CAR-positive T cells identified in the mouse blood as human CD3ε+ EGFRt+ events and calculated as absolute numbers per 100 μL of whole blood. Upon euthanasia or at the end of study on day 38, total tumor load in THP1-FRβ tumor-bearing mice was assessed by measuring GFP+ tumor cells in the blood by flow cytometry and collecting liver weight (with metastatic lesions) and total weight of nonliver macrometastases found in the body. Tumor fragments of liver metastases were enzymatically digested into single-cell suspensions and viable cell populations were analyzed for the status of CAR-T cell exhaustion using anti-human PD1, LAG3 and TIM3 (clones EH12.1, T47-530 and 7D3, respectively).

For the osteosarcoma study (FIG. 14), two cohorts of mice were subcutaneously implanted with HOS-FRα tumor cells 3 days prior to receiving ~6 million of the same CAR-T cell preparation used in the THP1-FRβ study (FIG. 13). At ~3.5 days post CAR-T cell infusion, one cohort of mice was given up to 3 cycles of EC17 at 5/10/100 nmol/kg in Cycle 1, 5/30/300 nmol/kg in Cycle 2, and 5/50/500 nmol/kg in Cycle 3, all following the Monday/Thursday/Monday regimen with a 6-day break in-between cycles. At the end of study, circulating CD3ε+ EGFRt+ CAR-T cells per 100 μL of mouse blood were enumerated. HOS-FRα tumors (+/− EC17 treatment) were also harvested and digested for flow cytometric analysis of tumor-infiltrating CAR-T cells.

A Dose Escalation Trial Against an Aggressive Osteosarcoma Model

For our intended purpose, HOS-FRα is a low FR-expressing but most aggressive tumor model with a functional FR level of ~5.82±1.45 pmol/mg protein. In parallel to the THP1-FRβ study described above, two cohorts of mice with 3-day-old HOS-FRα tumors were given the same E2-CAR-T cells at the same dose (~6 million). One cohort was treated with the same accelerated EC17 dose escalation regimen at 5/10/100 nmol/kg in Cycle 1, 5/30/300 nmol/kg in Cycle 2, and 5/50/500 nmol/kg in Cycle 3, on Monday/Thursday/Monday schedule followed by a 6-day break (FIG. 14, panel A). As HOS-FRα tumors grew aggressively without EC17 treatment, accelerating EC17 dose escalation at this CAR-T cell dose was safe (no CRS or body weight loss) and resulted in a significant delay in tumor growth within the first two cycles of treatment (FIG. 14, panel B). Upon protocol-mandated euthanasia due only to tumor size (≥1500 mm³), flow cytometric analyses performed on whole blood showed an EC17-dependent CAR-T cell expansion up to day 47 but higher on day 33 (FIG. 14, panel C, left bar graph). Ex vivo tumor analysis on day 33 indicated a low but significant intratumoral CD3ε+ EGFRt+ CAR-T cell population in EC17-treated animals which amounted to ~1% total viable digested tumor-derived cells (FIG. 14, panel C, right bar graph). As large HOS-FRα tumors stopped responding to treatment in Cycle 3 (FIG. 14, panel B), intratumoral CAR-T cells also diminished on day 47 (FIG. 14, panel C) Notably, HOS-FRα tumors analyzed by a ³H-FA radioligand assay upon disease progression showed similar FRα levels with and without EC17 treatment. Thus, it appeared that HOS-FRα tumors in NSG mice quickly outgrew the tumor infiltrating capability of CAR-T cells and may have decreased cytolytic activity due to T cell exhaustion as suggested by in vitro co-culture studies.

EC17 Dose Finding Study in Tumor-Containing and Tumor-Free Mice

The initial EC17 dose finding studies were conducted in MDA-MB-231 tumor bearing mice as shown by the schematic diagram of the experimental layout (FIG. 12, panel A). NSG mice without or with MDA-MB-231 tumors (~211±65 mm³) were engrafted on day 0 with ~10 million of a "clinical facsimile" batch of E2-CAR-T cells (~39% EGFRt+, 51:49 CD4/CD8). This batch of CAR-T cells consisted of mostly $T_{SCM}$ and $T_{CM}$ phenotypes (see FIG. 9). Two days after the CAR-T cell injection, one cohort of tumor-bearing mice were left untreated while three cohorts were treated with different regimens of EC17, including single injection per week (SIW) at 500 nmol/kg, or as escalating EC17 dose levels of 5/50/500 (Escalation-1) or 5/100/1000 nmol/kg (Escalation-2) given on a Monday/Thursday/Monday schedule with 1-week drug-free intervals. For comparison, two tumor-free cohorts were either untreated or treated with EC17 SIW at 500 nmol/kg.

Human T cell-derived IFNγ levels in mouse blood were measured in all cohorts using satellite animals on days 11 and 12 (~20 and 42 hours after the previous EC17 dose). Compared to tumor-bearing mice that received CAR-T cells only, all EC17 treated tumor cohorts had ~30× (day 11) and ~10× (day 12) higher IFNγ production in mouse plasma, and the levels of this cytokine decreased naturally from 20 hours to 42 hours later (FIG. 12, panel B). In accordance with IFNγ release, EC17 also triggered CAR-T cell expansion identified as human CD3ε+ EGFRt+ events in mouse blood, and cells persisted up to 54 days in tumor-bearing animals (last measurement) (FIG. 12, panel C). In tumor-free cohorts, no CAR-T cell expansion was detected by flow cytometry, but low levels of IFNγ were detected on days 11 and 12 in animals that received the same number of CAR-T cells plus EC17 (FIG. 12, panels B-C). Moreover, no CRS symptoms (grade 0 out of a 0-5 scale) or body weight loss was observed in tumor-free mice that received two weekly doses of EC17 at 500 nmol/kg.

Moderate-to-severe CRS symptoms (grades 2-3) and significant body weight losses (FIG. 12, panel D) were observed in tumor-bearing cohorts with continued EC17 dosing independent of the regimen. While EC17 SIW at 500 nmol/kg caused the earliest onset of CRS and body weight loss, the aggressive EC17 Escalation-2 regimen (up to 1000 nmol/kg) caused persistent body weight loss with animal recovery occurring after EC17 dose cessation (FIG. 12, panel D, top row). Notably, symptoms of graft-versus-host disease (GVHD) included red itching skin and hairlessness and became obvious at ~1 month after CAR-T cell engraftment. Although animals receiving only CAR-T cells showed signs of nonspecific CAR-T cell/tumor alloreactivity, only EC17-treated cohorts produced 100% cures (FIG. 12, panel D, bottom row). Therefore, EC17 administration in the presence of FR+ tumors was the key to drive i) CAR-T cell activation, ii) cytokine production, and iii) in vivo CAR-T cell expansion and persistence. Under specific conditions, however, severe CRS (grade ≥3) was triggered by a high CAR-T cell dose in combination with EC17 doses equal to or greater than 500 nmol/kg.

EC17 CAM Dosing Control in Anti-Leukemic Activity

Intravenously implanted GFP-expressing THP1-FRβ tumor cells developed disseminated diseases in NSG mice with tumor cells in the circulation and liver/non-liver metastases throughout the body. THP1-FRβ tumor cells could also localize to the mouse ovary which appeared inflamed during the early stage of tumor progression. Therefore, total tumor burden in each animal in study cohorts was assessed by quantitating circulating GFP+ tumor cells in the blood, liver weights, and all-inclusive non-liver macrometastases visible to the naked eye. Although THP1-FRβ expressed a low level of FR in vitro, THP1-FRβ tumor metastases were found to express a higher than expected functional FRs level at ~8.9±2.8 pmol/mg membrane protein. Thus, THP1-FRβ tumor-bearing mice were engrafted with a research batch of EGFRt-unsorted E2-CAR-T cells (~23% EGFRt+, 1:1 CD4: CD8) at ~6 million/animal and then treated with 3 different EC17 dosing regimens (FIG. 13). Starting 3 days after CAR-T cell injection, EC17 dosing regimens began as SIW at 500 nmol/kg continuously, three times a week (TIW) at 5/50/500 nmol/kg on Monday/Wednesday/Friday followed by a 9-day break, or by an accelerated dose escalation regimen at 5/10/100 nmol/kg in Cycle 1, 5/30/300 nmol/kg in Cycle 2, and 5/50/500 nmol/kg in Cycle 3, on Monday/Thursday/Monday (M/Th/M) followed by a 6-day break (FIG. 13, panel A). While some body weight loss and grade 1-2 CRS in Cycles 2 and 3 were observed in animals receiving EC17 SIW treatment, animals that received EC17 TIW had the least body weight loss with grade 0-1 CRS only (FIG. 13, panel B). Amongst the animals that received the 3 cycles of EC17 M/Th/M dose escalation, grade 0-1 CRS and very mild body weight loss were observed in Cycle 2 after the last dose of EC17 of 300 nmol/kg. Using satellite animals on day 31, CAR-T cells were enumerated in the blood and the data demonstrated EC17-dependent CAR-T cell expansion and persistence in all treated cohorts (FIG. 13, panel C). Compared to control animals that received tumor cells only or tumor cells plus CAR-T cells without EC17, EC17 dosed with any of the 3 "intra-patient" escalation formats effectively reduced circulating THP1-FRβ tumor cells in the blood and showed similar activities against liver tumor metastases (FIG. 13, panel D, left and middle bar graphs). Only minor allogeneic reactivity was seen against THP1-FRβ liver metastases in mice that received CAR-T cells only. While EC17 SIW and TIW at 10-fold dose escalation (on/off) successfully controlled non-liver macrometastases, EC17 M/Th/M dose escalation at a slow pace per cycle (FIG. 13, panel A) failed to control the non-liver macrometastases (FIG. 13, panel D, far right panel). At the end of study (i.e., 39 days post CAR-T cell injection), CAR-T cells isolated from liver THP1-FRβ tumor metastases appeared to have the least expression of double- and triple-positive T cell inhibitory receptors, PD1, LAG3 and TIM3 (FIG. 13, panel E). Overall, no severe CRS (i.e., grades ≥3) was observed in any EC17 treated cohorts. Nevertheless, the more aggressive EC17 TIW dose escalation (on/off) schedule trended to be the best regimen for reducing overall THP1-FRβ tumor burden in these mice.

Example 24

Functional FR Assessments

These functional FR assessments apply to examples described herein. Besides pediatric cancer cell lines transfected with FRα (HOS-FRα) and FRβ (THP1-FRβ), cancer cell lines of different histology and FR expression levels (FIG. 11) were included. As estimated by a radioligand binding assay (100 nM $^3$H-FA, 1 h at 37° C.), the ranking order of total available FRs on these cell lines was: 9×10$^4$ (OV90, a low-FR expressing ovarian cancer cell line), 1.9×10$^5$ (THP1-FRβ), 2.4×10$^5$ (HOS-FRα$^{fLuc}$), 7×10$^5$ (HOS-FRα), 2.1×10$^6$ (MDA-MB-231) and 4.8×10$^6$ (KB) FA molecules/cell. Also included as FR-negative controls were HOS-143b$^{(fLuc)}$ and THP1-FG12 parent cell lines. Thus, the general ranking of functional FR expression on co-cultured FR+ cancer cell lines was: KB>MDA-MB-231>HOS-FRα>HOS-FRα$^{fLuc}$>THP1-FRβ (AML)>OV90.

Example 25

Statistics

Statistical analyses were performed using the computer program GraphPad Prism (GraphPad Software Inc., San Diego, CA). Data were analyzed using Student's t-test or one-way ANOVA. If applicable, data were further analyzed across treatment groups using appropriate multiple comparison post-test. *=p<0.05 was considered statistically significant in all tests.

What is claimed is:

1. A method of treating a patient for cancer, the method comprising
   i) administering to the patient at least one dose of a chimeric antigen receptor T cell (CAR T cell) composition comprising CAR T cells comprising a chimeric antigen receptor (CAR) directed to a targeting moiety; and
   ii) administering to the patient a compound, or a pharmaceutically acceptable salt thereof, wherein the compound comprises a small molecule ligand linked to the targeting moiety by a linker, wherein the small molecule ligand is folate and wherein the targeting moiety is fluorescein, or a pharmaceutically acceptable salt thereof, fluorescein isothiocyanate (FITC), or NHS-fluorescein, and wherein the compound, or the pharmaceutically acceptable salt thereof, is administered in at least a first dose escalation sequence and a second dose escalation sequence, wherein a full dose of the compound, or the pharmaceutically acceptable salt thereof, is 10 μg/kg to 50 μg/kg of the compound, or the pharmaceutically acceptable salt thereof;
   wherein the first dose escalation sequence for the compound, or the pharmaceutically acceptable salt thereof, comprises administering 3 separate escalating doses up to the full dose of the compound on three separate days in a first two-week cycle; and
   wherein the second dose escalation sequence for the compound, or the pharmaceutically acceptable salt thereof, comprises administering 3 separate escalating doses up to the full dose of the compound on three separate days in a second two-week cycle,
   whereupon the patient is treated for cancer, and wherein the patient is a human.

2. The method of claim 1 wherein the compound, or the pharmaceutically acceptable salt thereof, is administered in at least a first dose escalation sequence, a second dose escalation sequence, and a third dose escalation sequence.

3. The method of claim 1 wherein a first dose of the CAR T cells and a second dose of the CAR T cells are administered to the patient.

4. The method of claim 3 wherein the first dose of the CART cells is a test dose to monitor the patient for tolerability to the CAR T cells.

5. The method of claim 4 wherein the second dose of the CAR T cells comprises a higher dose of the CAR T cells than the first dose of the CAR T cells.

6. The method of claim 1 wherein the first dose escalation sequence is followed by a period of time during which the compound, or the pharmaceutically acceptable salt thereof, is not administered.

7. The method of claim 6 wherein the period of time is about 7 days.

8. The method of claim 1 wherein the first dose escalation sequence comprises administering to the patient about 1 percent, about 10 percent, and about 100 percent of a full dose of the compound, or the pharmaceutically acceptable salt thereof, on three separate days.

9. The method of claim 2 wherein the second dose escalation sequence comprises administering to the patient about 1 percent, about 30 percent, and about 300 percent of a full dose of the compound, or the pharmaceutically acceptable salt thereof, on three separate days.

10. The method of claim 2 wherein the third dose escalation sequence comprises administering to the patient about 1 percent, about-50 percent, and about 500 percent of a full dose of the compound, or the pharmaceutically acceptable salt thereof, on three separate days.

11. The method of claim 1 wherein, if no cytokine release syndrome (CRS) or neurotoxicity is observed in the patient during the first dose escalation sequence, the method is advanced to the second dose escalation sequence.

12. The method of claim 1 wherein, if no CRS or neurotoxicity is observed in the patient during the second dose escalation sequence, the method is advanced to the third dose escalation sequence.

13. The method of claim 1 wherein if fever without hypotension is observed in the patient and no neurotoxicity is observed in the patient during any one of the dose escalation sequences, all subsequent doses of the compound, or the pharmaceutically acceptable salt thereof, are administered to the patient at the dose escalation sequence level that caused the fever without hypotension.

14. The method of claim 1 wherein, if serious CRS or neurotoxicity occurs in the patient in any dose escalation sequence, all subsequent doses of the compound, or the pharmaceutically acceptable salt thereof, are administered to the patient at the dose escalation sequence level below the dose escalation sequence level that caused the serious CRS or neurotoxicity in the patient.

\* \* \* \* \*